United States Patent
Tsai et al.

(10) Patent No.: US 12,311,194 B2
(45) Date of Patent: *May 27, 2025

(54) SYSTEMS AND METHODS FOR PREVENTING, MITIGATING, AND/OR TREATING DEMENTIA

(71) Applicant: Massachusetts Institute of Technology, Cambridge, MA (US)

(72) Inventors: Li-Huei Tsai, Cambridge, MA (US); Anthony James Martorell, Cambridge, MA (US); Ho-Jun Suk, Cambridge, MA (US); Ed Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 224 days.

This patent is subject to a terminal disclaimer.

(21) Appl. No.: 17/666,153

(22) Filed: Feb. 7, 2022

(65) Prior Publication Data

US 2022/0233879 A1  Jul. 28, 2022

Related U.S. Application Data

(63) Continuation of application No. 16/135,938, filed on Sep. 19, 2018, now Pat. No. 11,241,586.
(Continued)

(51) Int. Cl.
*A61N 5/06* (2006.01)
*A61M 21/00* (2006.01)

(52) U.S. Cl.
CPC ......... *A61N 5/0618* (2013.01); *A61N 5/0622* (2013.01); *A61M 2021/0022* (2013.01);
(Continued)

(58) Field of Classification Search
CPC ........ A61N 5/06; A61N 5/0618; A61N 5/062; A61N 5/0622; A61N 2005/0626;
(Continued)

(56) References Cited

U.S. PATENT DOCUMENTS

| 4,315,502 A | 2/1982 | Gorges |
| 4,449,047 A | 5/1984 | Monroe |

(Continued)

FOREIGN PATENT DOCUMENTS

| AU | 2017363200 A1 | 6/2019 |
| AU | 2018347870 A1 | 4/2020 |

(Continued)

OTHER PUBLICATIONS

Gualdi et al., "Wound Repair and Extremely Low Frequency-Electromagnetic Field: Insight from In Vitro Study and Potential Clinical Application" Int. J. Mol Sci. 2021, 22, 5027.*
(Continued)

*Primary Examiner* — Ahmed M Farah
(74) *Attorney, Agent, or Firm* — Smith Baluch LLP

(57) ABSTRACT

Devices, systems, and methods for a treating dementia or Alzheimer's disease in a subject in need thereof. In one example, combined auditory and visual stimuli having a frequency of about 20 Hz to about 60 Hz, and more specifically about 40 Hz, are non-invasively delivered to the subject to induce synchronized gamma oscillations in at least one brain region of the subject. In particular, pursuant to various treatment and exposure protocols, combined auditory and visual stimulation (as opposed to auditory or visual stimulation alone) promotes a microglia response in the medial prefrontal cortex (mPFC). More generally, combined auditory and visual stimulation induces an extended microglia clustering response in the auditory cortex, the visual cortex, and the mPFC.

58 Claims, 128 Drawing Sheets
(41 of 128 Drawing Sheet(s) Filed in Color)

Related U.S. Application Data

(60) Provisional application No. 62/570,929, filed on Oct. 11, 2017, provisional application No. 62/570,250, filed on Oct. 10, 2017.

(52) U.S. Cl.
CPC .............. *A61M 2021/0027* (2013.01); *A61M 2210/0693* (2013.01); *A61N 5/062* (2013.01); *A61N 2005/0626* (2013.01); *A61N 2005/063* (2013.01); *A61N 2005/0647* (2013.01); *A61N 2005/0651* (2013.01); *A61N 2005/0667* (2013.01)

(58) Field of Classification Search
CPC ...... A61N 2005/0627; A61N 2005/063; A61N 2005/0643; A61N 2005/0647; A61N 2005/065; A61N 2005/0658; A61M 2021/0005; A61M 2021/0022; A61M 2021/0027; A61M 2021/0055; A61M 2210/069
USPC ...................................... 607/88, 89, 101, 109
See application file for complete search history.

(56) References Cited

U.S. PATENT DOCUMENTS

| | | |
|---|---|---|
| 4,456,910 A | 6/1984 | DiMassimo et al. |
| 4,674,852 A | 6/1987 | Tanaka |
| 5,151,687 A | 9/1992 | Younger |
| 5,534,953 A | 7/1996 | Schmielau |
| 5,659,287 A | 8/1997 | Donati et al. |
| 5,923,398 A | 7/1999 | Goldman |
| 5,934,967 A | 8/1999 | Brown et al. |
| 6,066,163 A | 5/2000 | John |
| 6,071,229 A | 6/2000 | Rubins |
| 6,113,537 A | 9/2000 | Castano |
| 6,167,298 A | 12/2000 | Levin |
| 6,206,537 B1 | 3/2001 | Hauck |
| 6,234,953 B1 | 5/2001 | Thomas et al. |
| 6,443,977 B1 | 9/2002 | Jaillet |
| 6,463,328 B1 | 10/2002 | John |
| 6,539,263 B1 | 3/2003 | Schiff et al. |
| 6,733,490 B1 | 5/2004 | Falsini et al. |
| 7,010,356 B2 | 3/2006 | Jog et al. |
| 7,361,074 B1 | 4/2008 | Periman et al. |
| 7,446,785 B1 | 11/2008 | Hewlett et al. |
| 7,569,545 B2 | 8/2009 | Li et al. |
| 7,645,226 B2 | 1/2010 | Shealy et al. |
| 7,715,910 B2 | 5/2010 | Hargrove et al. |
| 7,748,846 B2 | 7/2010 | Todd |
| 7,769,439 B2 | 8/2010 | Vesely et al. |
| 7,798,982 B2 | 9/2010 | Zets et al. |
| 8,070,669 B2 | 12/2011 | Brunelle et al. |
| 8,083,392 B2 | 12/2011 | Chien |
| 8,121,694 B2 | 2/2012 | Molnar et al. |
| 8,239,030 B1 | 8/2012 | Hagedorn et al. |
| 8,267,851 B1 | 9/2012 | Kroll |
| 8,280,502 B2 | 10/2012 | Hargrove et al. |
| 8,328,420 B2 | 12/2012 | Abreu |
| 8,380,314 B2 | 2/2013 | Panken et al. |
| 8,396,545 B2 | 3/2013 | Berridge et al. |
| 8,423,144 B2 | 4/2013 | Tass et al. |
| 8,543,219 B2 | 9/2013 | Tass |
| 8,577,470 B2 | 11/2013 | Assaf et al. |
| 8,579,793 B1 | 11/2013 | Honeycutt et al. |
| 8,591,392 B2 | 11/2013 | Baror et al. |
| 8,636,640 B2 | 1/2014 | Chang |
| 8,700,167 B2 | 4/2014 | Sabel |
| 8,845,704 B2 | 9/2014 | Dunning et al. |
| 8,892,207 B2 | 11/2014 | Nelson et al. |
| 8,894,696 B2 | 11/2014 | Hurst |
| 8,914,119 B2 | 12/2014 | Wu et al. |
| 8,932,218 B1 | 1/2015 | Thompson |
| 8,942,809 B2 | 1/2015 | Assaf et al. |
| 9,119,583 B2 | 9/2015 | Tass |
| 9,272,118 B1 | 3/2016 | Acton |
| 9,302,069 B2 | 4/2016 | Tass et al. |
| 9,629,976 B1 | 4/2017 | Acton |
| 10,159,816 B2 * | 12/2018 | Tsai ..................... A61N 5/0622 |
| 10,265,497 B2 | 4/2019 | Tsai et al. |
| 10,279,192 B2 | 5/2019 | Malchano et al. |
| 10,293,177 B2 | 5/2019 | Malchano et al. |
| 10,307,611 B2 | 6/2019 | Malchano et al. |
| 10,518,063 B1 | 12/2019 | Noftsker |
| 10,682,490 B2 * | 6/2020 | Tsai ..................... A61N 5/0622 |
| 10,702,705 B2 | 7/2020 | Malchano et al. |
| 10,745,479 B2 | 8/2020 | Jaminet et al. |
| 10,843,006 B2 | 11/2020 | Malchano et al. |
| 10,960,225 B2 * | 3/2021 | Adaikkan ............ A61N 5/1001 |
| 11,141,604 B2 | 10/2021 | Malchano et al. |
| 11,241,586 B2 * | 2/2022 | Tsai ..................... A61N 5/0618 |
| 2001/0027278 A1 | 10/2001 | Kaufman et al. |
| 2001/0039012 A1 | 11/2001 | Lapidus |
| 2004/0097841 A1 | 5/2004 | Saveliev et al. |
| 2004/0158119 A1 | 8/2004 | Osorio et al. |
| 2005/0070977 A1 | 3/2005 | Molina |
| 2005/0234286 A1 | 10/2005 | Riehl et al. |
| 2006/0047324 A1 | 3/2006 | Tass |
| 2006/0173510 A1 | 8/2006 | Besio et al. |
| 2006/0263332 A1 | 11/2006 | Li et al. |
| 2007/0038142 A1 | 2/2007 | Todd et al. |
| 2007/0156182 A1 | 7/2007 | Castel et al. |
| 2007/0179557 A1 | 8/2007 | Maschino et al. |
| 2007/0191727 A1 | 8/2007 | Fadem |
| 2007/0218994 A1 | 9/2007 | Goto et al. |
| 2007/0225773 A1 | 9/2007 | Shen et al. |
| 2007/0253561 A1 | 11/2007 | Williams et al. |
| 2008/0055541 A1 | 3/2008 | Coulter et al. |
| 2008/0181882 A1 | 7/2008 | Hahn |
| 2008/0227139 A1 | 9/2008 | Deisseroth et al. |
| 2008/0249439 A1 | 10/2008 | Tracey et al. |
| 2008/0255949 A1 | 10/2008 | Genco et al. |
| 2009/0005837 A1 | 1/2009 | Olmstead |
| 2009/0018419 A1 | 1/2009 | Torch |
| 2009/0023977 A1 | 1/2009 | Sperling et al. |
| 2009/0030476 A1 | 1/2009 | Hargrove |
| 2009/0093403 A1 | 4/2009 | Zhang et al. |
| 2009/0153800 A1 | 6/2009 | Bassi et al. |
| 2009/0237563 A1 | 9/2009 | Doser |
| 2009/0270776 A1 | 10/2009 | Chang |
| 2009/0306555 A1 | 12/2009 | Goto |
| 2009/0312624 A1 | 12/2009 | Berridge et al. |
| 2010/0013402 A1 | 1/2010 | Chaffai et al. |
| 2010/0109541 A1 | 5/2010 | Roberts et al. |
| 2010/0174344 A1 | 7/2010 | Dadd et al. |
| 2010/0190129 A1 | 7/2010 | Paz |
| 2010/0217358 A1 | 8/2010 | Hebert et al. |
| 2010/0241021 A1 | 9/2010 | Morikawa et al. |
| 2010/0274329 A1 | 10/2010 | Bradley et al. |
| 2010/0331912 A1 | 12/2010 | Tass et al. |
| 2011/0009922 A1 | 1/2011 | Assaf et al. |
| 2011/0066586 A1 | 3/2011 | Sabel et al. |
| 2011/0105998 A1 | 5/2011 | Zhang et al. |
| 2011/0118534 A1 | 5/2011 | Baror et al. |
| 2011/0122396 A1 | 5/2011 | Ivaldi et al. |
| 2011/0152967 A1 | 6/2011 | Simon et al. |
| 2011/0280932 A1 | 11/2011 | Garcia et al. |
| 2012/0016174 A1 | 1/2012 | Taboada et al. |
| 2012/0065709 A1 | 3/2012 | Dunning et al. |
| 2012/0150545 A1 | 6/2012 | Simon |
| 2012/0253236 A1 | 10/2012 | Snow et al. |
| 2012/0271374 A1 | 10/2012 | Nelson et al. |
| 2012/0289869 A1 | 11/2012 | Tyler |
| 2013/0004517 A1 * | 1/2013 | Tsai ..................... A61K 31/00 514/315 |
| 2013/0021138 A1 | 1/2013 | Ezzat et al. |
| 2013/0066392 A1 | 3/2013 | Simon et al. |
| 2013/0066395 A1 | 3/2013 | Simon et al. |
| 2013/0083173 A1 | 4/2013 | Geisner et al. |
| 2013/0084299 A1 | 4/2013 | Maze et al. |
| 2013/0211238 A1 | 8/2013 | deCharms |
| 2013/0211277 A1 | 8/2013 | Berg et al. |

(56) References Cited

U.S. PATENT DOCUMENTS

| | | |
|---|---|---|
| 2013/0216055 A1 | 8/2013 | Wanca |
| 2013/0253338 A1 | 9/2013 | Kang et al. |
| 2013/0267759 A1 | 10/2013 | Jin |
| 2013/0317569 A1 | 11/2013 | Deisseroth et al. |
| 2013/0328490 A1 | 12/2013 | Chen |
| 2013/0338738 A1 | 12/2013 | Molina et al. |
| 2014/0081347 A1 | 3/2014 | Nelson et al. |
| 2014/0085446 A1 | 3/2014 | Hicks |
| 2014/0107525 A1 | 4/2014 | Tass |
| 2014/0135680 A1 | 5/2014 | Peyman |
| 2014/0194957 A1 | 7/2014 | Rubinfeld et al. |
| 2014/0200432 A1 | 7/2014 | Banerji et al. |
| 2014/0257438 A1 | 9/2014 | Simon et al. |
| 2014/0303025 A1 | 10/2014 | Keuren-Jensen et al. |
| 2014/0303424 A1 | 10/2014 | Glass |
| 2014/0316192 A1 | 10/2014 | Zambotti et al. |
| 2014/0324138 A1 | 10/2014 | Wentz et al. |
| 2014/0330335 A1 | 11/2014 | Errico et al. |
| 2014/0336514 A1 | 11/2014 | Peyman |
| 2014/0347265 A1 | 11/2014 | Aimone et al. |
| 2015/0002025 A1 | 1/2015 | Maricic et al. |
| 2015/0088212 A1 | 3/2015 | De Ridder |
| 2015/0157604 A1 | 6/2015 | Morozova et al. |
| 2015/0196762 A1 | 7/2015 | Amurthur et al. |
| 2015/0235597 A1 | 8/2015 | Meng et al. |
| 2015/0305667 A1 | 10/2015 | Durand |
| 2015/0337030 A1 | 11/2015 | Abeliovich |
| 2015/0342495 A1 | 12/2015 | Davis et al. |
| 2016/0051793 A1 | 2/2016 | Gibson-Horn |
| 2016/0067087 A1 | 3/2016 | Tedford et al. |
| 2016/0091758 A1 | 3/2016 | Yoneyama |
| 2016/0220821 A1 | 8/2016 | O'connell et al. |
| 2016/0235980 A1 | 8/2016 | Berman et al. |
| 2017/0072162 A1 | 3/2017 | Kim et al. |
| 2017/0082255 A1 | 3/2017 | Bentley et al. |
| 2017/0143934 A1* | 5/2017 | Tsai ............ A61M 21/00 |
| 2017/0143966 A1 | 5/2017 | Reymers et al. |
| 2017/0151436 A1 | 6/2017 | Flaherty et al. |
| 2017/0182285 A1* | 6/2017 | Tyler ............ A61B 5/4806 |
| 2017/0266443 A1 | 9/2017 | Rajguru et al. |
| 2018/0133431 A1 | 5/2018 | Malchano et al. |
| 2018/0133507 A1 | 5/2018 | Malchano et al. |
| 2018/0206737 A1 | 7/2018 | Colman |
| 2018/0236262 A1 | 8/2018 | Morries et al. |
| 2018/0277377 A1 | 9/2018 | Eto et al. |
| 2018/0286188 A1 | 10/2018 | Novak et al. |
| 2019/0030190 A1 | 1/2019 | Peyman |
| 2019/0062425 A1 | 2/2019 | Jaminet et al. |
| 2019/0076670 A1 | 3/2019 | Vyshedskiy |
| 2019/0105509 A1 | 4/2019 | Tsai et al. |
| 2019/0126056 A1 | 5/2019 | Bogdan |
| 2019/0126062 A1 | 5/2019 | Adaikkan et al. |
| 2019/0215926 A1 | 7/2019 | Lay et al. |
| 2019/0240443 A1 | 8/2019 | Tsai et al. |
| 2019/0254775 A1 | 8/2019 | Gregg et al. |
| 2019/0314641 A1 | 10/2019 | Malchano et al. |
| 2019/0388020 A1 | 12/2019 | Stauch et al. |
| 2020/0038658 A1* | 2/2020 | Tyler ............ A61M 21/02 |
| 2020/0069808 A1 | 3/2020 | Luehr et al. |
| 2020/0164220 A1 | 5/2020 | Broeng et al. |
| 2020/0171267 A1 | 6/2020 | Millard et al. |
| 2020/0269065 A1 | 8/2020 | Broeng et al. |
| 2020/0316334 A1 | 10/2020 | Tsai et al. |
| 2020/0316335 A1 | 10/2020 | Tsai et al. |
| 2021/0030998 A1 | 2/2021 | Wong |
| 2021/0121713 A1 | 4/2021 | Malchano et al. |
| 2021/0236837 A1 | 8/2021 | Lu |
| 2021/0339043 A1* | 11/2021 | Malchano ........ A61N 1/36092 |
| 2022/0008746 A1 | 1/2022 | Malchano et al. |
| 2022/0040496 A1 | 2/2022 | Adaikkan et al. |
| 2022/0151864 A1 | 5/2022 | Tsai et al. |
| 2023/0166072 A1 | 6/2023 | Malchano et al. |
| 2023/0173295 A1 | 6/2023 | Kim et al. |
| 2023/0181905 A1 | 6/2023 | Tsai et al. |
| 2024/0293680 A1 | 9/2024 | Malchano et al. |
| 2024/0325780 A1 | 10/2024 | Malchano et al. |

FOREIGN PATENT DOCUMENTS

| | | |
|---|---|---|
| CA | 2979686 A1 | 9/2016 |
| CA | 2979687 A1 | 9/2016 |
| CA | 3078704 A1 | 4/2019 |
| CN | 102791332 A | 11/2012 |
| CN | 103298480 A | 9/2013 |
| CN | 103492564 A | 1/2014 |
| CN | 104039353 A | 9/2014 |
| CN | 104783788 A | 7/2015 |
| CN | 103932701 B | 9/2015 |
| CN | 105278387 A | 1/2016 |
| CN | 106103711 A | 11/2016 |
| CN | 107002076 A | 8/2017 |
| CN | 108725462 A | 11/2018 |
| CN | 111655319 A | 9/2020 |
| EP | 0911398 A3 | 4/1999 |
| EP | 1642609 A1 | 4/2006 |
| EP | 2075035 A1 | 7/2009 |
| EP | 2489402 A2 | 8/2012 |
| EP | 3694464 A4 | 8/2020 |
| EP | 3694593 A1 | 8/2020 |
| EP | 3541467 B1 | 1/2024 |
| IT | RM20090027 A1 | 7/2010 |
| JP | 108150210 A | 6/1996 |
| JP | 2006525039 A | 11/2006 |
| JP | 2008520280 A | 6/2008 |
| JP | 2011514194 A | 5/2011 |
| JP | 2014071825 A | 4/2014 |
| JP | 2015519096 A | 7/2015 |
| JP | 2018525754 A | 9/2018 |
| KR | 1020020025884 A | 4/2002 |
| KR | 1020130101596 A | 9/2013 |
| KR | 1020140144272 A | 12/2014 |
| KR | 20160129752 A | 11/2016 |
| WO | 1997016196 A1 | 5/1997 |
| WO | 0184141 A1 | 11/2001 |
| WO | 2007062367 A2 | 5/2007 |
| WO | 2008041129 A2 | 4/2008 |
| WO | 2008101128 A1 | 8/2008 |
| WO | 2008147958 A1 | 12/2008 |
| WO | 2010123577 A2 | 10/2010 |
| WO | 2008041129 A3 | 3/2011 |
| WO | 2011042908 A1 | 4/2011 |
| WO | 2011057028 A1 | 5/2011 |
| WO | 2012024243 A1 | 2/2012 |
| WO | 2013061597 A1 | 5/2013 |
| WO | 2013152348 A1 | 10/2013 |
| WO | 2014040175 A1 | 3/2014 |
| WO | 2014107795 A1 | 7/2014 |
| WO | 2014130960 A1 | 8/2014 |
| WO | 2014162271 A2 | 10/2014 |
| WO | 2014179331 A2 | 11/2014 |
| WO | 2015034673 A1 | 3/2015 |
| WO | 2015066679 A2 | 5/2015 |
| WO | 2015149170 A1 | 10/2015 |
| WO | 2015066679 A3 | 11/2015 |
| WO | 2017091698 A1 | 6/2017 |
| WO | 2017091758 A1 | 6/2017 |
| WO | 2017172728 A1 | 10/2017 |
| WO | 2018094226 A1 | 5/2018 |
| WO | 2019046338 A1 | 3/2019 |
| WO | 2019074637 A1 | 4/2019 |
| WO | 2019075094 A1 | 4/2019 |
| WO | 2019241430 A2 | 12/2019 |
| WO | 2020041502 A1 | 2/2020 |
| WO | 2021216957 A1 | 10/2021 |
| WO | 2021221879 A1 | 11/2021 |
| WO | 2022027030 A1 | 2/2022 |
| WO | 2022192277 A1 | 9/2022 |

(56) References Cited

OTHER PUBLICATIONS

Acharya, et al. "Stem cell transplantation reverses chemotherapy-induced cognitive dysfunction." Cancer research 75.4 (2015): 676-686.

Amazon-listed product. "Mindplace Kasina DeepVision Bundle—Light and Sound Meditation Aid"; https://a.co/d/6nu7NcP; Date First Available: Nov. 6, 2015, retreived Jul. 23, 2023, 10 pages.

Callaghan, et al. "Long-term cognitive dysfunction in the rat following docetaxel treatment is ameliorated by the phosphodiesterase-4 inhibitor, rolipram." Behavioural brain research 290 (2015): 84-89, 6 pages.

Cheng, et al. "Neo-adjuvant chemotherapy with cisplatin induces low expression of NMDA receptors and postoperative cognitive impairment." Neuroscience Letters 637 (2017): 168-174, 7 pages.

Corrected Notice of Allowance for U.S. Appl. No. 16/427,276, dated May 6, 2020, 2 pages.

El-Agamy, et al. "Astaxanthin ameliorates doxorubicin-induced cognitive impairment (chemobrain) in experimental rat model: impact on oxidative, inflammatory, and apoptotic machineries." Molecular neurobiology 55 (2018): 5727-5740, 14 pages.

Elbeltagy, et al. "Fluoxetine improves the memory deficits caused by the chemotherapy agent 5-fluorouracil." Behavioural brain research 208.1 (2010): 112-117.

Extended European Search Report with Written Opinion in European App. No. 23150106.5 dated Jul. 5, 2023, 7 pages.

Fardell, et al. "Cognitive impairments caused by oxaliplatin and 5-fluorouracil chemotherapy are ameliorated by physical activity." Psychopharmacology 220 (2012): 183-193, 12 pages.

Final Office Action for U.S. Appl. No. 15/816,238 dated Nov. 30, 2018, 9 pages.

Final Office Action for U.S. Appl. No. 16/404,302, dated Jan. 28, 2020, 17 pages.

Final Office Action for U.S. Appl. No. 16/415,825, dated Jan. 27, 2020, 7 pages.

Final Office action for U.S. Appl. No. 16/427,276, dated Nov. 22, 2019, 7 pages.

Huehnchen, et al. "A novel preventive therapy for paclitaxel-induced cognitive deficits: preclinical evidence from C57BL/6 mice." Translational psychiatry 7.8 (2017): e1185-e1185, 11 pages.

International Preliminary Report on Patentability for PCT Appl. No. PCT/US2017/062328, dated May 21, 2019, 11 pages.

International Preliminary Report on Patentability for PCT Appl. No. PCT/US2017/062333, mailed on May 21, 2019, 16 pages.

International Search Report and Written Opinion for International Appl. No. PCT/US2017/062328, mailed on May 3, 2018, 16 pages.

International Search Report and Written Opinion for International Appl. No. PCT/US2017/062333, mailed on Jun. 20, 2018, 24 pages.

International Search Report and Written Opinion for International Appl. No. PCT/US2017/062335, mailed on Apr. 12, 2018, 12 pages.

International Search Report and Written Opinion in International Appl. No. PCT/US2022/044755 mailed Dec. 22, 2022, 16 pages.

International Search Report and Written Opinion in International Appl. No. PCT/US2022/044760 mailed Dec. 23, 2022, 17 pages.

International Search Report and Written Opinion in International Appl. No. PCT/US2022/081353 mailed May 26, 2023, 20 pages.

Invitation to pay Additional Search Fees in International Application No. PCT/US2022/081353 dated Mar. 15, 2023, 3 pages.

Johnston, et al. "Ibudilast reduces oxaliplatin-induced tactile allodynia and cognitive impairments in rats." Behavioural Brain Research 334 (2017): 109-118, 10 pages.

Kasina Manual. MindPlace. Updated: Jan. 2020. [Online]. Available: https://mindplacesupport.com/download/1244/?tmstv=1687473751, 26 pages.

Korean Office Action in Korean Application No. 10-2023-7001501 dated Apr. 25, 2023, 7 pages.

Korean_IUPTAB_Appeal Decision with translation in Korean Application No. 10-2020-7013291 dated May 16, 2023, 36 pages.

Lim, et al. "PET evidence of the effect of donepezil on cognitive performance in an animal model of chemobrain." BioMed research international 2016 (2016), 8 pages.

Lyons, et al. "Fluoxetine counteracts the cognitive and cellular effects of 5-fluorouracil in the rat hippocampus by a mechanism of prevention rather than recovery." PloS one 7.1 (2012): e30010, 8 pages.

Mathys et al. "Single-cell transcriptomic analysis of Alzheimer's disease." Nature 570.7761 (2019): 332-337, 25 pages.

Nguyen, et al. "Cellular mechanisms and treatments for chemobrain: insight from aging and neurodegenerative diseases." EMBO molecular medicine 12.6 (2020): e12075, 17 pages.

Non-Final Office action for U.S. Appl. No. 15/816,222, dated Jun. 15, 2018, 16 pages.

Non-Final Office Action for U.S. Appl. No. 15/816,238, dated Feb. 28, 2018, 7 pages.

Non-Final Office Action for U.S. Appl. No. 15/816,233, dated Sep. 21, 2018, 7 pages.

Non-Final Office Action for U.S. Appl. No. 16/404,302, dated Sep. 6, 2019, 22 pages.

Non-Final Office Action for U.S. Appl. No. 16/415,825, dated Jun. 13, 2019, 8 pages.

Non-Final Office Action for U.S. Appl. No. 16/427,276, dated Jul. 31, 2019, 6 pages.

Non-Final Office Action for U.S. Appl. No. 18/160,674 dated Jun. 8, 2023, 9 pages.

Non-Final Office Action on U.S. Appl. No. 16/404,302, dated Jul. 24, 2020, 15 pages.

Notice of Allowance for U.S. Appl. No. 15/816,222 dated Jan. 24, 2019, 7 pages.

Notice of Allowance for U.S. Appl. No. 15/816,222, dated Mar. 4, 2019, 8 pages.

Notice of Allowance for U.S. Appl. No. 15/816,233, dated Jan. 10, 2019, 9 pages.

Notice of Allowance for U.S. Appl. No. 15/816,238, dated Mar. 19, 2019, 7 pages.

Notice of Allowance for U.S. Appl. No. 16/427,276, dated Feb. 24, 2020, 7 pages.

Notice of Allowance for U.S. Appl. No. 16/415,825, dated Jul. 20, 2020, 7 pages.

Notice of Allowance in Canadian Application No. 3003183, dated Jun. 27, 2023 1 page.

Notice of Allowance with translation in Korean Application No. 10-2022-7037169 dated Aug. 14, 2023, 5 pages.

Office Action (Final Rejection) with translation in Chinese Application no. 201880077874.3 dated May 20, 2023, 21 pages.

Office Action with translation for corresponding Japanese Application No. JP2019-547581, dated Jul. 3, 2021, 31 pages.

Park, et al. "Physical exercise prevents cognitive impairment by enhancing hippocampal neuroplasticity and mitochondrial function in doxorubicin-induced chemobrain." Neuropharmacology 133 (2018): 451-461, 11 pages.

Fries, P. et al., "The gamma cycle," Trends in Neurosciences, vol. 30 (Jul. 2007): 309-316.

Geraghty et al., "Loss of adaptive myelination contributes to methotrexate chemotherapy-related cognitive impairment." Neuron 103.2 (2019): 250-265.

Gibson et al., "Methotrexate chemotherapy induces persistent triglial dysregulation that underlies chemotherapy-related cognitive impairment." Cell 176.1-2 (2019): 43-55.

Gibson et al., "Neuronal activity promotes oligodendrogenesis and adaptive myelination in the mammalian brain." Science 344.6183 (2014). 27 pages.

Gillepsie, A. et al., "Apolipoprotein E4 Causes Age-Dependent Disruption of Slow Gamma Oscillations during Hippocampal Sharp-Wave Ripples," Neuron, vol. 90 (May 2016): 740-751.

Gjoneska, E. et al., "Conserved epigenomic signals in mice and humans reveal immune basis of Alzheimer's disease," Nature, vol. 518 (Feb. 2015): 365-369.

Gosselin, D. et al., "Environment drives selection and function of enhancers controlling tissue-specific macrophage identities," Cell, vol. 159 (Dec. 2014): 1327-1340.

Goutagny, R. et al., "Alterations in hippocampal network oscillations and theta-gamma coupling arise before Aβ overproduction in a mouse model of Alzheimer's disease," European Journal of Neuroscience, vol. 37 (Jun. 2013): 1896-1902.

(56) References Cited

OTHER PUBLICATIONS

Gray, C. et al., "Chattering cells: superficial pyramidal neurons contributing to the generation of synchronous oscillations in the visual cortex," Science, vol. 274 (Oct. 1996): 109-113.
Gray, C. et al., "Oscillatory responses in cat visual cortex exhibit inter-columnar synchronization which reflects global stimulus properties," Nature, vol. 338 (Mar. 1989): 334-337.
Harvey, C. et al., "Intracellular dynamics of hippocampal place cells during virtual navigation," Nature, vol. 461 (Oct. 2009): 941-946.
Jelwig, M. et al., "The neuroendocrine protein 7B2 suppresses the aggregation of neurodegenerative disease-related proteins," The Journal of Biological Chemistry, vol. 288 (Jan. 2013): 1114-1124.
Hen Eka, M. et al., "Innate immune activation in neurodegenerative disease," Nature Reviews Immunology, vol. 14 (Jul. 2014): 463-477.
Hermann, C. et al., "Human Eeg gamma oscillation in neuropsychiatric disorders," Clinical Neurophysiology, vol. 116 (Sep. 2006): 2719-2733.
Hermann, C. et al., "Human EEG responses to 1-100 Hz flicker: resonance phenomena in visual cortex and their potential correlation to cognitive phenomena," Experimental Brain Research, vol. 137 (Apr. 2001): 346-353.
Hermelink, "Chemotherapy and cognitive function in breast cancer patients: the so-called chemo brain." Journal of the National Cancer Institute Monographs 2015.51 (2015): 67-69.
Hsiao, F. et al., "Altered Oscillation and Synchronization of Default-Mode Network Activity in Mild Alzheimer's Disease Compared to Mild Cognitive Impairment: an Electrophysiological Study," PLOS One, vol. 8 (Jul. 2013): 1-10.
Huang, S. et al., "Cell-intrinsic lysosomal lipolysis is essential for alternative activation of macrophages," Nature Immunology, vol. 15 (Sep. 2014): 846-855.
Iliff, J. et al., "A Paravascular Pathway Facilitates CSF Flow Through the Brain Parenchyma and the Clearance of Interstitial Solutes, Including Amyloid β," Science Trandlational Medicine, vol. 4 (Aug. 2012): 147.
International Search Report and Written Opinion in International Patent Application No. PCT/US 18/55258 mailed Dec. 27, 2018. 16 pages.
International Search Report and Written Opinion in International Patent Application No. PCT/US2018/051785 mailed Jan. 24, 2019, 16 pages.
International Search Report and Written Opinion in International Patent Application No. PCT/US2021/028776 mailed Aug. 13, 2021, 19 pages.
International Search Report and Written Opinion issued by the International Searching Authority for Internaltional Application No. PCT/US16/63536, dated Mar. 27, 2017, 19 pages.
Israel, M. et al., "Probing sporadic and familial Alzheimer's disease using induced pluripotent stem cells," Nature, vol. 482 (Jan. 2012): 216-220.
Japanese Office Action in Japanese Patent Application No. 2018-525754 dated Nov. 2, 2020, 13 pages.
Jeong, J. "EEG dynamics in patients with Alzheimer's disease," Clinical Neurophysiology, vol. 115 (Aug. 2004): 1490-1505.
Jiang et al., "PAN-811 prevents chemotherapy-induced cognitive impairment and preserves neurogenesis in the hippocampus of adult rats." Plos one 13.1 (2018): e0191866.
Khasabova et al., "Pioglitazone, a PPARγ agonist, reduces cisplatin-evoked neuropathic pain by protecting against oxidative stress." Pain 160.3 (2019): 688-701.
Koenig, T. et al., "Decreased EEG synchronization in Alzheimer's disease and mild cognitive impairment," Neurobiology of Aging, vol. 26 (Feb. 2005): 165-171.
Kreutzberg, G. "Microglia: a sensor for pathological events in the CNS," Trends in Neurosciences, vol. 19 (Sep. 1996): 312-318.
Krynetskiy et al., "Establishing a model for assessing DNA damage in murine brain cells as a molecular marker of chemotherapy-associated cognitive impairment." Life sciences 93.17 (2013): 605-610.
Kumburovic et al., "Antioxidant effects of *Satureja hortensis* L. attenuate the anxiogenic effect of cisplatin in rats." Oxidative medicine and cellular longevity 2019 (2019). 15 pages.
Kurudenkandy, F. et al., "Amyloid-β-Induced Action Potential Desynchronization and Degradation of Hippocampal Gamma Oscillations is Prevented by Interference with Peptide Conformation Change and Aggregation," The Journal of Neuroscience, vol. 34 (Aug. 2014): 11416-11425.
Laumet et al., "Cisplatin educates CD8+ T cells to prevent and resolve chemotherapy-induced peripheral neuropathy in mice." Pain 160.6 (2019): 1459. 19 pages.
Leinenga, G. et al., "Scanning ultrasound removes amyloid-β and restores memory in an Alzheimer's disease mouse model," Science Translational Medicine, vol. 7 (Mar. 2015): 12 pages.
Leo et al., "Cisplatin-induced neuropathic pain is mediated by upregulation of N-type voltage-gated calcium channels in dorsal root ganglion neurons." Experimental neurology 288 (2017): 62-74.
Li, F. et al., "Effect of electroacupuncture stimulation of "Baihui" (GV 20) and "Yongquan" (KI 1) on expression of hippocampal amyloid-β and low density lipoprotein receptor-related protein-1 in APP/PS 1 transgenic mice," Zhen Ci Yan Jiu, vol. 40 (Feb. 2015), 1 page.
Lok, K. et al., "Characterization of the APP/PS1 mouse model of Alzheimer's disease in senescence accelerated background," Neuroscience Letters, vol. 557 (Dec. 2013): 84-89.
Martorell et al., "Multi-sensory gamma stimulation ameliorates Alzheimer's-associated pathology and improves cognition." Cell 177.2 (2019): 256-271.
Martorell et al., Multi-sensory Gamma Stimulation Ameliorates Alzheimer's—Associated Pathology and Improves Cognition. Cell. Mar. 14, 2019. https://doi.org/10.1016/j.cell.2019.02.014. 39 pages.
Mastrangelo, M. et al., "Detailed immunohistochemical characterization of temporal and spatial progression of Alzheimer's disease-related pathologies in male triple-transgenic mice," BMC Neuroscience, vol. 9 (Aug. 2008): 1-31.
Meyers, "How chemotherapy damages the central nervous system." Journal of biology 7.4 (2008): 11. 3 pages.
Mind Alive Inc. http://mindalive.com/ Internet Archive Wayback Machine earliest Internet archived date Mar. 2, 2001, 2 pages.
Mind Gear http://Mindlightz.com, Internet Archive Wayback Machine earliest Internet archived date Mar. 1, 2015, 5 pages.
Mind Machines http://www.mindmachines.com/, Internet Archive Wayback Machine earliest Internet archived date Dec. 7, 1998, 4 pages.
Mind Mods http://www.mindmods.com/, Internet Archive Wayback Machine earliest. Internet archived date Mar. 12, 2008, 2 pages.
Mind Place http://mindplace.com/, Internet Archive Wayback Machine earliest Internet archived date Dec. 2, 1998, 4 pages.
Mitrasinovic, O. et al., "Microglial overexpression of the M-CSF receptor augments phagocytosis of opsonized Aβ," Neurobiology of Aging, vol. 24 (Oct. 2003): 807-815.
Neuro Alpha (Brain PBM). Vielight the Life Light 2019. Accessed at https://vielight.com/devices/vielight-neuro-alpha/ on Aug. 22, 2019. 7 pages.
Neuronix http://neuronixmedical.com, Internet Archive Wayback Machine earliest Internet archived date Nov. 16, 2009, 2 pages.
Neurotronics http://www.neurotronics.eu/, Internet Archive Wayback Machine earliest Internet archived date Sep. 24, 2008, 2 pages.
Next Wave Physioacoustic MX therapy chair. Nextwave. Accessed at http://www.nextwaveworldwide.com/products/physioacoustic-mx-therapy-chair/ on Nov. 18, 2020. 2 pages.
Notice of Allowance dated Apr. 25, 2018 for U.S. Appl. No. 15/647,157, 5 pages.
Oakley, H. et al., "Intraneuronal beta-amyloid aggregates, neurodegeneration, and neuron loss in transgenic mice with five familial Alzheimer's disease mutations: potential factors in amyloid plaque formation," Journal of Neuroscience, vol. 26 (Oct. 2006): 10129-10140.
O'Connor et al., "The use of the puzzle box as a means of assessing the efficacy of environmental enrichment." JoVE (Journal of Visualized Experiments) 94 (2014): e52225. 8 pages.

(56) References Cited

OTHER PUBLICATIONS

Ohmi, K. et al., "Defects in the medial entorhinal cortex and dentate gyrus in the mouse model of Sanfilippo syndrome type B," Plos One, vol. 6 (Nov. 2011): 1-10.
Palop, J. et al., "Aberrant excitatory neuronal activity and compensatory remodeling of inhibitory hippocampal circuits in mouse models of Alzheimer's disease," Neuron, vol. 55 (Sep. 2007): 697-711.
Palpagama et al., "The role of microglia and astrocytes in Huntington's disease." Frontiers in molecular neuroscience 12 (2019): 258. 15 pages.
Paro Therapeutic Robot http://www.parorobots.com/: Internet Archive Wayback Machine earliest Internet Archived date Dec. 4, 2008, 2 pages.
Pericic, D. et al., "Sex differences in the response to GABA antagonists depend on the route of drug administration," Experimental Brain Research, vol. 115 (Jun. 1997): 187-190.
Quietmind Foundation Launches World's First Clinical Trial of Drug-Free Infrared Light Therapy to Treat Dementia. Global News Wire, Feb. 17, 2011. Accessed at http://www.globenewswire.com/news-release/2011/02/17/1182914/0/en/Quietmind-Foundation-Launches-World-s-First-Clinical-Trial-of-Drug-Free-Infrared-Light-Therapy-to-Treat-Dementia.html on Aug. 22, 2019. 2 pages.
Raivich, G. et al., "Neuroglial activation repertoire in the injured brain: graded response, molecular mechanisms and cues to physiological function," Brain Research Reviews, vol. 30 (Aug. 1999): 77-105.
Ravassard, P. et al., "Multisensory control of hippocampal spatiotemporal selectivity," Science, vol. 340 (Jun. 2013): 1342-1346.
Sauer et al., "Impaired fast-spiking interneuron function in a genetic mouse model of depression." Elife 4 (2015): e04979. 20 pages.
Seibenhener et al., "Use of the open field maze to measure locomotor and anxiety-like behavior in mice." JoVE (Journal of Visualized Experiments) 96 (2015): e52434. 9 pages.
Selkoe, D. et al., "The role of APP processing and trafficking pathways in the formation of amyloid beta-protein," Annals of the New York Academy of Sciences (Jan. 1996): 57-64.
Siegle, J. et al., "Enhancement of Encoding and retrieval functions through theta phase-specific manipulation of hippocampus," ELife Sciences Publications (Jul. 2014).
Smith et al., "The validity of neuropathy and neuropathic pain measures in patients with cancer receiving taxanes and platinums." Oncology nursing forum. Vol. 38. No. 2. 2011. 10 pages.
Snailax Massage Mat with Heat. Snailax. Accessed at https://www.amazon.com/Snailax-Massage-Mat-Heat-Relaxation/dp/B07MNZ5Z6P on Nov. 18, 2020. 10 pages.
Stam, C. et al., "Generalized synchronization of MEG recordings in Alzheimer's Disease: evidence for involvement of the gamma band," Journal of Clinical Neurophysiology, vol. 19 (Dec. 2002): 562-574.
Subramanian, A. et al., "Gene set enrichment analysis: A knowledge-based approach for interpreting genorne-wide expression profiles," PNAS, vol. 102 (Aug. 2005): 15545-15550.
Sudol, K. et al., "Generating Differentially Targeted Amyloid-β Specific Intrabodies as a Passive Vaccination Strategy for Alzheimer's Disease," Molecular Therapy, vol. 17 (Dec. 2009): 2031-2040.
Tanaka et al., "Analysis of MEG Auditory 40-Hz Response by Event-Related Coherence." ITEIS 125.6 (2005): 898-903.
Tanaka et al., "Analysis of MEG Auditory 40-Hz Response by Event-Related Coherence." ITEIS 125.6 (2005): 898-903. English Translation 7 pages.
Thakurela, S. et al., "Dynamics and function of distal regulatory elements during neurogenesis and neuroplasticity," Genome Research, vol. 25 (Sep. 2015): 1309-1324.
Theragun by Therabody. Accessed at https://www.theragun.com/us/en-us/4th-generation-devices/ on Nov. 18, 2020. 26 pages.
Transparent Corporation https://www.transparentcorp.com/, Internet Archive Wayback Machine earliest Internet archived date Jan. 10, 1998, 3 pages.

Trapnell, C. et al., "Differential gene and transcript expression analysis of RNA-seq experiments with TopHat and Cufflinks," Nature Protocols, vol. 7 (2012): 562-578.
Trapnell, C. et al., "Transcript assembly and quantification by RNA-Seq reveals unannotated transcripts and isoforrn switching during cell differentiation," Nature Biotechnology, vol. 28 (May 2010): 511-515.
Traub, R. et al., "Analysis of gamma rhythms in the rat hippocampus in vitro and in vivo," the Journal of Physiology, vol. 493 (Jun. 1996): 471-484.
Verret, L. et al., "Inhibitory interneuron deficit links altered network activity and cognitive dysfunction in Alzheimer model," Cell, vol. 149 (Apr. 2012): 708-721.
Vibration Plate Model VT003F. Vibration Therapeutic. Accessed at https://vibrationtherapeutic.com/_Products-Vibration-Plate/Vibration-Plate-VT003F.html on Nov. 19, 2020, 17 pages.
Vielight Neuro Gamma (40hz). QuietMIND Foundation 2019. Accessed at https://www.quietmindfdn.org/store/p5/Vielight_Neuro_Gamma_%2840hz%29_-_20%25_Off_for_Clinical_Trial_Participants.html on Aug. 22, 2019. 3 pages.
Walsh et al., "The open-field test: a critical review." Psychological bulletin 83.3 (1976): 482. 23 pages.
Wang et al., "The gamma frequency band neural oscillation: generation mechanisms and functions." Progress in Biochemistry and Biophysics 38.8 (2011): 688-693.
Wang, Y. et al., "TREM2 lipid sensing sustains the microglial response in an Alzheimer's disease model," Cell, vol. 160 (Mar. 2015): 1061-1071.
Ylinen, A. et al., "Sharp wave-associated high-frequency oscillation (200 Hz) in the intact hippocampus: network and intracellular mechanisms," Journal of Neuroscience, vol. 15 (Jan. 1995): 30-46.
Yoshiyama, Y. et al., "Synapse loss and microglial activation precede tangles in a P301S tauopathy mouse model," Neuron, vol. 53 (Feb. 2007): 337-351.
Yu, H. et al., "Tet3 regulates synaptic transmission and homeostatic plasticity via Dna oxidation and repair," Nature Neuroscience, vol. 18 (Jun. 2015): 836-843.
Zhang, Y. et al., "An RNA-sequencing transcriptome and splicing database of glia, neurons, and vascular cells of the cerebral cortex," Journal of Neuroscience, vol. 34 (Sep. 2014): 11929-11947.
Zheng et al., Rhythmic light flicker rescues hippocampal low gamma and protects ischemic neurons by enhancing presynaptic plasticity. Nat Commun. 2020; 11(1):3012. Published Jun. 15, 2020. doi: 10.1038/s41467-020-16826-0. 16 pages.
Agosta, et al. "White matter damage in Alzheimer disease and its relationship to gray matter atrophy." Radiology 258.3 (2011): 853-863.
Ancoli-Israel, et al. "Cognitive effects of treating obstructive sleep apnea in Alzheimer's disease: a randomized controlled study." Journal of the American Geriatrics Society 56.11 (2008): 2076-2081.
Cajal Santiago. "Degeneration and regeneration of the nervous system." (1928). Oxford University Press, Humphrey Milford; 1928, 429 pages.
Deschenes, et al. "Current treatments for sleep disturbances in individuals with dementia." Current psychiatry reports 11.1 (2009): 20-26.
Doody, et al. "A phase 3 trial of semagacestat for treatment of Alzheimer's disease." New England Journal of Medicine 369.4 (2013): 341-350.
Doody, et al. "Phase 3 trials of solanezumab for mild-to-moderate Alzheimer's disease." New England Journal of Medicine 370.4 (2014): 311-321.
European Office Action in European App. No. 18866506.1 dated Oct. 4, 2023, 5 pages.
Final Office Action in Japanese App. No. 2022-81038 dated Oct. 16, 2023, 10 pages.
First Examination Report in European App. No. 18866752.1 dated Oct. 4, 2023, 5 pages.
Herring, et al. "Polysomnographic assessment of suvorexant in patients with probable Alzheimer's disease dementia and insomnia: a randomized trial." Alzheimer's & Dementia 16.3 (2020): 541-551.

(56) References Cited

OTHER PUBLICATIONS

Kang, et al. "Norepinephrine metabolite DOPEGAL activates AEP and pathological Tau aggregation in locus coeruleus." The Journal of clinical investigation 130.1 (2020): 422-437, 17 pages.
Koenig, "Cholesterol of myelin is the determinant of gray-white contrast in MRI of brain." Magnetic resonance in medicine 20.2 (1991): 285-291.
Loy, et al. "Galantamine for Alzheimer's disease and mild cognitive impairment." Cochrane database of systematic reviews 1 (2006), 89 pages.
McFadden, et al. "Test-retest reliability of the 40 Hz EEG auditory steady-state response." PLoS One 9.1 (2014): e85748, 10 pages.
Most, et al. "Discrepancy between subjective and objective sleep disturbances in early-and moderate-stage Alzheimer disease." The American Journal of Geriatric Psychiatry 20.6 (2012): 460-467.
Notice of Allowance in Australian App. No. 2021215128 dated Oct. 24, 2023, 3 pages.
Ooms, et al. "Treatment of sleep disorders in dementia." Current treatment options in neurology 18 (2016): 1-17.
Ouslander, et al. "A nonpharmacological intervention to improve sleep in nursing home patients: results of a controlled clinical trial." Journal of the American Geriatrics Society 54.1 (2006): 38-47.
Peskind, et al. "Memantine treatment in mild to moderate Alzheimer disease: a 24-week randomized, controlled trial." The American Journal of Geriatric Psychiatry 14.8 (2006): 704-715.
Richard, et al. "Steady-state visual evoked potential temporal dynamics reveal correlates of cognitive decline." Clinical Neurophysiology 131.4 (2020): 836-846.
Solveig, et al. "Current radiotracers to image neurodegenerative diseases." EJNMMI Radiopharmacy and Chemistry 4.1 (2019), 23 pages.
Tada, et al. "Gamma-band auditory steady-state response as a neurophysiological marker for excitation and inhibition balance: a review for understanding schizophrenia and other neuropsychiatric disorders." Clinical EEG and Neuroscience 51.4 (2020): 234-243.
USPTO e-Office Action: CTFR—Final Rejection in U.S. Appl. No. 16/375,393 dated Jan. 9, 2020.
USPTO e-Office Action: CTFR—Final Rejection in U.S. Appl. No. 15/360,637 dated Jun. 4, 2018.
USPTO e-Office Action: CTNF—Non-Final Rejection in U.S. Appl. No. 16/901,592 dated Oct. 6, 2023.
USPTO e-Office Action: CTNF—Non-Final Rejection Jun. 26, 2019 in U.S. Appl. No. 16/375,393 dated Jun. 26, 2019.
USPTO e-Office Action: CTNF—Non-Final Rejection in U.S. Appl. No. 15/360,637 Dated Sep. 8, 2017.
USPTO e-Office Action: CTNF—Non-Final Rejection in U.S. App. No. 15/647,157 dated Sep. 11, 2017.
USPTO e-Office Action: CTNF—Non-Final Rejection in U.S. Appl. No. 16/135,938 dated Mar. 18, 2021.
USPTO e-Office Action: CTNF—Non-Final Rejection in U.S. Appl. No. 16/156,833 dated Apr. 20, 2020.
USPTO e-Office Action: CTNF—Non-Final Rejection in U.S. Appl. No. 16/901,628 dated Sep. 1, 2023.
USPTO e-Office Action: CTNF—Non-Final Rejection in U.S. Appl. No. 17/217,789 dated Dec. 22, 2022.
USPTO e-Office Action: CTNF—Non-Final Rejection in U.S. Appl. No. 16/156,833 dated Jul. 9, 2019.
USPTO e-Office Action: NOA—Notice of Allowance and Fees Due (Ptol-85) in U.S. Appl. No. 16/375,393 dated Feb. 3, 2020.
USPTO e-Office Action: NOA—Notice of Allowance and Fees Due (Ptol-85) in U.S. Appl. No. 15/360,637 dated Sep. 24, 2018.
USPTO e-Office Action: NOA—Notice of Allowance and Fees Due (Ptol-85) in U.S. Appl. No. 16/135,938 dated Sep. 21, 2021.
USPTO e-Office Action: NOA—Notice of Allowance and Fees Due (Ptol-85) in U.S. Appl. No. 16/156,833 dated Nov. 3, 2020.
USPTO e-Office Action: NOA—Notice of Allowance and Fees Due (Ptol-85) in U.S. Appl. No. 16/156,833 dated Feb. 3, 2021.
USPTO e-Office Action: NOA—Notice of Allowance and Fees Due (Ptol-85) in U.S. Appl. No. 17/217,789 dated Oct. 18, 2023.
USPTO e-Office Action: NOA—Notice of Allowance and Fees Due (Ptol-85) in U.S. Appl. No. 17/217,789 dated Jul. 31, 2023.
USPTO e-Office Action: NOA—Notice of Allowance and Fees Due in (Ptol-85) U.S. App. No. 15/647, 157 dated Sep. 24, 2018.
Van Erum, et al. "Sleep and Alzheimer's disease: a pivotal role for the suprachiasmatic nucleus." Sleep Medicine Reviews 40 (2018): 17-27.
Vialatte, et al. "Steady-state visually evoked potentials: focus on essential paradigms and future perspectives." Progress in neurobiology 90.4 (2010): 418-438.
Vitiello, et al. "Sleep disturbances in patients with Alzheimer's disease: epidemiology, pathophysiology and treatment." CNS drugs 15 (2001): 777-796.
Chinese Second Office Action with English Translation in Chinese Application No. 201880073535.8 dated May 25, 2022, 5 pages.
Korean Office Action with English translation thereof in Korean Application No. 10-2020-7013291, dated Jun. 2, 2022, 11 pages.
Mosabbir et al. "The effects of long-term 40-Hz physioacoustic vibrations on motor impairments in Parkinson's disease: a double-blinded randomized control trial." Healthcare. vol. 8. No. 2. MDPI, 2020, 13 pages.
Notice of Allowance (with Search Report) with English Translation dated May 17, 2022 in Chinese Application No. 201680075447.2 8 pages.
Poza et al. "Analysis of spontaneous MEG activity in patients with Alzheimer's disease using spectral entropies." 2007 29th Annual International Conference of the IEEE Engineering in Medicine and Biology Society. IEEE, 2007, 4 pages.
Third Office Action in CA Application No. 3003183, dated Jun. 20, 2022, 4 pages.
Product Comparison. (Jan. 2020). MindPlace. https://mindplace.com/pages/product, accessed on Aug. 31, 2023 at Wayback Machine, 5 pages.
Shop 40 Hertz Light & Sound at MindPlace. (Jan. 2020). MindPlace. https://mindplace.com/collections/light-sound/40-hertz, 5 pages.
Sosna et al. "Early long-term administration of the CSF1R inhibitor PLX3397 ablates microglia and reduces accumulation of intraneuronal amyloid, neuritic plaque deposition and pre-fibrillar oligomers in 5XFAD mouse model of Alzheimer's disease." Molecular neurodegeneration 13 (2018): 1-11.
Mjayanathan, et al. "Persistent cognitive deficits, induced by intrathecal methotrexate, are associated with elevated CSF concentrations of excitotoxic glutamate analogs and can be reversed by an NMDA antagonist." Behavioural brain research 225.2 (2011): 491-497, 7 pages.
Winocur et al. "Environmental enrichment protects against cognitive impairment following chemotherapy in an animal model." Behavioral Neuroscience 130.4 (2016): 428-436, 9 pages.
Winocur, et al. "Donepezil reduces cognitive impairment associated with anti-cancer drugs in a mouse model." Neuropharmacology 61.8 (2011): 1222-1228, 7 pages.
Winocur, et al. "Physical exercise prevents suppression of hippocampal neurogenesis and reduces cognitive impairment in chemotherapy-treated rats." Psychopharmacology 231 (2014): 2311-2320.
Zhou, et al. "Metformin prevents cisplatin-induced cognitive impairment and brain damage in mice." PloS one 11.3 (2016): e0151890, 15 pages.
"40hz Light Therapy addressing Alzheimer's news!" Indiegogo https://www.indiegogo.com/projects/40hz-light-therapy-addressing-alzheimer-s-news##/, https://www.indiegogo.com, Internet Archive Wayback Machine earliest Internet archived date Oct. 29, 2017, 6 pages.
"Brainsway: Deep TMS Therapy," Brainsway (2014): http://www.brainsway.com/us.
"Good Vibrations Can Help Alzheimer's Patients," Awakening from Alzheimer's http://www.awakeningfromalzheimers.com/good-vibrations-can-help-alzheimers-patients/, Internet Archive Wayback Machine earliest Internet archived date Nov. 2, 2016, 8 pages.
"PSIO Manual," PSiO http://www.psioplanet.com/download/manuals/manuel-psio-1.1-EN.pdf, http://www.psoplanet.com/, Internet Archive Wayback Machine earliest Internet archived date Mar. 2, 2013, 16 pages.

(56) References Cited

OTHER PUBLICATIONS

Adaikkan et al., "Gamma entrainment binds higher-order brain regions and offers neuroprotection." Neuron 102.5 (2019): 929-943.
Alzheimer's Life Therapy App. Apple Store. Current version 1.5.7 released Aug. 6, 2019, earliest version 1.0.3 released Jan. 17, 2018. Accessed at https://apps.apple.com/us/app/alzheimers-light-therapy/id1327175926. 3 pages.
Aronov, D. et al., "Engagement of neural circuits underlying 2D spatial navigation in a rodent virtual reality system," Neuron, vol. 84 (Oct. 2014): 442-456.
Barton, A. "Sound vibration treatment may boost brain activity in Alzheimer's patients," The Globe and Mail (2016): http://www.theglobeandmail.com/life/health-and-fitness/health/sound-vibration-treatment-may-boost-brain-activity-in-alzheimers-patients/article29771676/.
Bartos, M. et al., "Synaptic mechanisms of synchronized gamma oscillations in inhibitory interneuron networks," Nature Reviews Neuroscience, vol. 8 (Jan. 2007): 45-56.
Basar, E. et al., "Delay of cognitive gamma responses in Alzheimer's disease," NeuroImage: Clinical, vol. 11 (2016): 106-115.
BEBOP. MACE Virtual Labs. Accessed at https://www.macevl.com/bebop on Nov. 18, 2020. 4 pages.
Berman et al., "Photobiomodulation with near infrared light helmet in a pilot, placebo controlled clinical trial in dementia patients testing memory and cognition." Journal of neurology and neuroscience 8.1 (2017). 15 pages.
Berman et al., Chapter 32—Noninvasive neurotherapeutic treatment of neurodegeneration: integrating photobiomodulation and neurofeedback training in Photobiomodulation in the Brain Low-Level Laser (Light) Therapy in Neurology and Neuroscience 2019, pp. 447-462.
Berman et al., Chapter 4—Photobiomodulation and Other Light Stimulation Procedures in Rhythmic Stimulation Procedures in Neuromodulation 2017, pp. 97-129.
Bero, A. et al., "Neuronal activity regulates the regional vulnerability to amyloid-β deposition," Nature Neuroscience, vol. 14 (May 2011): 750-756.
Boissonneault, V. et al., "Powerful beneficial effects of macrophage colony-stimulating factor on beta-amyloid deposition and cognitive impairment in Alzheimer's disease," Brain, vol. 132 (Apr. 2009): 1078-1092.
Bragin, A. et al., "Gamma (40-100 Hz) oscillation in the hippocampus of the behaving rat," Journal of Neuroscience, vol. 15 (Jan. 1995): 47-60.
Briones et al., "Dysregulation in myelination mediated by persistent neuroinflammation: possible mechanisms in chemotherapy-related cognitive impairment." Brain, behavior, and immunity 35 (2014): 23-32.
Busche, M. et al., "Decreased amyloid-β and increased neuronal hyperactivity by immunotherapy in Alzheimer's models," Nature Neuroscience, vol. 18 (Dec. 2015): 1725-1727.
Buzsaki et al., "Mechanisms of Gamma Oscillations," Rev. Neurosci. 35, 203-23 (2012).
Buzsaki, G. "Rhythms of the Brain," Oxford University Press (2006).
Buzsaki, G. "Theta oscillations in the hippocampus," Neuron, vol. 33 (Jan. 2002): 325-340.
Buzsaki, G. et al., "Hippocampal network patterns of activity in the mouse," Neuroscience, vol. 116 (2003): 201-211.
Buzsaki, G. et al., "Scaling brain size, keeping timing: evolutionary preservation of brain rhythms," Neuron, vol. 80 (Oct. 2013): 751-764.
Cardin, J. et al., "Driving fast-spiking cells induces gamma rhythm and controls sensory responses," Nature, vol. 459 (Apr. 2009): 663-667.
Carr, M. et al., "Hippocampal replay in the awake state: a potential substrate for memory consolidation and retrieval," Nature Neuroscience, vol. 14 (Feb. 2011): 147-153.
Carr, M. et al., "Transient slow gamma synchrony underlies hippocampal memory replay," Neuron, vol. 75 (Aug. 2012): 700-713.
Cataldo, A. et al., "Endocytic pathway abnormalities precede amyloid beta deposition in sporadic Alzheimer's disease and Down syndrome: differential effects of APOE genotype and presenilin mutations," American Journal of Pathology, vol. 157 (2000): 277-286.
Chinese Office Action and English Translation Thereof in Chinese Patent Application No. 201680075447.2 dated Jun. 1, 2021, 31 pages.
Chitu, V. et al., "Colony-stimulating factor-1 in immunity and inflammation," Current Opinion in Immunology, vol. 18 (Feb. 2006): 39-48.
Chiu et al., "Nasal administration of mesenchymal stem cells restores cisplatin-induced cognitive impairment and brain damage in mice." Oncotarget 9.85 (2018): 35581. 17 pages.
Chiu, I. et al., "A neurodegeneration-specific gene-expression signature of acutely isolated microglia from an amyotrophic lateral sclerosis mouse model," Cell Reports, vol. 4 (Jul. 2013): 385-401.
Chung, K. et al., "Structural and molecular interrogation of intact biological systems," Nature, vol. 497 (May 2013): 332-337.
Cirrito, J. et al., "In vivo assessment of brain interstitial fluid with microdialysis reveals plaque-associated changes in amyloid-beta metabolism and half-life," The Journal of Neuroscience, vol. 23 (Oct. 2003): 8844-8853.
Clements-Cortes et al., "Short-term effects of rhythmic sensory stimulation in Alzheimer's disease: An exploratory pilot study." Journal of Alzheimer's Disease 52.2 (2016): 651-660.
Clements-Cortes, A. "Sound Stimulation in Patients With Alzheimer's Disease," Annals of Long-Term Care: Clinical Care and Aging, vol. 23 (May 2015): 10-16.
Colgin, L. et al., "Frequency of gamma oscillations routes flow of information in the hippocampus," Nature, vol. 462 (Nov. 2009): 353-357.
Colgin, L. et al., "Gamma oscillations in the hippocampus," Physiology, vol. 25 (Oct. 2010): 319-329.
Correa et al., "A prospective evaluation of changes in brain structure and cognitive functions in adult stem cell transplant recipients." Brain imaging and behavior 7.4 (2013): 478-490.
Cronk, J. et al., "Methyl-CpG binding protein 2 regulates microglia and macrophage gene expression in response to inflammatory stimuli," Immunity, vol. 42 (Apr. 2015): 679-691.
Crotti, A. et al., "Mutant Huntingtin promotes autonomous microglia activation via myeloid lineage-determining factors," Nature Neuroscience, vol. 17 (Apr. 2014): 513-521.
Das, U. et al., "Activity-induced convergence of App and Bace-1 in acidic microdomains via an endocytosis-dependent pathway," Neuron, vol. 79 (Aug. 2013): 447-460.
Eckhorn, R. et al., "Coherent Oscillations: a Mechanism of Feature Linking in the Visual Cortex," Biological Cybernetics, vol. 60 (1988): 121-130.
Erny, D. et al., "Host microbiota constantly control maturation and function of microglia in the CNS," Nature Neuroscience, vol. 18 (Jun. 2015): 965-977.
Extended European Search Report in European Patent Application No. 16869248.1 dated Jul. 15, 2019, 7 pages.
Extended European Search Report in European Patent Application No. 18866506.1 dated Jun. 9, 2021, 8 pages.
Extended European Search Report in European Patent Application No. 18866752.1 dated Jun. 22, 2021, 7 pages.
Final Office Action dated Jun. 4, 2018 for U.S. Appl. No. 15/360,637, 11 pages.
Fisher Wallace Stimulator http://www.fisherwallace.com/, Internet Archive Wayback Machine earliest Internet archived date Jul. 13, 2017, 7 pages.
Foster, D. et al., "Reverse replay of behavioural sequences in hippocampal place cells during the awake state," Nature. vol. 440 (Mar. 2006):680-683.
Adaikkan et al. "Gamma entrainment: impact on neurocircuits, glia, and therapeutic opportunities." Trends in neurosciences 43.1 (2020): 24-41.
Carstensen et al. "40 Hz invisible spectral flicker and its potential use in Alzheimer's light therapy treatment." Mechanisms of Photobiomodulation Therapy XV. vol. 11221. SPIE, 2020, 14 pages.
Carstensen et al. "Wavelength dependency of the critical flicker-fusion frequency: therapeutic 40 Hz light source in Alzheimer's

(56) References Cited

OTHER PUBLICATIONS disease." Mechanisms and Techniques in Photodynamic Therapy and Photobiomodulation. vol. 11628. SPIE, 2021, 9 pages.
Cimenser et al. "Sensory-evoked 40-Hz gamma oscillation improves sleep and daily living activities in Alzheimer's disease patients." Frontiers in systems neuroscience (2021): 103, 11 pages.
Fan et al. "New insights into the pathogenesis of Alzheimer's disease." Frontiers in Neurology 10 (2020): 1312, 12 pages.
Garza et al. "Gamma visual stimulation induces a neuroimmune signaling profile distinct from acute neuroinflammation." Journal of Neuroscience 40.6 (2020): 1211-1225.
Korean Notice of Final Rejection (with translation) in Korean Application No. 10-2020-7013291 dated Oct. 13, 2022, 6 pages.
Lee et al. "Optimal flickering light stimulation for entraining gamma waves in the human brain." Scientific Reports 11.1 (2021): 1-10.
Mcdermott et al. "Gamma band neural stimulation in humans and the promise of a new modality to prevent and treat Alzheimer's disease." Journal of Alzheimer's Disease 65.2 (2018): 363-392.
OptoCeutics ApS homepage 2022 accessed at https://optoceutics.com on Nov. 29, 2022, 7 pages.
Singer et al. "Noninvasive 40-Hz light flicker to recruit microglia and reduce amyloid beta load." Nature protocols 13.8 (2018): 1850-1868.
Zibrandtsen et al. "Gamma entrainment in a large retrospective cohort: implications for photic stimulation therapy for Alzheimer's disease." Journal of Alzheimer's Disease 75.4 (2020): 1181-1190.
Japanese Office Action and English Translation thereof in Japanese App. No. 2020-520207 dated May 9, 2022 13 pages.
Office Action with translation in Korean App. No. 10-2022-7036866 dated Aug. 24, 2023, 12 pages.
Examination Report No. 2 for Australian Application 2021215128 dated Jan. 27, 2023, 3 pages.
Fourth Office Action in Canadian Application No. 3003183, dated Jan. 27, 2023, 4 pages.
Fourth Office Action with translation in Chinese Application No. 201880077874.3 dated Jan. 28, 2023, 23 pages.
Japanese Office Action with machine translation in Japanese Application No. 2021-188541 dated Jan. 23, 2023, 12 pages.
Notification of Refusal with English translation in Japanese Application No.2020-520265 dated Mar. 6, 2023, 6 pages.
Office Action and Translation thereof in Korean Application No. 10-2022-7037169 dated Feb. 27, 2023, 10 pages.
Iaccarino et al. "Gamma frequency entrainment attenuates amyloid load and modifies microglia." Nature 540.7632 (2016): 230-235.
Korean Office Action with English Translation in Korean Application No. 10-2018-7017689 dated Mar. 23, 2022, 31 pages.
Korean Office Action with English Translation in Korean Application No. KR 10-2020-7013288 dated Mar. 16, 2022, 16 pages.
Pastor et al. "Activation of human cerebral and cerebellar cortex by auditory stimulation at 40 Hz." Journal of Neuroscience 22.23 (2002): 10501-10506.
Santarnecchi "Individual differences and specificity of prefrontal gamma frequency-tACS on fluid intelligence capabilities." Cortex 75 (2016): 33-43.
Wang, "Neurophysiological and computational principles of cortical rhythms in cognition." Physiological reviews 90.3 (2010): 1195-1268.
Chinese Office Action and English Translation Thereof in Chinese Patent Application No. 201680075447.2 dated Jan. 29, 2022, 27 pages.
International Search Report in PCT Application No. PCT/US2021/060146 mailed Feb. 11, 2022 15 pages.
Examination Report No. 1 in Australian App. No. 2023200711 dated Feb. 22, 2024, 3 pages.
Japanese Office Action with machine translation in Japanese Application No. 2021-188541 dated Mar. 25, 2024, 11 pages.
Korean Office Action in Korean App. No. 10-2023-7001501 dated Feb. 23, 2024, 8 pages.
Non-Final Rejection in U.S. Appl. No. 16/901,628 dated May 23, 2024, 6 pages.
Notice of Allowance in U.S. Appl. No. 16/901,628 dated Jun. 13, 2024, 12 pages.
Notice of Allowance in U.S. Appl. No. 17/217,789 dated Mar. 13, 2024, 7 pages.
Office Action (NOA) with translation in Korean App. No. 10-2022-7036866 dated Jun. 7, 2024, 8 pages.
Office Action (Notice of Allowance) in Canadian App. No. 3,078,739 dated Mar. 19, 2024, 1 page.
Notice of Allowance in Canadian App. No. 3,078,704 dated Jun. 12, 2024, 1 page.
Office Action in Canadian App. No. 3,078,704 dated Nov. 10, 2023, 8 pages.
Supplemental Notice of Allowance in U.S. Appl. No. 17/217,789 dated Jun. 14, 2024, 2 pages.
Non-Final Office Action in U.S. Appl. No. 16/901,628 dated Dec. 15, 2023, 9 pages.
Examination Report of Australian App. No. 2022271389 dated Nov. 29, 2023, 3 pages.
Office Action (Refusal) with translation in Japanese App. No. 2020-520265) dated Nov. 24, 2023, 9 pages.
Office Action in Canadian App. No. 3,078,739 dated Oct. 26, 2023, 6 pages.
Japanese Office Action with machine translation in Japanese App. No. 2020-520207 dated Jan. 22, 2024, 32 pages.
Notice of Allowance in Canadian App. No. 3003183 mailed Dec. 1, 2023, 1 page.
Notice of Acceptance in Australian App. No. 2023200711 dated Oct. 10, 2024, 3 pages.
Adduru, et al. "A method to estimate brain vol. from head CT images and application to detect brain atrophy in Alzheimer disease." American Journal of Neuroradiology 41.2 (2020): 224-230, 7 pages.
Boublay, et al. "Brain vol. predicts behavioral and psychological symptoms in Alzheimer's disease." Journal of Alzheimer's Disease 73.4 (2020): 1343-1353.
CDR(R) Dementia Staging Instrument [1-4] Department of Neurology, Knight Alzheimer Disease Research Center webpage accessed at https://knightadrc.wustl.edu/cdr/cdr.htm on Dec. 5, 2024, 2 pages.
Cholerton, et al. "Total brain and hippocampal vols. and cognition in older American Indians: the Strong Heart Study." Alzheimer Disease & Associated Disorders 31.2 (2017): 94-100, 16 pages.
Cognito Therapeutics to Advance Digital Therapeutic for Alzheimer's into Pivotal Studies Based on Positive Clinical Results Announced at AD/PD 2021, Business Wire, 2 pages.
Extended European Search Report in European App. No. EP24150119.6 dated Apr. 24, 2024, 9 pages.
Gray, et al. "Full-length human mutant huntingtin with a stable polyglutamine repeat can elicit progressive and selective neuropathogenesis in BACHD mice." Journal of Neuroscience 28.24 (2008): 6182-6195.
Gunter, et al. "Methodological considerations for measuring rates of brain atrophy." Journal of Magnetic Resonance Imaging: An Official Journal of the International Society for Magnetic Resonance in Medicine 18.1 (2003): 16-24.
HALE: Cognito's light-and-sound therapy slows Alzheimer's declines in clinical study. Fierce Biotech: MedTech [1-4] (2021), 2 pages.
Harris, et al. "The shrinking brain: cerebral atrophy following traumatic brain injury." Annals of biomedical engineering 47.9 (2019): 1941-1959, 19 pages.
International Search Report and Written Opinion in International App. No. PCT/US2021/0171003 (WO2022027030) dated Nov. 22, 2022, 8 pages.
International Search Report and Written Opinion in International App. No. PCT/US2022/018370 dated Jun. 8, 2022, 11 pages.
Japanese Office Action with translation in Japanese Application No. 2021-188541 dated Nov. 11, 2024, 5 pages.
Korean Office Action with Google Translation in Korean App. No. 10-2023-7039330 dated Nov. 14, 2024, 8 pages.
Marasco, "Current and evolving treatment strategies for the Alzheimer disease continuum." The American Journal of Managed Care 26.8 Suppl (2020): S167-S176, 28 pages.

(56) References Cited

OTHER PUBLICATIONS

McDougall, et al. "Psychometric properties of the Clinical Dementia Rating—Sum of Boxes and other cognitive and functional outcomes in a prodromal Alzheimer's disease population." The Journal of Prevention of Alzheimer's Disease 8 (2021): 151-160.
Neuropsychiatric Inventory (NPI): Construct: Behavioral disturbances in dementia patients. American Psychological Association, APA [1-3] (2011).
Nguyen, et al. "Behavioral abnormalities precede neuropathological markers in rats transgenic for Huntington's disease." Human molecular genetics 15.21 (2006): 3177-3194, 18 pages.
Non-Final Office Action in U.S. Appl. No. 17/531,616 dated Nov. 5, 2024, 15 pages.
Non-Final Rejection in U.S. Appl. No. 17/217,789 dated Nov. 26, 2024, 9 pages.
Notice of Acceptance in Australian App. No. 2022271389 dated Sep. 4, 2024, 3 pages.
Office Action in U.S. Appl. No. 16/901,592 dated Mar. 29, 2024.
Osmand, et al. "Imaging polyglutamine deposits in brain tissue." Methods in enzymology 412 (2006): 106-122, 17 pages.
Petrasch-Parwez, et al. "Cellular and subcellular localization of Huntington aggregates in the brain of a rat transgenic for Huntington disease." Journal of Comparative Neurology 501.5 (2007): 716-730.
Schwarz, et al. "Magnetic resonance imaging measures of brain atrophy from the EXPEDITION3 trial in mild Alzheimer's disease." Alzheimer's & Dementia: Translational Research & Clinical Interventions 5 (2019): 328-337.
Siemers, et al. "Phase 3 solanezumab trials: secondary outcomes in mild Alzheimer's disease patients." Alzheimer's & Dementia 12.2 (2016): 110-120.
Smeets, et al. "Reliable measurements of brain atrophy in individual patients with multiple sclerosis." Brain and behavior 6.9 (2016): e00518, 12 pages.
Storelli, et al. "Measurement of whole-brain and gray matter atrophy in multiple sclerosis: assessment with MR imaging." Radiology 288.2 (2018): 554-564, 11 pages.
Sungura, et al. "A case-control study on the driving factors of childhood brain vol. loss: What pediatricians must explore." Plos One 17.12 (2022): e0276433, 15 pages.
Sur, et al. "BACE inhibition causes rapid, regional, and non-progressive volume reduction in Alzheimer's disease brain." Brain 143.12 (2020): 3816-3826.
Van de Weijer, et al. "The Parkin'Play study: protocol of a phase II randomized controlled trial to assess the effects of a health game on cognition in Parkinson's disease." BMC neurology 16 (2016): 1-11.
Vonsattel, et al. "Huntington disease." Journal of neuropathology and experimental neurology 57.5 (1998): 369, 16 pages.
Wang, et al. "ADCOMS: a composite clinical outcome for prodromal Alzheimer's disease trials." Journal of Neurology, Neurosurgery & Psychiatry 87.9 (2016): 993-999.
Wessels, et al. "A combined measure of cognition and function for clinical trials: the Integrated Alzheimer's Disease Rating Scale (iADRS)." The journal of prevention of Alzheimer's disease 2.4 (2015): 227-241, 29 pages.
Whitwell, et al. "Rates of cerebral atrophy differ in different degenerative pathologies." Brain 130.4 (2007): 1148-1158.
Wujek, et al. "Axon loss in the spinal cord determines permanent neurological disability in an animal model of multiple sclerosis." Journal of Neuropathology & Experimental Neurology 61.1 (2002): 23-32.
Young, Brain Changes Speak vols. About Normal Aging and Dementia. ALZFORUM (2013), 5 pages.
Yu, et al. "Interferon-β inhibits progression of relapsing-remitting experimental autoimmune encephalomyelitis." Journal of neuroimmunology 64.1 (1996): 91-100.
Yu-Taeger, et al. "A novel BACHD transgenic rat exhibits characteristic neuropathological features of Huntington disease." Journal of Neuroscience 32.44 (2012): 15426-15438, 13 pages.

\* cited by examiner

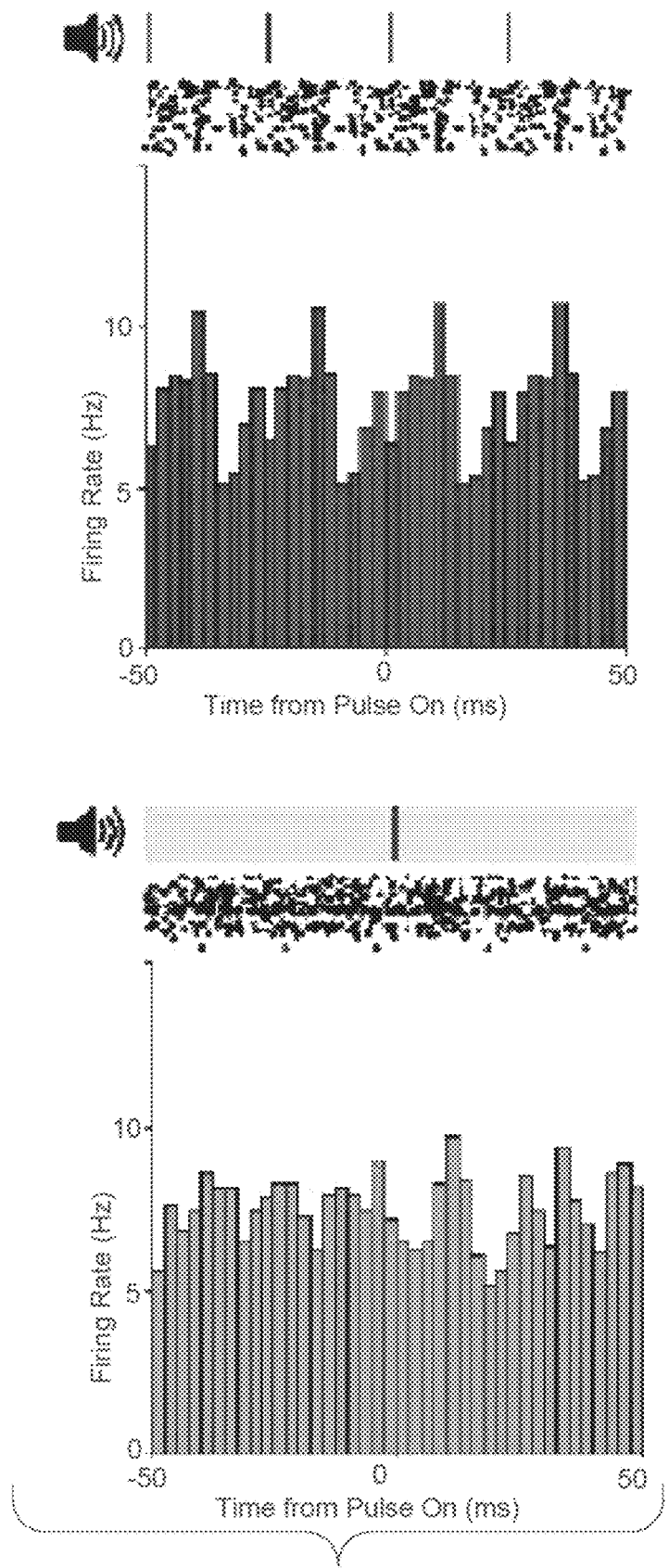
FIG. 1A-Cont'd

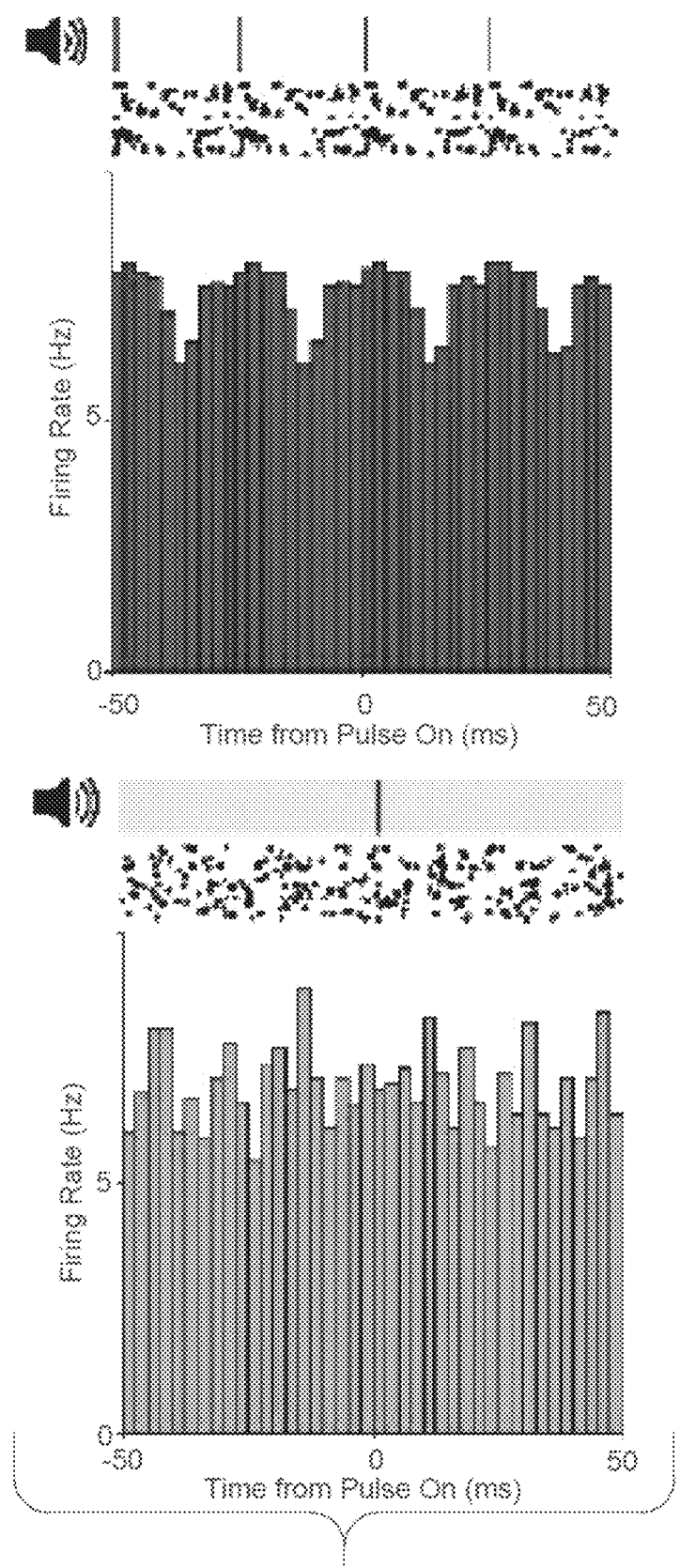
FIG. 1E-Cont'd

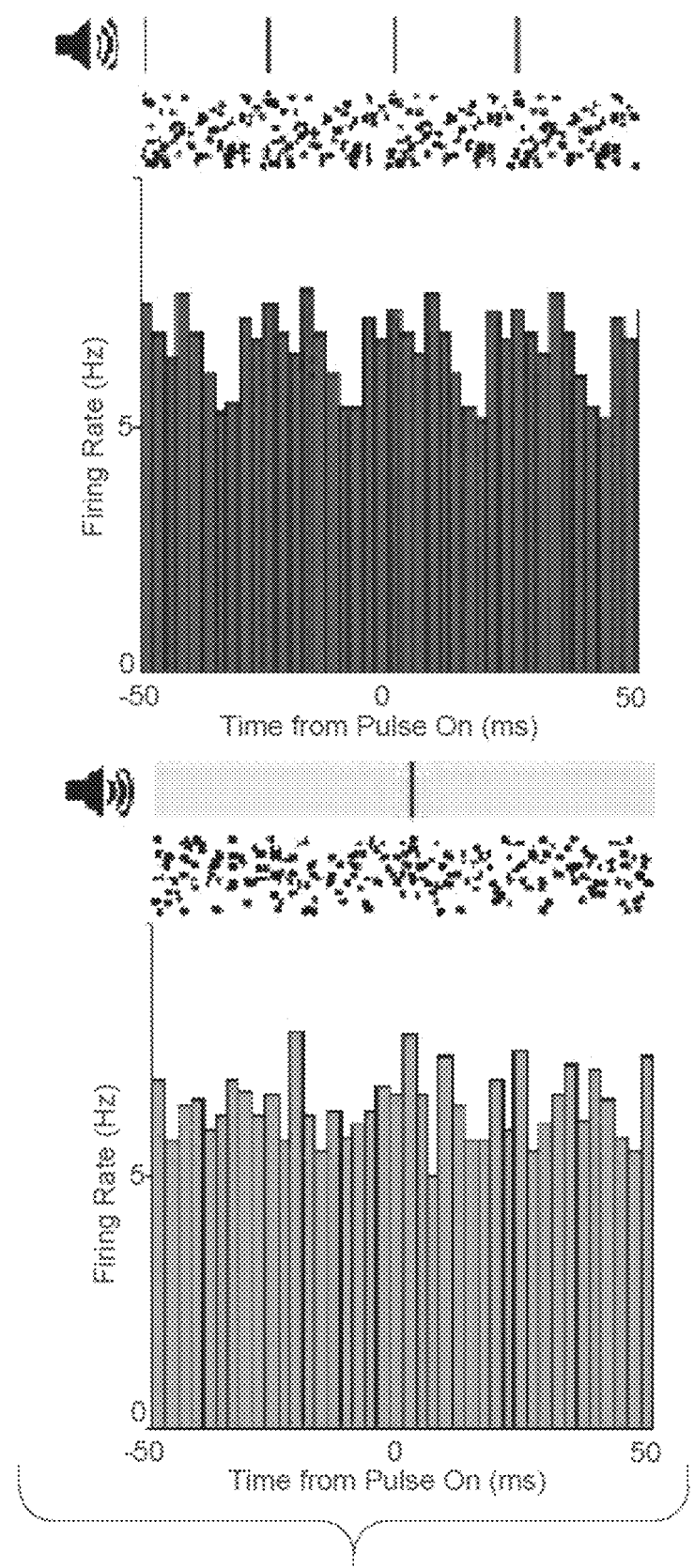
FIG. 1I-Cont'd

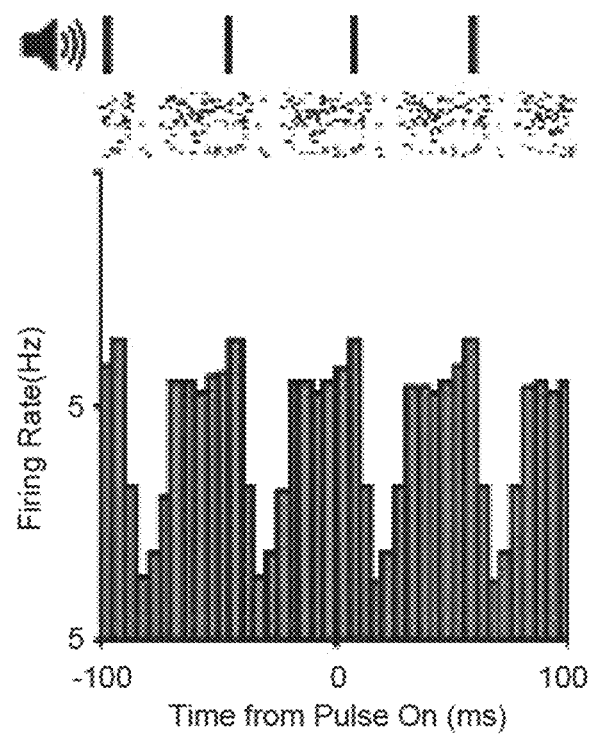
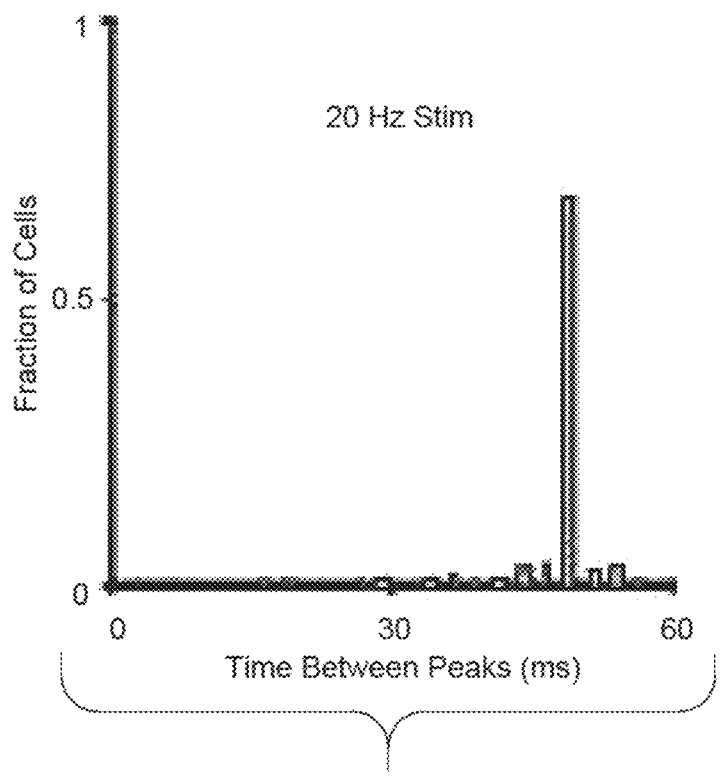
FIG. 8D

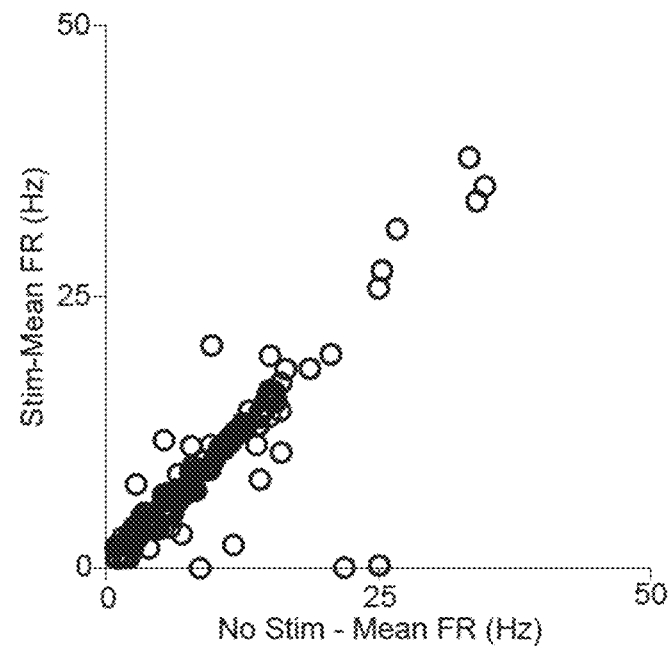
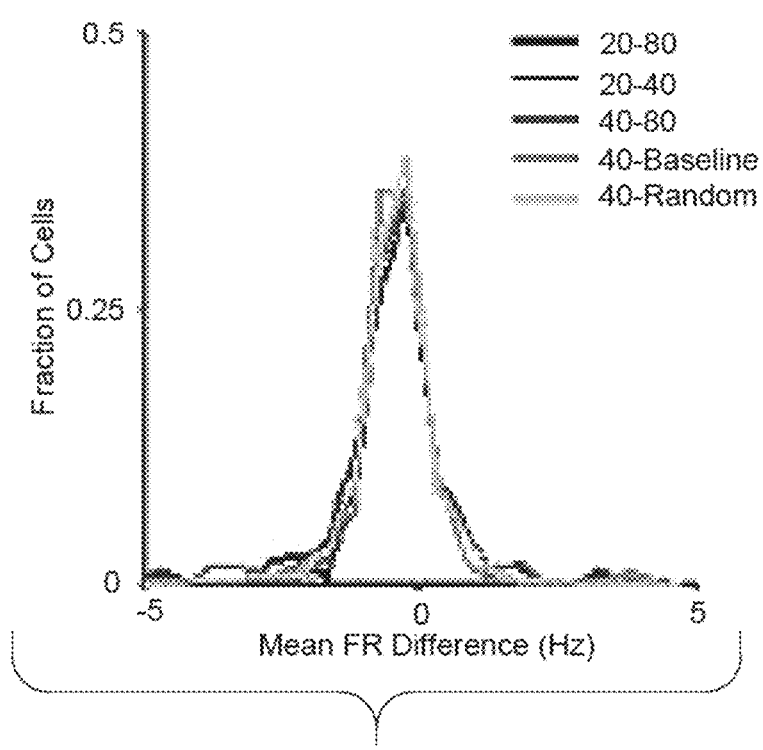
FIG. 8I

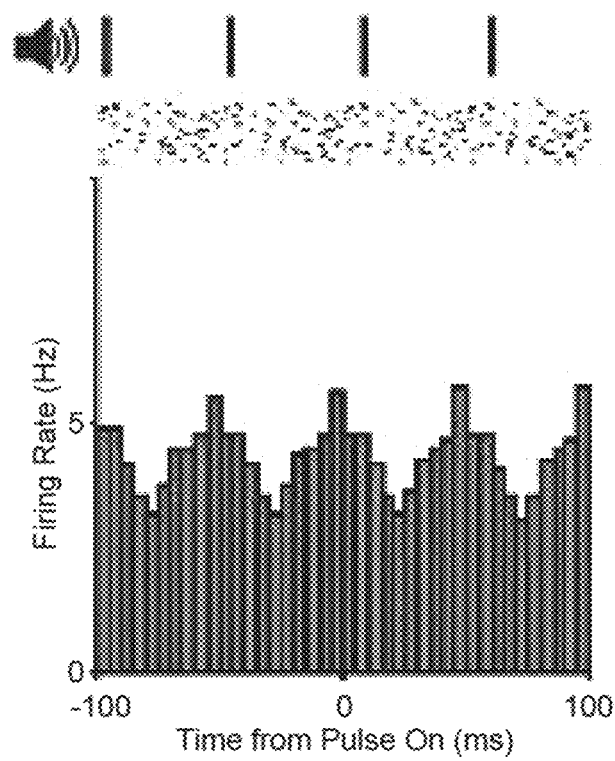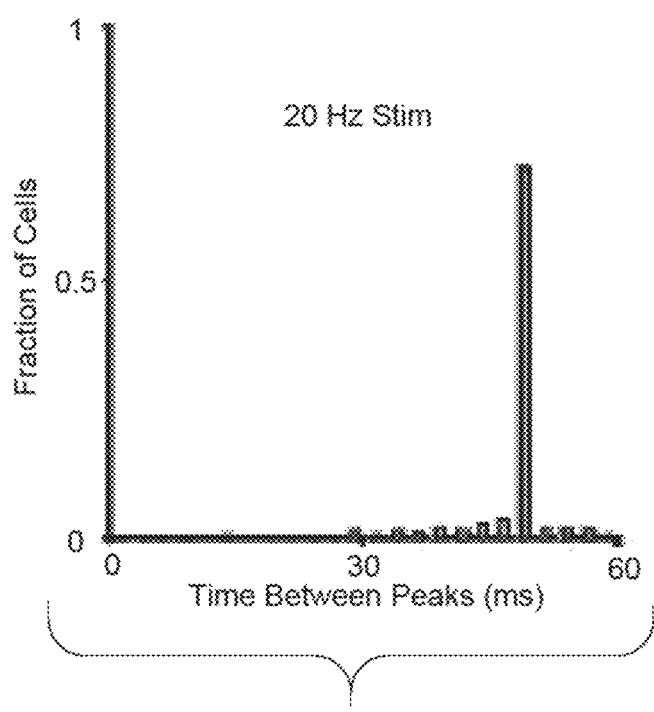
FIG. 8J

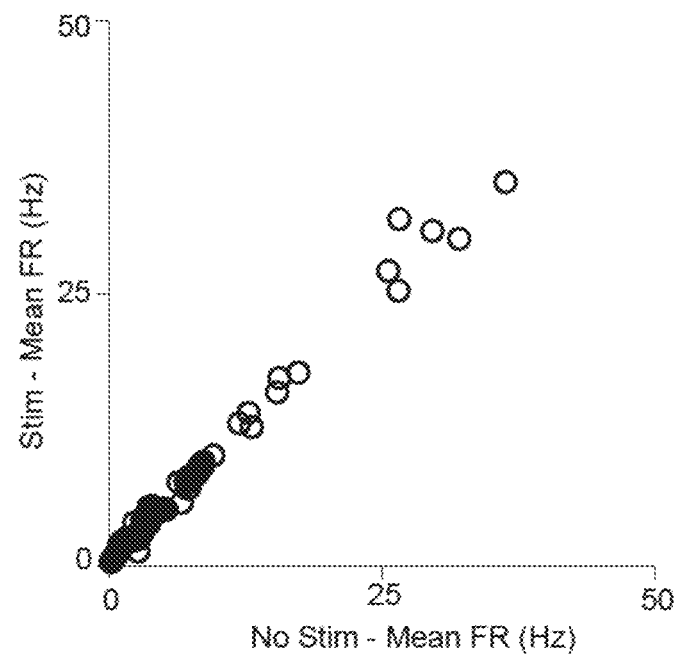
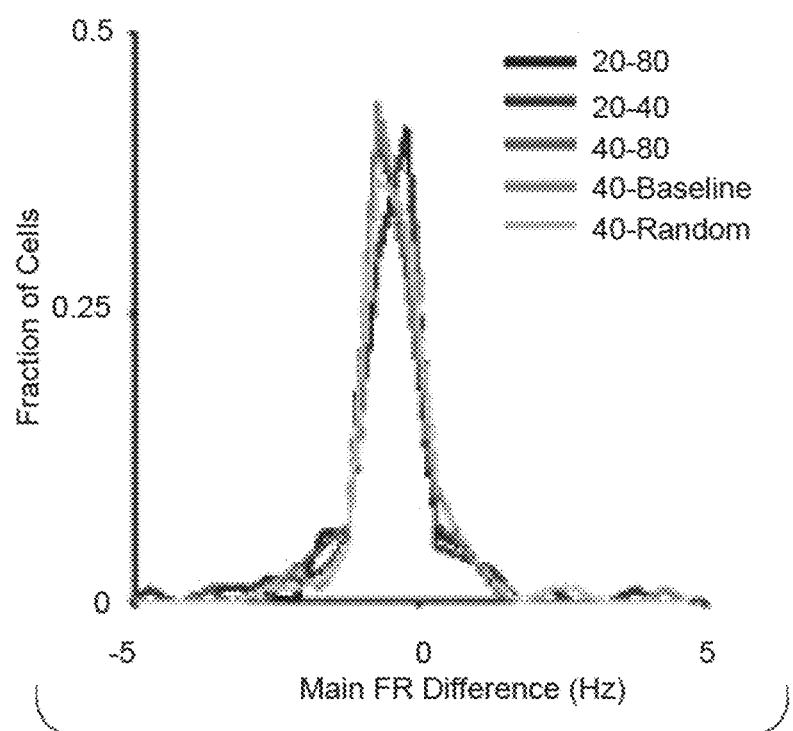
FIG. 80

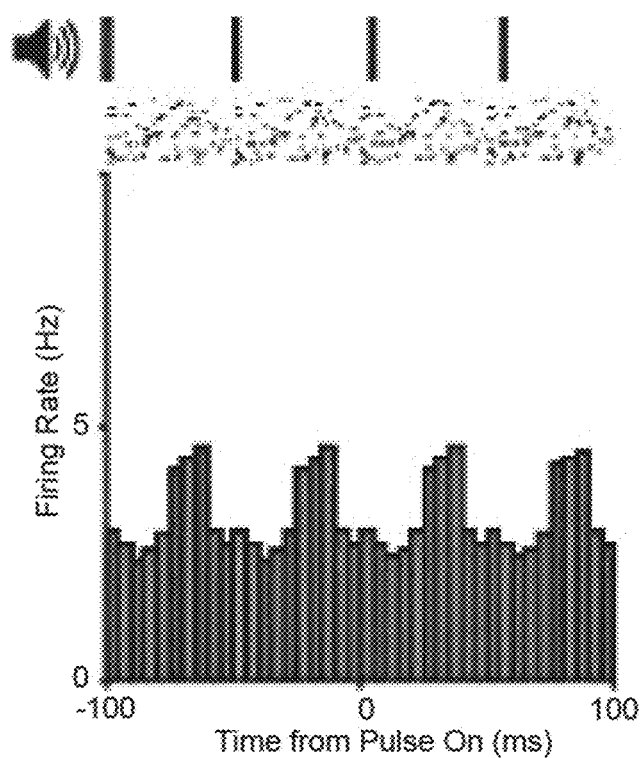
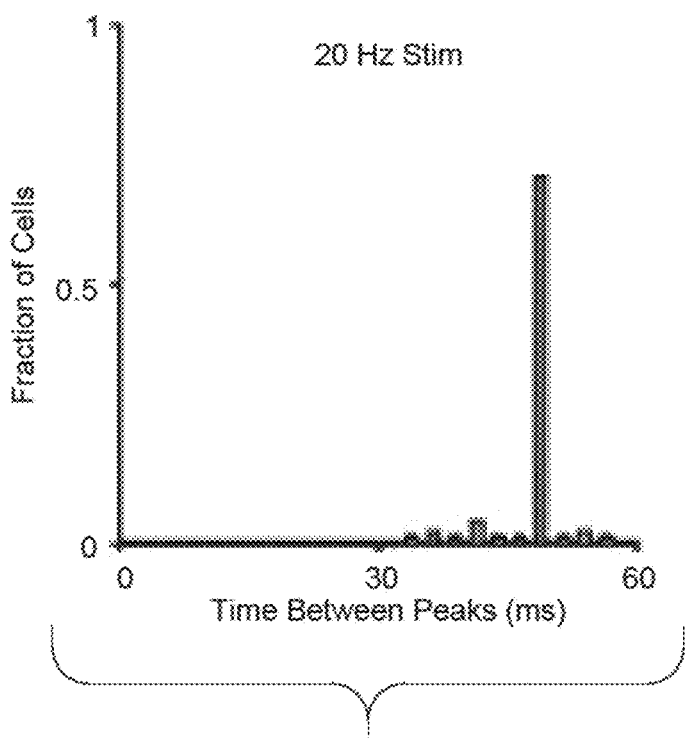
*FIG. 8P*

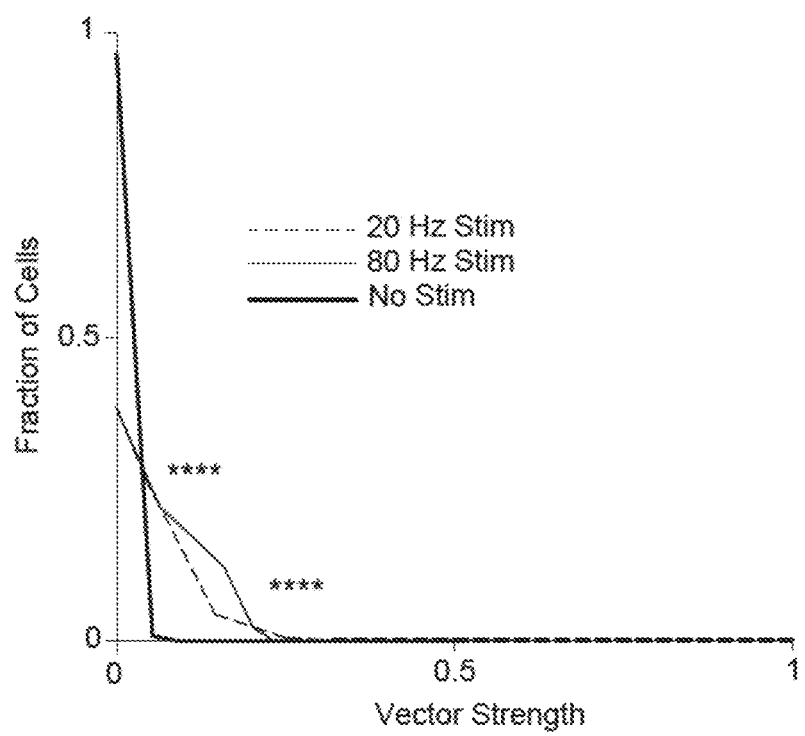
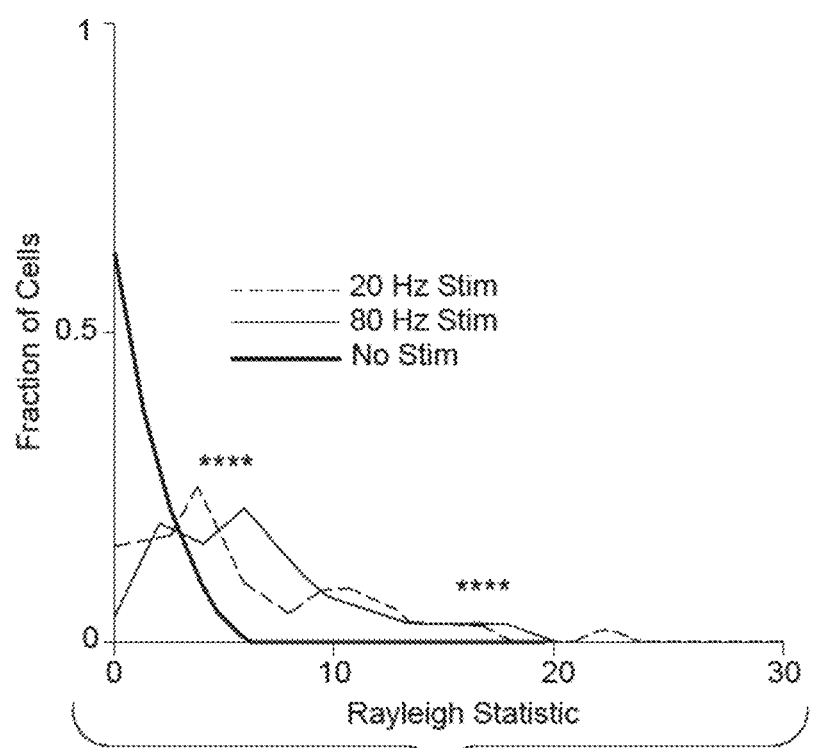
FIG. 8R

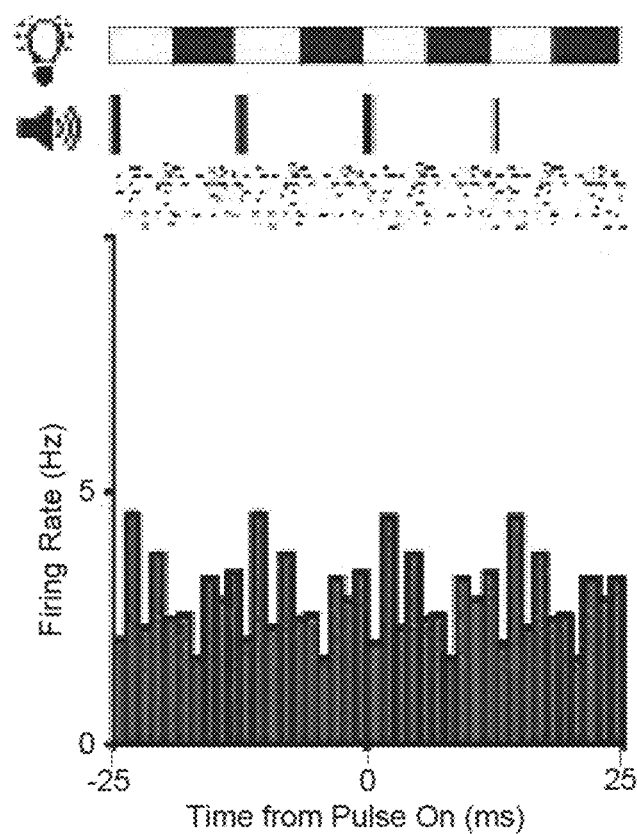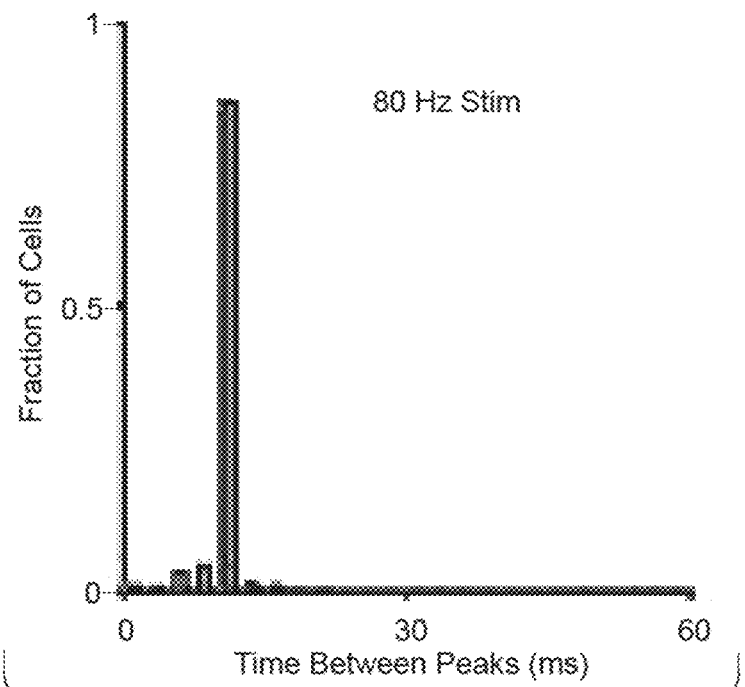
FIG. 13E

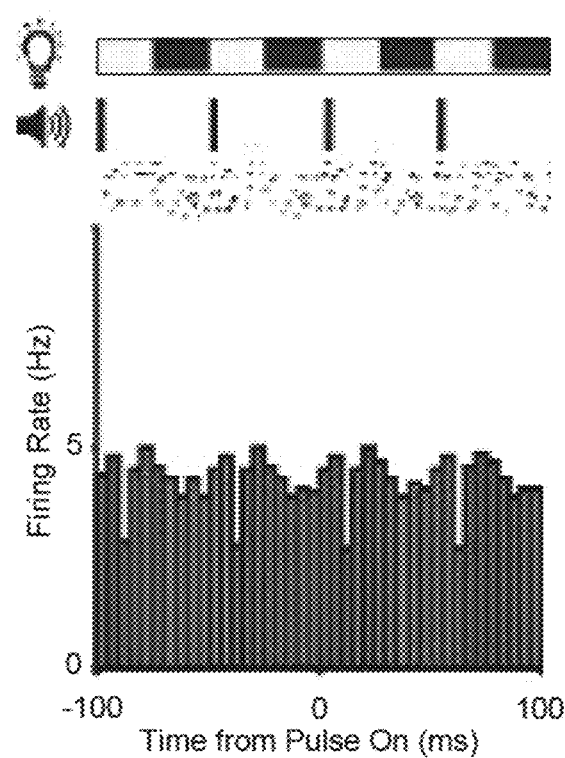
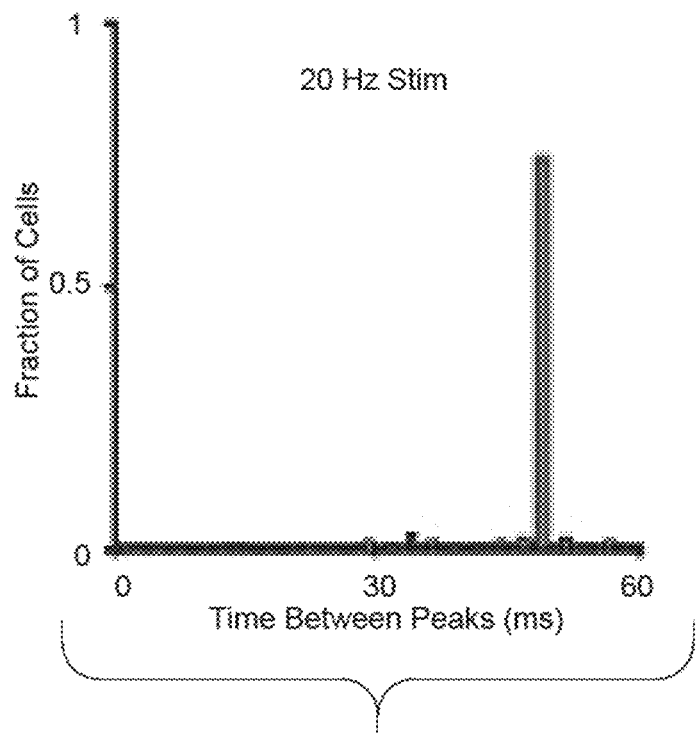
FIG. 13K

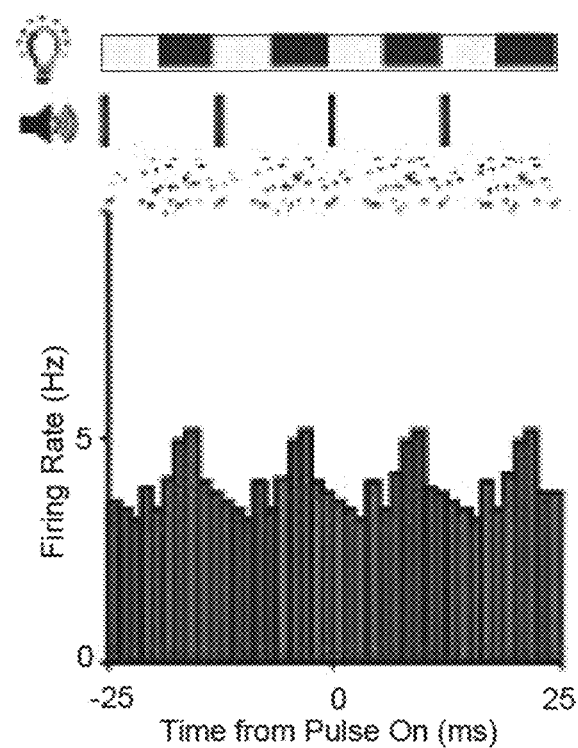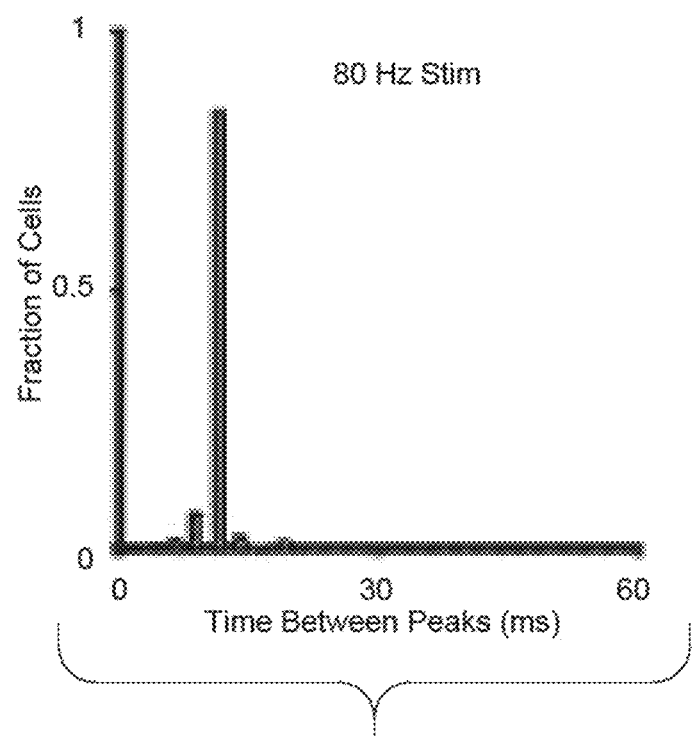
FIG. 13L

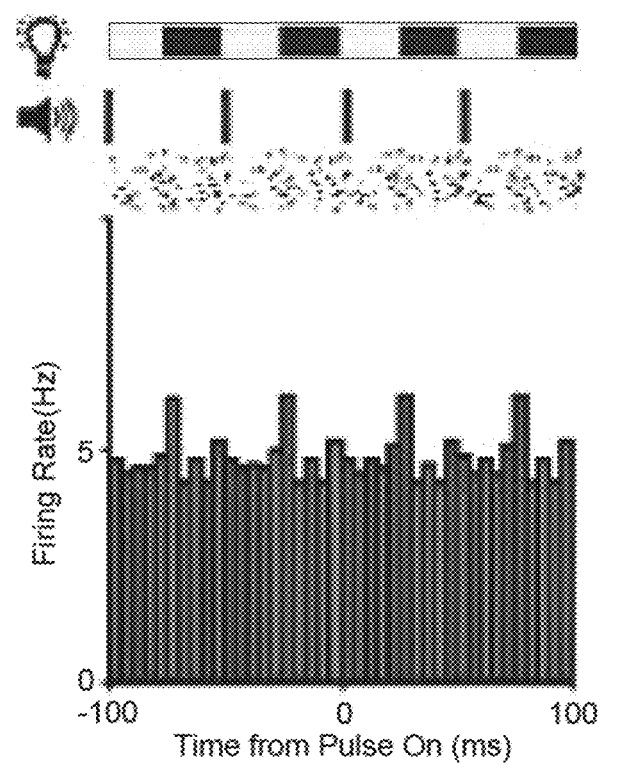
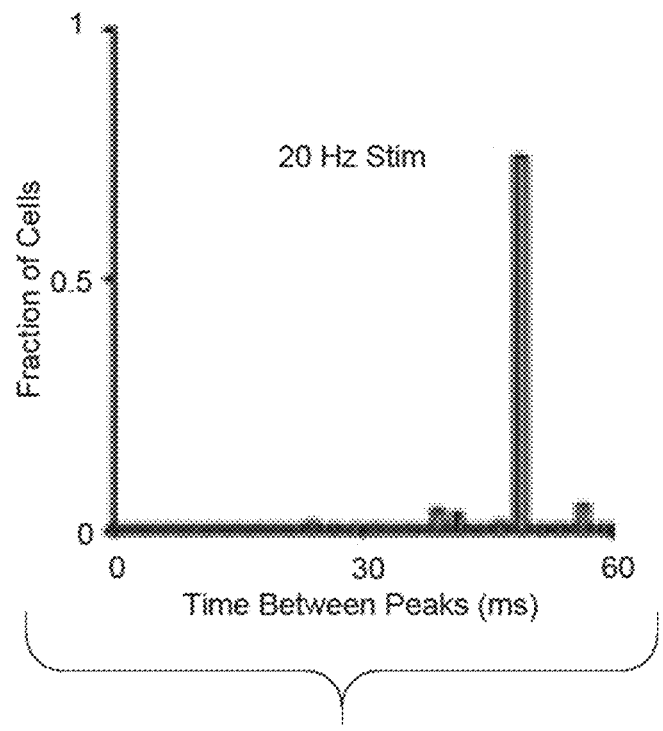
FIG. 13R

SYSTEMS AND METHODS FOR PREVENTING, MITIGATING, AND/OR TREATING DEMENTIA

CROSS-REFERENCES TO RELATED APPLICATIONS

The present application is a continuation of, and claims priority to, U.S. Ser. No. 16/135,938, filed on Sep. 19, 2018, and entitled "SYSTEMS AND METHODS FOR PREVENTING, MITIGATING, AND/OR TREATING DEMENTIA," which claims a priority benefit to each of the following U.S. provisional applications: Ser. No. 62/570,250, filed on Oct. 10, 2017, and entitled "NEUROPROTECTIVE EFFECTS OF COMBINED SENSORY STIMULATION"; and Ser. No. 62/570,929, filed on Oct. 11, 2017, and entitled GAMMA ENTRAINMENT BINDS HIGHER ORDER BRAIN REGIONS AND OFFERS NEUROPROTECTION". Each of these provisional applications is incorporated herein by reference in its entirety.

GOVERNMENT SUPPORT STATEMENT

This invention was made with government support under DA045549, EY023173, and AG047661 awarded by the National Institutes of Health. The government has certain rights in the invention.

BACKGROUND

Alzheimer's disease (AD) is a progressive neurodegenerative disease characterized by a decline in memory, orientation, and reasoning. It is the most common form of dementia in the world, affecting approximately one in eight people over the age of 65, and the sixth leading cause of death in the United States. The prevalence of this progressive neurodegenerative disorder is estimated to increase by 40% in the next ten years.

Histopathologically, AD may be characterized by the accumulation of amyloid plaques comprising the amyloid-$\beta$ (A$\beta$) peptide and neurofibrillary tangles (NFTs) made of the tau protein. The A$\beta$ peptide is a 36-43 amino acid protein whose normal physiological function remains unidentified. The A$\beta$ peptide is formed by the sequential proteolytic cleavage of the amyloid precursor protein (APP) by $\beta$-secretase 1 (BACE1) and $\gamma$-secretase. C-terminal fragment $\beta$ ($\beta$-CTF) is an APP derivative produced during amyloidogenic cleavage of APP by BACE1 and thus another indicator of A$\beta$ peptide production. Under normal conditions, the soluble A$\beta$ peptide is produced and secreted by neurons and subsequently cleared from the brain via cerebral spinal fluid (CSF) pathways. However, in subjects with AD, the A$\beta$ peptide appears to aggregate into higher-order species to form soluble oligomers and insoluble plaques in a concentration-dependent manner. This aggregation may initiate many neurotoxic events including disrupted brain metabolism, neuroinflammation, reduced functional connectivity, synaptic and neuronal loss, and/or formation of NFTs.

A fundamental relationship between A$\beta$ concentration and neuronal activity has been demonstrated. First, treatment of organotypic hippocampal slices prepared from transgenic (Tg) mice overexpressing APP with tetrodotoxin decreased neuronal activity and subsequently A$\beta$ levels. Then, the opposite effect—increased neuronal activity—was observed upon treatment with picrotoxin. Dynamic modulation of the A$\beta$ peptide concentration and eventual plaque deposition in vivo also has been demonstrated using neuronal activity. In human AD patients, neural imaging shows that the most severe plaque deposition may align with the most consistently active brain areas, known as the "default-mode network."

Currently AD has no cure, and treatment options do not inhibit the pathological progression of AD, are mainly palliative, and/or may have multiple, troubling side effects. For example, preventative and/or therapeutic strategies targeting the A$\beta$ peptide and/or its precursors (e.g., A$\beta$ immunotherapy and inhibition of $\beta$- and $\gamma$-secretases) have been toxic and/or ineffective at reducing AD pathology in clinical trials. Clinical trials involving amyloid beta vaccines (e.g., bapineuzumab) have failed due to lack of cognitive benefit. Gamma-secretase inhibitors (e.g., semagacestat) have failed clinical trials for worsening of cognitive deficits in subjects. Even existing medications like acetylcholinesterase inhibitors (e.g., donepezil and rivastigmine) and N-methyl-D-aspartate (NMDA)-receptor antagonists (e.g., memantine) demonstrate only mild cognitive benefits.

SUMMARY

As disclosed in U.S. patent application Ser. No. 15/360,637, filed on Nov. 23, 2016, and entitled "SYSTEMS AND METHODS FOR PREVENTING, MITIGATING, AND/OR TREATING DEMENTIA" (hereby incorporated herein by reference in its entirety), inducing synchronized gamma oscillations in the brain via visual or auditory stimulus results in reduced amyloid load and morphological changes in some brain regions. The Inventors have recognized and appreciated, however, that there remains a need for systems and methods of treating dementia and Alzheimer's disease that address circuit-wide disease affecting multiple brain centers significantly responsible for learning and memory and other higher-order brain functions.

In view of the foregoing, the present disclosure relates at least in part to combined auditory and visual stimuli that induce gamma oscillations in the brain of a subject according to various techniques referred to generally herein as "Gamma ENtrainment Using Sensory stimuli (GENUS)." Combined auditory and visual stimuli as disclosed herein (e.g., combined visual and auditory GENUS) unexpectedly generates positive physiological and behavioral changes not observed for visual or auditory GENUS alone. Positive effects on the brain arising from combined auditory and visual GENUS are not confined to the auditory cortex (AC) and hippocampus (HPC), but notably they extended to inducing a microglia-clustering response in the medial prefrontal cortex (mPFC) and reducing amyloid load throughout the neocortex. Furthermore, effects of combined auditory and visual GENUS are observed over short time frames of treatment/exposure (on the order of weeks).

In one aspect, the disclosure provides devices, methods, and systems for a treating dementia or Alzheimer's disease in a subject in need thereof, the method comprising non-invasively delivering combined auditory and visual stimuli having a frequency of about 20 Hz to about 60 Hz to the subject to induce synchronized gamma oscillations in at least one brain region of the subject. In some embodiments, the dementia is associated with AD, vascular dementia, frontal temporal dementia, Lewy Body dementia, and/or age-related cognitive decline. The subject may be a human or an animal.

In some embodiments, the combined auditory and visual stimuli have a frequency of about 35 Hz to about 45 Hz, or of about 40 Hz.

In some embodiments, the non-invasively delivering combined auditory and visual stimuli induces periodic spiking response in 5% of more of recording sites in at least one cortex region selected from the auditory cortex (AC), the visual cortex (VC), the hippocampus (HPC), and the medial prefrontal cortex (mPFC). In some embodiments, the non-invasively delivering combined auditory and visual stimuli induces local field potential (LFP) at about 40 Hz in the mPFC.

In some embodiments, the non-invasively delivering combined auditory and visual stimuli increases microglial response in at least one cortex region. The cortex region may include the neocortex, the AC, the VC, the HPC, and the mPFC. In some embodiments, the microglial response is induced in the mPFC. In some embodiments, the microglial response is induced in multiple cortex regions. In some embodiments, the microglial response is induced across the entire neocortex.

In some embodiments, increasing microglial response comprises at least one effect selected from increasing in the number of microglia within 25 micrometers of an amyloid plaque; increasing microglia cell body diameter; decreasing microglial projection length; and increasing microglia cell count. In an embodiment, the increasing microglial response comprises an at least 10%, 20%, 30%, 40%, or 50% of increase in microglia cell body diameter. In an embodiment, the increasing microglial response comprises an at least 10%, 20%, 30%, 40%, or 50% of decrease in microglial projection length. In an embodiment, the increasing microglial response comprises an at least 10%, 20%, 30%, 40%, or 50% of increase in microglia cell count.

In some embodiments, the increasing microglial response results after 1, 2, 3, 4, 5, 6, 7, 8, 9, or 10 days of non-invasively delivering combined auditory and visual stimuli.

In some embodiments, the non-invasively delivering combined auditory and visual stimuli comprises reducing amyloid plaques in at least one cortex region selected from the neocortex, the AC, the VC, the HPC, and the mPFC. The cortex region may include the neocortex, the AC, the VC, the HPC, and the mPFC. In some embodiments, the microglial response is induced in the mPFC. In some embodiments, the microglial response is induced in multiple cortex regions. In some embodiments, the microglial response is induced across the entire neocortex.

In an embodiment, the reducing amyloid plaques comprises at least about 5, 10, 15, 20, 25, 30, 35, 40, 45, 50, 55, or 60% reduction in plaque size. In an embodiment, the reducing amyloid plaques comprises at least about 5, 10, 15, 20, 25, 30, 35, 40, 45, 50, 55, or 60% reduction in plaque number.

In some embodiments, the increasing microglial response results after 1, 2, 3, 4, 5, 6, 7, 8, 9, or 10 days of non-invasively delivering combined auditory and visual stimuli.

In some embodiments, the non-invasively delivering combined auditory and visual stimuli comprises reducing an amount of amyloid-β (Aβ) peptide in at least one cortex region selected from the neocortex, the AC, the VC, the HPC, and the mPFC. The cortex region may include the neocortex, the AC, the VC, the HPC, and the mPFC. In some embodiments, the microglial response is induced in the mPFC. In some embodiments, the microglial response is induced in multiple cortex regions. In some embodiments, the microglial response is induced across the entire neocortex.

In an embodiment, the reducing an amount of Aβ peptide comprises at least about 5, 10, 15, 20, 25, 30, 35, 40, 45, 50, 55, or 60% reduction in amount. In some embodiments, the Aβ peptide include at least one of isoform Aβ1 40 peptide and isoform Aβ1-42 peptide. In some embodiments, the Aβ peptide includes at least one of soluble Aβ peptide and insoluble Aβ peptide.

In some embodiments, the increasing microglial response results after 1, 2, 3, 4, 5, 6, 7, 8, 9, or 10 days of non-invasively delivering combined auditory and visual stimuli.

In a second aspect, the disclosure provides a method for a treating dementia or Alzheimer's disease in a subject in need thereof, the method comprising controlling at least one visual stimulator to emit a visual stimulus at a frequency of about 35 Hz to about 45 Hz; controlling at least one electroacoustic transducer to convert an electrical audio signal into a corresponding auditory stimulus at a frequency of about 35 Hz to about 45 Hz; and non-invasively delivering a combined stimulus to the subject, the combined stimulus including the visual stimulus and the sound stimulus synchronously aligned, the combined stimulus to induce synchronized gamma oscillations in at least one brain region of the subject. The synchronized gamma oscillations result in an improvement of the cognitive function in the subject.

In some embodiments, the visual stimulus comprises repeated 12.5 ms light on then 12.5 ms light off. In some embodiments, the optogenetic stimulator is a light-emitting diode with 40-80 W power. In some embodiments, the auditory stimulus comprises a 10 kHz tone played at 40 Hz with a duty cycle of about 4% to about 80%. In some embodiments, the visual stimulus comprises a light flickered at 40 Hz for 10 s period with a duty cycle of about 10% to about 80%.

In some embodiments, the visual stimulus and the auditory stimulus are synchronized. In some embodiments, the visual stimulus and the auditory stimulus are out of phase by from −180 to 0 degrees or from 0 to 180 degrees.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally see, e.g., like features (e.g., functionally similar and/or structurally similar elements).

FIG. 3A-3I show auditory GENUS reduces amyloid load in AC and HPC in 5XFAD mice.

FIG. 10A-10ll show auditory GENUS ameliorates plaque load in APP/PS1 mice.

FIG. 11A-11ll show auditory GENUS induces microglia response in APP/PS1 mice.

DETAILED DESCRIPTION

Figure 1A:
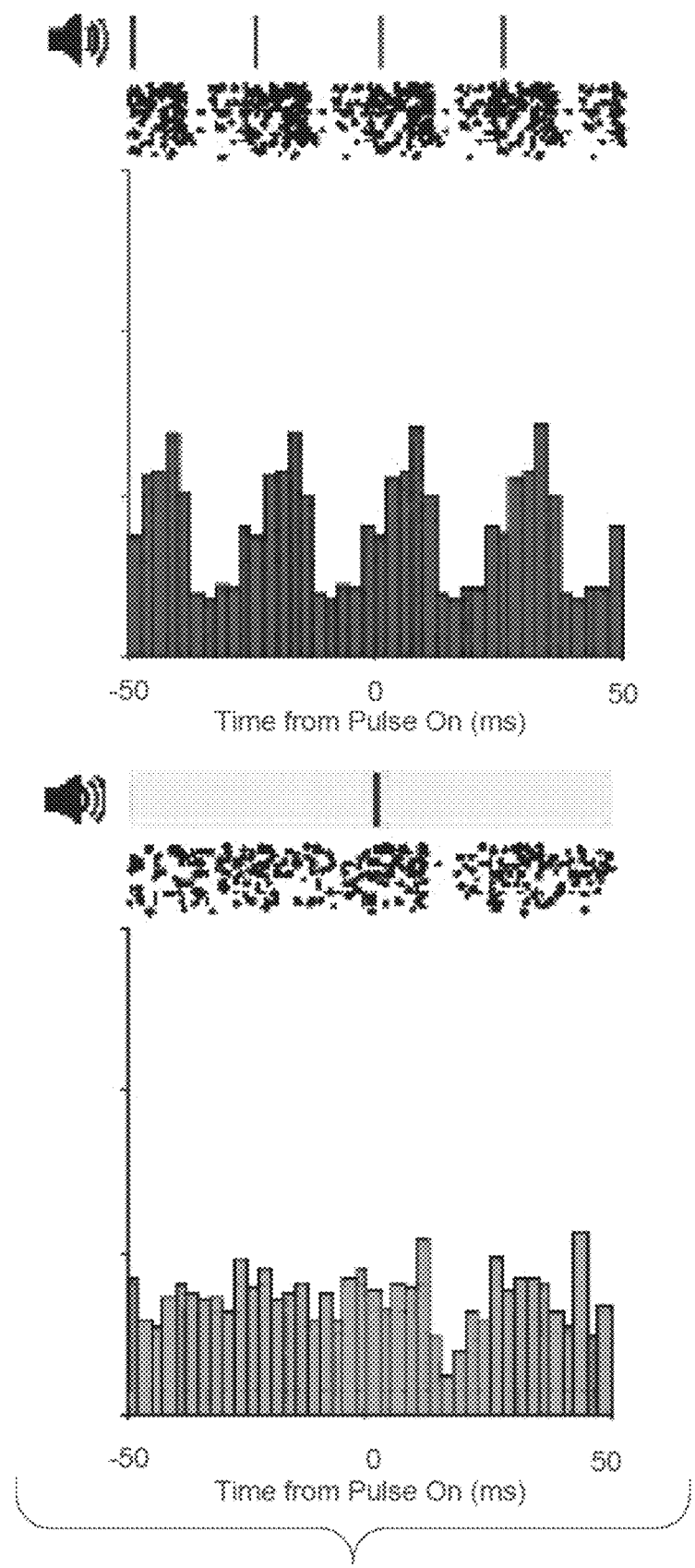
FIG. 1A-1L show 40 Hz auditory stimulation modulates spiking activity in AC, CA1, and mPFC.

Combined auditory and visual Gamma ENtrainment Using Sensory stimuli (GENUS) unexpectedly generates positive physiological and behavioral changes not observed for visual or auditory GENUS alone. Positive effects on the brain are not confined to the auditory cortex (AC) and hippocampus (HPC), but rather they extended to inducing a microglia-clustering response in the medial prefrontal cortex (mPFC) and reducing amyloid load throughout the neocortex. Furthermore, effects of combined auditory and visual GENUS are observed over short time frames (on the order of weeks). Combined auditory and visual GENUS for about one week ameliorates Alzheimer's Disease (AD) pathology in brain regions spanning a large circuit network. In particular, combined auditory and visual GENUS results in a significant reduction in amyloid load in the AC, visual cortex (VC), hippocampal subregion CA1, and mPFC. Combined auditory and visual GENUS produces microglial-clustering responses and decreased amyloid in medial prefrontal cortex. Combined auditory and visual GENUS results in widespread reduction of amyloid plaques throughout the neocortex.

In one aspect, the disclosure provides devices, methods, and systems for a treating dementia or Alzheimer's disease in a subject in need thereof, the method comprising non-invasively delivering combined auditory and visual stimuli having a frequency of about 20 Hz to about 60 Hz to the subject to induce synchronized gamma oscillations in at least one brain region of the subject. In some embodiments, the dementia is associated with AD, vascular dementia, frontal temporal dementia, Lewy Body dementia, and/or age-related cognitive decline. The subject may be a human or an animal.

In some embodiments, the combined auditory and visual stimuli have a frequency of about 35 Hz to about 45 Hz, or of about 40 Hz.

In some embodiments, the non-invasively delivering combined auditory and visual stimuli induces periodic spiking response in 5% of more of recording sites in at least one cortex region selected from the auditory cortex (AC), the visual cortex (VC), the hippocampus (HPC), and the medial prefrontal cortex (mPFC). In some embodiments, the non-invasively delivering combined auditory and visual stimuli induces local field potential (LFP) at about 40 Hz in the mPFC.

In some embodiments, the non-invasively delivering combined auditory and visual stimuli increases microglial response in at least one cortex region. The cortex region may include the neocortex, the AC, the VC, the HPC, and the mPFC. In some embodiments, the microglial response is induced in the mPFC. In some embodiments, the microglial response is induced in multiple cortex regions. In some embodiments, the microglial response is induced across the entire neocortex.

In some embodiments, increasing microglial response comprises at least one effect selected from increasing in the number of microglia within 25 micrometers of an amyloid plaque; increasing microglia cell body diameter; decreasing microglial projection length; and increasing microglia cell count. In an embodiment, the increasing microglial response comprises an at least 10%, 20%, 30%, 40%, or 50% of increase in microglia cell body diameter. In an embodiment, the increasing microglial response comprises an at least 10%, 20%, 30%, 40%, or 50% of decrease in microglial projection length. In an embodiment, the increasing microglial response comprises an at least 10%, 20%, 30%, 40%, or 50% of increase in microglia cell count.

In some embodiments, the increasing microglial response results after 1, 2, 3, 4, 5, 6, 7, 8, 9, or 10 days of non-invasively delivering combined auditory and visual stimuli. In some embodiments, the increasing microglial response results after 1, 2, 3, 4, 5, 6, 7, 8, 9, or 10 weeks of non-invasively delivering combined auditory and visual stimuli. In some embodiments, the increasing microglial response results after 1, 2, 3, 4, 5, 6, 7, 8, 9, or 10 months of non-invasively delivering combined auditory and visual stimuli. In some embodiments, the increasing microglial response results after 1, 2, 3, 4, 5, 6, 7, 8, 9, or 10 years of non-invasively delivering combined auditory and visual stimuli.

In some embodiments, the non-invasively delivering combined auditory and visual stimuli comprises reducing amyloid plaques in at least one cortex region selected from the neocortex, the AC, the VC, the HPC, and the mPFC. The cortex region may include the neocortex, the AC, the VC, the HPC, and the mPFC. In some embodiments, the microglial response is induced in the mPFC. In some embodiments, the microglial response is induced in multiple cortex regions. In some embodiments, the microglial response is induced across the entire neocortex.

In an embodiment, the reducing amyloid plaques comprises at least about 5, 10, 15, 20, 25, 30, 35, 40, 45, 50, 55, or 60% reduction in plaque size. In an embodiment, the reducing amyloid plaques comprises at least about 5, 10, 15, 20, 25, 30, 35, 40, 45, 50, 55, or 60% reduction in plaque number.

In some embodiments, the increasing microglial response results after 1, 2, 3, 4, 5, 6, 7, 8, 9, or 10 days of non-invasively delivering combined auditory and visual stimuli. In some embodiments, the increasing microglial response results after 1, 2, 3, 4, 5, 6, 7, 8, 9, or 10 weeks of non-invasively delivering combined auditory and visual stimuli. In some embodiments, the increasing microglial response results after 1, 2, 3, 4, 5, 6, 7, 8, 9, or 10 months of non-invasively delivering combined auditory and visual stimuli. In some embodiments, the increasing microglial response results after 1, 2, 3, 4, 5, 6, 7, 8, 9, or 10 years of non-invasively delivering combined auditory and visual stimuli.

In some embodiments, the non-invasively delivering combined auditory and visual stimuli comprises reducing an amount of amyloid-β (Aβ) peptide in at least one cortex region selected from the neocortex, the AC, the VC, the HPC, and the mPFC. The cortex region may include the neocortex, the AC, the VC, the HPC, and the mPFC. In some embodiments, the microglial response is induced in the mPFC. In some embodiments, the microglial response is induced in multiple cortex regions. In some embodiments, the microglial response is induced across the entire neocortex.

In an embodiment, the reducing an amount of Aβ peptide comprises at least about 5, 10, 15, 20, 25, 30, 35, 40, 45, 50, 55, or 60% reduction in amount. In some embodiments, the Aβ peptide include at least one of isoform Aβ1 40 peptide and isoform Aβ1-42 peptide. In some embodiments, the Aβ peptide includes at least one of soluble Aβ peptide and insoluble Aβ peptide.

In some embodiments, the increasing microglial response results after 1, 2, 3, 4, 5, 6, 7, 8, 9, or 10 days of non-invasively delivering combined auditory and visual stimuli. In some embodiments, the increasing microglial response results after 1, 2, 3, 4, 5, 6, 7, 8, 9, or 10 weeks of non-invasively delivering combined auditory and visual stimuli. In some embodiments, the increasing microglial response results after 1, 2, 3, 4, 5, 6, 7, 8, 9, or 10 months of non-invasively delivering combined auditory and visual stimuli. In some embodiments, the increasing microglial response results after 1, 2, 3, 4, 5, 6, 7, 8, 9, or 10 years of non-invasively delivering combined auditory and visual stimuli.

In a second aspect, the disclosure provides a method for a treating dementia or Alzheimer's disease in a subject in need thereof, the method comprising controlling at least one visual stimulator to emit a visual stimulus at a frequency of about 35 Hz to about 45 Hz; controlling at least one electroacoustic transducer to convert an electrical audio signal into a corresponding auditory stimulus at a frequency of about 35 Hz to about 45 Hz; and non-invasively delivering a combined stimulus to the subject, the combined stimulus including the visual stimulus and the sound stimulus synchronously aligned, the combined stimulus to induce synchronized gamma oscillations in at least one brain region of the subject. The synchronized gamma oscillations result in an improvement of the cognitive function in the subject.

In some embodiments, the visual stimulus comprises repeated 12.5 ms light on then 12.5 ms light off. In some embodiments, the optogenetic stimulator is a light-emitting diode with 40-80 W power. In some embodiments, the auditory stimulus comprises a 10 kHz tone played at 40 Hz with a duty cycle of about 4% to about 80%. In some embodiments, the visual stimulus comprises a light flickered at 40 Hz for 10 s period with a duty cycle of about 10% to about 80%.

In some embodiments, the visual stimulus and the auditory stimulus are synchronized. In some embodiments, the visual stimulus and the auditory stimulus are out of phase by from −180 to 0 degrees or from 0 to 180 degrees. As used herein, "phase" refers to lag between the auditory stimulus and the visual stimulus expressed in degrees, where 0 degrees means simultaneous auditory and visual stimulus and −180 or +180 refers to alternating visual and auditory stimulus.

As used herein, the terms "treatment" or "treating" refers to both therapeutic treatment and prophylactic or preventive measures. In some embodiments, subjects in need of treatment include those subjects that already have the disease or condition as well as those subjects that may develop the disease or condition and in whom the object is to prevent, delay, or diminish the disease or condition. For example, in some embodiments, the devices, methods, and systems disclosed herein may be employed to prevent, delay, or diminish a disease or condition to which the subject is genetically predisposed, such as AD. In some embodiments, the devices, methods, and systems disclosed herein may be employed to treat, mitigate, reduce the symptoms of, and/or delay the progression of a disease or condition with which the subject has already been diagnosed, such as AD.

As used herein, the term "subject" denotes a mammal, such as a rodent, a feline, a canine, or a primate. Preferably, a subject according to the invention is a human.

The term "about," as used herein, refers to plus or minus ten percent of the object that "about" modifies.

Dementias are disorders characterized by loss of intellectual abilities and/or memory impairments. Dementias include, for example, AD, vascular dementia, Lewy body dementia, Pick's disease, fronto-temporal dementia (FTD), AIDS dementia, age-related cognitive impairments, and age-related memory impairments. Dementias may also be associated with neurologic and/or psychiatric conditions such, as, for example, brain tumors, brain lesions, epilepsy, multiple sclerosis, Down's syndrome, Rett's syndrome, progressive supranuclear palsy, frontal lobe syndrome, schizophrenia, and traumatic brain injury.

AD is the most frequent neurodegenerative disease in developed countries. AD is histopathologically characterized by the accumulation of amyloid plaques comprised of the Aβ peptide and NFTs made of the tau protein. Clinically, AD is associated with progressive cognitive impairment characterized by loss of memory, function, language abilities, judgment, and executive functioning. AD often leads to severe behavioral symptoms in its later stages.

Vascular dementia can also be referred to as cerebrovascular dementia and refers to cerebrovascular diseases (e.g., infarctions of the cerebral hemispheres), which generally have a fluctuating course with periods of improvement and stepwise deterioration. Vascular dementia can include one or more symptoms of disorientation, impaired memory and/or impaired judgment. Vascular dementia can be caused by discrete multiple infarctions, or other vascular causes including, for example, autoimmune vasculitis, such as that found in systemic lupus erythematosus; infectious vasculitis, such as Lyme's disease; recurrent intracerebral hemorrhages; and/or strokes.

Frontal temporal dementia (FTD) is a progressive neurodegenerative disorder. Subjects with FTD generally exhibit prominent behavioral and personality changes, often accompanied by language impairment.

Lewy body dementia is characterized by one or more symptoms of the development of dementia with features overlapping those of AD; development of features of Parkinson's disease; and/or early development of hallucinations. Lewy body dementia is generally characterized by day-to-day fluctuations in the severity of the symptoms.

In some aspects, the present disclosure provides methods for preventing, mitigating, and/or treating dementia in a subject, comprising inducing synchronized gamma oscillations in the brain of the subject. In some embodiments, the induction of gamma oscillations in the subject suffering from a neurological disease or disorder or age-related decline acts to restore gamma oscillatory rhythms that are disrupted in the subject as a result of or in association with the disease or disorder or age-related decline.

In some embodiments, the induction of gamma oscillations reduces generation of isoforms $A\beta_{1-40}$ and $A\beta_{1-42}$. In some embodiments, the induction of gamma oscillations enhances clearance of $A\beta$ (e.g., isoforms $A\beta_{1-40}$ and $A\beta_{1-42}$) from the brain of the subject. In some embodiments, the induction of gamma oscillations prevents accumulation of $A\beta$ in the brain of the subject. In some embodiments, the methods provided herein reduce the level of $A\beta$ in the brain of the subject by about 10%, about 20%, about 30%, about 40%, about 50%, about 60%, about 70%, or more, relative to the level of $A\beta$ in the brain of the subject prior to treatment. In some embodiments, the level of $A\beta$ in the brain of the subject is reduced by at least about 50% relative to the level of $A\beta$ in the brain of the subject prior to treatment.

In some embodiments, the level of $A\beta$ in the brain of the subject is reduced via reduction in the cleavage of APP in the brain of the subject. In some embodiments, the methods provided herein reduce the cleavage of APP in the brain of the subject by about 10%, about 20%, about 30%, about 40%, about 50%, about 60%, about 70%, or more, relative to the level of APP cleavage in the brain of the subject prior to treatment. In some embodiments, the level of APP cleavage in the brain of the subject is reduced by at least about 50% relative to the level of APP cleavage in the brain of the subject prior to treatment. In some embodiments, the level of APP cleavage is measured by the level of C-terminal fragment $\beta$ ($\beta$-CTF) in the brain of the subject. In some embodiments, the level of APP cleavage in the brain is reduced via inhibition of $\beta$- and/or $\gamma$-secretases, such as by increasing the level of inhibition of $\beta$- and/or $\gamma$-secretase activity. In some embodiments, the methods provided herein reduce the aggregation of $A\beta$ plaques in the brain of the subject.

In some embodiments, the methods improve cognitive ability and/or memory in the subject.

In another aspect, the present disclosure provides methods for inducing a neuroprotective profile or neuroprotective environment in the brain of a subject, comprising inducing synchronized gamma oscillations in the brain of the subject. For example, in some embodiments, the neuroprotective profile is associated with a neuroprotective microglial cell profile. In further embodiments, the neuroprotective profile is induced by or associated with an increase in activity of the M-CSF pathway. In some embodiments, the neuroprotective environment is associated with anti-inflammatory signaling pathways. For example, in some embodiments, the anti-inflammatory signaling pathways are anti-inflammatory microglia signaling pathways.

In some embodiments, the neuroprotective profile is associated with a reduction in or a lack of pro-inflammatory glial cell activity. Pro-inflammatory glial cell activity is associated with an M1 phenotype in microglia, and includes production of reactive species of oxygen (ROS), neurosecretory protein Chromogranin A, secretory cofactor cystatin C, NADPH oxidase, nitric oxide synthase enzymes such as iNOS, NF-κB-dependent inflammatory response proteins, and pro-inflammatory cytokines and chemokines (e.g., TNF, IL-1β, IL-6, and IFNγ).

In contrast, an M2 phenotype of microglia is associated with downregulation of inflammation and repair of inflammation-induced damage. Anti-inflammatory cytokines and chemokines (IL-4, IL-13, IL-10, and/or TGFβ) as well as an increase in phagocytic activity are associated with an M2 phenotype. Thus, in some embodiments, the methods provided herein elicit a neuroprotective M2 phenotype in microglia. In some embodiments, the methods provided herein increase the phagocytic activity in the brain of the subject. For example, in some embodiments, the methods provided herein increase phagocytic activity of microglia such that the clearance of $A\beta$ is increased.

Gamma oscillations may include about 20 Hz to about 100 Hz. Thus, in some embodiments, the present disclosure provides methods for preventing, mitigating, or treating dementia in a subject comprising inducing gamma oscillations of about 20 Hz to about 100 Hz, or about 20 Hz to about 80 Hz, or about 20 Hz to about 50 Hz, or about 30 to about 60 Hz, or about 35 Hz to about 45 Hz, or about 40 Hz, in the brain of the subject. Preferably, the gamma oscillations are about 40 Hz.

A stimulus may include any detectable change in the internal or external environment of the subject that directly or ultimately induces gamma oscillations in at least one brain region. For example, a stimulus may be designed to stimulate electromagnetic radiation receptors (e.g., photoreceptors, infrared receptors, and/or ultraviolet receptors), mechanoreceptors (e.g., mechanical stress and/or strain), nociceptors (i.e., pain), sound receptors, electroreceptors (e.g., electric fields), magnetoreceptors (e.g., magnetic fields), hydroreceptors, chemoreceptors, thermoreceptors, osmoreceptors, and/or proprioceptors (i.e., sense of position). The absolute threshold or the minimum amount of sensation needed to elicit a response from receptors may vary based on the type of stimulus and the subject. In some embodiments, a stimulus is adapted based on individual sensitivity.

In some embodiments, gamma oscillations are induced in a brain region specific manner. For example, in some embodiments, the gamma oscillations are induced in the hippocampus, the visual cortex, the barrel cortex, the auditory cortex, or any combination thereof. By way of example, in some embodiments, the gamma oscillations are induced in the visual cortex using a flashing light; and in other embodiments, the gamma oscillations are induced in the auditory cortex using auditory stimulation at particular frequencies. In some embodiments, the gamma oscillations are induced in multiple brain regions simultaneously using a combination of visual, auditory, and/or other stimulations. In some embodiments, the gamma oscillations are induced in a virtual reality system.

In some embodiments, the subject receives a stimulus via an environment configured to induce gamma oscillations, such as a chamber that passively or actively blocks unrelated stimuli (e.g., light blocking or noise canceling). Alternatively or in addition, the subject may receive a stimulus via a system that includes, for example, light blocking or noise canceling aspects. In some embodiments, the subject receives a visual stimulus via a stimulus-emitting device, such as eyewear designed to deliver the stimulus. The device may block out other light. In some embodiments, the subject receives an auditory stimulus via a stimulus-emitting device, such as headphones designed to deliver the stimulus. The device may cancel out other noise.

In addition to at least one interface for emitting a stimulus, some embodiments may include at least one processor (to, e.g., generate a stimulus, control emission of the stimulus, monitor emission of the stimulus/results, and/or process feedback regarding the stimulus/results), at least one memory (to store, e.g., processor-executable instructions, at least one stimulus, a stimulus generation policy, feedback, and/or results), at least one communication interface (to communicate with, e.g., the subject, a healthcare provider, a caretaker, a clinical research investigator, a database, a monitoring application, etc.), and/or a detection device (to detect and provide feedback regarding, e.g., the stimulus and/or the subject, including whether gamma oscillations are induced, subject sensitivity, cognitive function, physical or chemical changes, stress, safety, etc.).

In some embodiments, the gamma oscillations are induced by a visual stimulus such as a flashing light at about 20 Hz to about 100 Hz. In particular embodiments, the gamma oscillations are induced by flashing light at about 20 Hz to about 50 Hz. In further embodiments, the gamma oscillations are induced by flashing light at about 35 Hz to about 45 Hz. In yet further embodiments, the gamma oscillations are induced by flashing light at about 40 Hz. In some embodiments, the subject receives (e.g., is placed in a chamber with or wears a light blocking device emitting) about 20 Hz to about 100 Hz flashing light, or about 20 Hz to about 50 Hz flashing light or about 35 Hz to about 45 Hz flashing light, or about 40 Hz flashing light.

In some embodiments, the gamma oscillations are induced by an auditory stimulus such as a sound at a frequency of about 20 Hz to about 100 Hz, or about 20 Hz to about 80 Hz, or about 20 Hz to about 50 Hz, or about 35 Hz to about 45 Hz, or about 40 Hz. In some embodiments, the subject receives (e.g., is placed in a chamber with or wears a noise canceling device emitting) an auditory stimulus of about 20 Hz to about 100 Hz, about 20 Hz to about 80 Hz, about 20 Hz to about 50 Hz, about 35 Hz to about 45 Hz, or about 40 Hz.

In some embodiments, the subject receives (e.g., is placed in a chamber with or wears a light blocking device emitting) the visual and/or auditory stimuli for about one hour, about 2 hours, about 3 hours, about 4 hours, about 5 hours, or more. In some embodiments, the subject receives (e.g., is placed in a chamber with or wears a light blocking device emitting) the stimuli for no more than about 6 hours, no more than about 5 hours, no more than about 4 hours, no more than about 3 hours, no more than about 2 hours, or no more than about one hour. In some embodiments, the subject receives (e.g., is placed in a chamber with or wears a light blocking device emitting) the stimuli for less than an hour.

In some embodiments, the subject undergoes with the methods provided herein. In other embodiments, the subject undergoes treatment with the methods provided herein on multiple separate occasions. Subjects may be treated on a regular schedule or as symptoms arise or worsen. In some embodiments, chronic treatment may be effective at reducing soluble Aβ peptide and/or insoluble Aβ peptide (i.e., plaques).

In some embodiments, the gamma oscillations are induced in a cell-type specific manner. In some embodiments, the gamma oscillations are induced in FS-PV-interneurons. The term "fast-spiking" (FS) when used to describe a class of neurons refers to the capacity of the neurons to discharge at high rates for long periods with little spike frequency adaptation or attenuation in spike height. Thus, these neurons are capable of sustained high frequency (e.g., equal to or greater than about 100 Hz or about 150 Hz) discharge without significant accommodation. This property of FS neurons is attributable in large measure to their expression of fast delayed rectifier channels, in other words, channels that activate and deactivate very quickly.

In one aspect, the stimulations may be non-invasive. The term "non-invasive," as used herein, refers to devices, methods, and systems which do not require surgical intervention or manipulations of the body such as injection or implantation of a composition or a device. For example, the stimulations may visual (e.g., flickering light), audio (e.g., sound vibrations), and/or haptic (mechanical stimulation with forces, vibrations, or motions).

In another aspect, the stimulations may be invasive or at least partially invasive. For example, visual, audio, and/or haptic stimulations may be combined with an injection or implantation of a composition (e.g., a light-sensitive protein) or a device (e.g., an integrated fiber optic and solid-state light source).

Experimental Data

Experimental data relating to the inventive concepts described herein is set forth below in connection with the various figures, which are first summarized and then followed with detailed explanations.

FIG. 1A shows firing rate modulation of two putative single units during 40 Hz auditory stimulation (left panel of each pair) and random stimulation (right panel of each pair) in AC. Ticks indicate auditory pulses; light bar indicates randomly distributed pulses. Raster plots show spiking response of two example putative single units to 10 seconds of 40 Hz auditory or random stimulation.

Figure 1B:
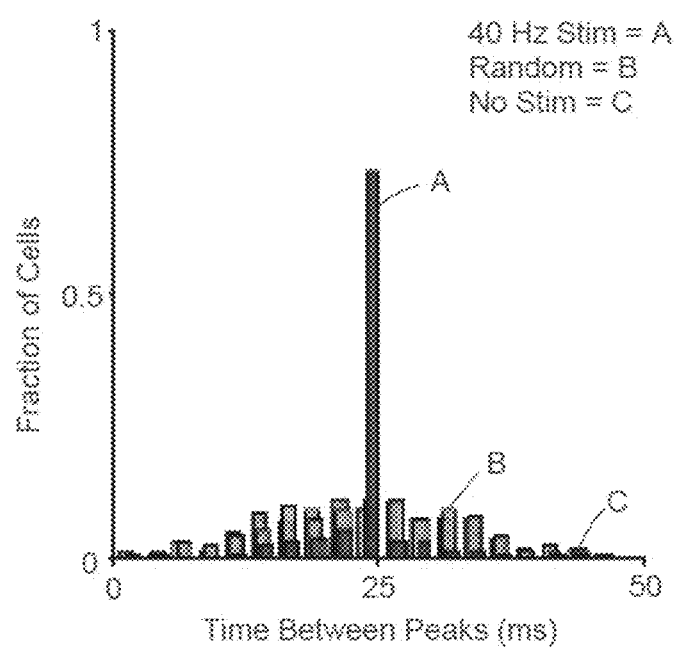

FIG. 1B shows distribution of intervals between peaks in firing rate in AC for no stimulation (labeled no stim), random (labeled random), and 40 Hz auditory stimulation (labeled 40 Hz stim) conditions for all single units (n=292 units in 9 recording sessions in 5 mice. Proportion of intervals around inter-stimulus interval: P=0 40 Hz vs. No stim, P=0 40 Hz vs. Random; z-Test for two proportions).

Figure 1C:
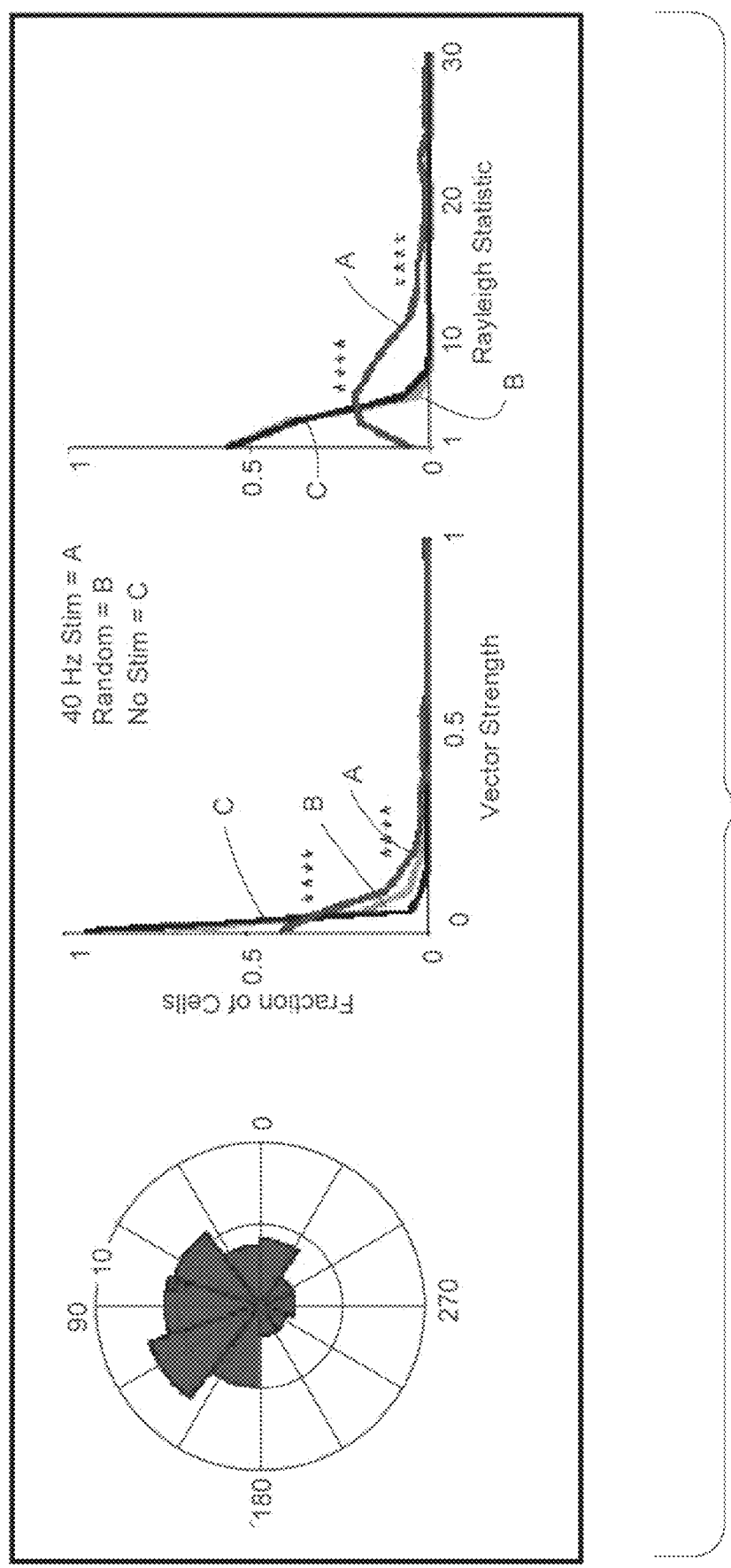

FIG. 1C shows example polar plot of firing rate modulation relative to the onset of the stimulus during 40 Hz auditory stimulation (left, stimulus onset at 0), vector strength distribution of single unit firing rate modulation during 40 Hz auditory stimulation, random, and no stimulation (center, **$P<0.0001$, $P=4\times10^{-54}$ 40 Hz vs. No Stim, $P=2\times10^{-13}$ 40 Hz vs. Random; Kolmogorov-Smirnov test), and distribution of Rayleigh statistic values of single unit firing rate modulation (right, **$P<0.0001$, $P=5\times10^{-68}$ 40 Hz vs. No Stim, $P=6\times10^{-72}$ 40 Hz vs. Random; Kolmogorov-Smirnov test; 26 units had 40 Hz stim RS values greater than 30; 1 unit had a random stim RS value greater than 30).

Figure 1D:
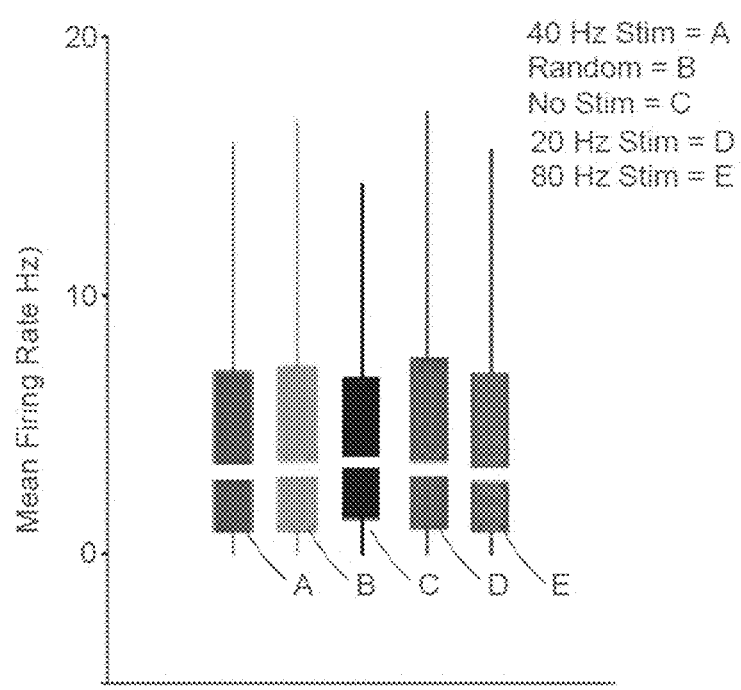

FIG. 1D shows distribution of mean firing rate values between stimulation conditions in AC.

Figure 1E:
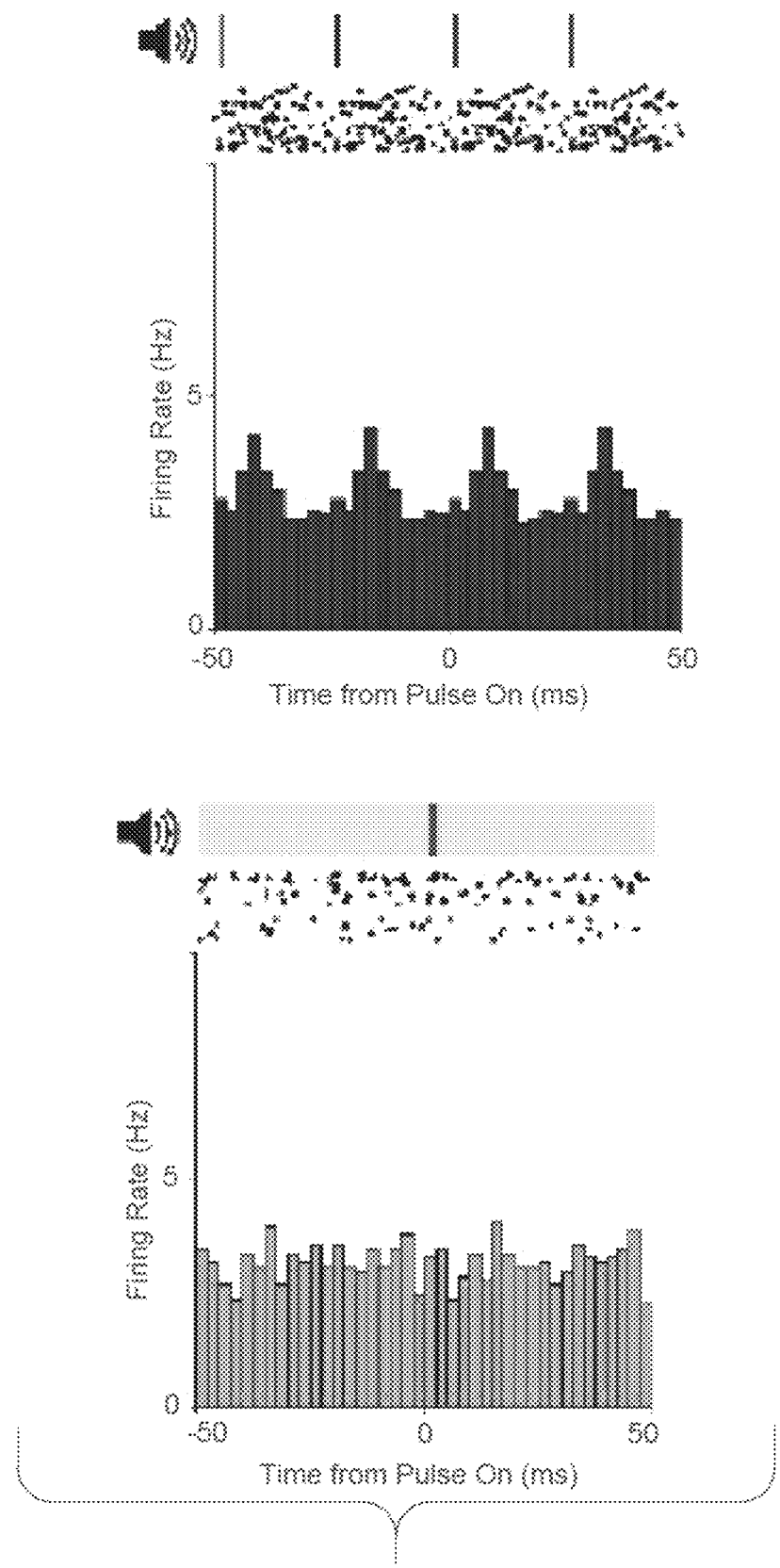

FIG. 1E shows same as FIG. 1A for CA1.

Figure 1F:
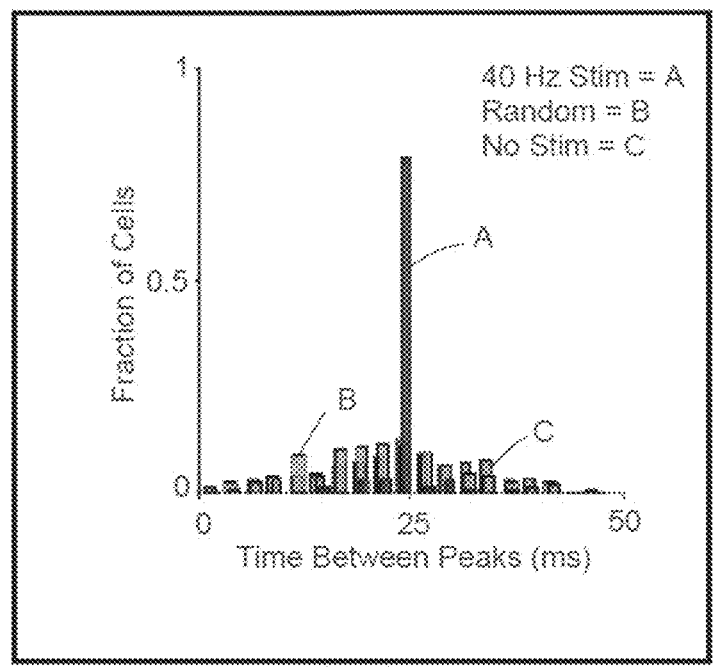

FIG. 1F shows same as FIG. 1B for CA1 (n=338 units in 10 recording sessions in 5 mice. P=0 40 Hz vs. No stim, P=0 40 Hz vs. Random; z-Test for two proportions).

Figure 1G:
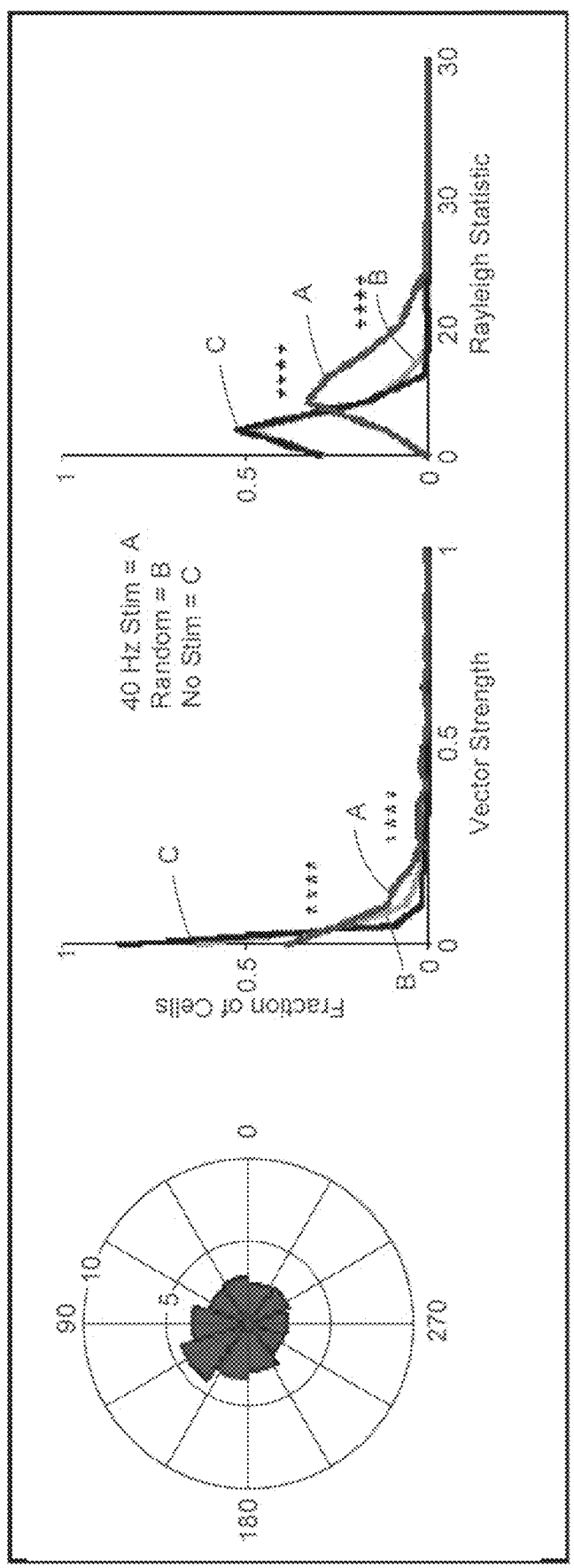

FIG. 1G shows same as FIG. 1C for CA1 (center, **$P<0.0001$, $P=4\times10^{-40}$ 40 Hz vs. No Stim, $P=9\times10^{-11}$ 40 Hz vs. Random; Kolmogorov-Smirnov test; right, **$P<0.0001$, $P=1\times10^{-74}$ 40 Hz vs. No Stim, $P=2\times10^{-73}$ 40 Hz vs. Random; Kolmogorov-Smirnov test).

Figure 1H:
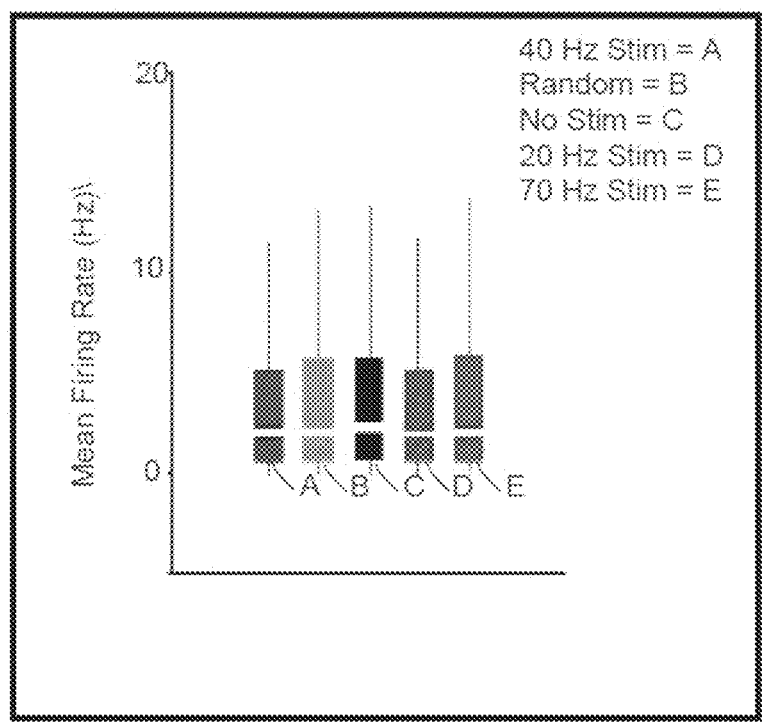

FIG. 1H shows same as FIG. 1D for CA1.

Figure 1I:
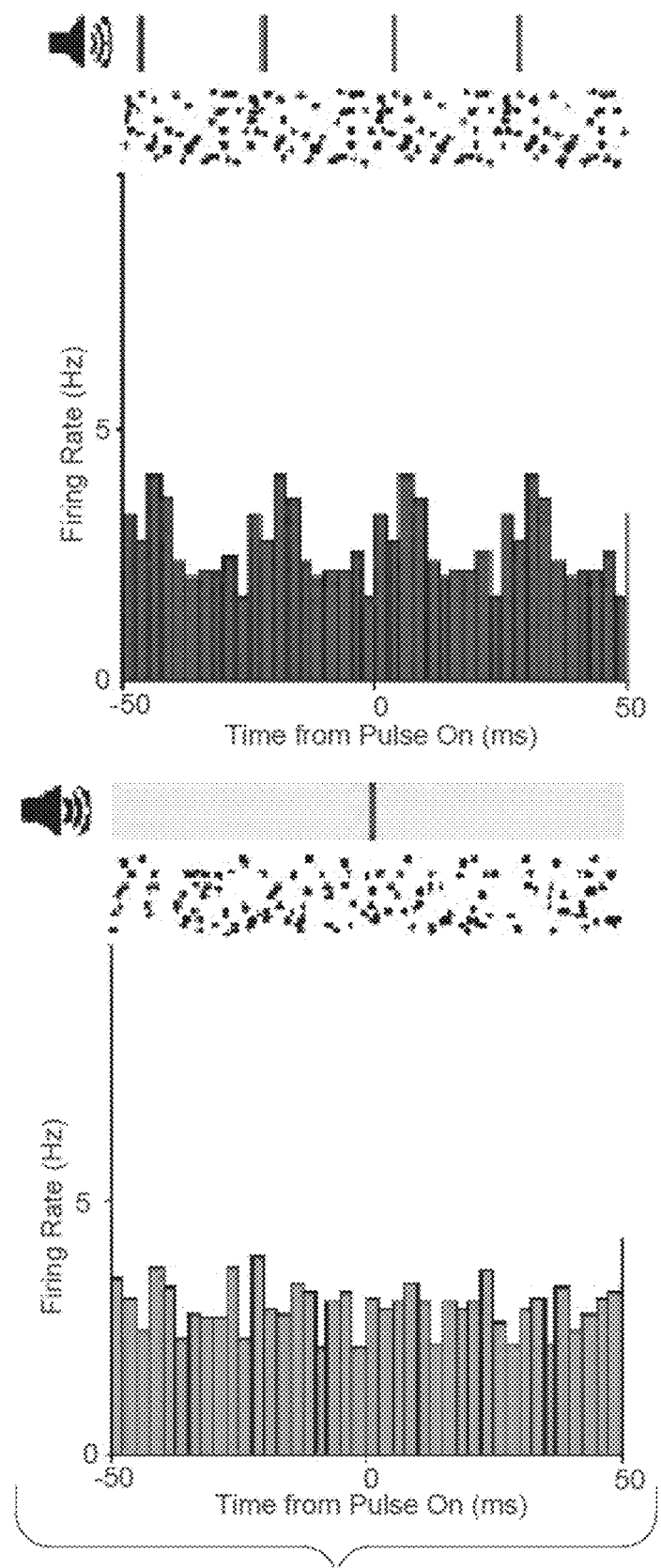

FIG. 1I shows same as FIG. 1A for mPFC.

Figure 1J:
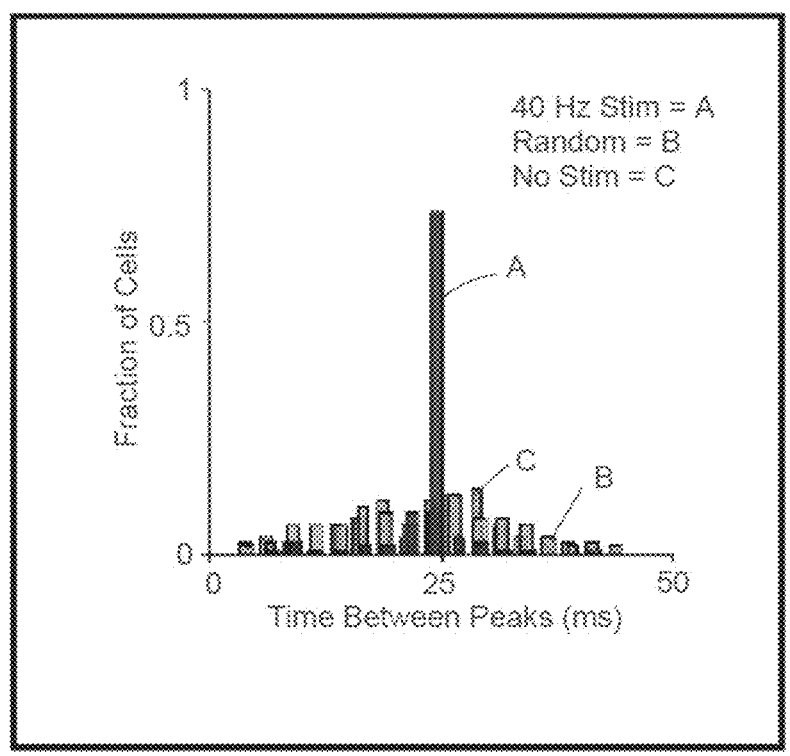

FIG. 1J shows same as FIG. 1B for mPFC (n=115 units in 7 recording sessions in 4 mice. P=0 40 Hz vs. No stim, P=0 40 Hz vs. Random; z-Test for two proportions).

Figure 1K:
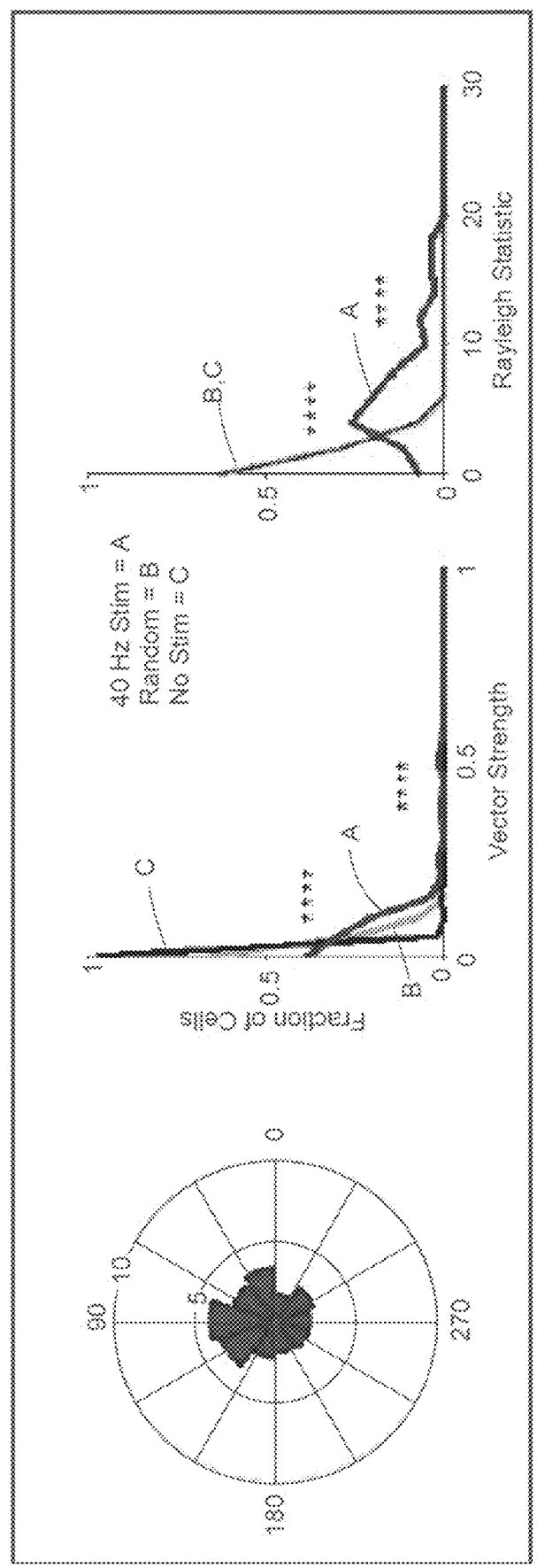

FIG. 1K shows same as FIG. 1C for mPFC (center, **P<0.0001, P=2×10$^{-27}$ 40 Hz vs. No Stim, P=4×10$^{-5}$ 40 Hz vs. Random; Kolmogorov-Smirnov test; right, **P<0.0001, P=1×10$^{-28}$ 40 Hz vs. No Stim, P=5×10$^{-30}$ 40 Hz vs. Random; Kolmogorov-Smirnov test).

Figure 1L:
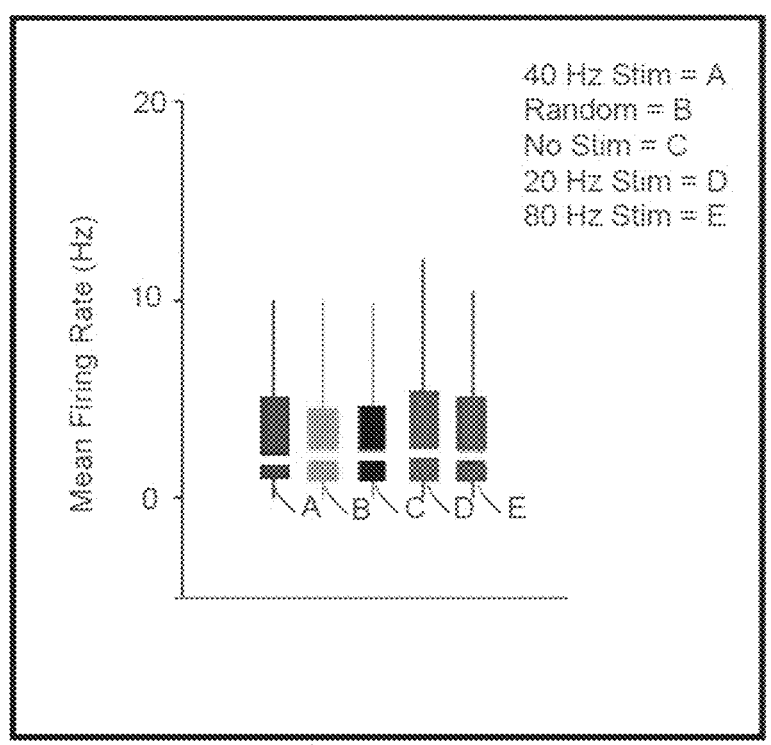

FIG. 1L shows same as FIG. 1D for mPFC.

Figure 2A:
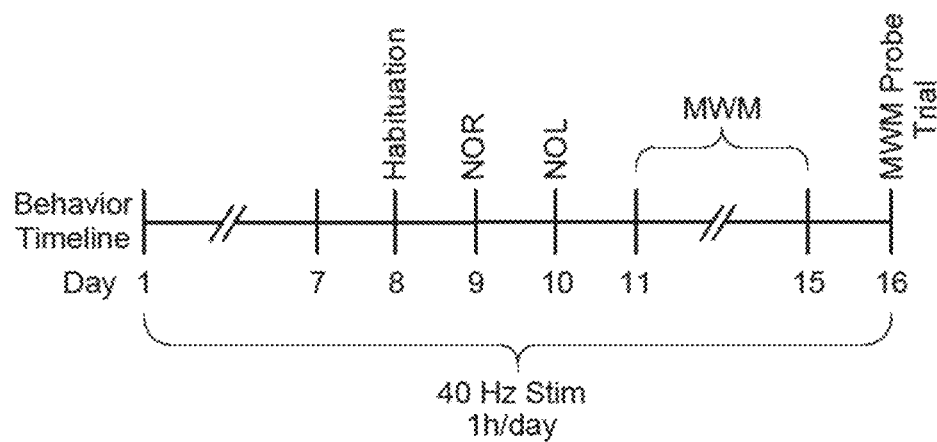
FIG. 2A-2J show auditory GENUS improves recognition and spatial memory tasks in 5XFAD mice.

FIG. 2A shows timeline of behavior experiments for 5XFAD auditory GENUS mice.

Figure 2B:
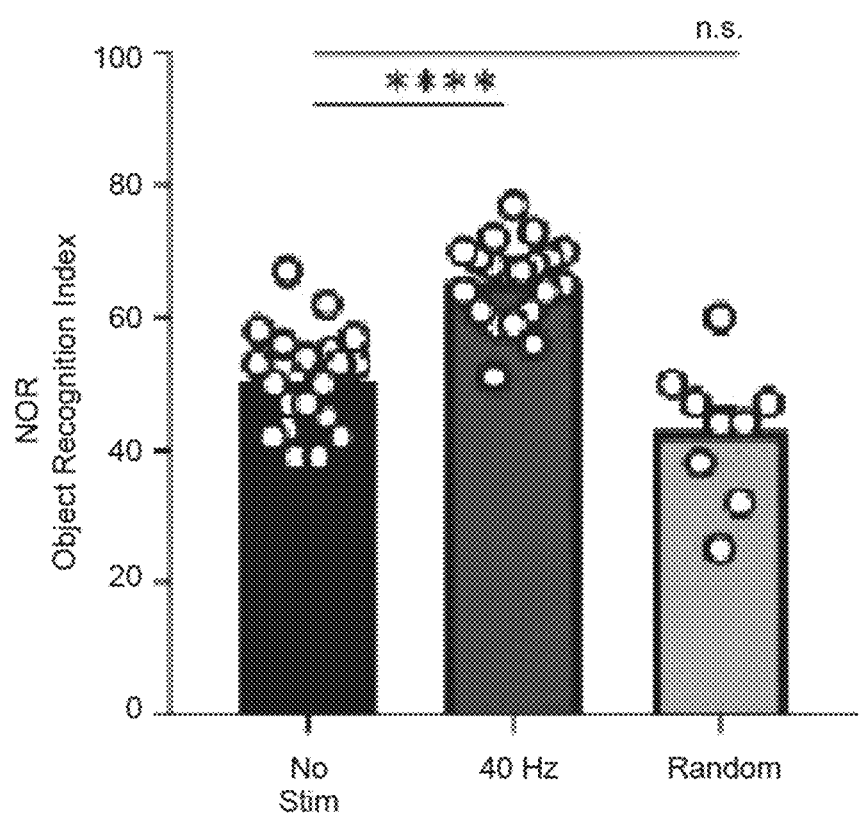

FIG. 2B shows recognition index of novel object recognition (NOR) test of 5XFAD auditory GENUS mice (n=20 mice in no stim group, n=20 mice in 40 Hz group, n=9 in random frequency group, circles indicate 'n', mean s.e.m. in bar graphs, ****P<0.0001, n.s.=not significant, Kruskal-Wallis test with Dunn's multiple comparison test).

Figure 2C:
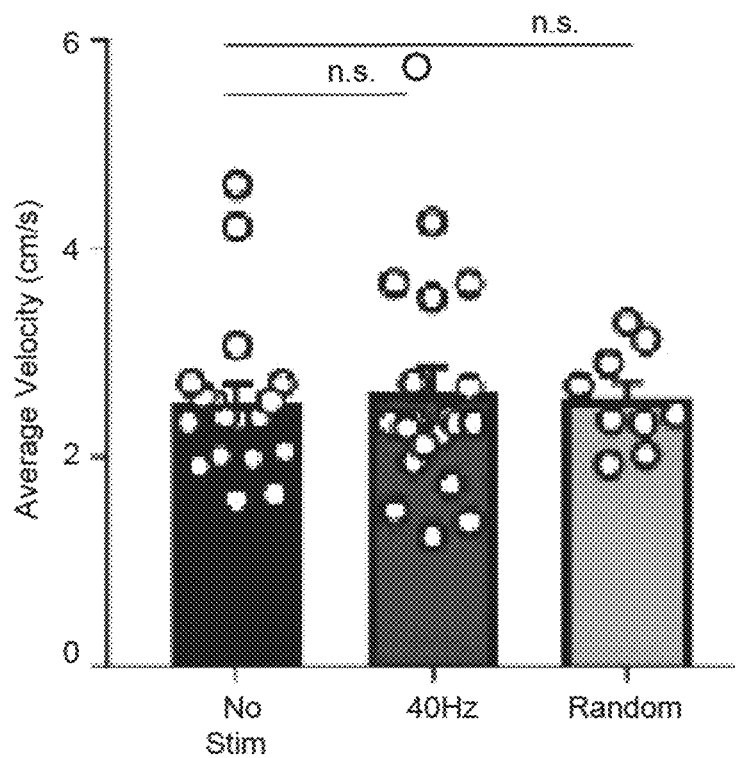

FIG. 2C shows average velocity (cm/s) during novel object recognition test (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 2D:
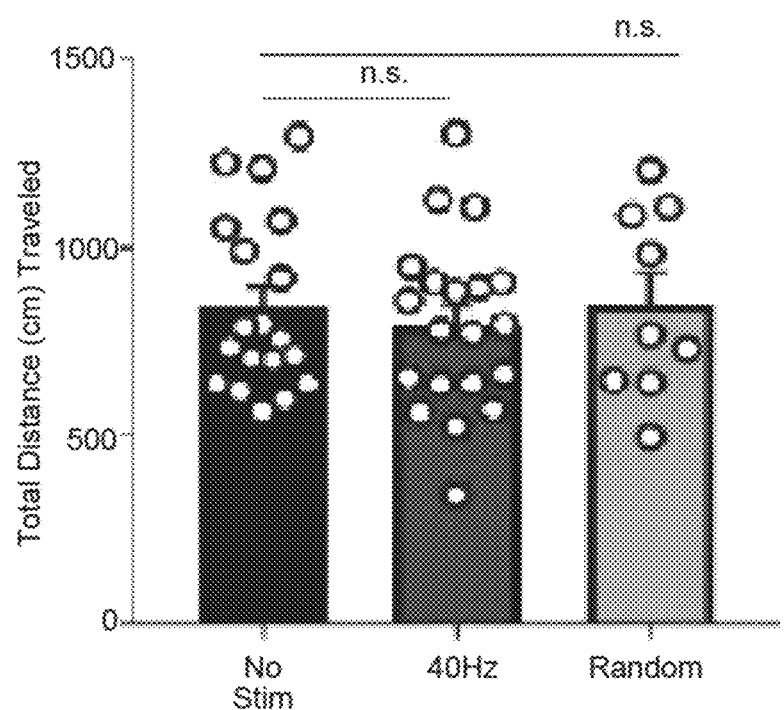

FIG. 2D shows total distance (cm) traveled during novel object recognition test (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 2E:
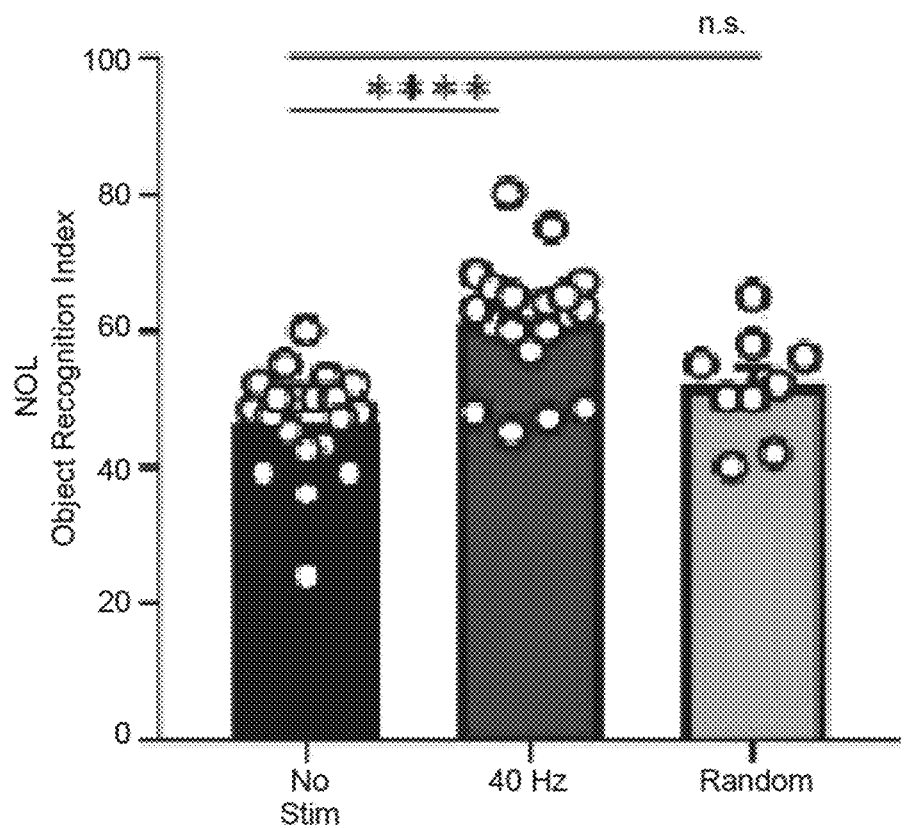

FIG. 2E shows recognition index of novel object location (NOL) test of 5XFAD auditory GENUS mice (n=20 mice in no stim group, n=20 mice in 40 Hz group, n=9 in random frequency group, mean s.e.m. in bar graphs, ****P<0.0001, n.s.=not significant, Kruskal-Wallis test with Dunn's multiple comparison test).

Figure 2F:
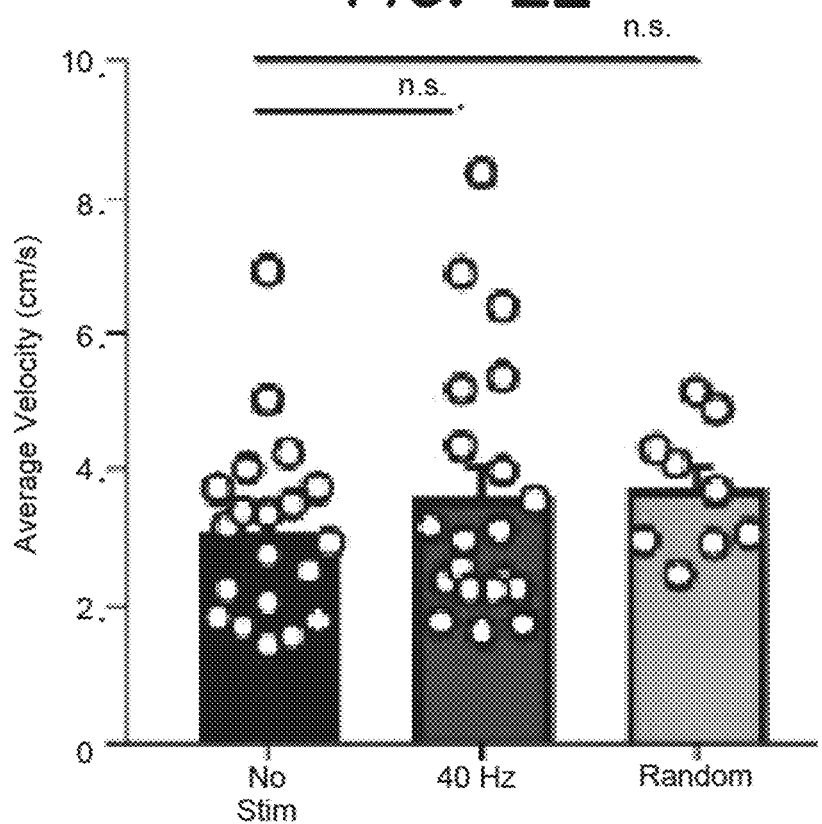

FIG. 2F shows average velocity (cm/s) during novel object location test (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 2G:
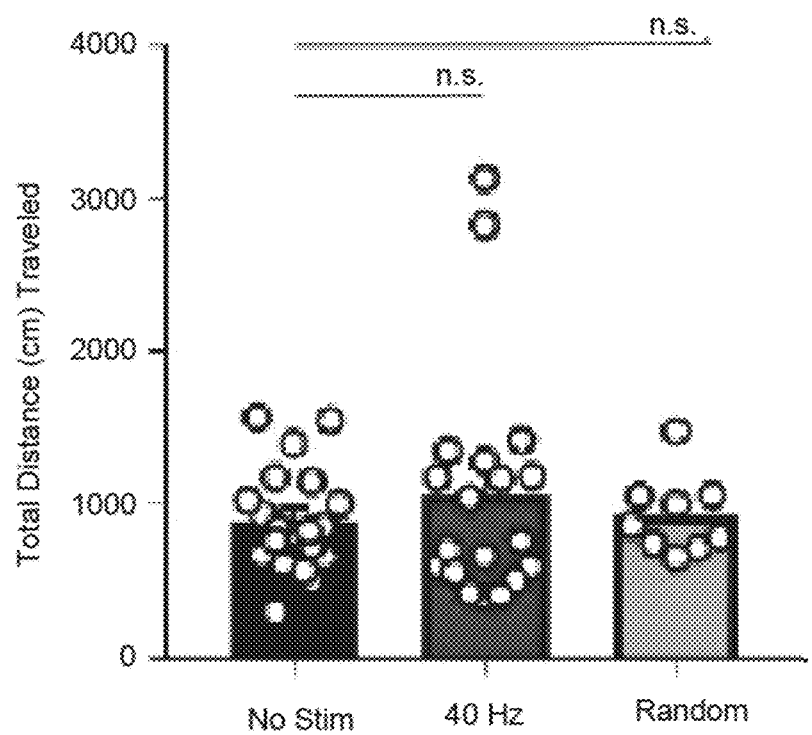

FIG. 2G shows total distance (cm) traveled during novel object location test (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 2H:
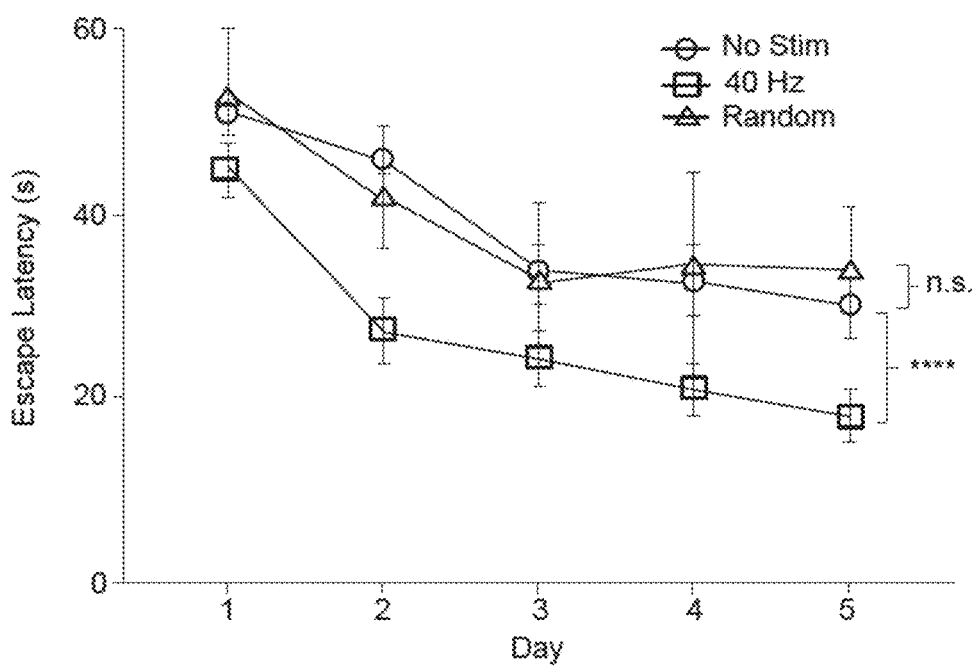

FIG. 2H shows escape latencies (s) of 5XFAD non-stimulated, random frequency, and 40 Hz auditory stimulated mice in the Morris Water Maze (n=25 mice in no stim group, n=28 mice in 40 Hz group, n=9 in random frequency group, mean s.e.m. in bar graphs, ****P<0.0001, n.s.=not significant, 2-way ANOVA with Tukey's multiple comparison test).

Figure 2I:
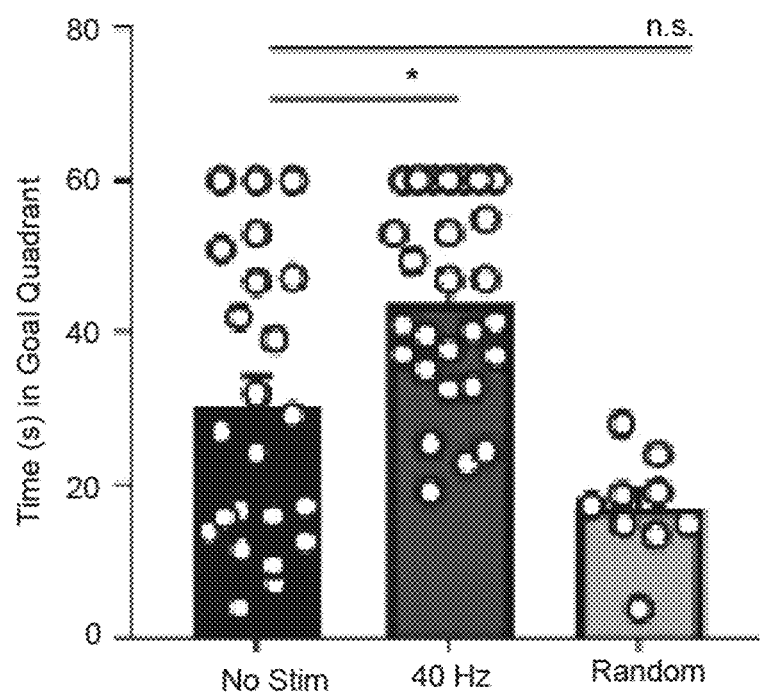

FIG. 2I shows time (s) spent swimming in the goal quadrant during the probe trial (n=25 mice in no stim group, n=28 mice in 40 Hz group, n=9 in random frequency group, mean s.e.m. in bar graphs, *P<0.05, Kruskal-Wallis test with Dunn's multiple comparison test).

Figure 2J:
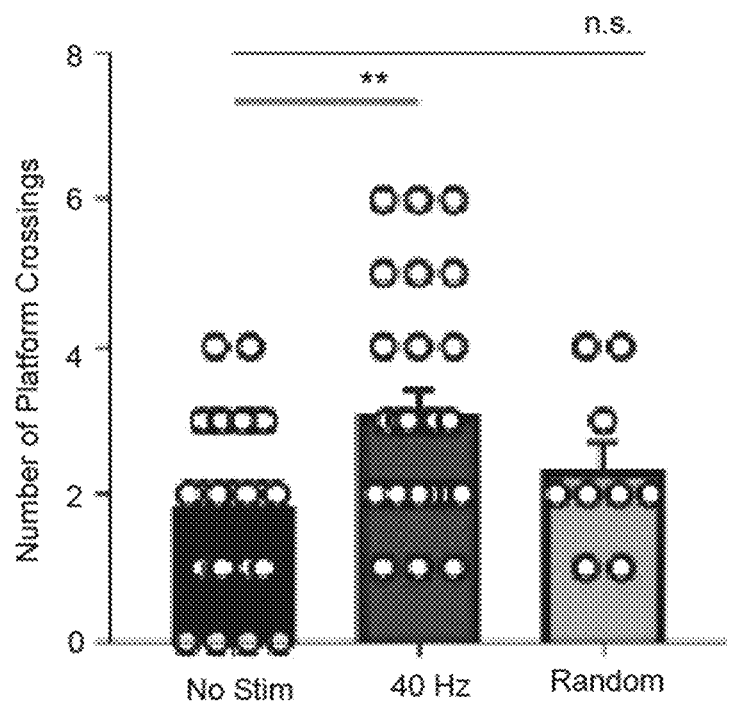

FIG. 2J shows number of platform crossings during the probe trial (n=25 mice in no stim group, n=28 mice in 40 Hz group, n=9 in random frequency group, mean s.e.m. in bar graphs, **P<0.01, Kruskal-Wallis test with Dunn's multiple comparison test).

Figure 3A:
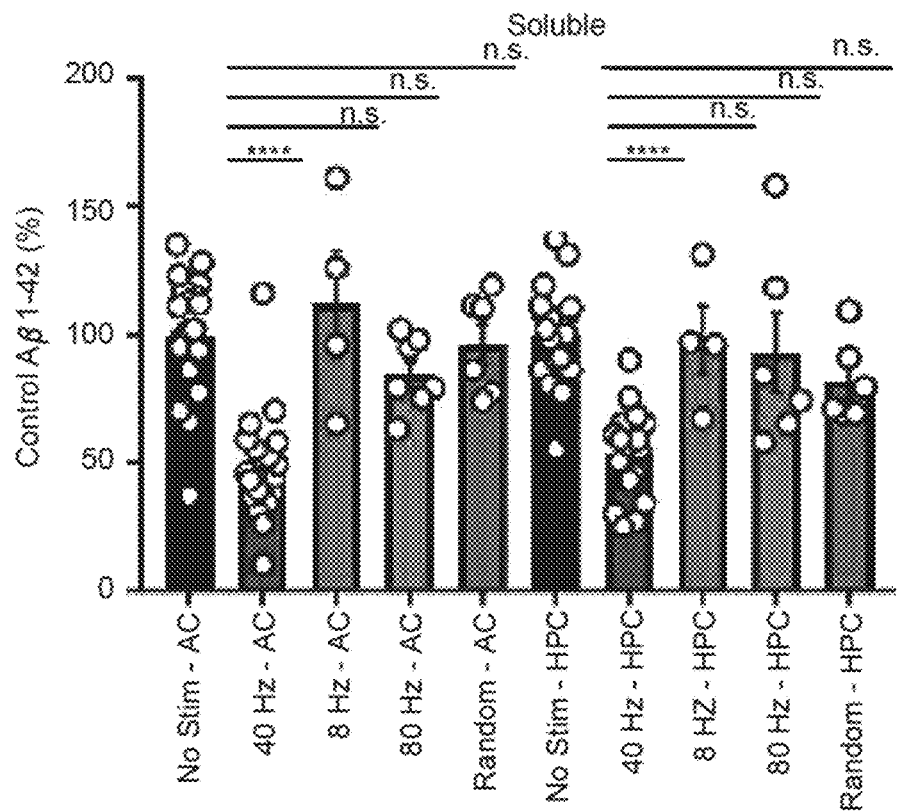

FIG. 3A shows relative soluble $A\beta_{1-42}$ levels in auditory cortex (AC) and hippocampus (HPC) in 6-month-old 5XFAD mice following 40 Hz, 8 Hz, 80 Hz, or random frequency auditory stimulation for 1 hour per day for 7 days, normalized to non-stimulation control (n=19 mice in no stim group, n=19 mice in 40 Hz group, n=4 mice in 8 Hz group, n=7 in 80 Hz group, n=6 in random frequency group, mean s.e.m. in bar graphs, ****P<0.0001, n.s.=not significant, Kruskal-Wallis test with Dunn's multiple comparison test).

Figure 3B:
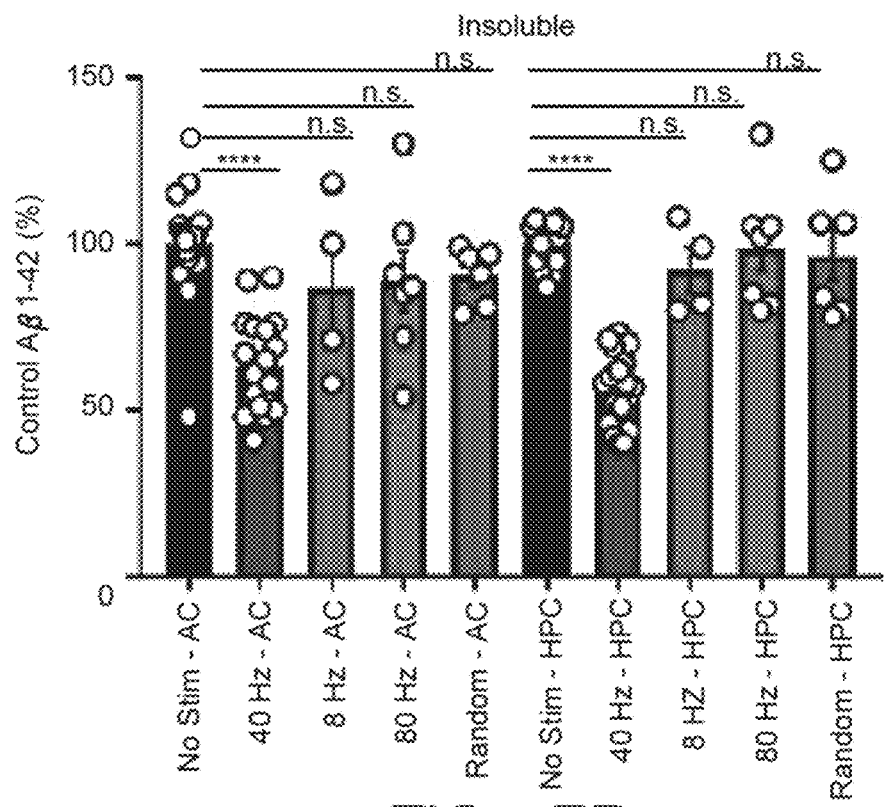

FIG. 3B shows as in FIG. 3A for insoluble $A\beta_{1-42}$.

Figure 3C:
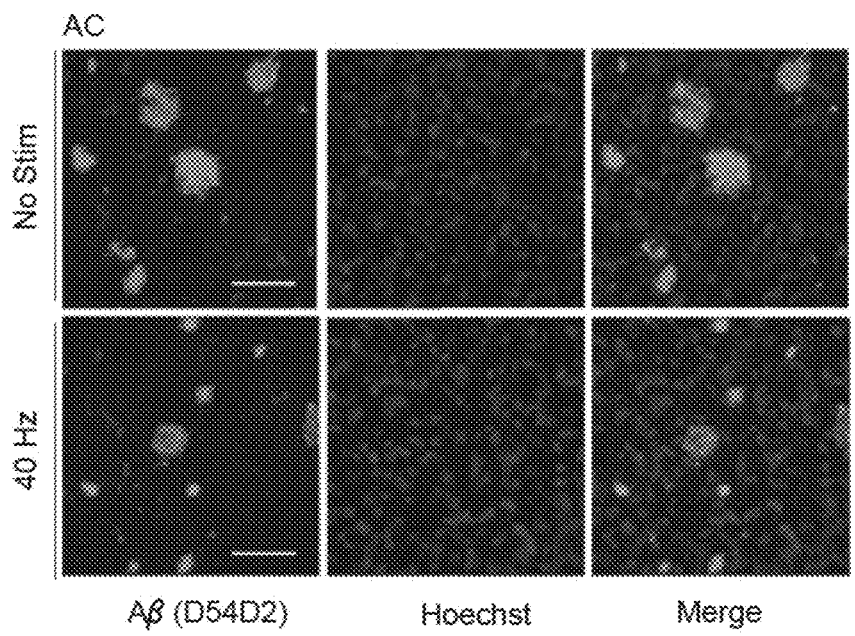

FIG. 3C shows immunohistochemistry with anti-Aβ (D54D2, green) antibody in 6-month-old AC of 5XFAD mice after auditory GENUS or no stimulation, for 1 hour per day for 7 days (n=7 mice per group, scale bar, 50 μm).

Figure 3D:
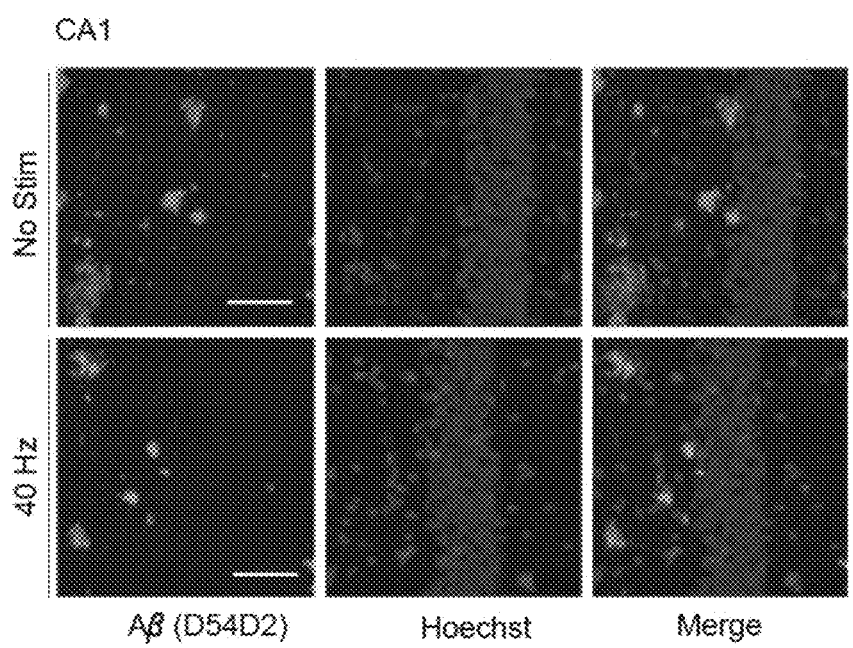

FIG. 3D shows as in FIG. 3C for CA1.

Figure 3E:
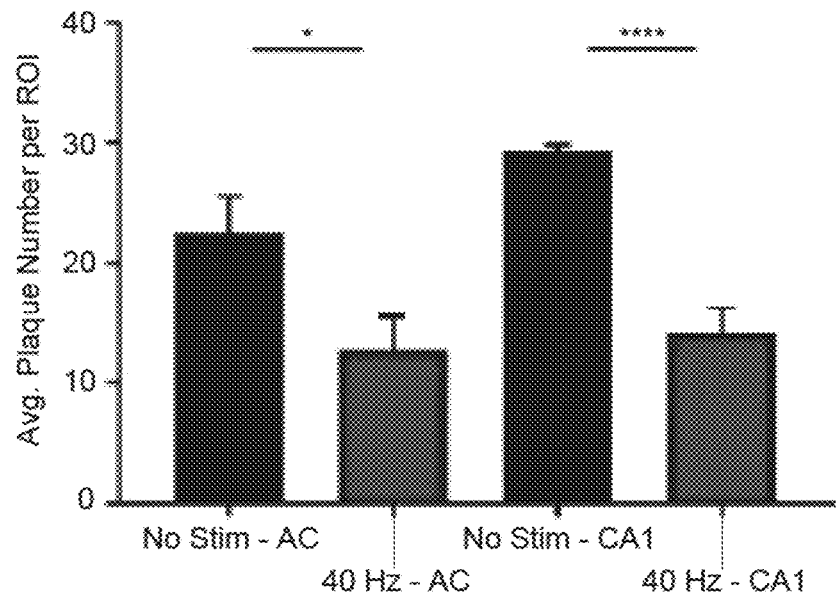

FIG. 3E shows average number of Aβ-positive plaques in AC and CA1 (n=7 mice per group, mean s.e.m. in bar graphs, *P<0.05, ****P<0.0001; unpaired Mann-Whitney Test).

Figure 3F:
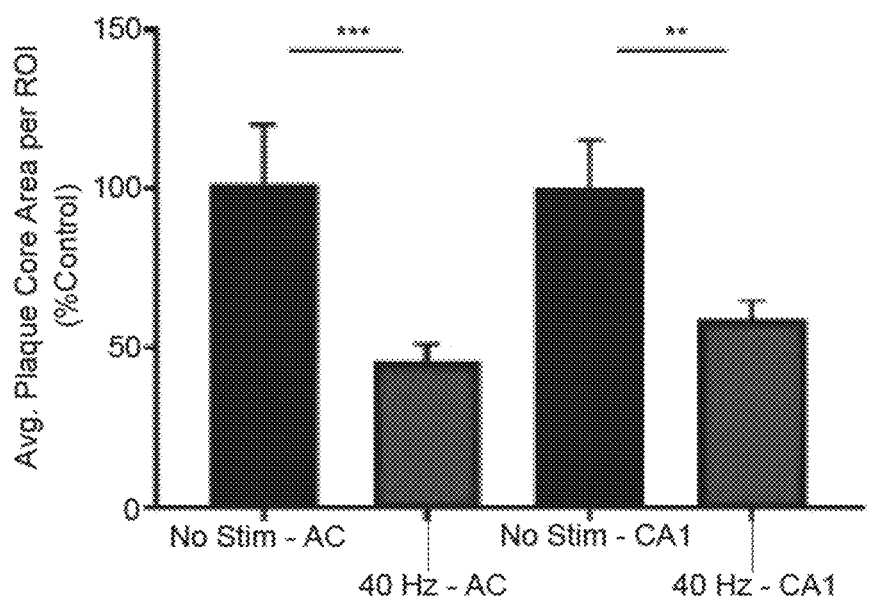

FIG. 3F shows average area of Aβ-positive plaques in AC and CA1 (n=7 mice per group, mean s.e.m. in bar graphs, P<0.01, *P<0.001; unpaired Mann-Whitney Test).

Figure 3G:
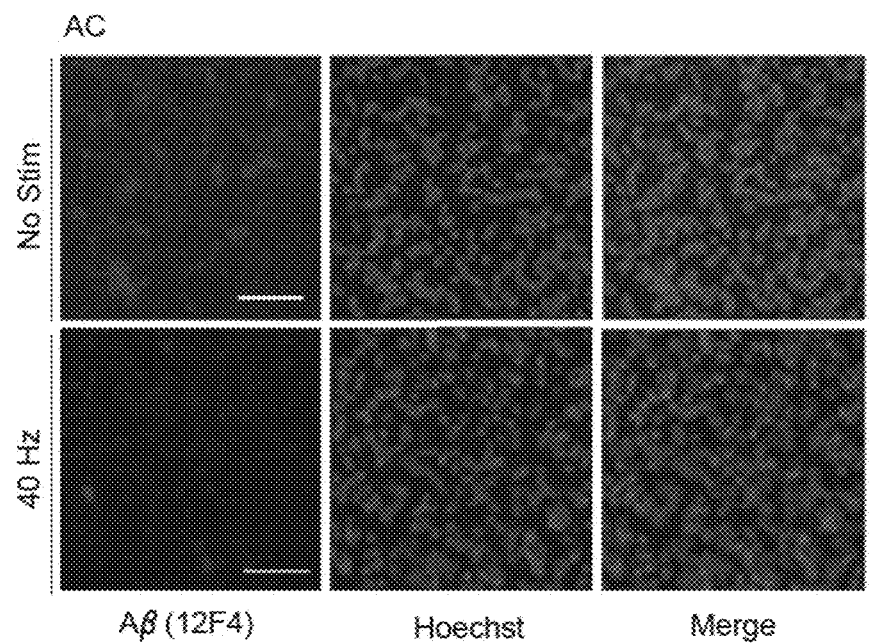

FIG. 3G shows immunohistochemistry with anti-Aβ (12F4, red) antibody in 6-month-old AC of 5XFAD mice after auditory GENUS or no stimulation, for 1 hour per day for 7 days (Inset, 20×, scale bar, 50 μm).

Figure 3H:
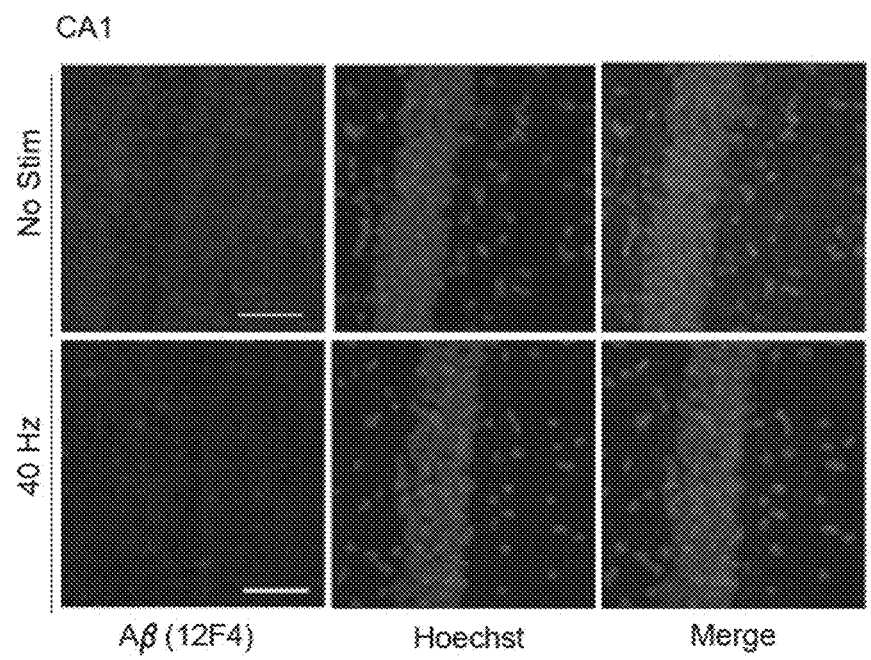
Figure 31:
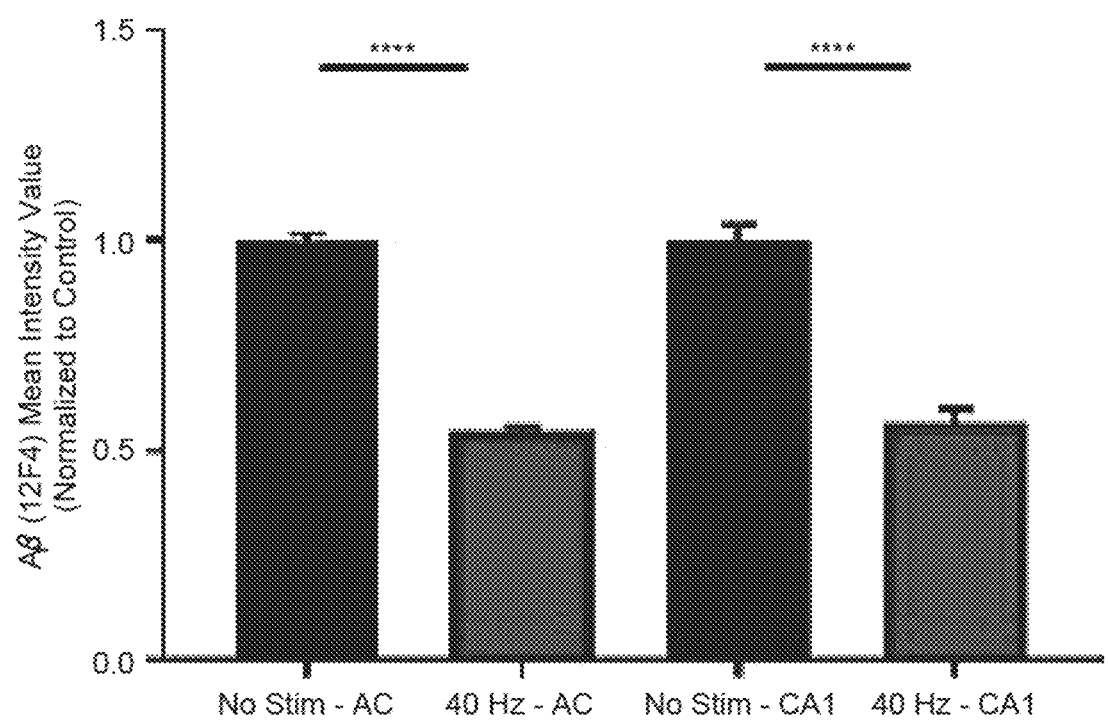

FIG. 3H shows as in FIG. 3G for CA1.

FIG. 3I shows Aβ (12F4) mean intensity value (12F4 antibody) normalized to non-stimulated controls (n=7 mice per group, mean s.e.m. in bar graphs, ****P<0.0001, unpaired Mann-Whitney Test).

Figure 4A:
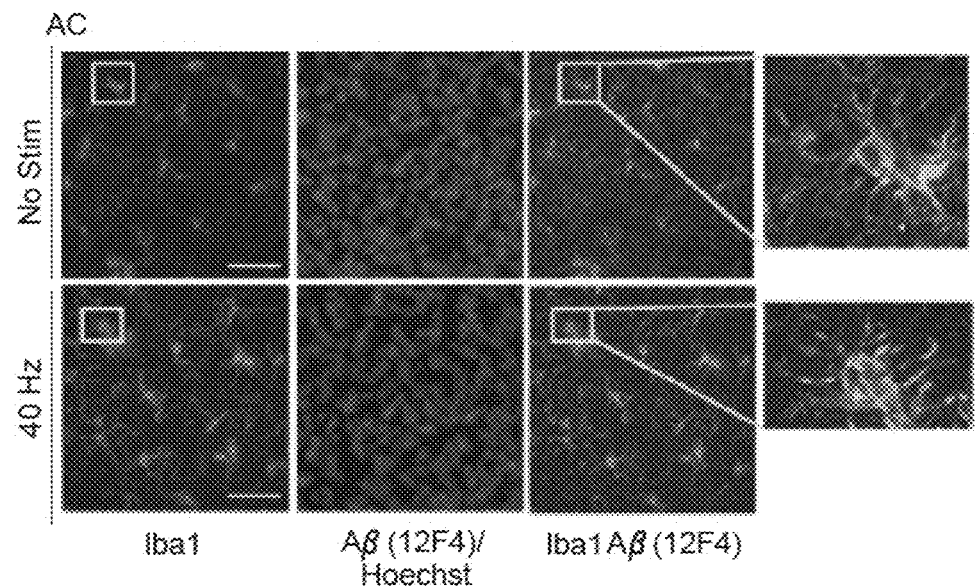
FIG. 4A-4K shows auditory GENUS induces glial response in AC and CA1 in 5XFAD mice.

FIG. 4A shows immunohistochemistry with anti-Iba1 (019-19741, green) and anti-Aβ (12F4, red) antibodies in AC of 5XFAD mice after 7 days of 1 hour per day no stimulation or auditory GENUS (n=8 mice per group, scale bar, 50 μm).

Figure 4B:
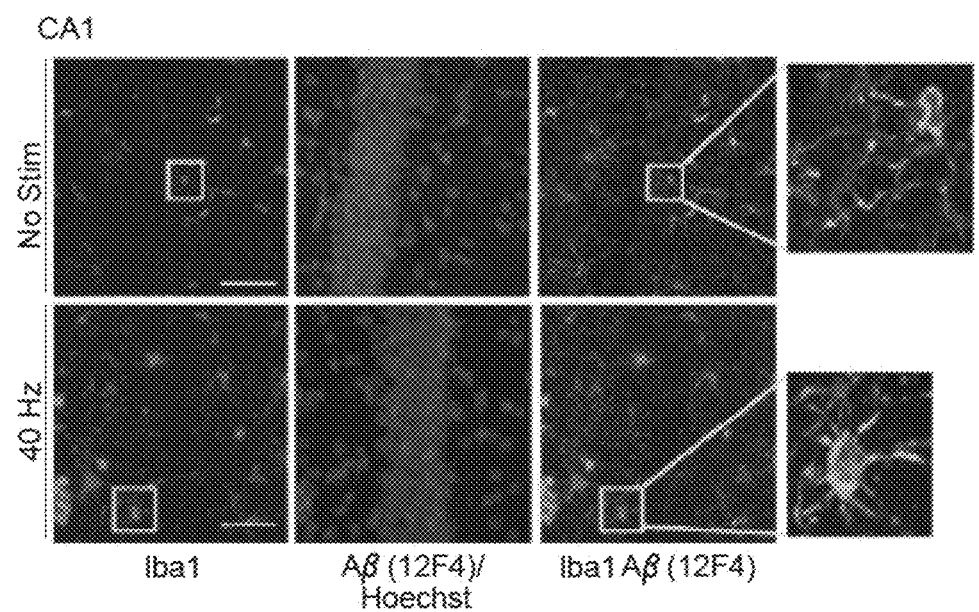

FIG. 4B shows as in FIG. 4A for CA1.

Figure 4C:
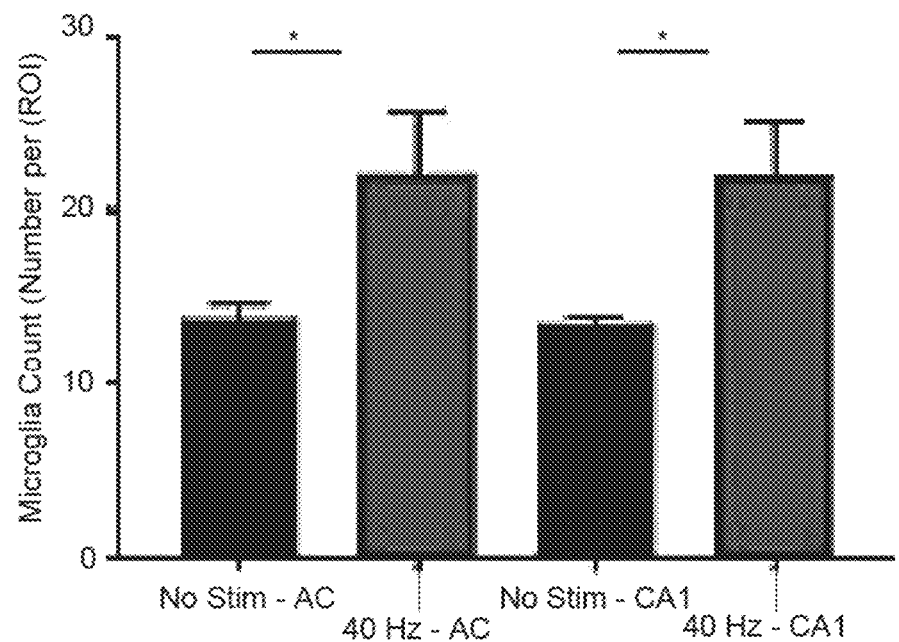

FIG. 4C shows number of Iba1-positive microglia in AC and CA1 (n=8 mice per group, mean s.e.m. in bar graphs, *P<0.05; unpaired Mann-Whitney Test).

Figure 4D:
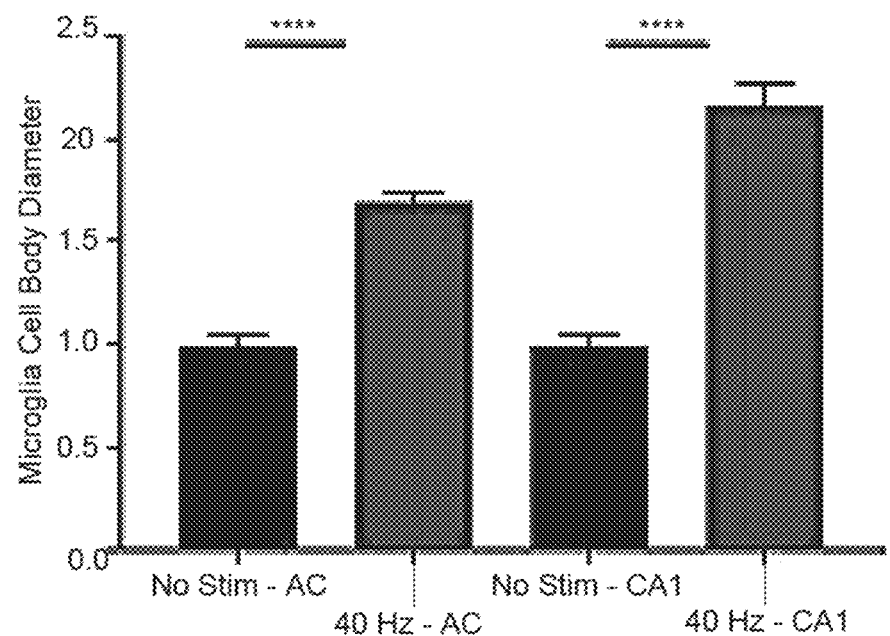

FIG. 4D shows diameter of Iba1-positive microglia cell bodies in AC and CA1 normalized to non-stimulated controls (n=8 mice per group, mean s.e.m. in bar graphs, ****P<0.0001; unpaired Mann-Whitney Test).

Figure 4E:
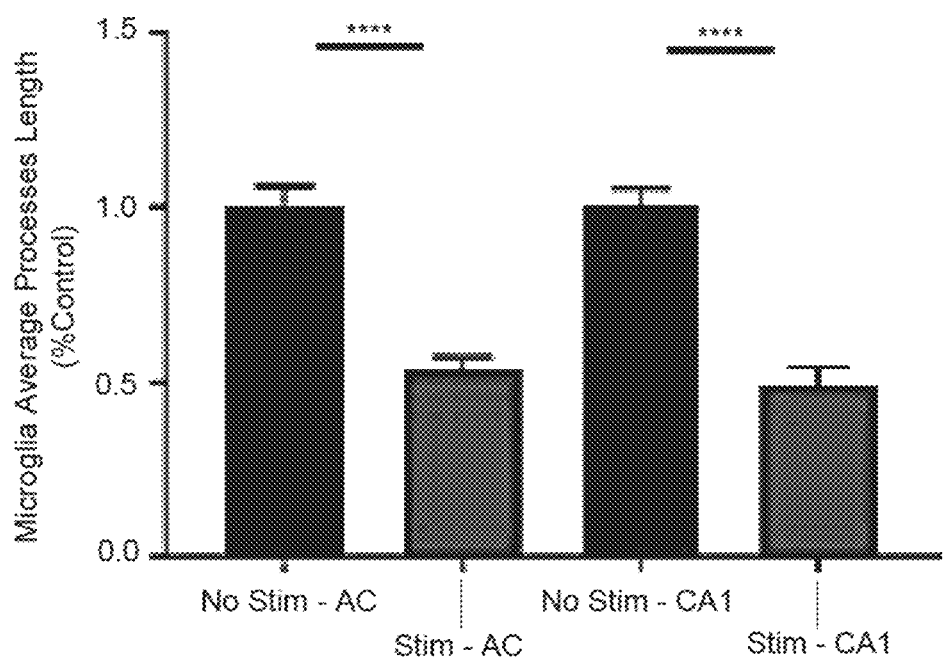

FIG. 4E shows average length of Iba1-positive microglia primary processes in AC and CA1 normalized to non-stimulated controls (n=8 mice per group, mean s.e.m. in bar graphs, ****P<0.0001; unpaired Mann-Whitney Test).

Figure 4F:
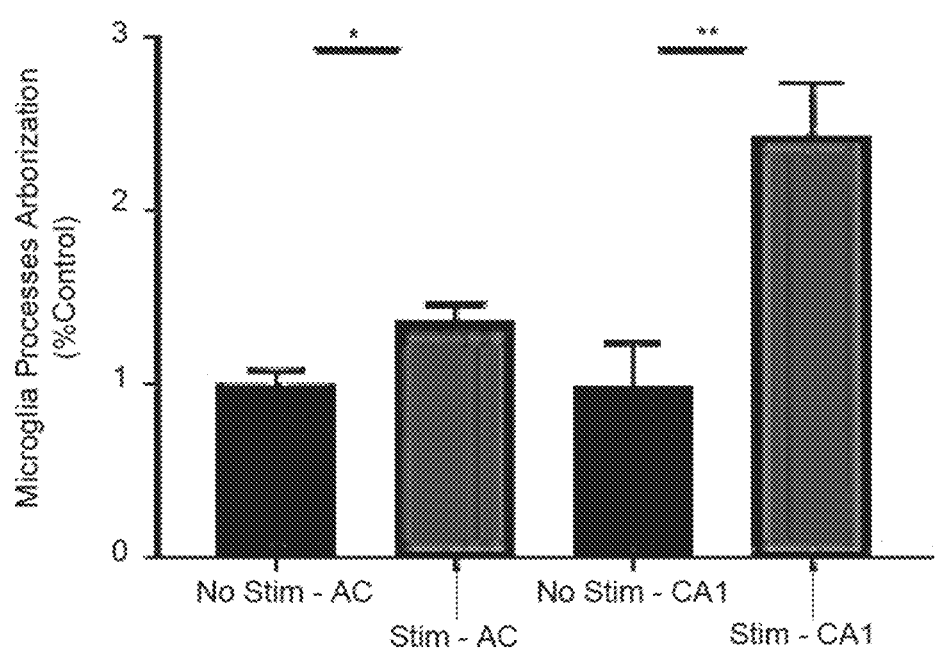

FIG. 4F shows average processes arborization of Iba1-positive microglia in AC and CA1 normalized to non-stimulated controls (n=8 mice per group, mean s.e.m. in bar graphs, *P<0.05, **P<0.01; unpaired Mann-Whitney Test).

Figure 4G:
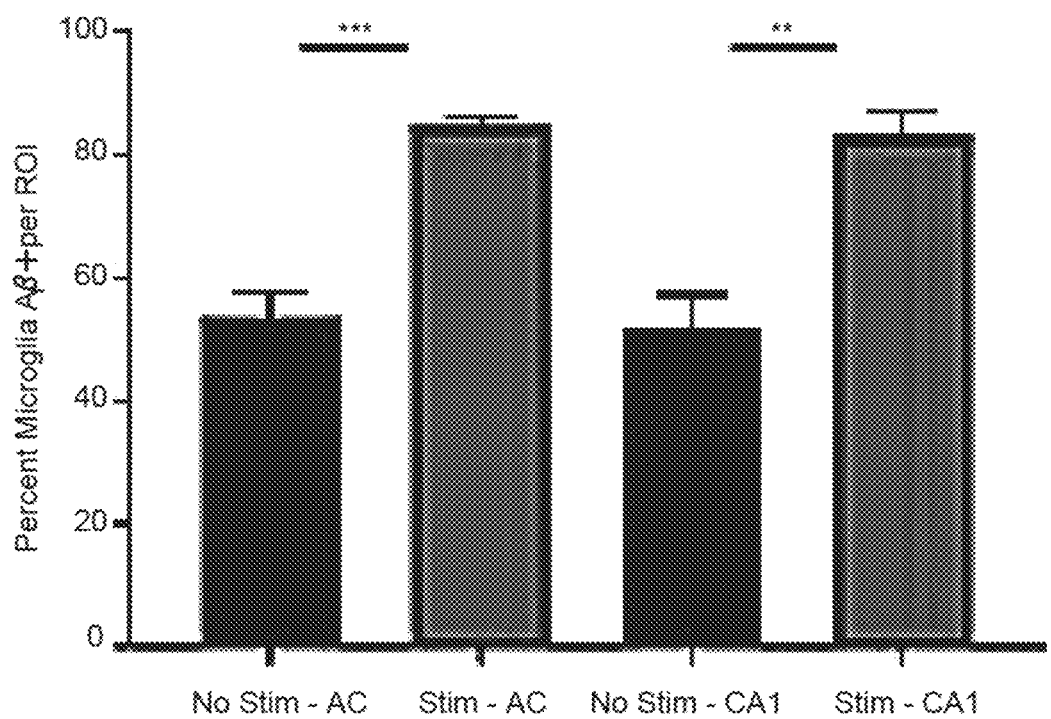

FIG. 4G shows percentage of Iba1-positive microglia cell bodies that are also Aβ-positive in AC and CA1 (n=8 mice per group, mean s.e.m. in bar graphs, P<0.01, *P<0.001; unpaired Mann-Whitney Test).

Figure 4H:
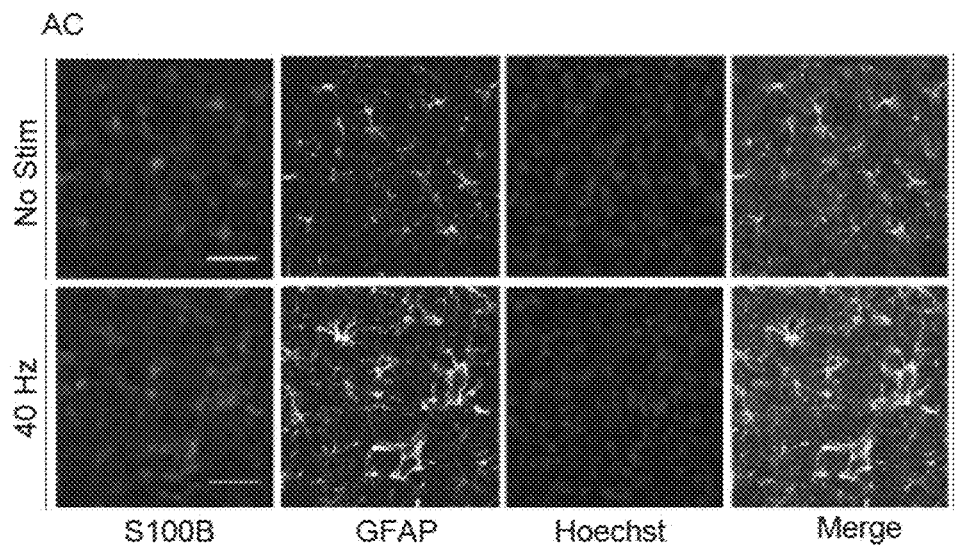

FIG. 4H shows immunohistochemistry with anti-S100B (ab868, purple) and anti-GFAP (ab4674, grey) antibodies in AC of 5XFAD mice after 7 days of 1 hour per day no stimulation or auditory GENUS (n=8 per group, scale bar, 50 μm).

Figure 4I:
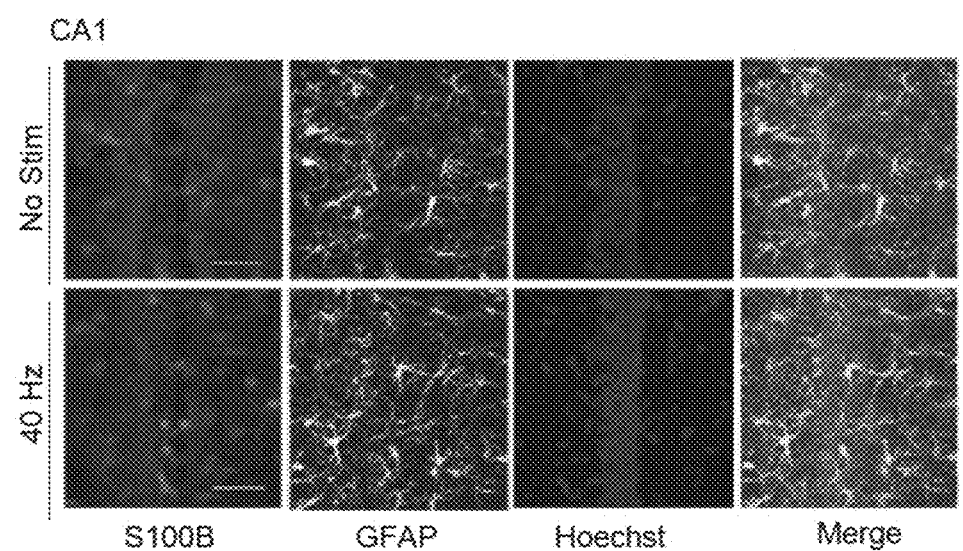

FIG. 4I shows as in FIG. 4H for CA1.

Figure 4J:
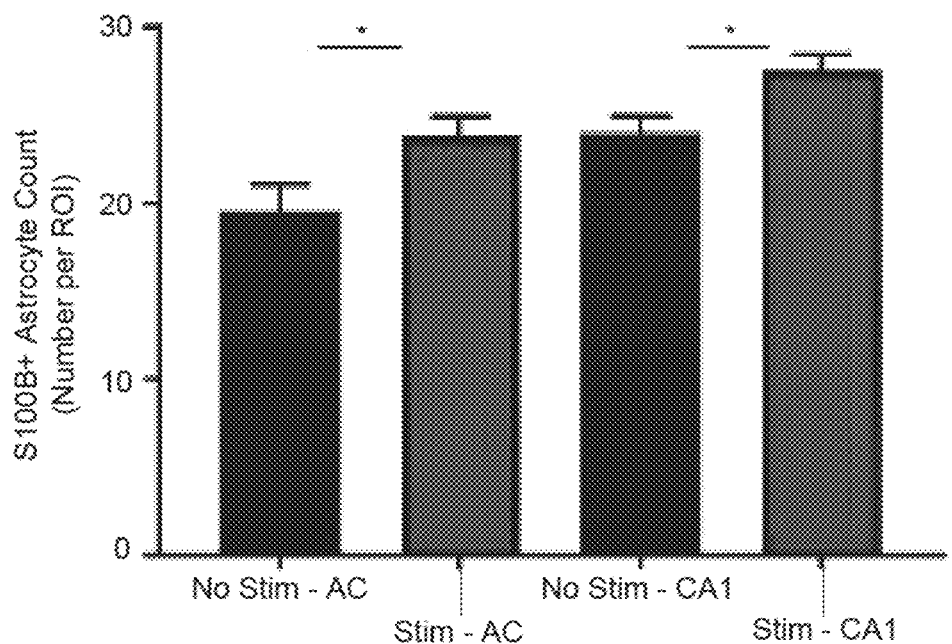

FIG. 4J shows number of S100B-positive astrocytes in AC and CA1 (n=8 mice per group, *P<0.05; unpaired Mann-Whitney Test).

Figure 4K:
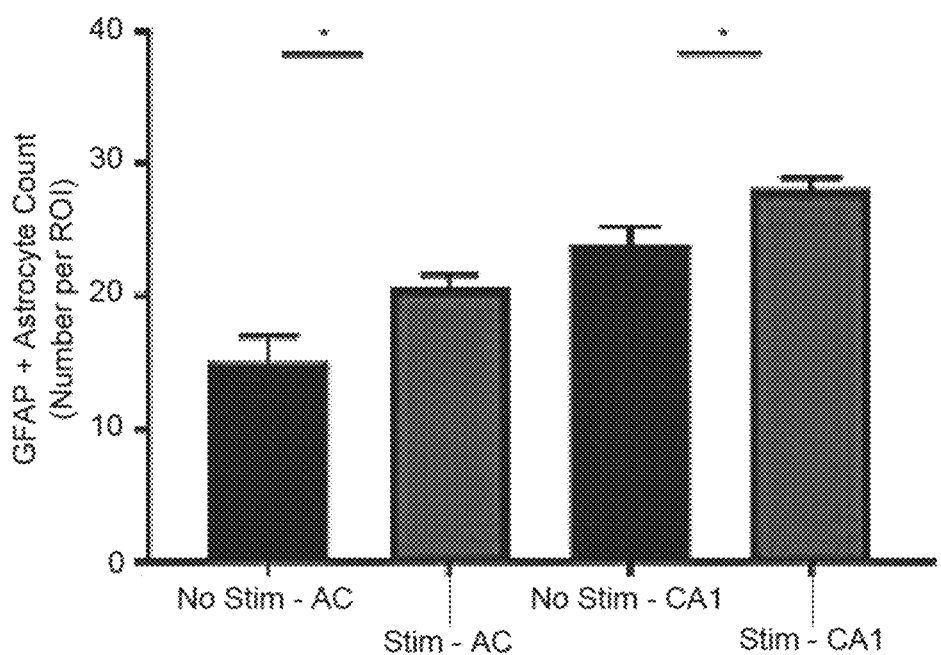

FIG. 4K shows as in FIG. 4J for GFAP-positive astrocytes.

Figure 5A:
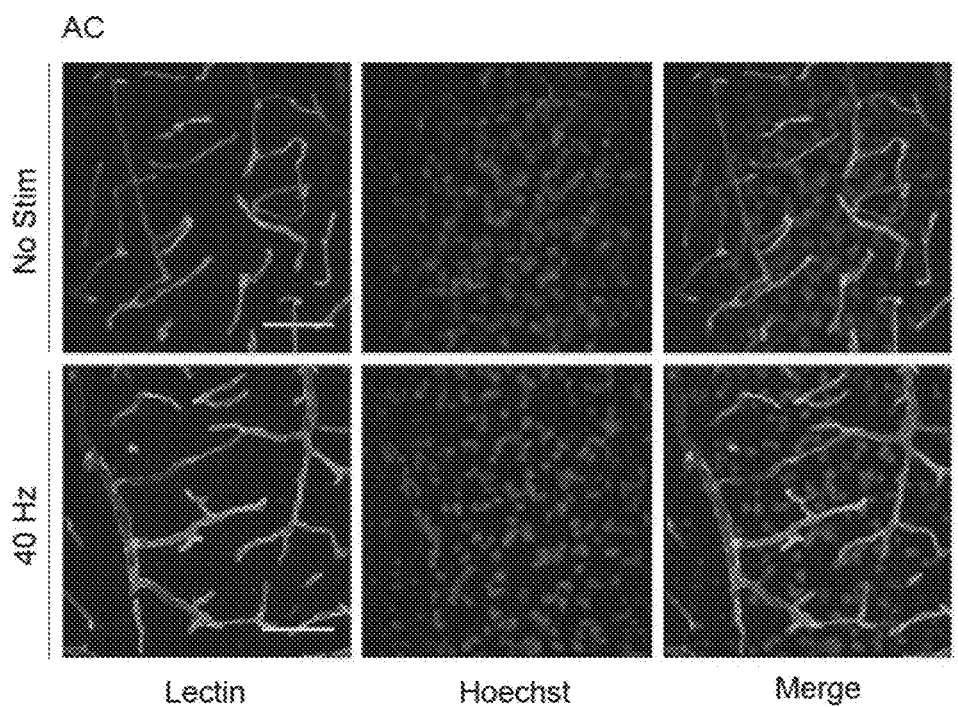
FIG. 5A-5F show auditory GENUS increases amyloid-vasculature associations.

FIG. 5A shows immunohistochemistry with lectin stain (DL-1174, green) in AC of 6-month-old 5XFAD mice after 7 days of 1 h per day no stimulation or auditory GENUS (scale bar, 50 μm).

Figure 5B:
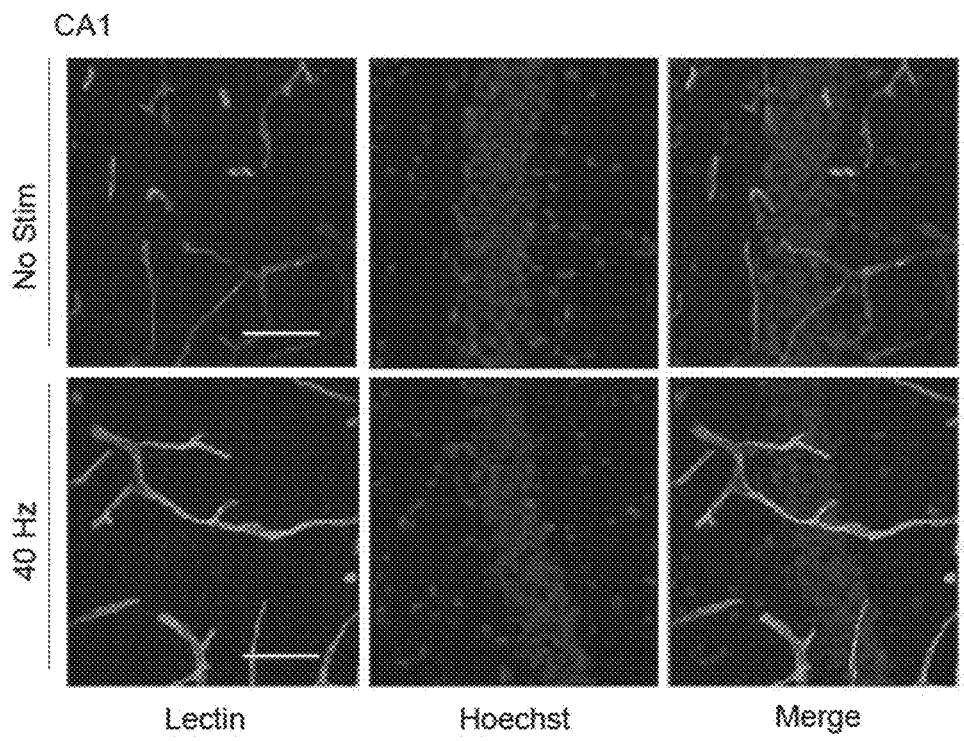

FIG. 5B shows as in FIG. 5A for CA1.

Figure 5C:
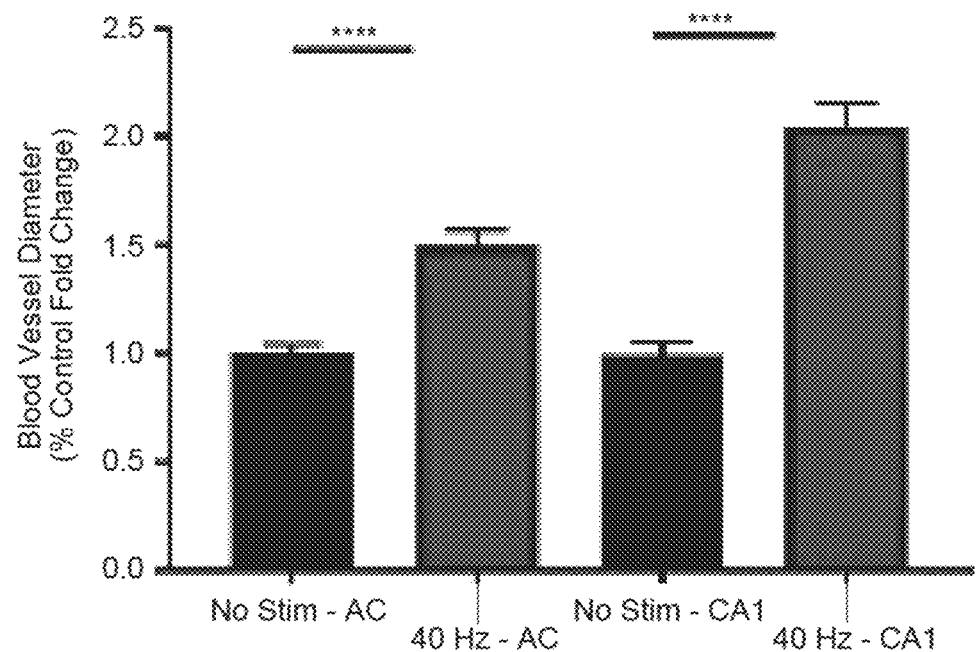

FIG. 5C shows percent fold change in blood vessel diameter in AC and CA1 of 6-month-old 5XFAD mice after 7 days of 1 hour per day no stimulation or auditory GENUS, normalized to no stimulation control (n=7 mice per group, mean s.e.m. in bar graphs, ****P<0.0001; unpaired Mann-Whitney Test).

Figure 5D:
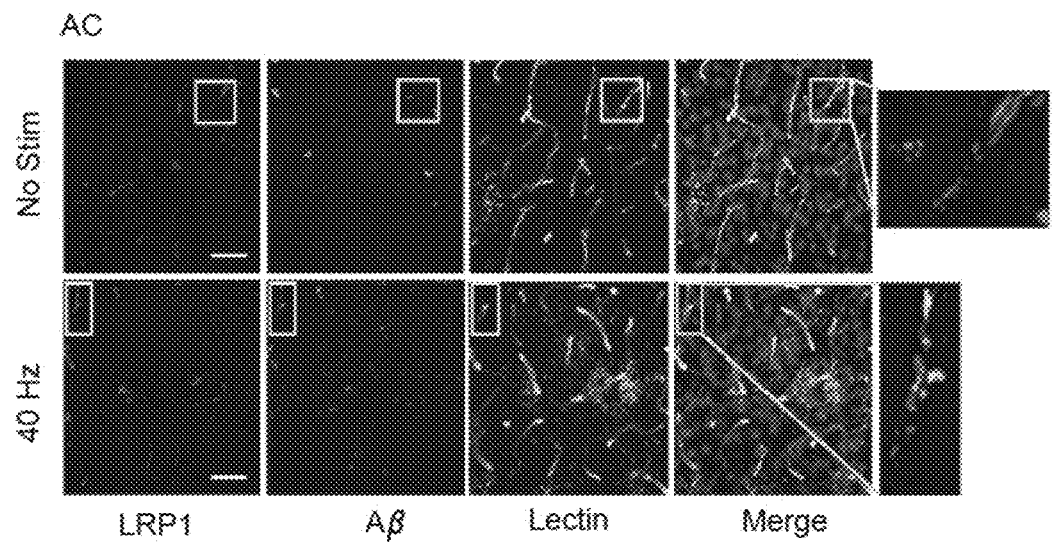

FIG. 5D shows immunohistochemistry with anti-LRP1 (28320, red), anti-Aβ (AB9234, green), and lectin stain (DL-1174, gray) antibodies in AC of 6-month-old 5XFAD mice after 7 days of 1 hour per day no stimulation or auditory GENUS (n=8 mice per group, scale bar, 50 μm).

Figure 5E:
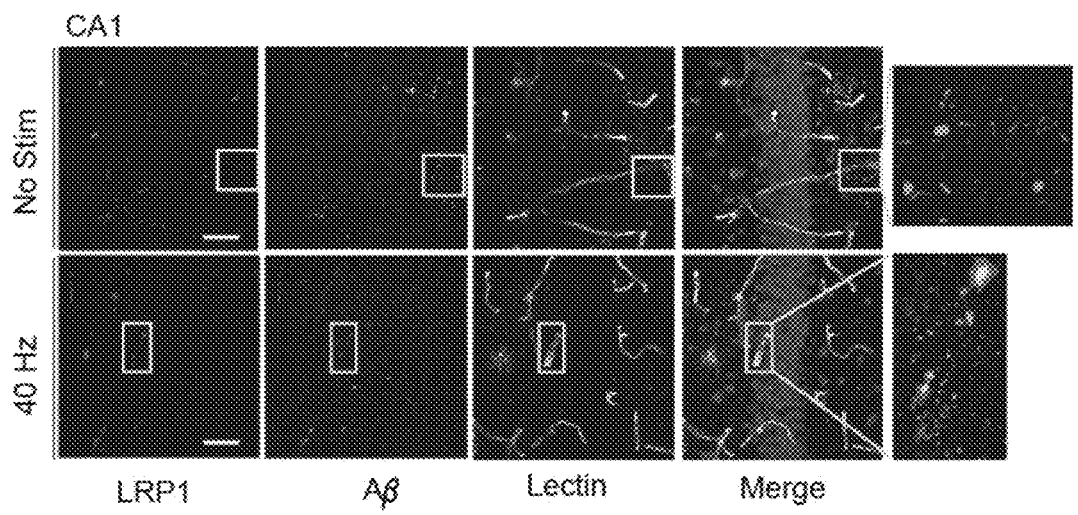

FIG. 5E shows as in FIG. 5D for CA1.

Figure 5F:
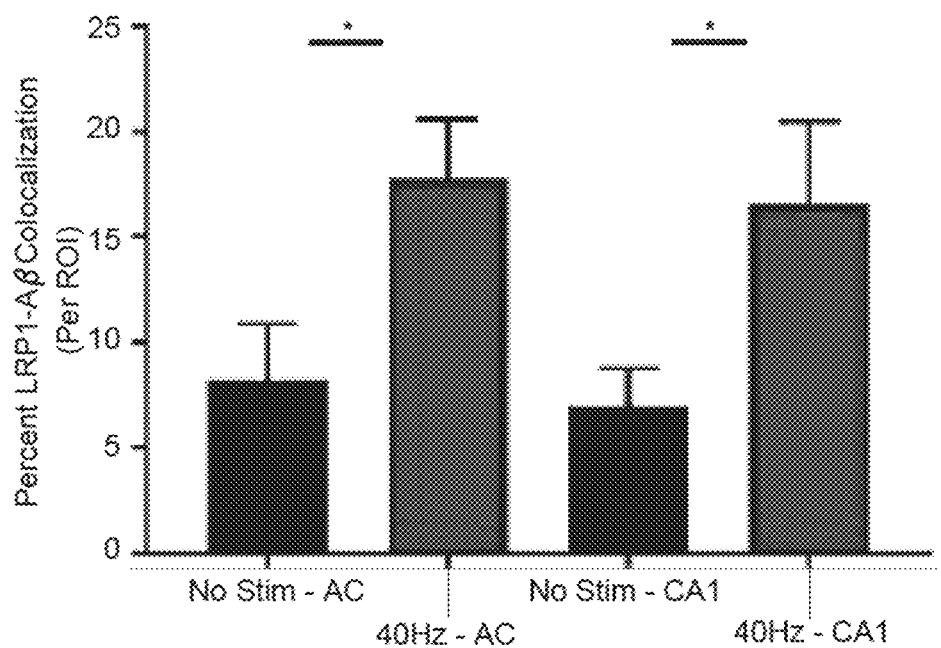

FIG. 5F shows percentage of Aβ-LRP1 co-localization in AC and CA1 of 5XFAD mice after 7 days of 1 hour per day no stimulation or auditory GENUS (n=8 mice per group, *P<0.05; unpaired Mann-Whitney Test).

Figure 6A:
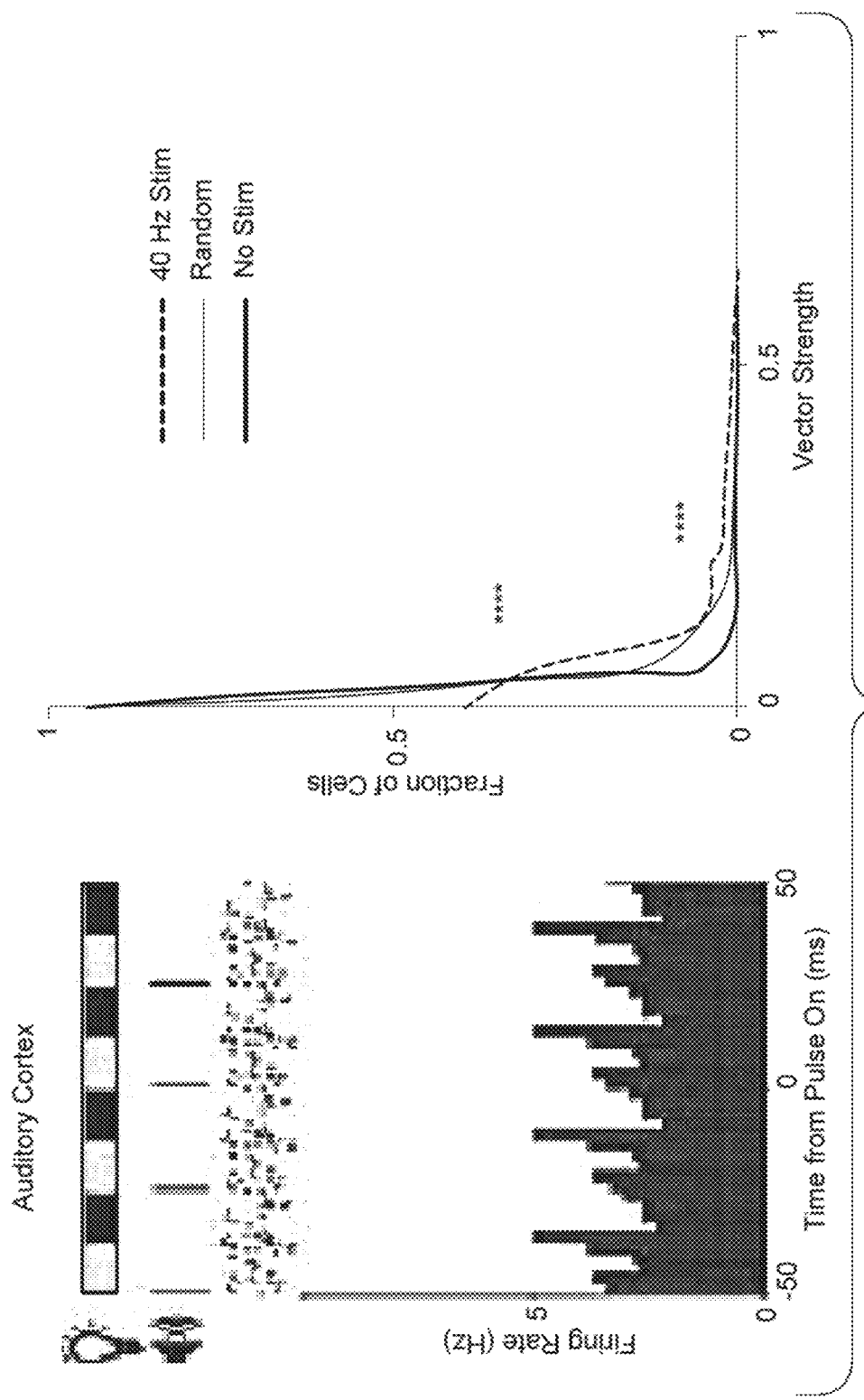
FIG. 6A-6I shows combined auditory and visual GENUS induces a clustering phenotype response by microglia.

FIG. 6A shows firing rate modulation of a single unit during 40 Hz audio-visual stimulation (left, below). Raster plots show spiking response of two example putative single units to 10 seconds of 40 Hz auditory or random stimulation (left, above). Vector strength distribution of 40 Hz audio-visual stimulation, random audio-visual stimulation, and no stimulation periods (right, ****P<0.0001, P=9×10$^{-59}$ 40 Hz vs. No Stim, P=1×10$^{-13}$ 40 Hz vs. Random; Kolmogorov-Smirnov test).

Figure 6B:
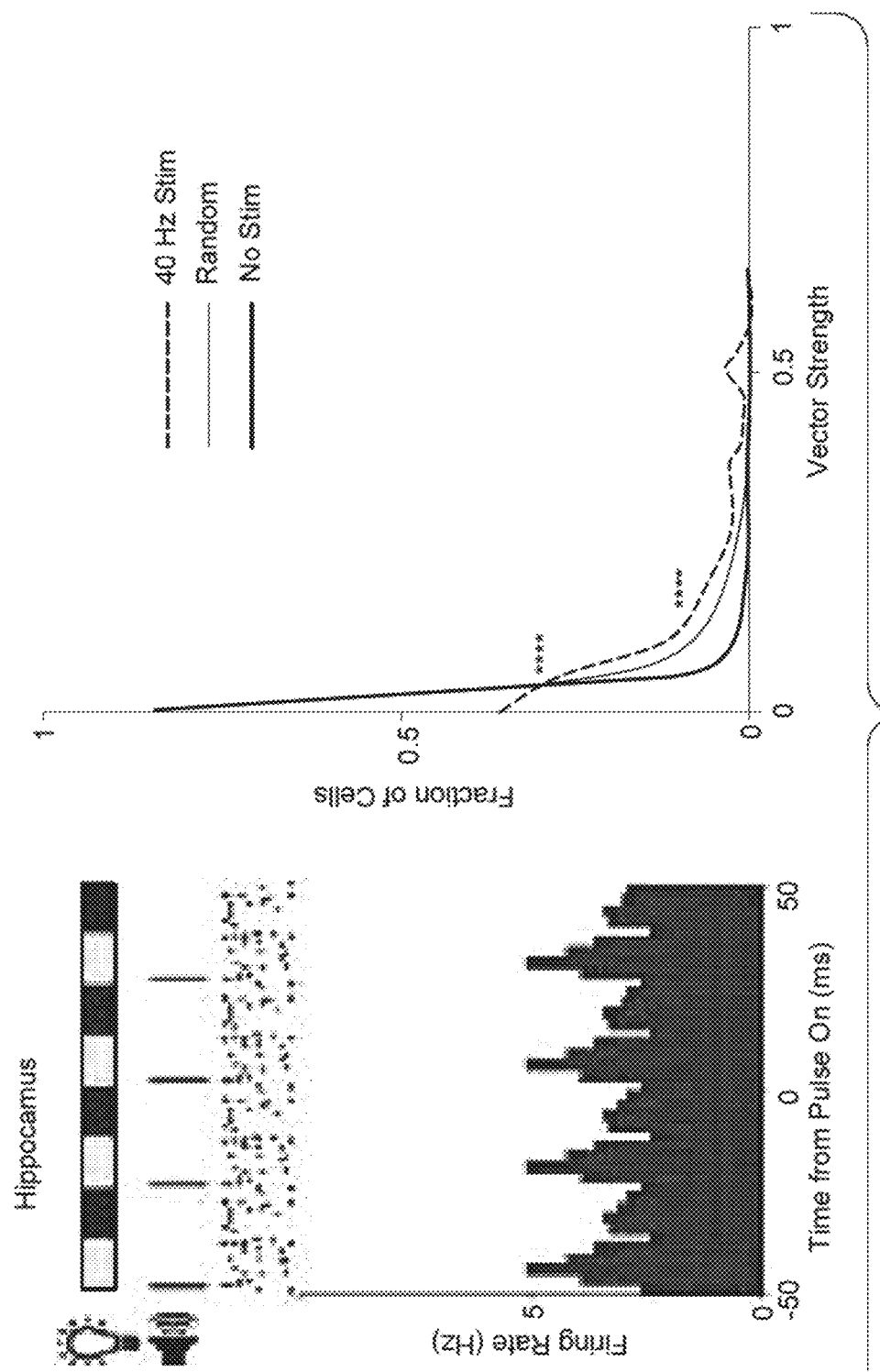

FIG. 6B shows same as FIG. 6A for CA1 (right, ****P<0.0001, P=6×10$^{-41}$ 40 Hz vs. No Stim, P=2×10$^{-11}$ 40 Hz vs. Random; Kolmogorov-Smirnov test).

Figure 6C:
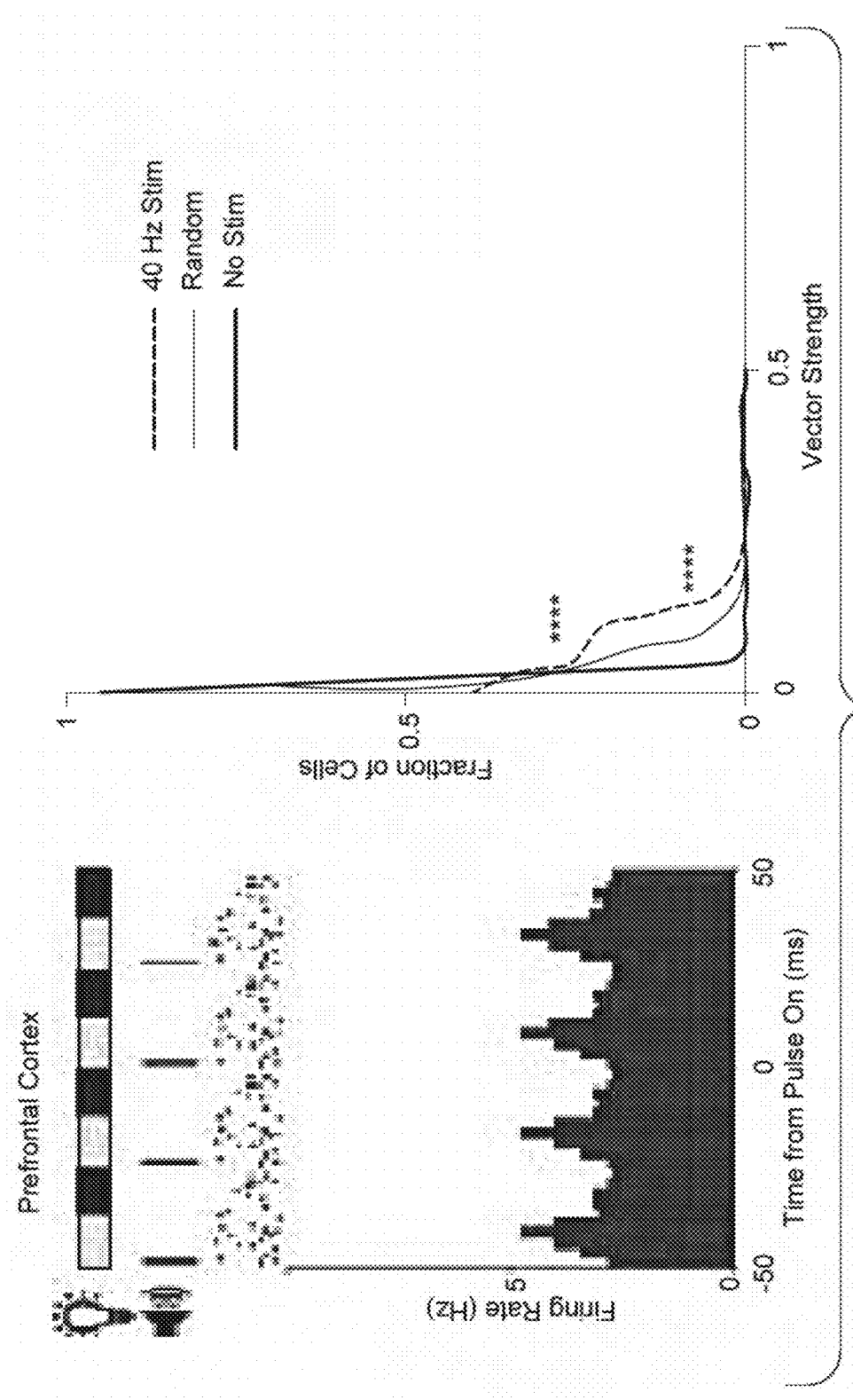

FIG. 6C shows same as FIG. 6A for mPFC (right, ****P<0.0001, P=2×10$^{-23}$ 40 Hz vs. No Stim, P=9×10$^{-5}$ 40 Hz vs. Random; Kolmogorov-Smirnov test).

Figure 6D:
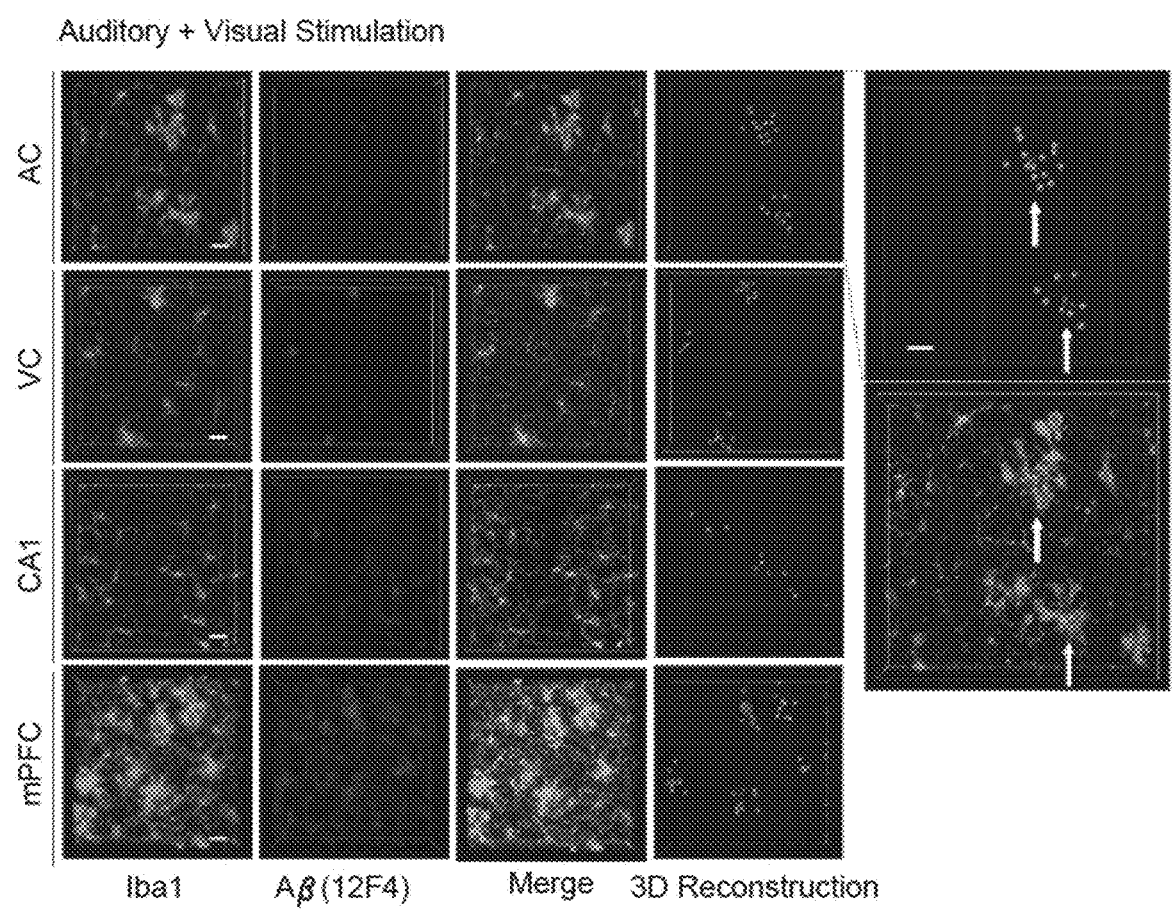

FIG. 6D shows immunohistochemistry and 3D reconstruction using IMARIS (Methods) of anti-Iba1 (019-19741) and anti-Aβ (12F4) antibodies in AC, VC, CA1, and mPFC of 6-month-old 5XFAD mice after 7 days of 1 hour per day of no stimulation (n=6 mice per group, top inset: example of using IMAMS to quantify the number of microglia surrounding a 25 μm radius around amyloid plaques. Plaques are demonstrated as red dots, microglia as green dots, and white arrows point to clusters. Bottom inset: enlarged merged image from AC. Scale bar, 20 μm).

Figure 6E:
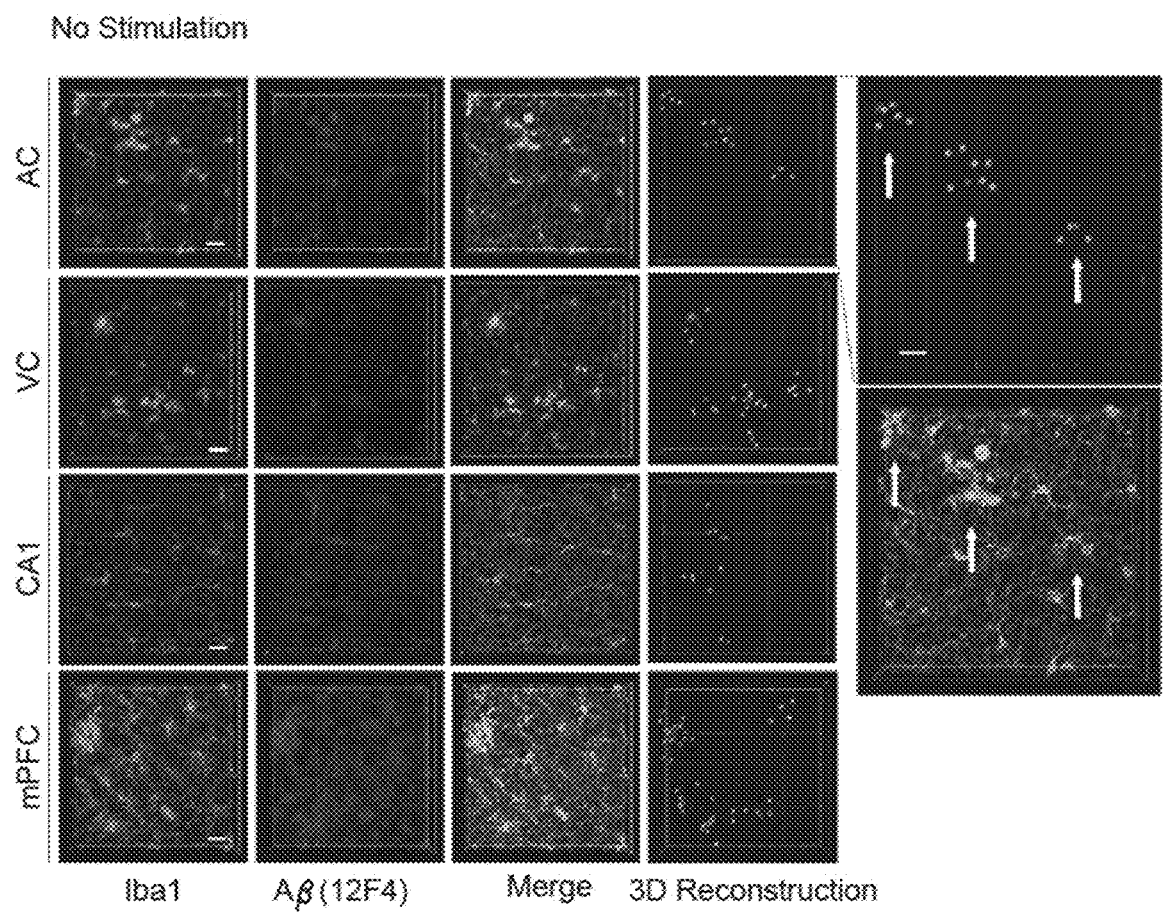

FIG. 6E shows as in FIG. 6D for combined GENUS.

Figure 6F:
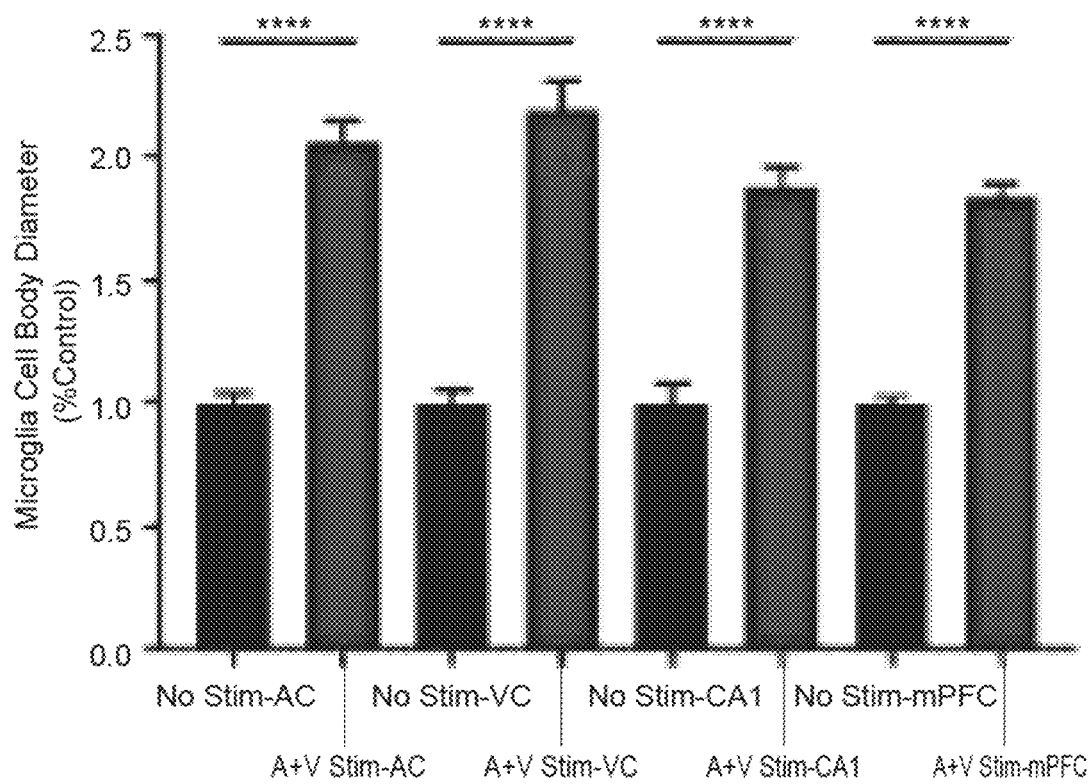

FIG. 6F shows average microglia cell body diameter in AC, VC, CA1, and mPFC of 6-month-old 5XFAD mice after 7 days of 1 hour per day of no stimulation or combined GENUS (A+V Stim), normalized to no stimulation control (n=6 mice in no control group, n=7 mice in combined GENUS group, mean s.e.m. in bar graphs, ****P<0.0001; unpaired Mann-Whitney test).

Figure 6G:
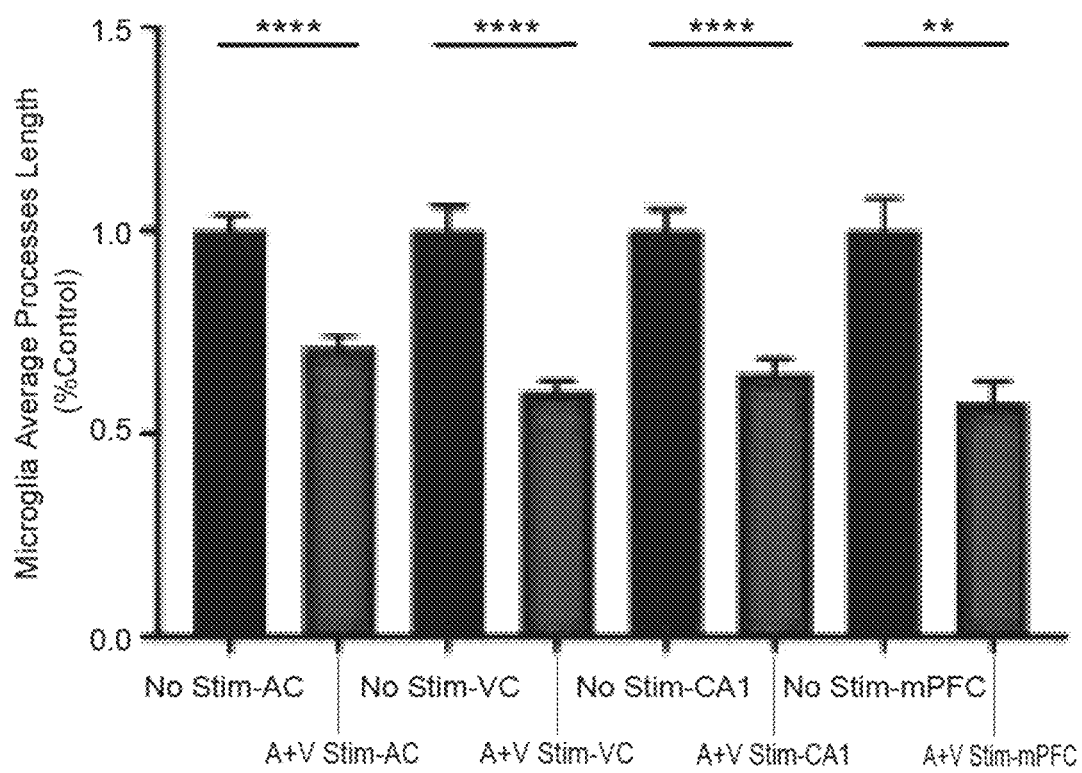

FIG. 6G shows average microglia process length in AC, VC, CA1, and mPFC of 6-month-old 5XFAD mice after 7 days of 1 hour per day of no stimulation or combined GENUS, normalized to no stimulation control (n=6 mice in no control group, n=7 mice in combined GENUS group, mean s.e.m. in bar graphs, P<0.01, **P<0.0001; unpaired Mann-Whitney test).

Figure 6H:
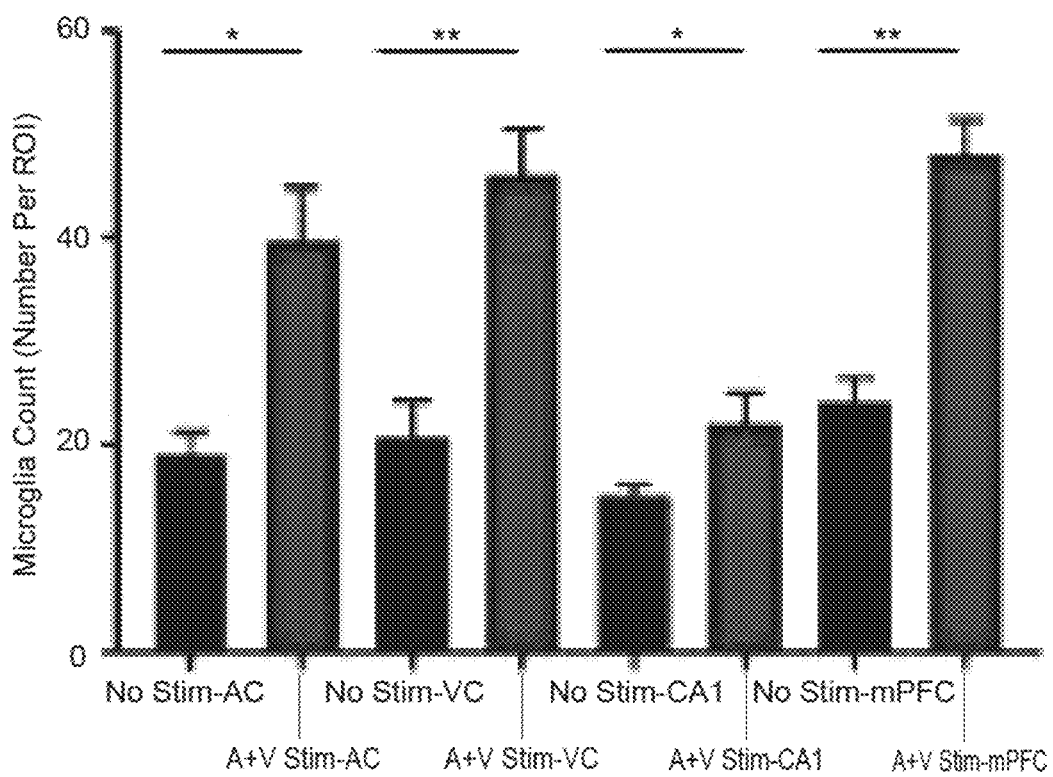

FIG. 6H shows microglia count per region of interest in AC, VC, CA1, and mPFC of 6-month-old 5XFAD mice after 7 days of 1 h per day of no stimulation or combined GENUS (n=6 mice in no control group, n=7 mice in combined GENUS group, mean s.e.m. in bar graphs, *P<0.05, **P<0.01, unpaired Mann-Whitney test).

Figure 6I:
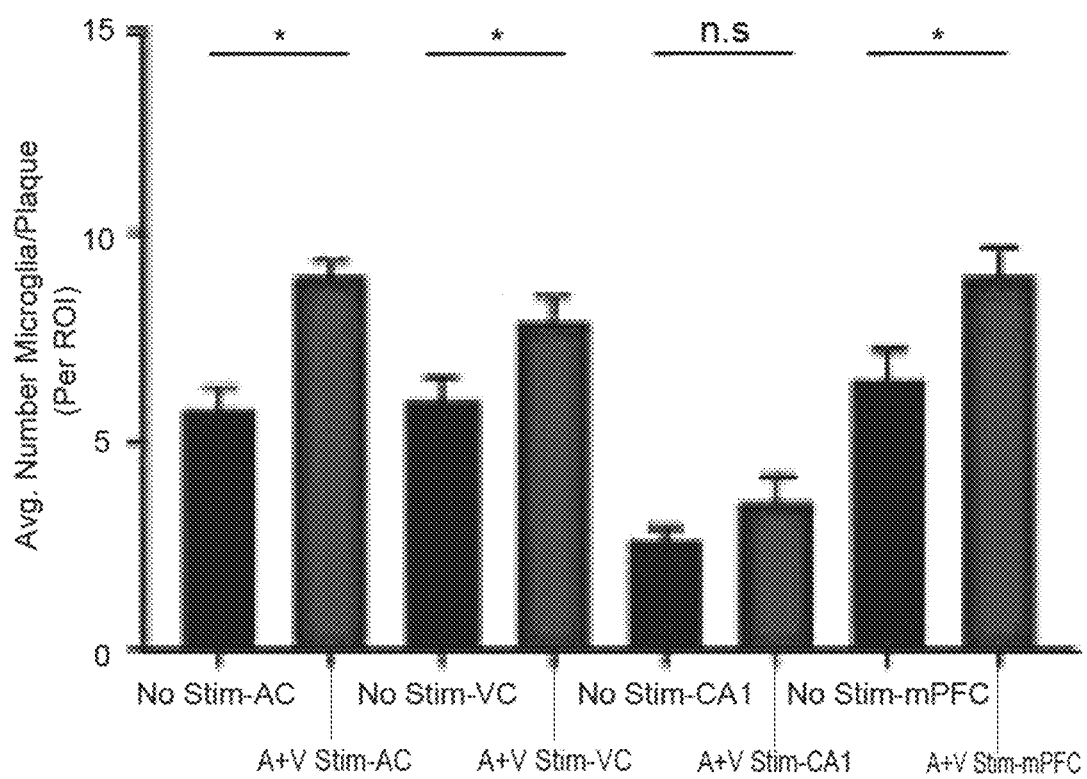

FIG. 6I shows average number of microglia surrounding 25 μm radium of a plaque in AC, VC, CA1, and mPFC following no stimulation or combined GENUS (n=6 mice per group, mean s.e.m. in bar graphs, n.s.=not significant, *P<0.05; unpaired Mann-Whitney test).

Figure 7A:
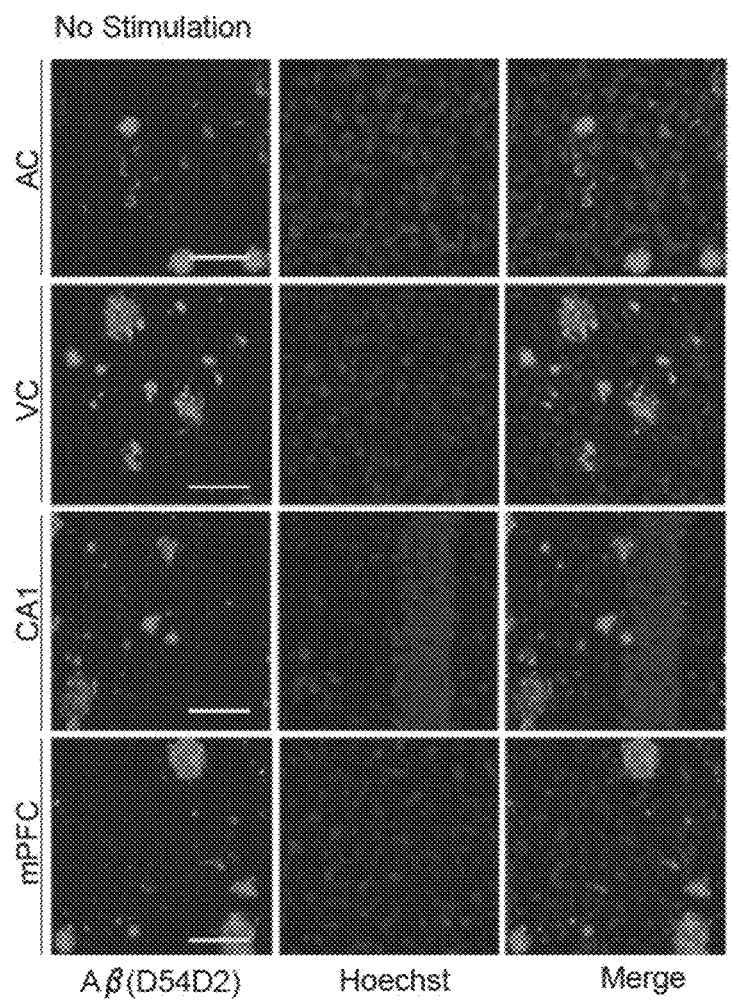
FIG. 7A-7J show combined auditory and visual GENUS reduces amyloid load in the mPFC and neocortex.

FIG. 7A shows immunohistochemistry of anti-Aβ plaques (D54D2, green) antibodies in AC, VC, CA1, and mPFC of 6-month-old 5XFAD mice after 7 days of 1 hour per day no stimulation (image taken with 40× objective, scale bar, 50 μm).

Figure 7B:
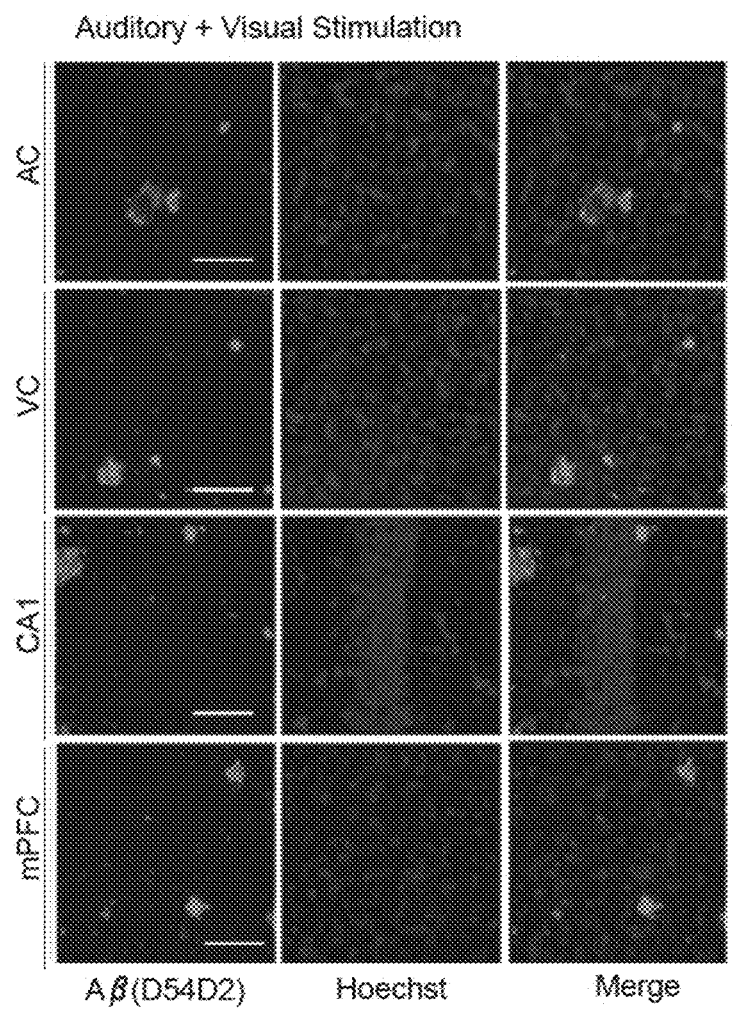

FIG. 7B shows as in FIG. 7A for combined GENUS.

Figure 7C:
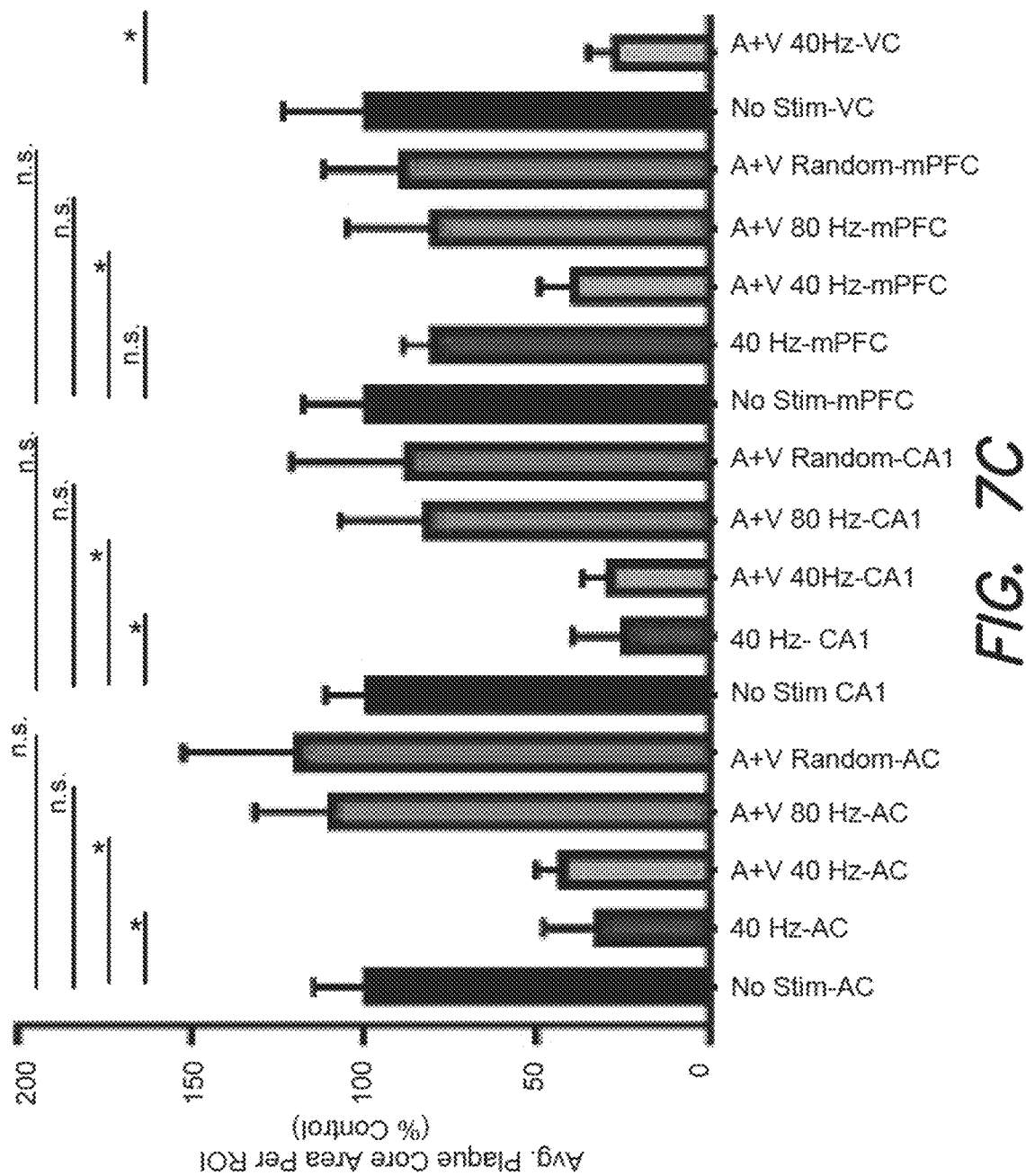

FIG. 7C shows average plaque core area in AC, CA1, mPFC, and VC in 6-month old 5XFAD mice following 7 days of 1 hour per day no stimulation, 40 Hz auditory stimulation, combined (A+V) GENUS, combined (A+V) 80 Hz, and combined (A+V) random frequency stimulation, normalized to no stimulation control (n=12 mice per group, mean s.e.m. in bar graphs, n.s.=not significant, *P<0.05, Kruskal-Wallis test with Dunn's multiple comparison test).

Figure 7D:
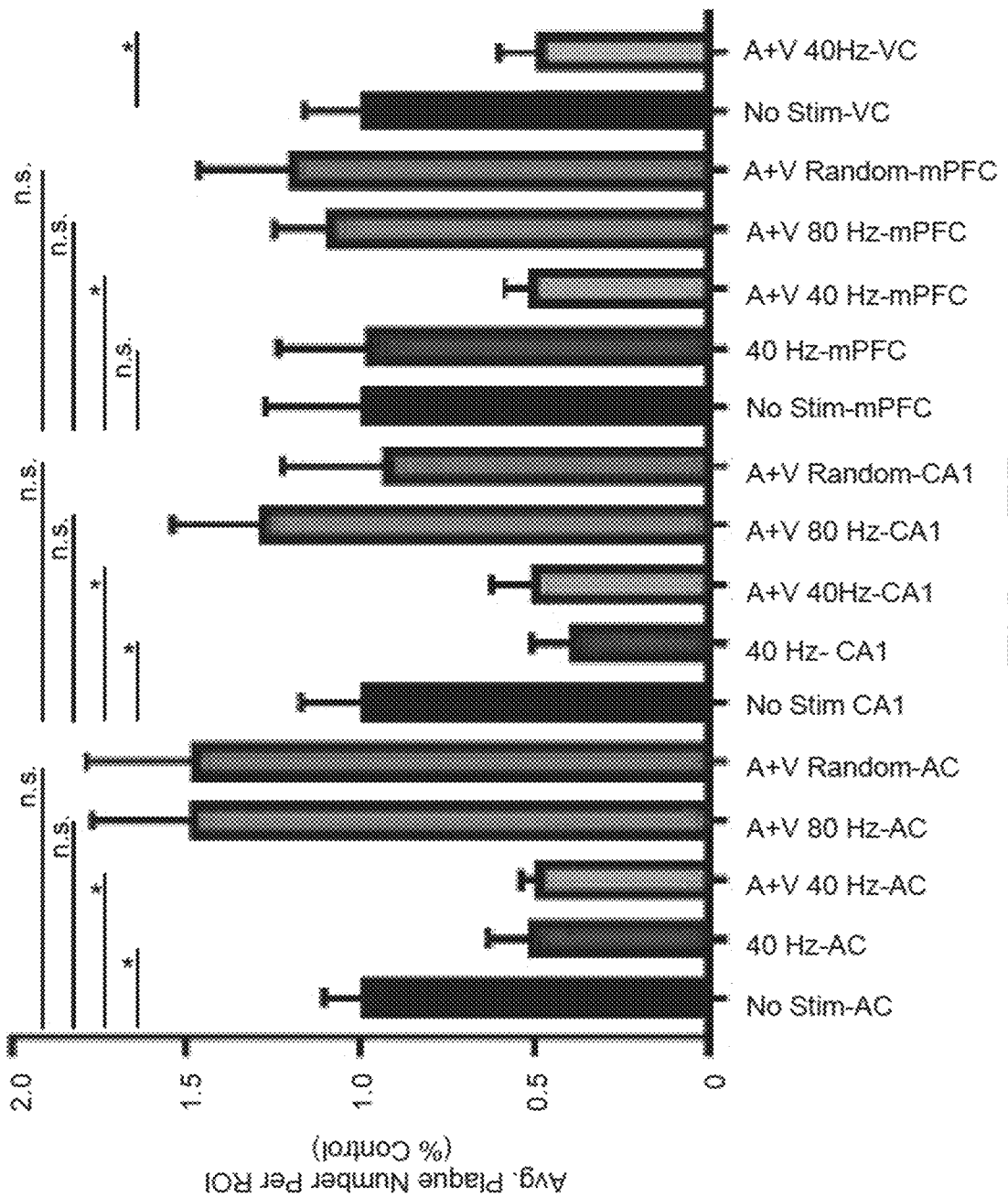

FIG. 7D shows average plaque number in AC, CA1, mPFC, and VC in 6-month old 5XFAD mice following 7 days of 1 hour per day no stimulation, 40 Hz auditory stimulation, combined (A+V) GENUS, combined (A+V) 80 Hz, and combined (A+V) random frequency stimulation, normalized to no stimulation control (n=12 mice per group, mean s.e.m. in bar graphs, n.s.=not significant, *P<0.05, Kruskal-Wallis test with Dunn's multiple comparison test).

Figure 7E:
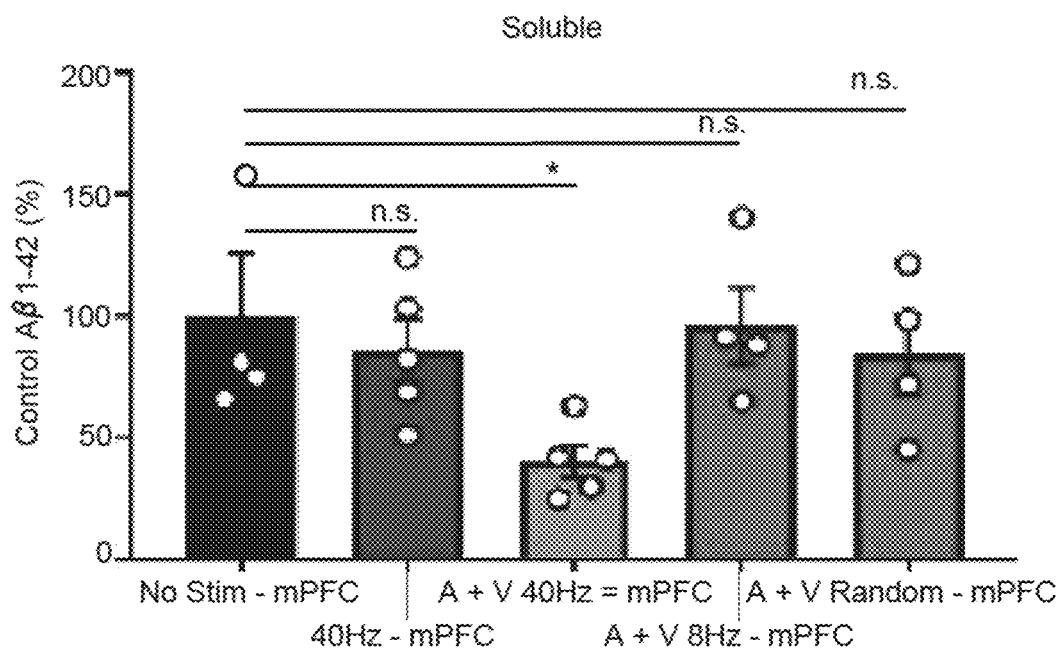

FIG. 7E shows relative soluble Aβ$_{1-42}$ levels in mPFC of 6-month-old 5XFAD mice following 7 days of 1 hour per day 40 Hz auditory stimulation, combined (A+V) GENUS, combined (A+V) 8 Hz, or combined (A+V) random frequency stimulation, normalized to non-stimulation control (n=4-5 mice per group, mean s.e.m. in bar graphs, n.s.=not significant, *P<0.05, Kruskal-Wallis test with Dunn's multiple comparison test).

Figure 7F:
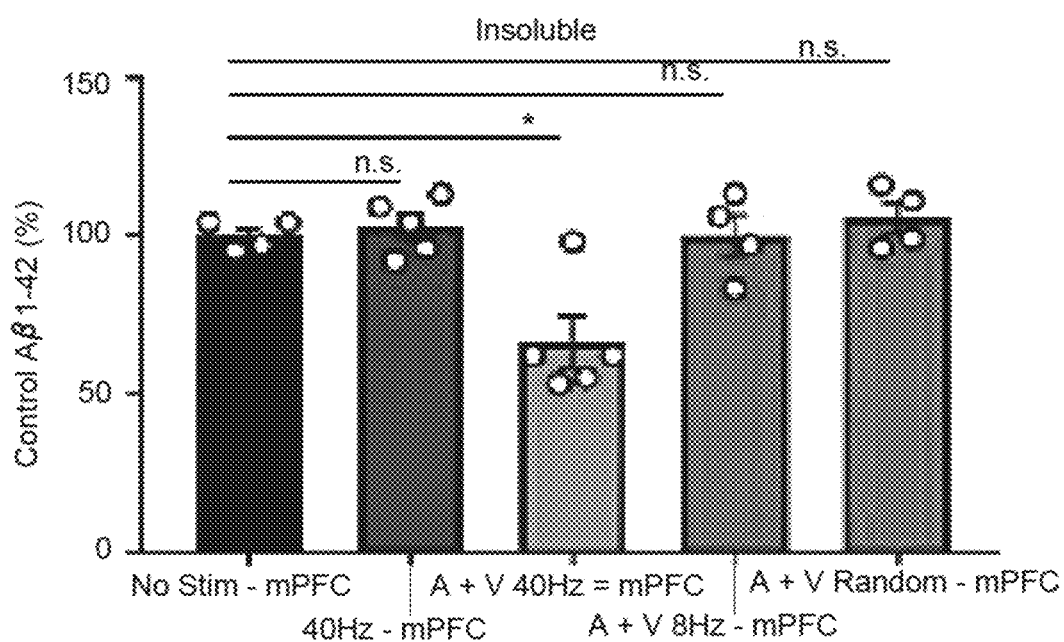

FIG. 7F shows as in FIG. 7E for insoluble Aβ$_{1-42}$ (n.s.=not significant, *P<0.05).

Figure 7G:
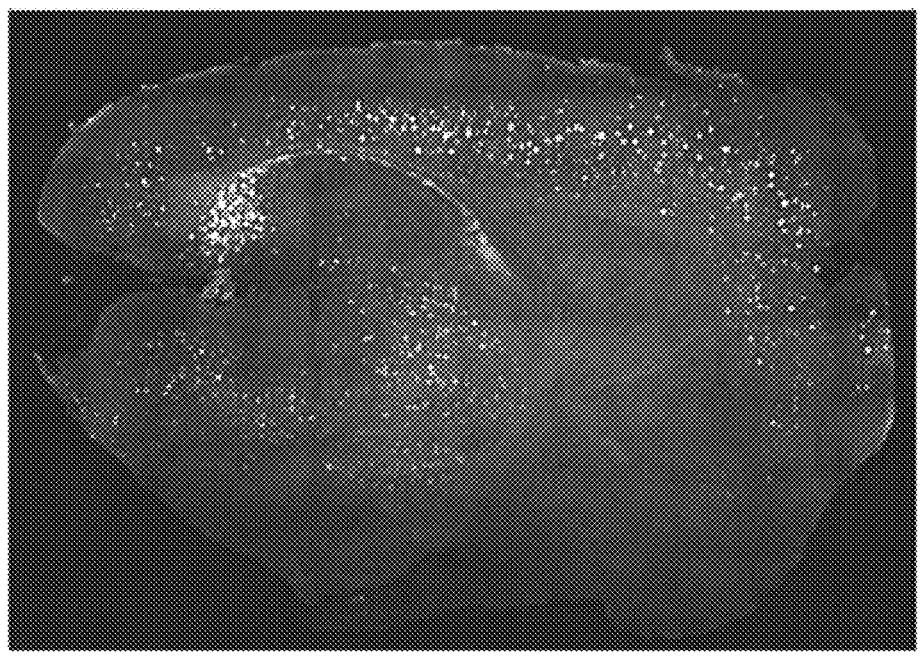

FIG. 7G shows immunohistochemistry of SHIELD treated whole brain (sagittal plane of 25 μm section of brain) of anti-Aβ plaques (D54D2, white) antibodies of 6-month-old 5XFAD mice after 7 days of 1 hour per day no stimulation (light-sheet microscope, scale bar, 700 μm).

Figure 7H:
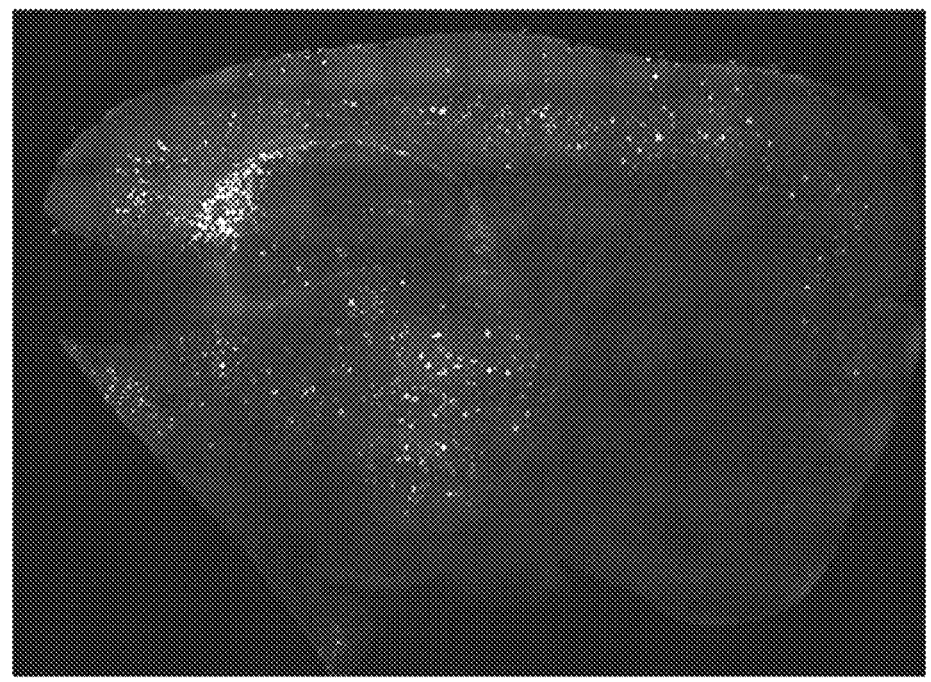

FIG. 7H shows as in FIG. 7G for combined (A+V) GENUS.

Figure 7I:
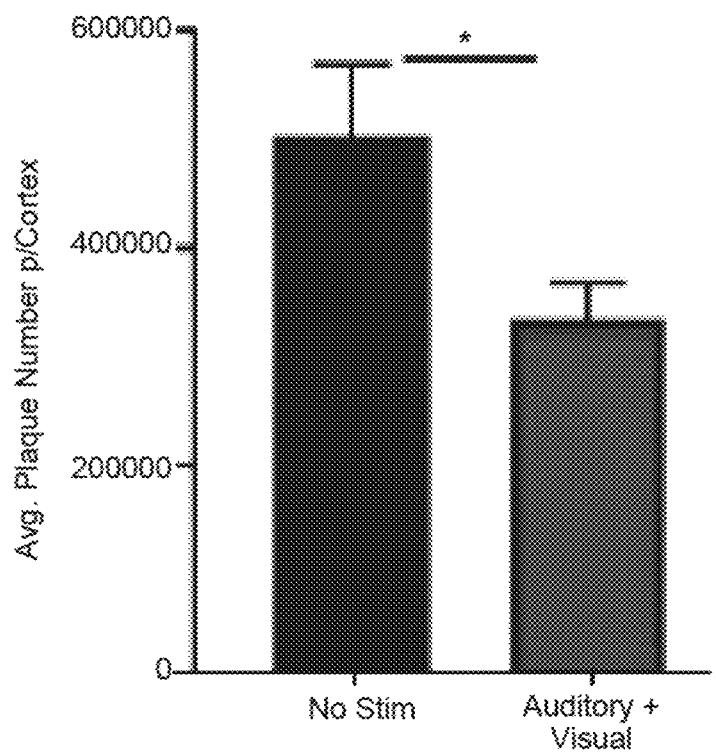

FIG. 7I shows average cortical plaque number following no stimulation or combined (A+V) GENUS (n=6 mice per group, mean s.e.m. in bar graphs, *P<0.05; unpaired Mann-Whitney Test).

Figure 7J:
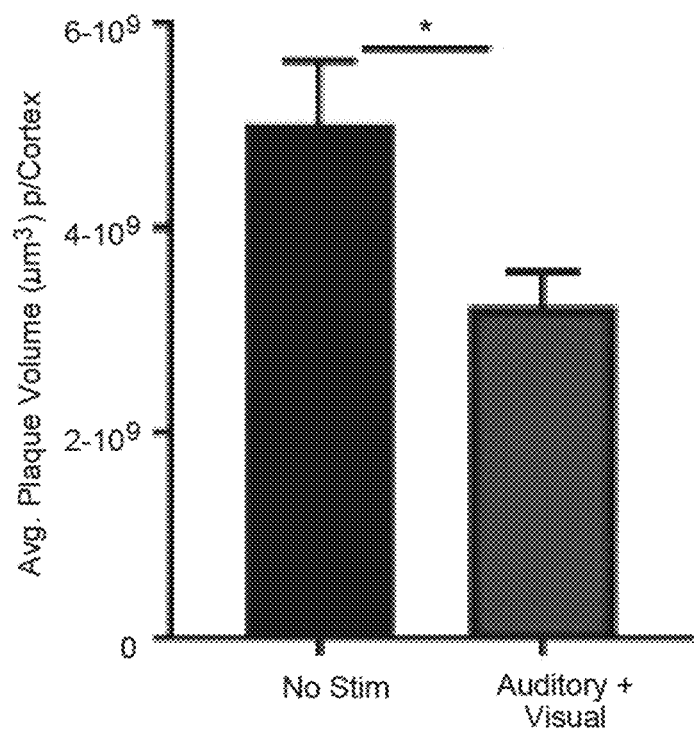

FIG. 7J shows average cortical plaque volume (μm$^3$) following combined (A+V) GENUS (n=6 mice per group, mean s.e.m. in bar graphs, *P<0.05; unpaired Mann-Whitney Test).

Figure 8A:
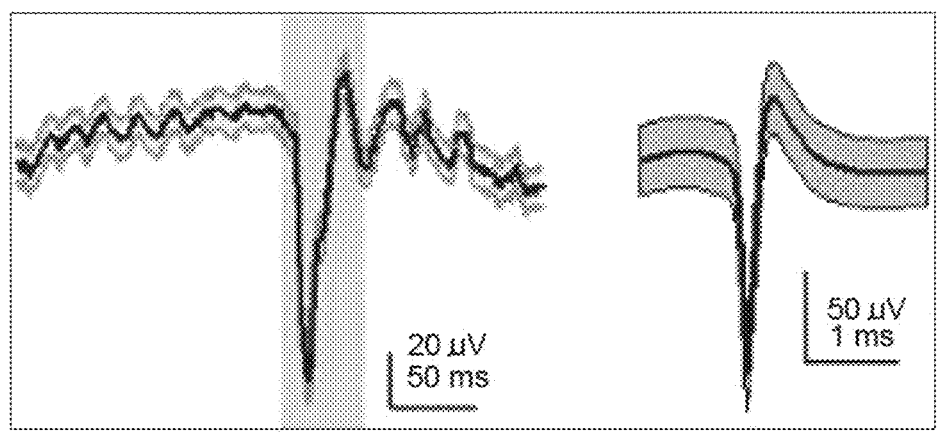
FIG. 8A-8R show 20 Hz and 80 Hz auditory stimulation modulates activity in AC, CA1, and mPFC.

FIG. 8A shows mean LFP response to auditory mapping tones used to detect auditory cortex (left). The blue region indicates when the 50 ms mapping tone played. Example of a clustered putative single unit (right).

Figure 8B:
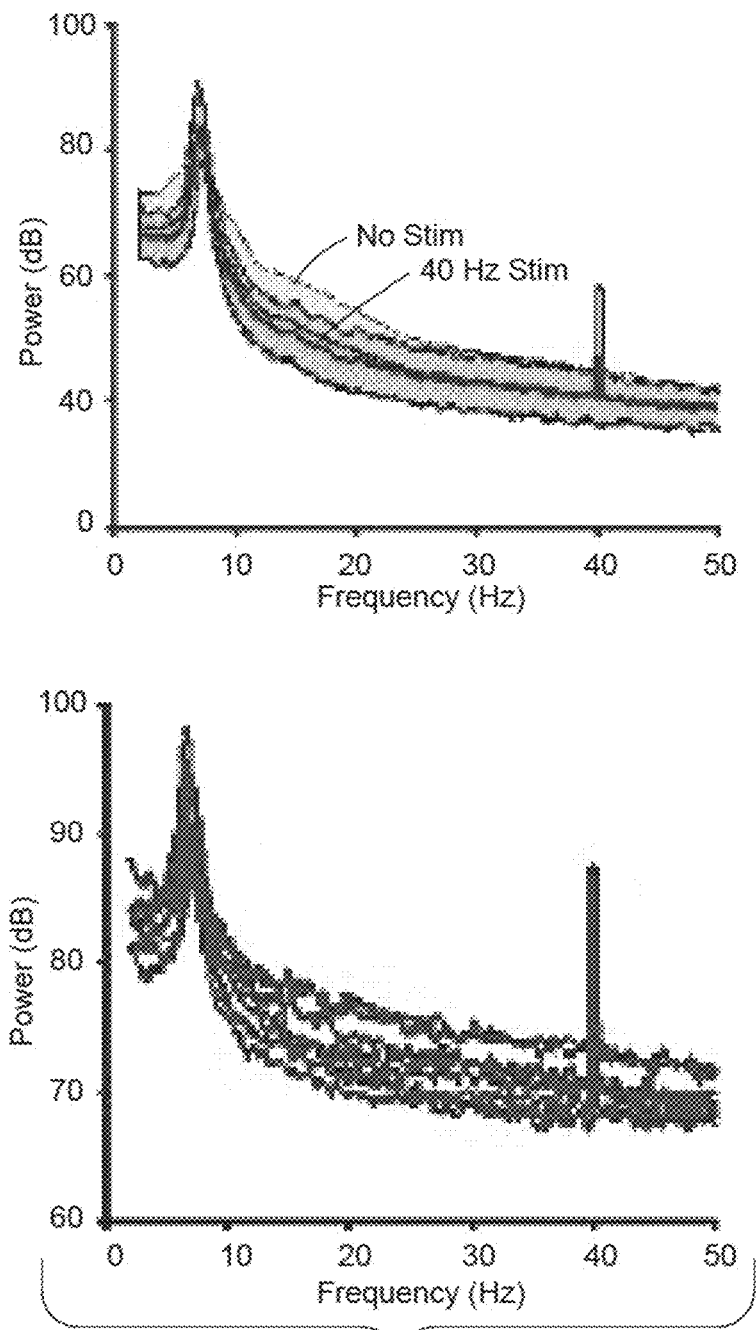

FIG. 8B shows power spectral density (PSD) response to 40 Hz auditory flicker stimuli and no stimulation periods, with mean and standard deviation across recording days (left), power spectrum LFP response to auditory flicker of all recording days in AC (recording site with largest 40 Hz peak during 40 Hz auditory flicker per recording depth is shown, see Methods) (right).

Figure 8C:
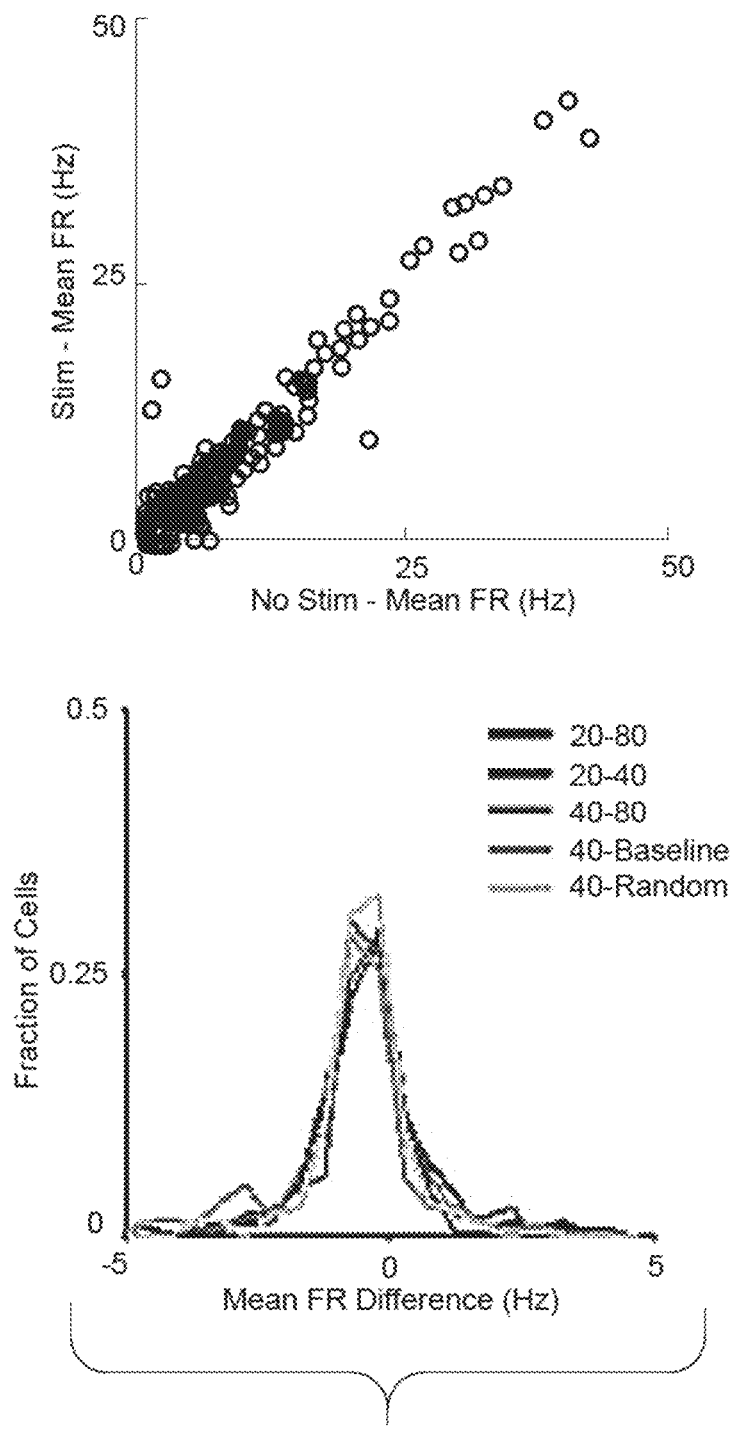

FIG. 8C shows mean firing rate (FR) of single units in AC during 40 Hz auditory stimulation vs. no stimulation periods (left), mean firing rate difference between multiple stimulation conditions of single units in AC centers around 0 Hz (right, ****P<0.0001 40 Hz—no stimulation, all others n.s.; Wilcoxon signed rank test for zero median).

FIG. 8D shows firing rate modulation of a putative single unit in response to 20 Hz audio flicker stimulation (left, below), raster plot shows spiking in response to 10 s of stimulation (left, above). Distribution of intervals between peaks in firing rate response to 20 Hz audio stimulation (right, proportion of intervals around inter-stimulus interval: P=0 20 Hz vs. No stim; z-Test for two proportions).

Figure 8E:
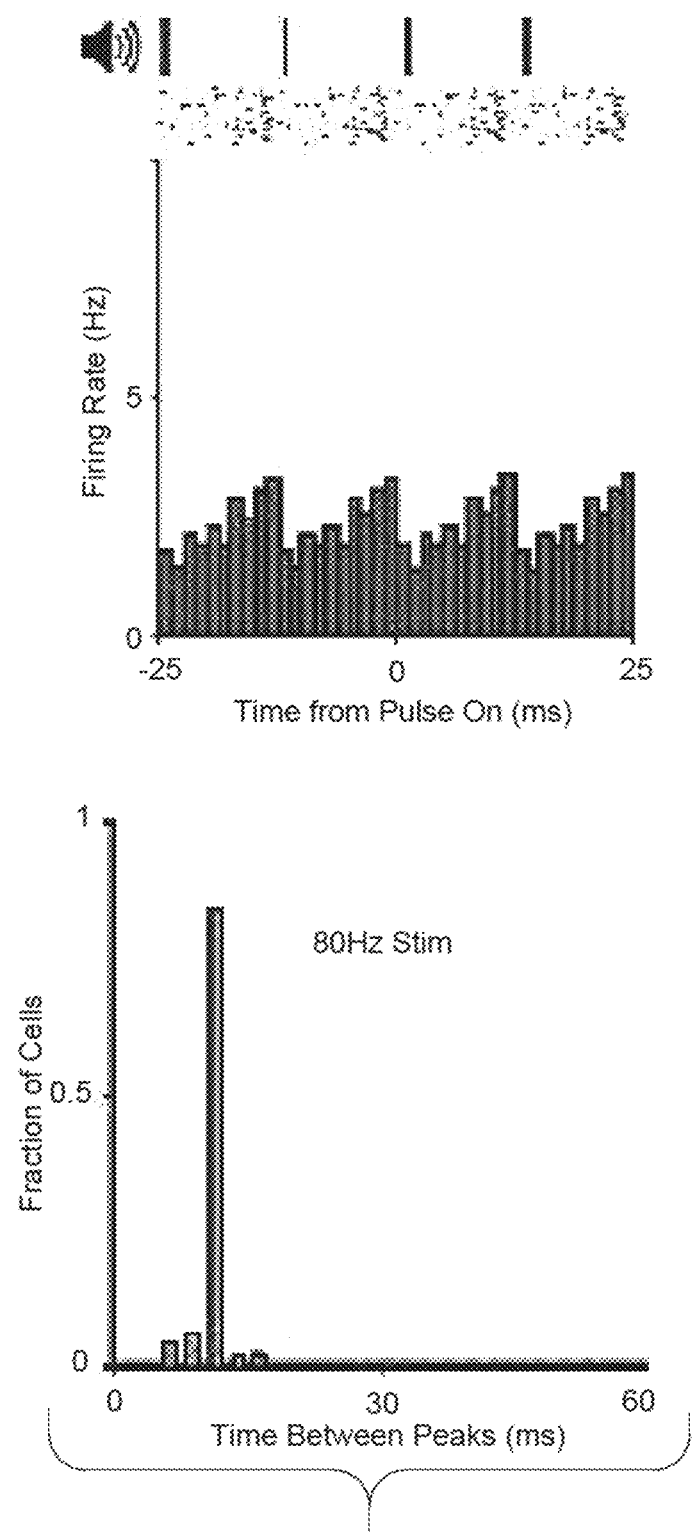

FIG. 8E shows firing rate modulation of the same unit shown in D in response to 80 Hz audio flicker stimulation (left, below), raster plot shows spiking in response to 10 s of stimulation (left, above). Distribution of intervals between peaks in firing rate response to 80 Hz audio stimulation (right, proportion of intervals around inter-stimulus interval: P=0 80 Hz vs. No stim; z-Test for two proportions).

Figure 8F:
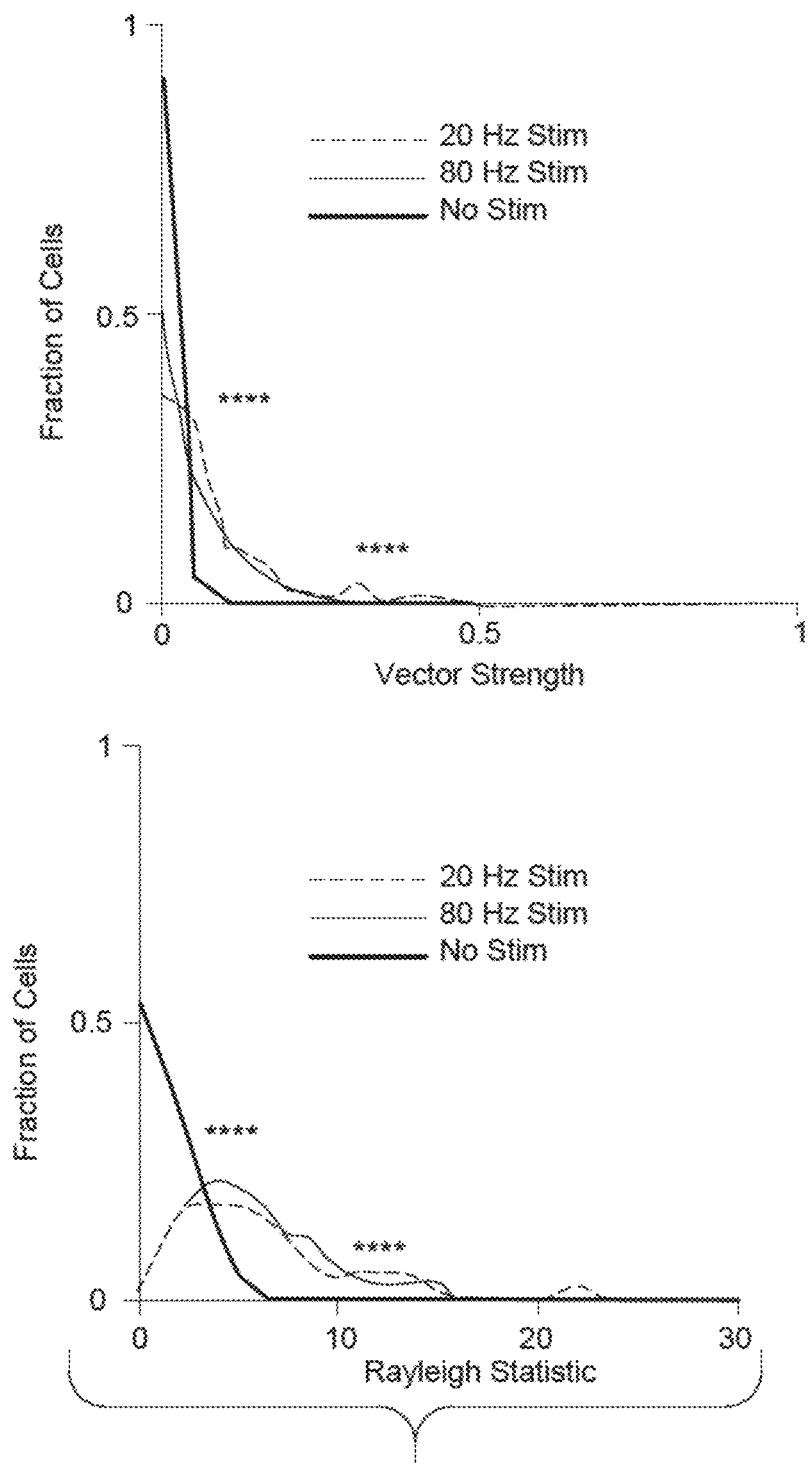

FIG. 8F shows vector strength distribution of 20 Hz and 80 Hz auditory stimulation vs. no stimulation condition (left, **P<0.0001, P=3×10$^{-61}$ 20 Hz vs. No Stim, P=3×10$^{-61}$ 80 Hz vs. No Stim; Kolmogorov-Smirnov test), and Rayleigh statistic distribution of 20 Hz and 80 Hz auditory stimulation vs. no stimulation (right, **P<0.0001, P=3×10$^{-73}$ 20 Hz vs. No Stim, P=1×10$^{-68}$ 80 Hz vs. No Stim; Kolmogorov-Smirnov test; 54 units had 20 Hz stim RS values greater than 30; 28 units had 80 Hz stim RS values greater than 30).

Figure 8G:
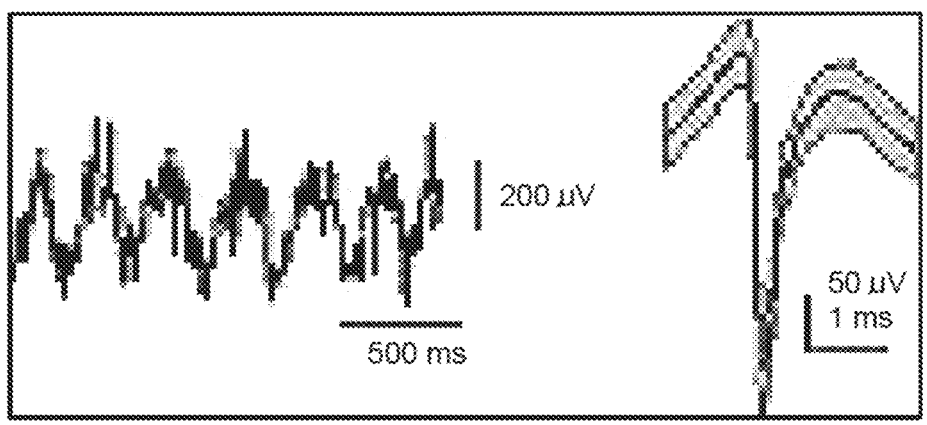

FIG. 8G shows example of theta rhythm, a hallmark of hippocampus, used to detect CA1.

Figure 8H:
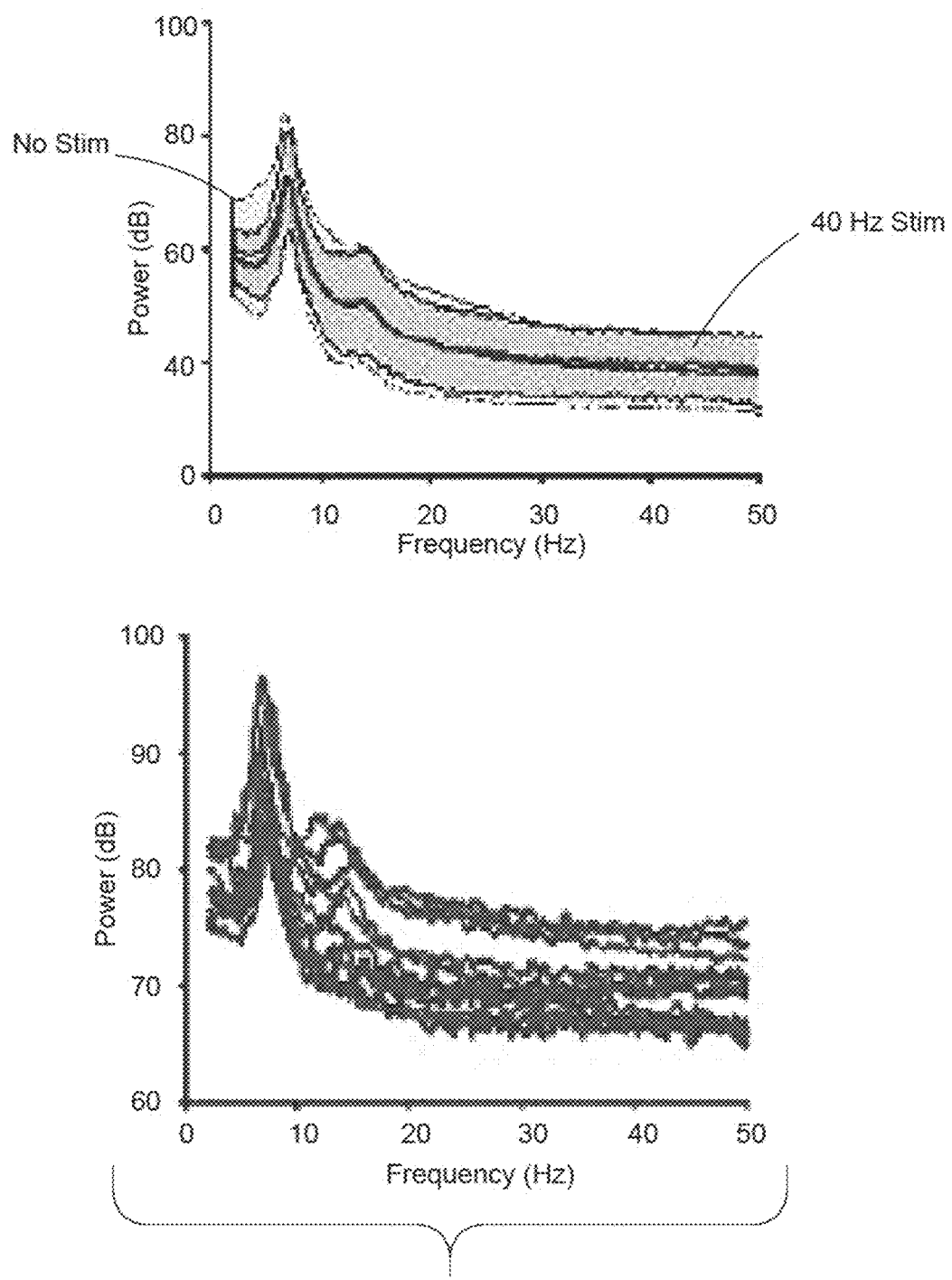

FIG. 8H shows same as B for CA1.

FIG. 8I shows same as C for CA1 (right, n.s.; Wilcoxon signed rank test for zero median).

FIG. 8J shows same as D for CA1 (right, P=0 20 Hz vs. No stim; z-Test for two proportions).

Figure 8K:
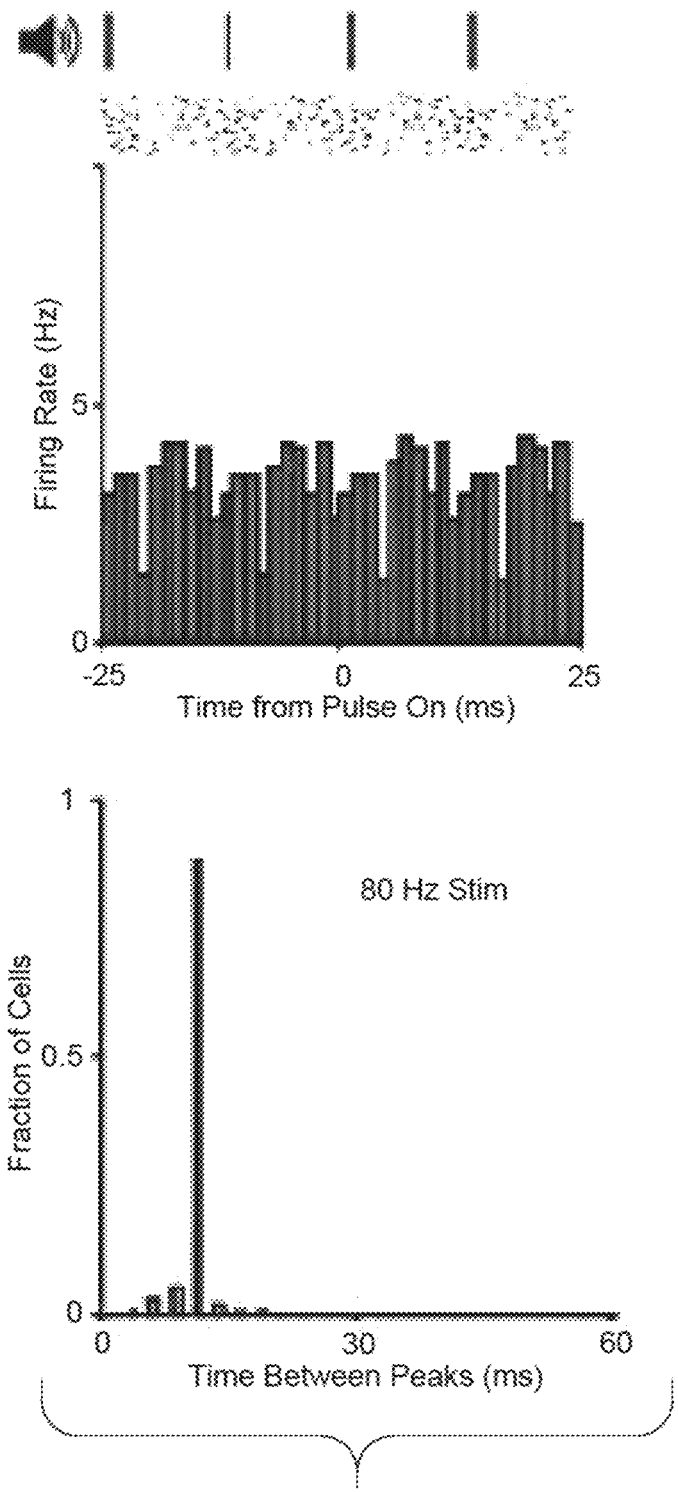

FIG. 8K shows same as E for CA1 (right, P=0 80 Hz vs. No stim; z-Test for two proportions).

Figure 8L:
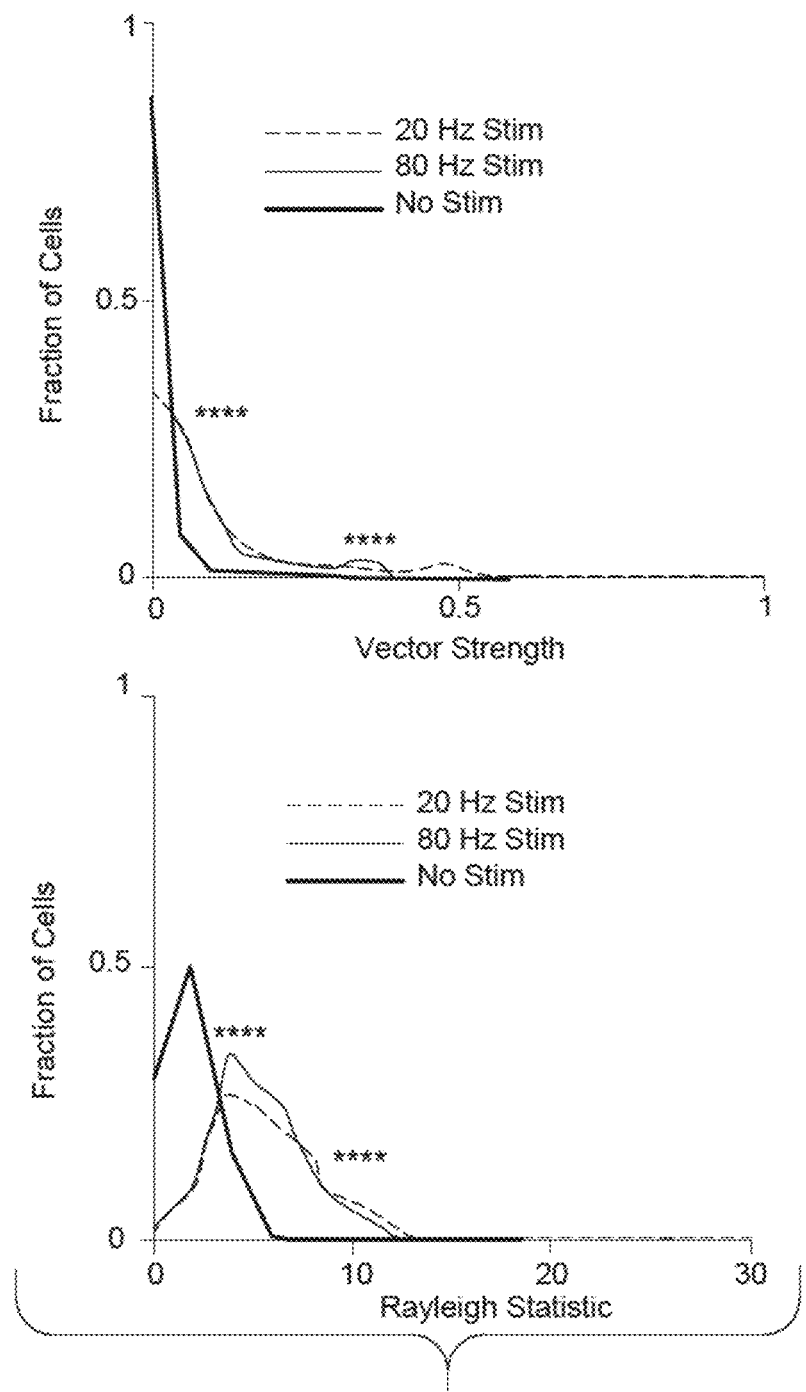

FIG. 8L shows same as F for CA1 (left, **P<0.0001, P=1×10$^{-40}$ 20 Hz vs. No Stim, P=9×10$^{-45}$ 80 Hz vs. No Stim; Kolmogorov-Smirnov test; right, **P<0.0001, P=1×10$^{-71}$ 20 Hz vs. No Stim, P=8×10$^{-73}$ 80 Hz vs. No Stim; Kolmogorov-Smirnov test).

Figure 8M:
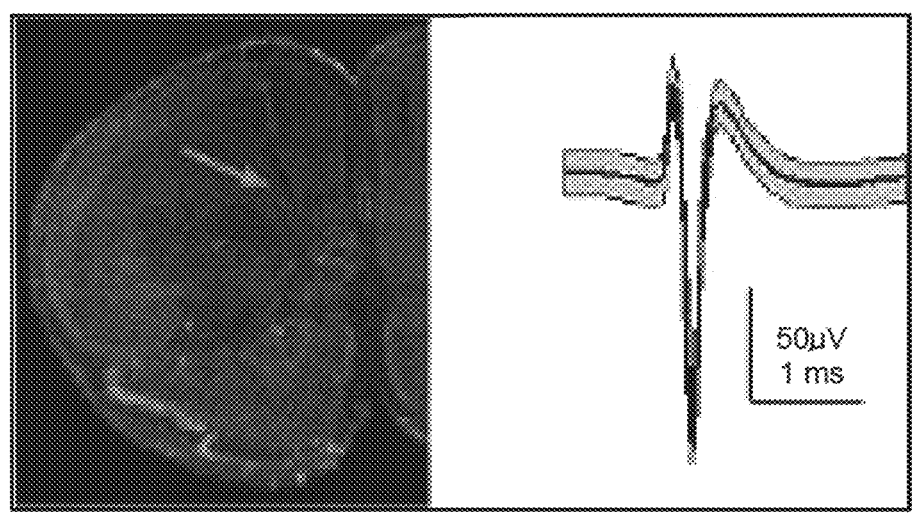

FIG. 8M shows histology image showing probe trace and recording location in mPFC. Red arrow indicates recording location.

Figure 8N:
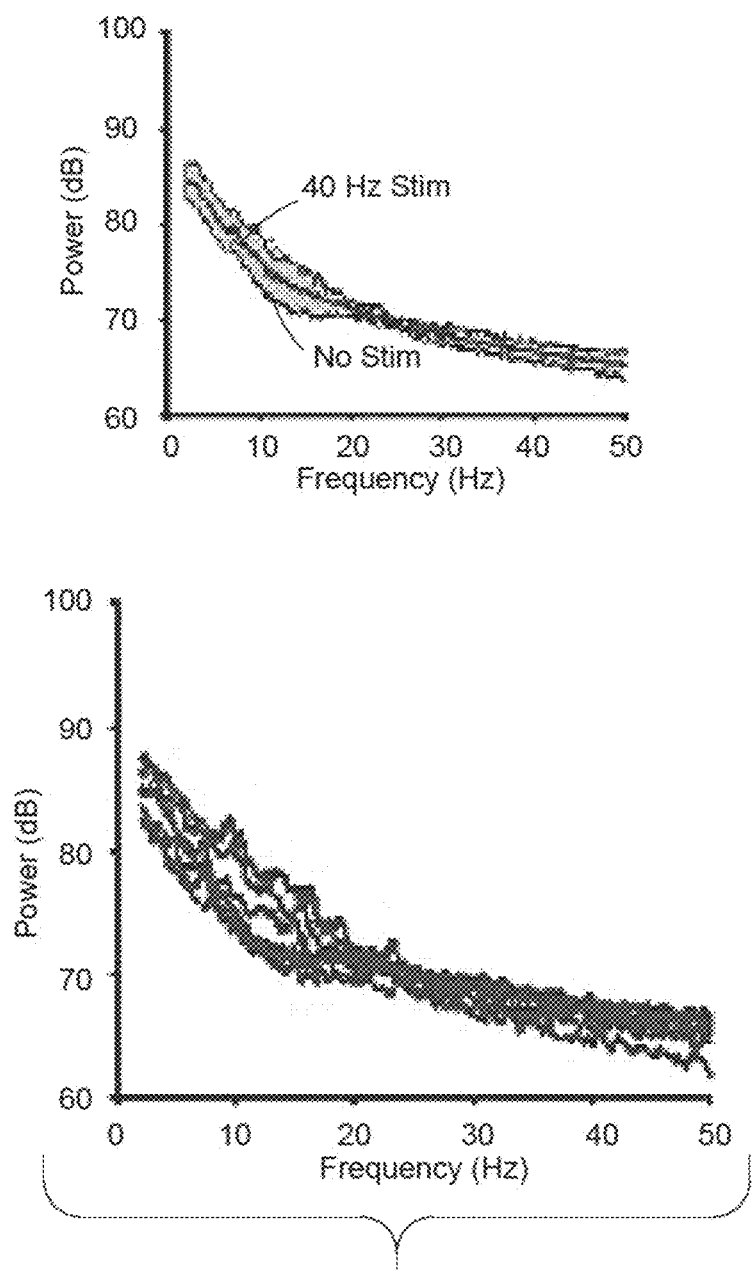

FIG. 8N shows same as B for mPFC.

FIG. 8O shows same as C for mPFC (right, n.s.; Wilcoxon signed rank test for zero median).

FIG. 8P shows same as D for mPFC (right, P=0 20 Hz vs. No stim; z-Test for two proportions).

Figure 8Q:
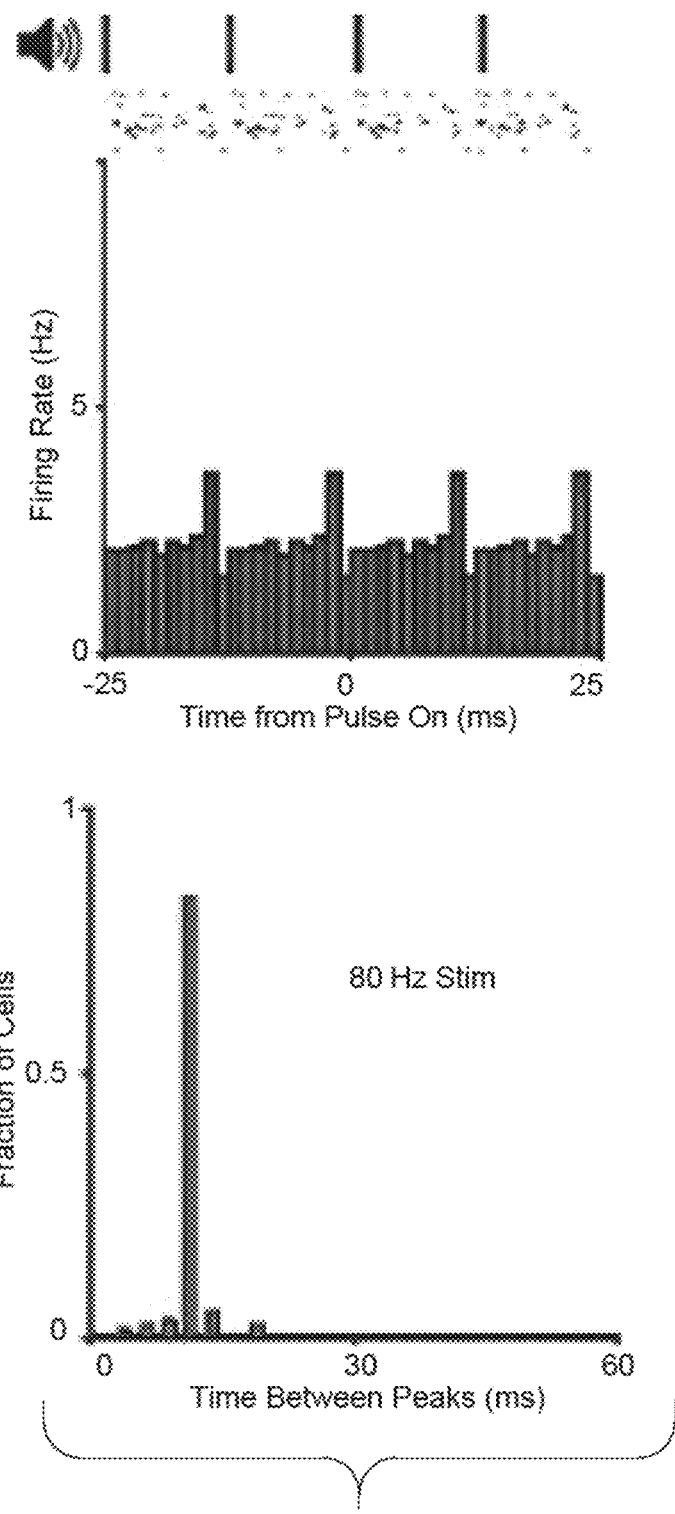

FIG. 8Q shows same as E for mPFC (right, P=0 80 Hz vs. No stim; z-Test for two proportions).

FIG. 8R shows same as F for mPFC (left, **P<0.0001, P=1×10$^{-23}$ 20 Hz vs. No Stim, P=6×10$^{-24}$ 80 Hz vs. No Stim; Kolmogorov-Smirnov test; right, **P<0.0001, P=2×10$^{-17}$ 20 Hz vs. No Stim, P=4×10$^{-26}$ 80 Hz vs. No Stim; Kolmogorov-Smirnov test).

Figure 9A:
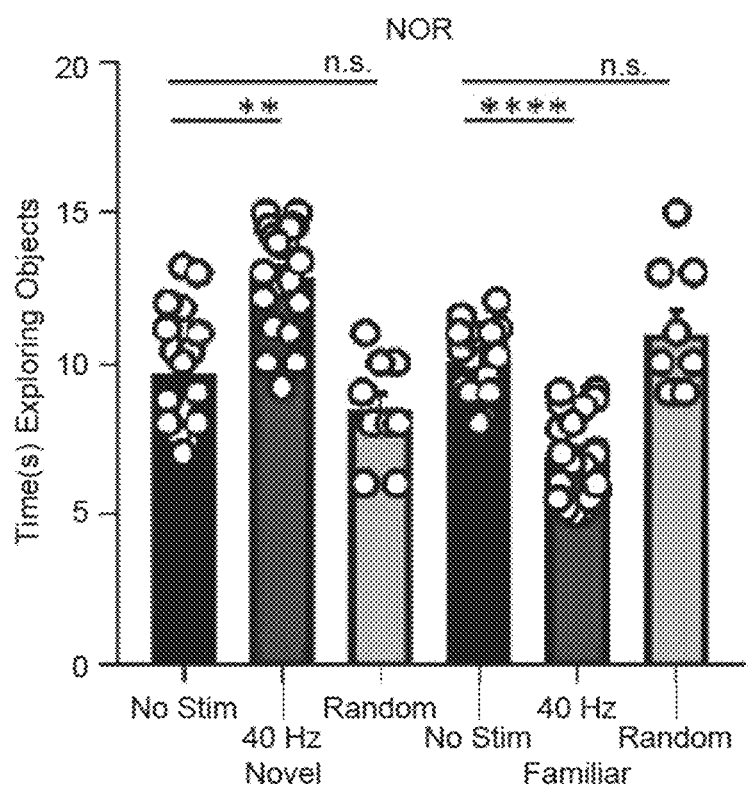
FIG. 9A-9L show auditory GENUS does not affect mouse behavior.

FIG. 9A shows time (seconds) spent exploring familiar and novel objects during NOR test of 5XFAD non-stimulated, 40 Hz, and random frequency stimulated mice (n=20 mice in no stim group, n=20 mice in 40 Hz group, n=9 in random frequency group, mean s.e.m. in bar graphs, P<0.01, **p<0.0001, n.s.=not significant, Kruskal-Wallis test with Dunn's multiple comparison test).

Figure 9B:
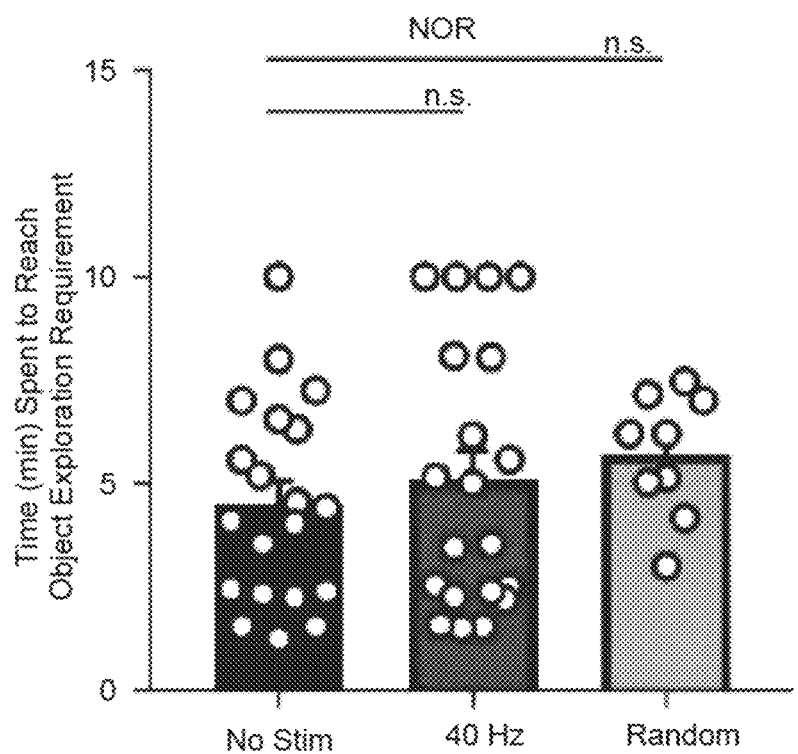

FIG. 9B shows time (min) mice required during NOR test to reach the total object exploration requirement of 20 s (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 9C:
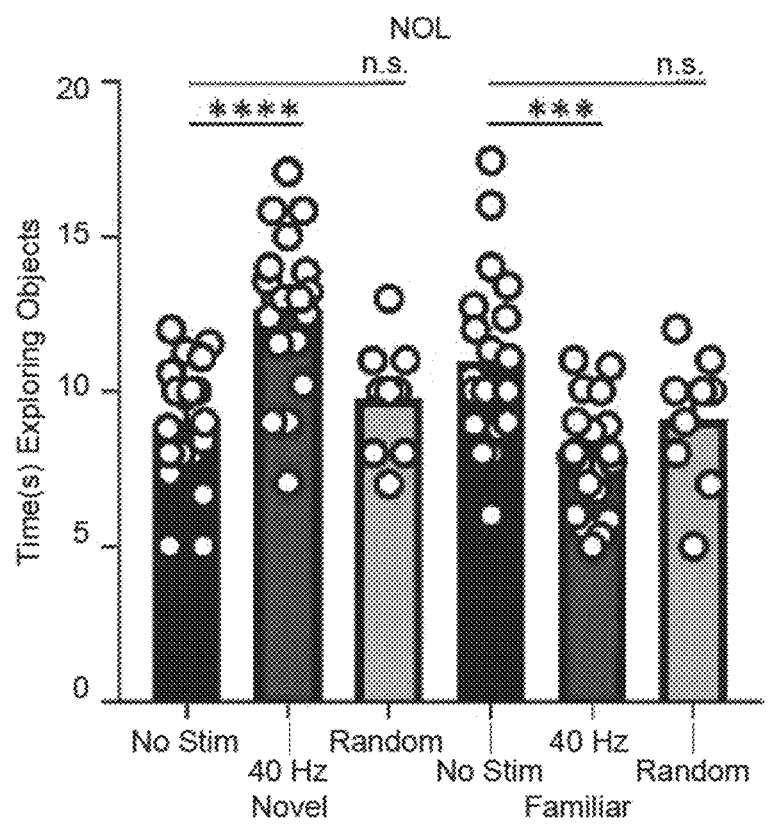

FIG. 9C shows time (seconds) spent exploring object in familiar and novel location during NOL test of 5XFAD non-stimulated, 40 Hz, and random frequency stimulated mice (n=20 mice in no stim group, n=20 mice in 40 Hz group, n=9 in random frequency group, mean s.e.m. in bar graphs, *P<0.001, **p<0.0001, n.s.=not significant, Kruskal-Wallis test with Dunn's multiple comparison test).

Figure 9D:
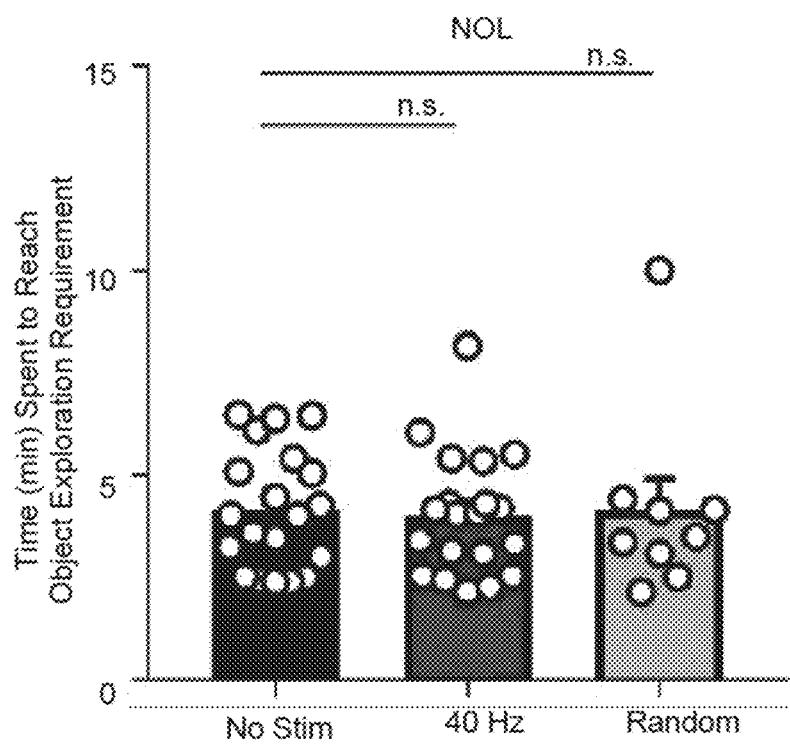

FIG. 9D shows time (min) mice required during NOL test to reach the total object exploration requirement of 20 s (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 9E:
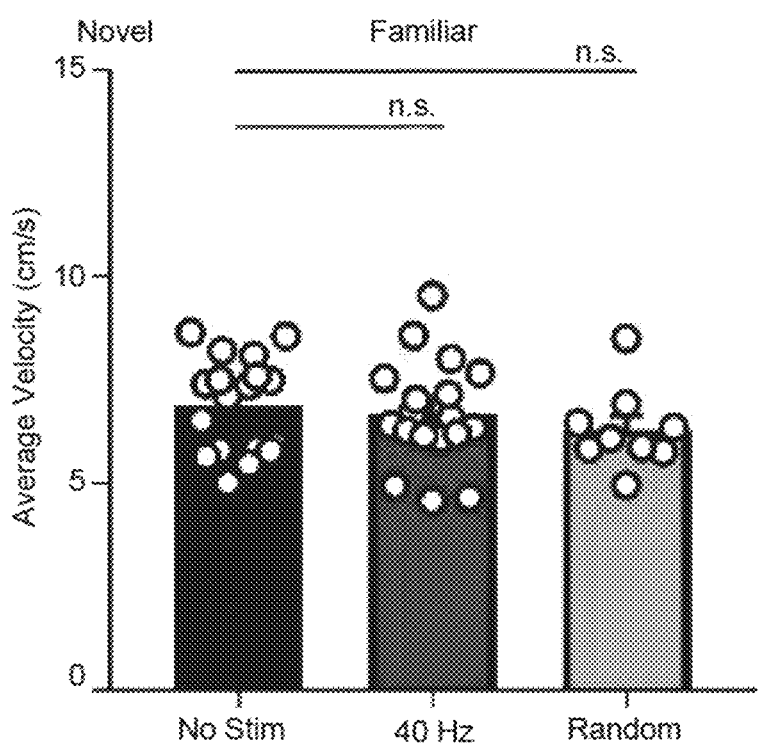

FIG. 9E shows average velocity (cm/s) during habituation ((n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 9F:
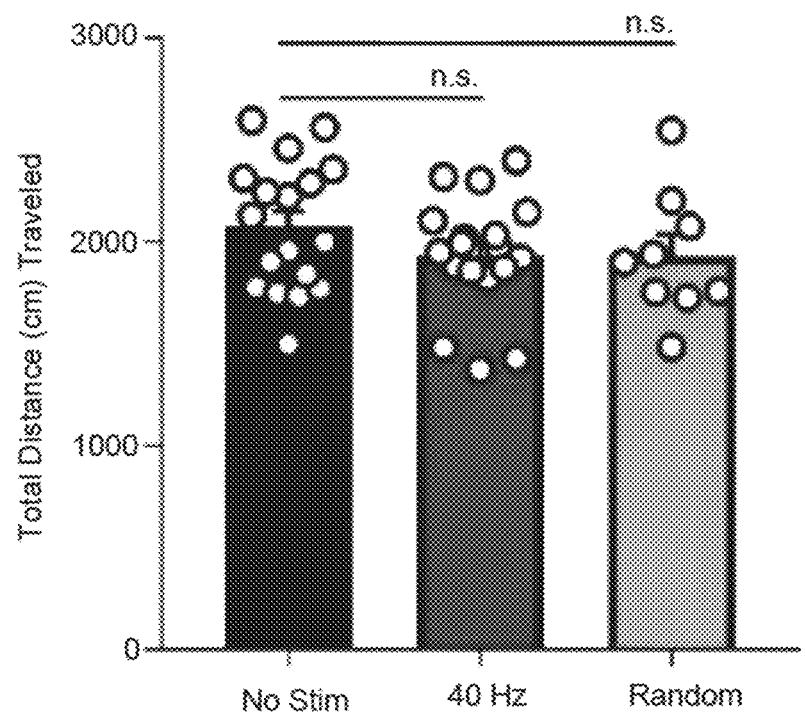

FIG. 9F shows total distance (cm) traveled during habituation (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 9G:
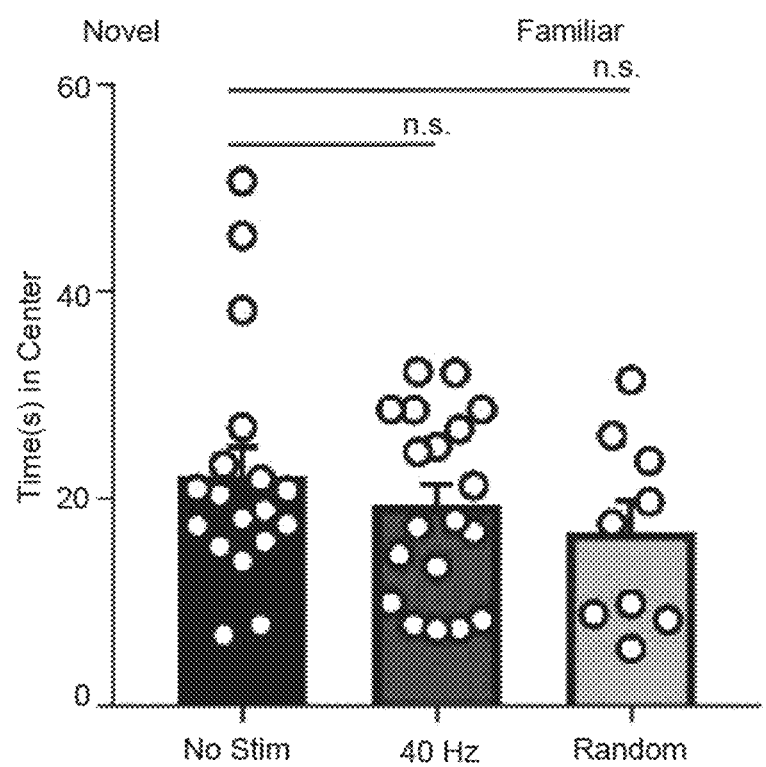

FIG. 9G shows time (seconds) spent in the center of the behavior chamber during habituation (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 9H:
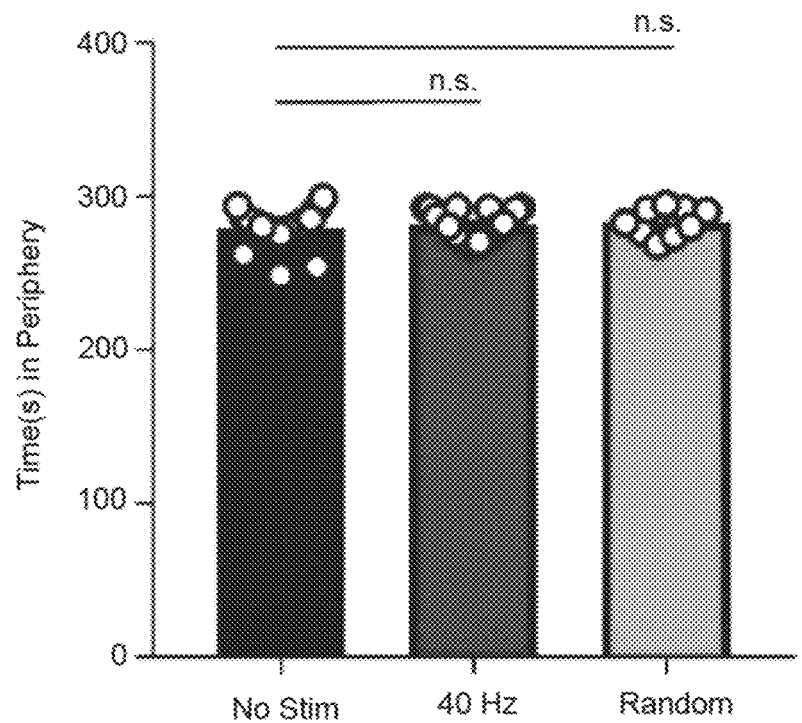

FIG. 9H shows time (seconds) spent in the periphery of the behavior chamber during habituation (n=20 mice in no stim group, n=20 mice in 40 Hz group, n=9 in random frequency group, mean s.e.m. in bar graphs, n.s.=not significant, Kruskal-Wallis test with Dunn's multiple comparison test).

Figure 9I:
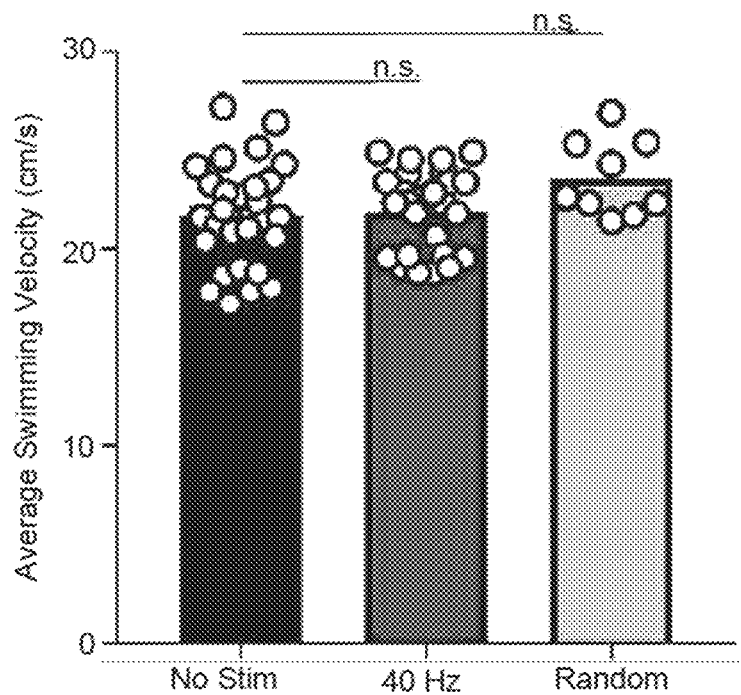

FIG. 9I shows average swimming velocity (cm/s) during Morris water maze (n=25 mice in no stim group, n=28 mice in 40 Hz group, n=9 in random frequency group, mean s.e.m. in bar graphs, n.s.=not significant, Kruskal-Wallis test with Dunn's multiple comparison test).

Figure 9J:
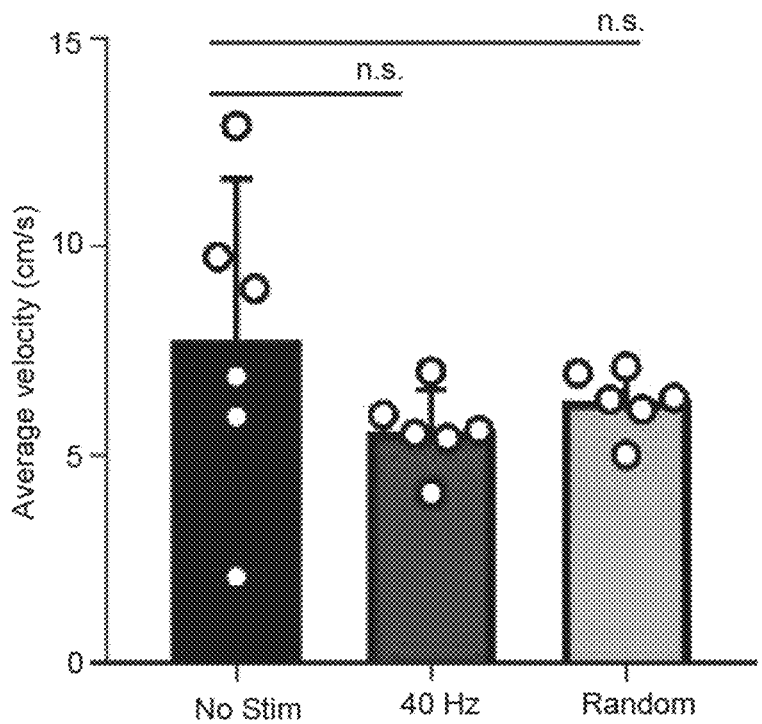

FIG. 9J shows average velocity (cm/s) during 1-hour no stimulation, auditory GENUS, or random frequency stimulation (n=6 mice in no stim group, n=6 mice in 40 Hz group, n=6 in random frequency group, mean s.e.m. in bar graphs, n.s.=not significant, Kruskal-Wallis test with Dunn's multiple comparison test).

Figure 9K:
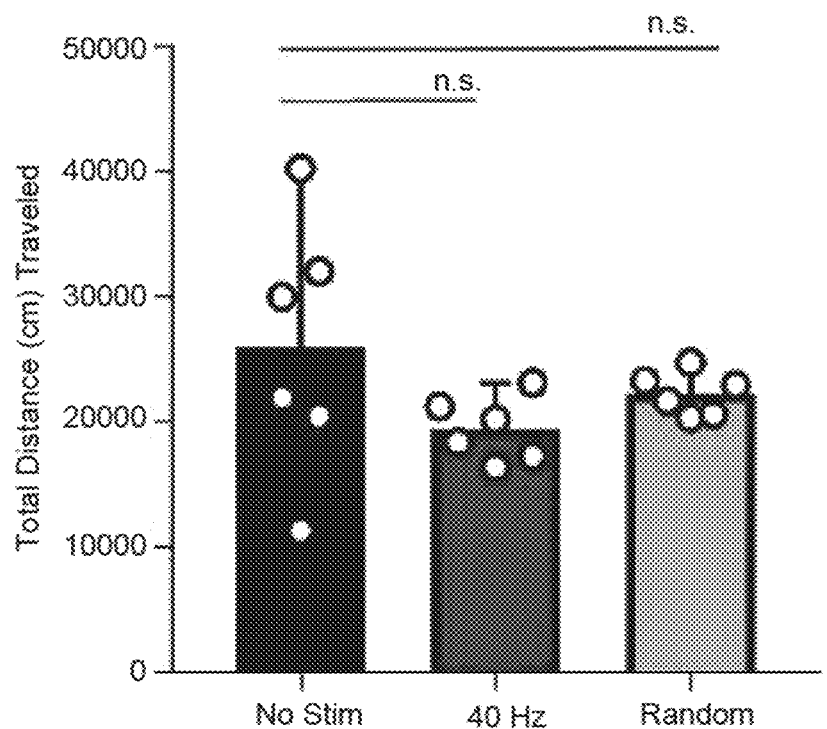

FIG. 9K shows total distance (cm) traveled during 1-hour no stimulation, auditory GENUS, or random frequency stimulation (n=6 mice in no stim group, n=6 mice in 40 Hz group, n=6 in random frequency group, mean s.e.m. in bar graphs, n.s.=not significant, Kruskal-Wallis test with Dunn's multiple comparison test).

Figure 9L:
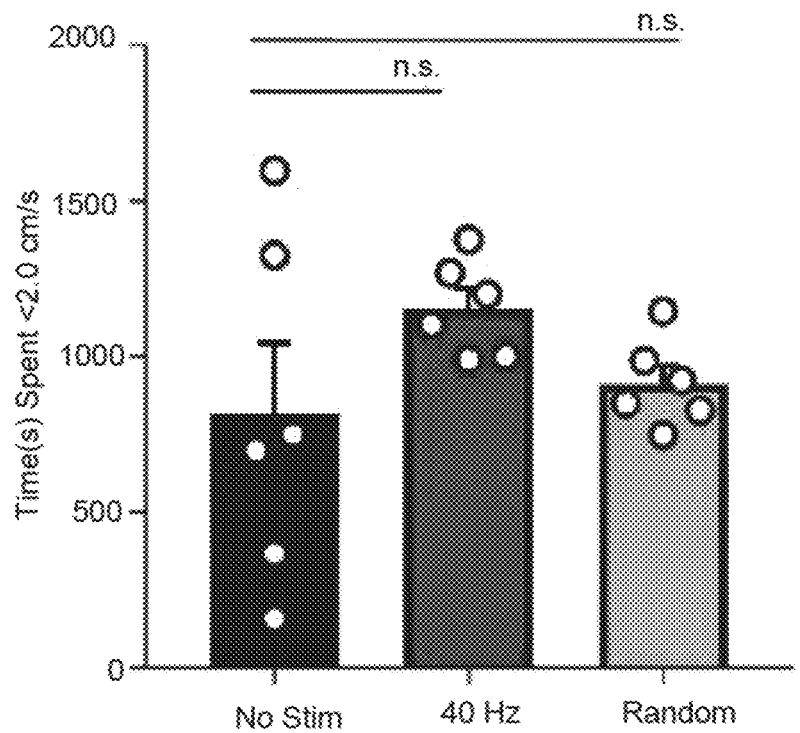

FIG. 9L shows time (seconds) spend under 2 cm/s during 1-hour no stimulation, auditory GENUS, or random frequency stimulation (n=6 mice in no stim group, n=6 mice in 40 Hz group, n=6 in random frequency group, mean s.e.m. in bar graphs, n.s.=not significant, Kruskal-Wallis test with Dunn's multiple comparison test).

Figure 10A:
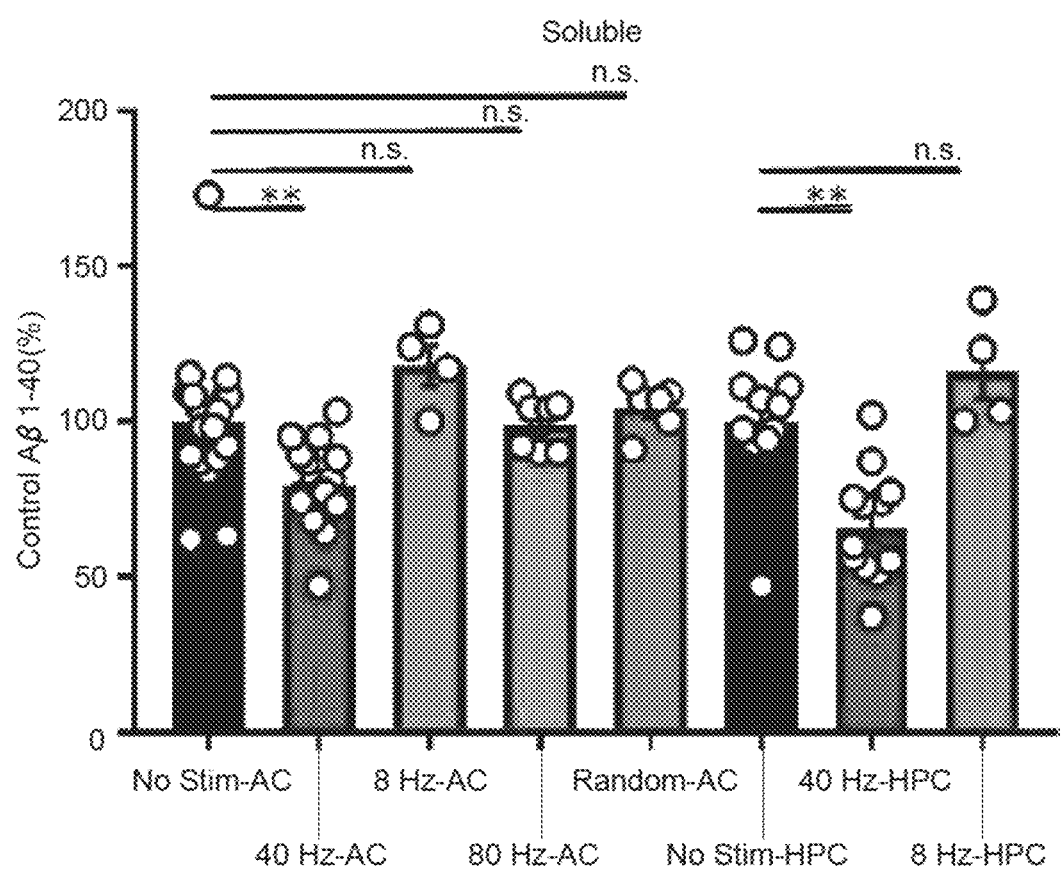

FIG. 10A shows relative soluble $A\beta_{1-40}$ levels in auditory cortex (AC) and hippocampus (HPC) in 6-month-old 5XFAD mice following 40 Hz, 8 Hz, 80 Hz, or random frequency auditory stimulation for 1 hour per day for 7 days, normalized to non-stimulation control (note: ELISA for 80 Hz and random frequency HPC samples were unsuccessful and were unable to be reported, n=19 mice in no stim group, n=19 mice in 40 Hz group, n=4 mice in 8 Hz group, n=7 in 80 Hz group, n=6 in random frequency group, mean s.e.m. in bar graphs, **P<0.01, n.s.=not significant, Kruskal-Wallis test with Dunn's multiple comparison test).

Figure 10B:
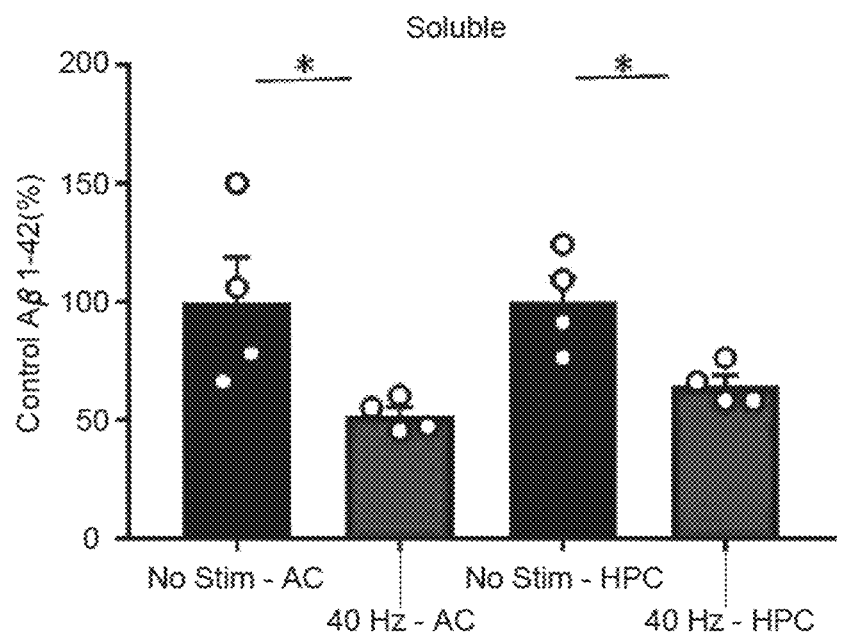

FIG. 10B shows relative soluble $A\beta_{1-42}$ levels in auditory cortex (AC) and hippocampus (HPC) in 6-month-old APP/PS1 mice following auditory GENUS for 1 hour per day for 7 days, normalized to non-stimulation control (n=4 mice in no stim group, n=4 mice in 40 Hz group, mean s.e.m. in bar graphs, *P<0.05, unpaired Mann-Whitney test).

Figure 10C:
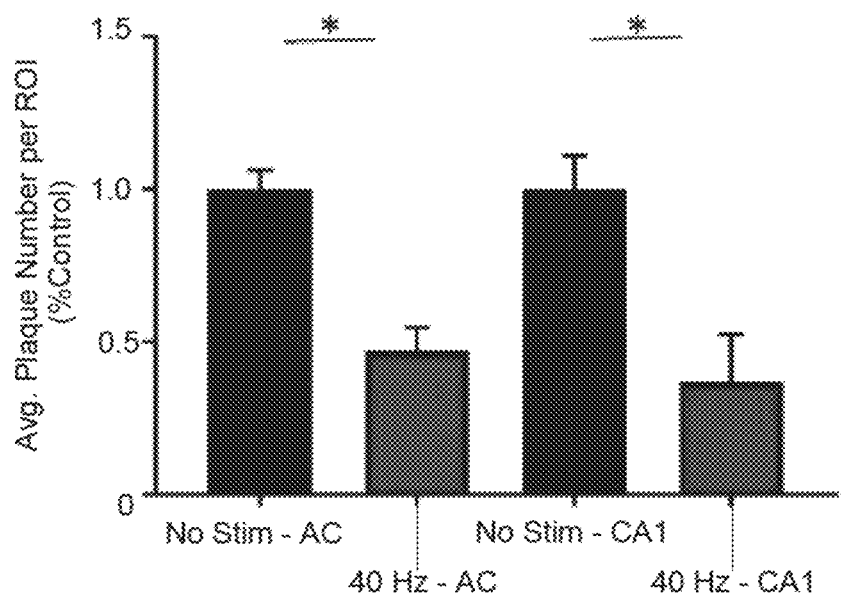

FIG. 10C shows average plaque number in AC and CA1 ('region of interest', ROI) in 9-month old APP/PS1 mice following auditory GENUS for 1 hour per day for 7 days, normalized to non-stimulation control (n=5 mice in no stim group, n=5 mice in 40 Hz group, mean s.e.m. in bar graphs, *P<0.05, unpaired Mann-Whitney test).

Figure 10D:
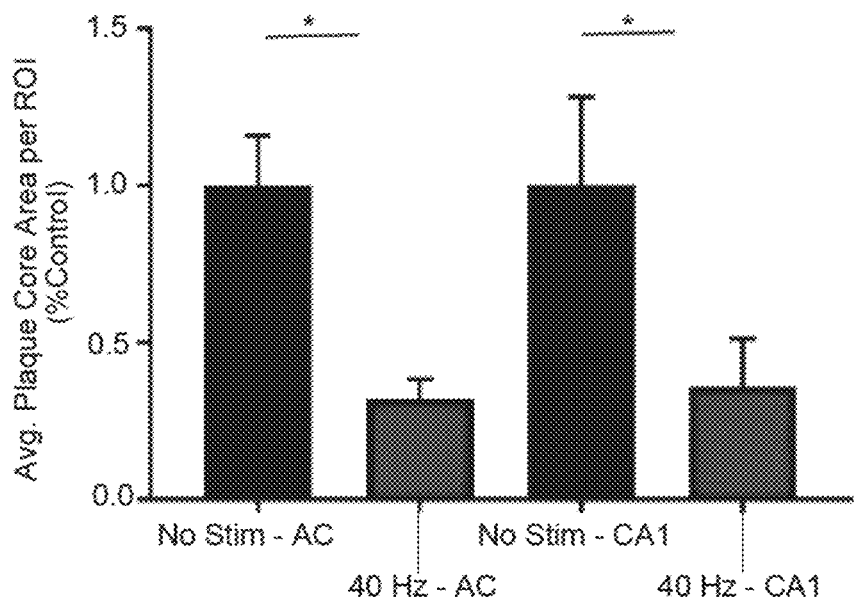

FIG. 10D shows average plaque core area in AC and CA1 in 9-month old APP/PS1 mice following auditory GENUS for 1 hour per day for 7 days, normalized to non-stimulation control (n=5 mice in no stim group, n=5 mice in 40 Hz group, mean s.e.m. in bar graphs, *P<0.05, unpaired Mann-Whitney test).

Figure 10E:
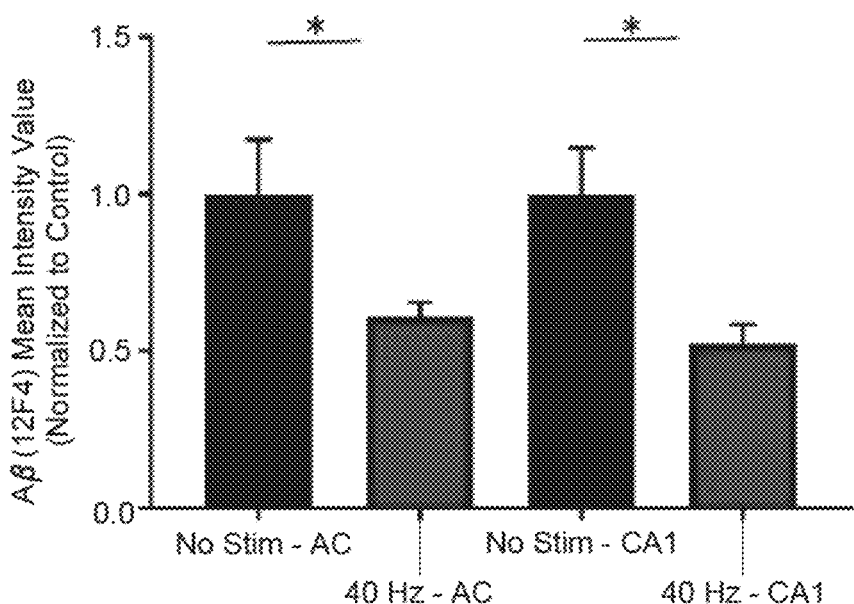

FIG. 10E shows Aβ (12F4) mean intensity value (12F4 antibody) in AC and CA1 in 9-month old APP/PS1 mice following auditory GENUS for 1 hour per day for 7 days, normalized to non-stimulation control (n=5 mice in no stim group, n=5 mice in 40 Hz group, mean s.e.m. in bar graphs, *P<0.05, unpaired Mann-Whitney test).

Figure 10F:
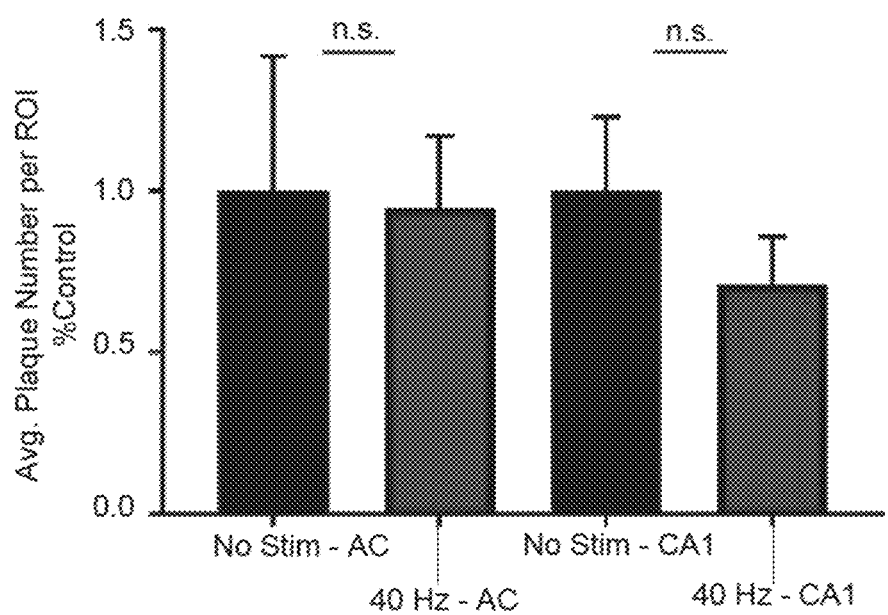

FIG. 10F shows average plaque number in AC and CA1 in 6-month old 5XFAD mice following 7 days no stimulation post auditory GENUS for 1 hour per day for 7 days, normalized to non-stimulation control (n=6 mice in no stim group, n=6 mice in 40 Hz group, mean s.e.m. in bar graphs, n.s.=not significant, unpaired Mann-Whitney test).

Figure 10G:
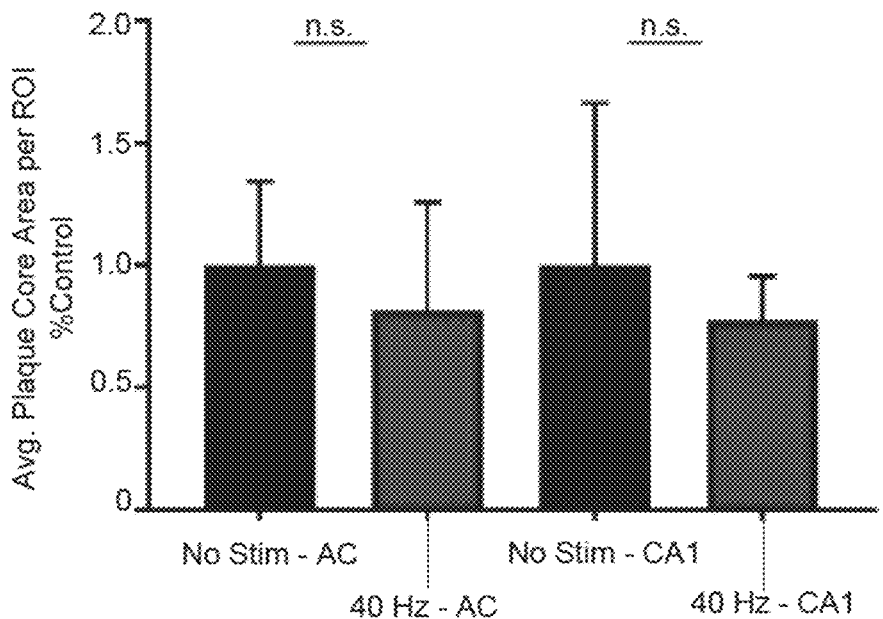

FIG. 10G shows average plaque core area in AC and CA1 in 6-month old 5XFAD mice following 7 days no stimulation post auditory GENUS for 1 hour per day for 7 days, normalized to non-stimulation control (n=6 mice in no stim group, n=6 mice in 40 Hz group, mean s.e.m. in bar graphs, n.s.=not significant, unpaired Mann-Whitney test).

Figure 10H:
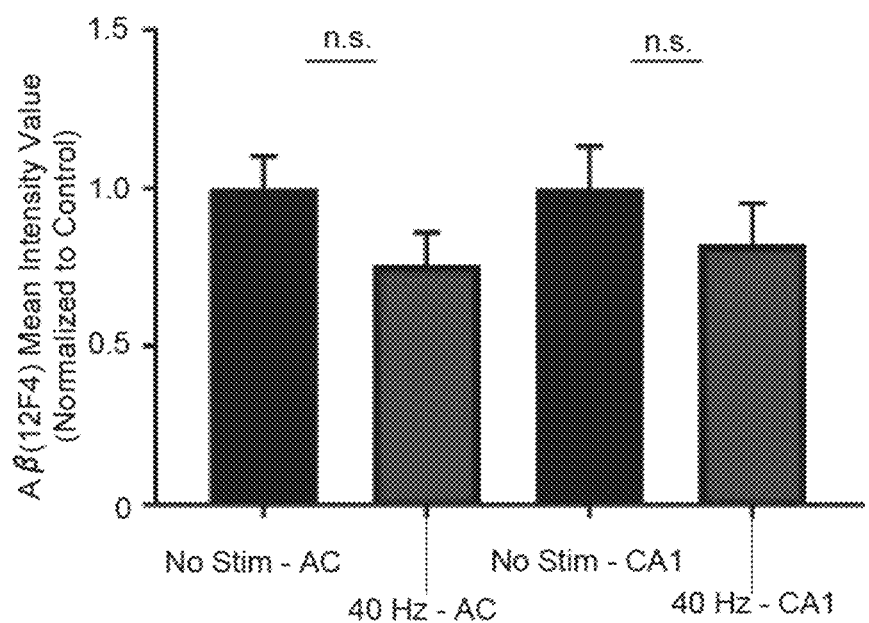

FIG. 10H shows Aβ (12F4) mean intensity value (12F4 antibody) in AC and CA1 in 6-month old 5XFAD mice following 7 days no stimulation post auditory GENUS for 1 hour per day for 7 days, normalized to non-stimulation control (n=6 mice in no stim group, n=6 mice in 40 Hz group, mean s.e.m. in bar graphs, n.s.=not significant, unpaired Mann-Whitney test).

Figure 11A:
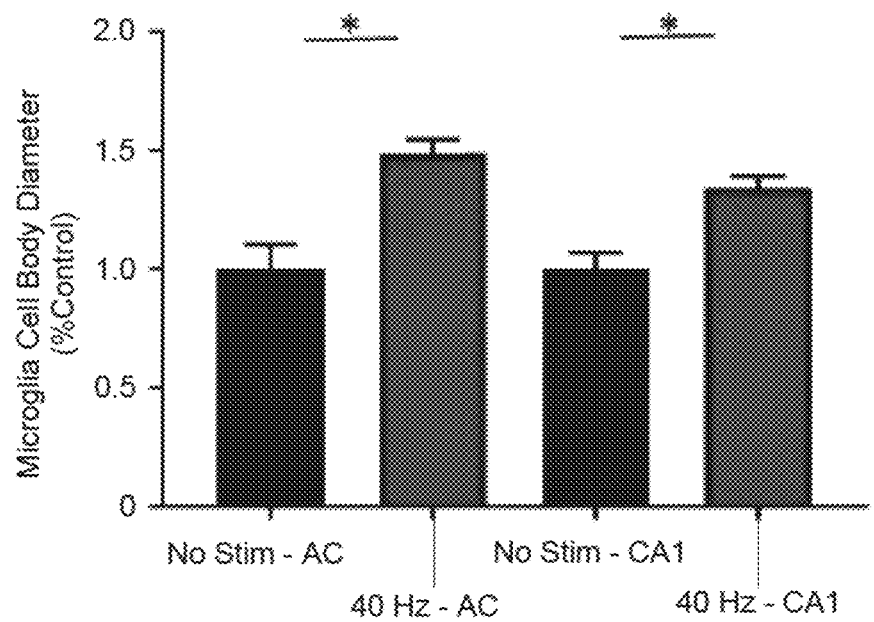

FIG. 11A shows diameter of Iba1-positive microglia cell bodies in AC and CA1 in 9-month old APP/PS1 mice following auditory GENUS for 1 hour per day for 7 days, normalized to non-stimulation control (n=5 mice per group, mean s.e.m. in bar graphs, *P<0.05, unpaired Mann-Whitney test).

Figure 11B:
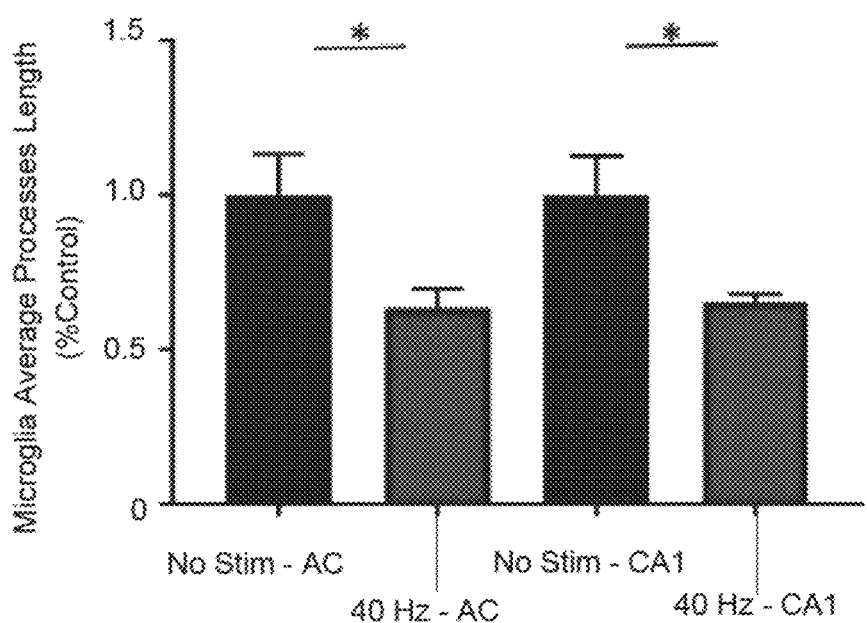

FIG. 11B shows average length of Iba1-positive microglia primary processes in AC and CA1 in 9-month old APP/PS1 mice following auditory GENUS for 1 hour per day for 7 days, normalized to non-stimulation control (n=5 mice per group, mean s.e.m. in bar graphs, *P<0.05, unpaired Mann-Whitney test).

Figure 11C:
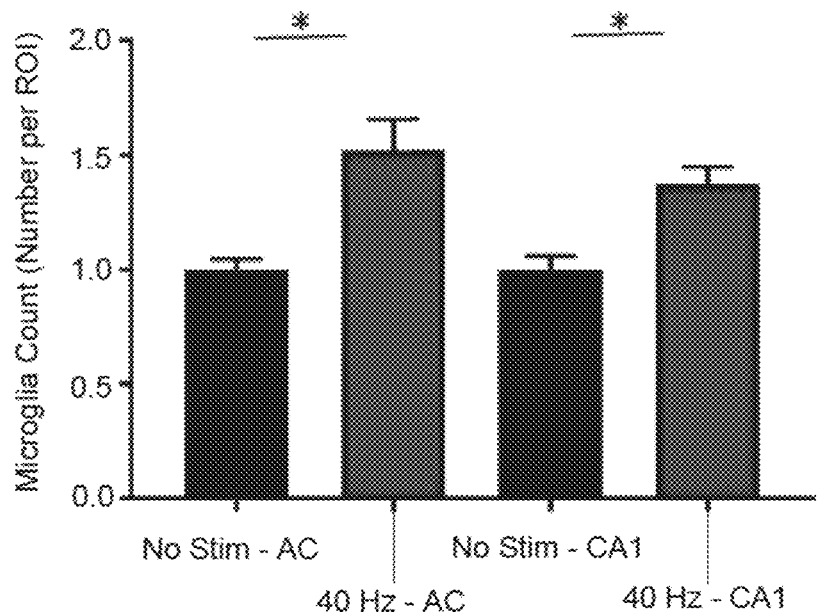

FIG. 11C shows number of Iba1-positive microglia in AC and CA1 in 9-month old APP/PS1 mice following auditory GENUS for 1 hour per day for 7 days, normalized to non-stimulation control (n=5 mice per group, mean s.e.m. in bar graphs, *P<0.05, unpaired Mann-Whitney test).

Figure 11D:
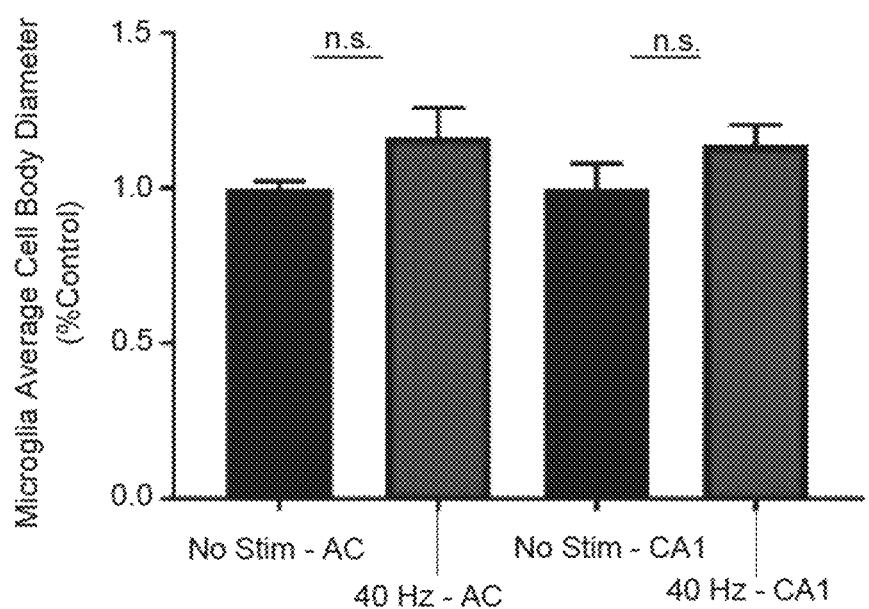

FIG. 11D shows diameter of Iba1-positive microglia cell bodies in AC and CA1 in 6-month old 5XFAD mice following 7 days no stimulation post auditory GENUS for 1 hour per day for 7 days, normalized to non-stimulation control (n=6 mice per group, mean s.e.m. in bar graphs, n.s.=not significant, unpaired Mann-Whitney test).

Figure 11E:
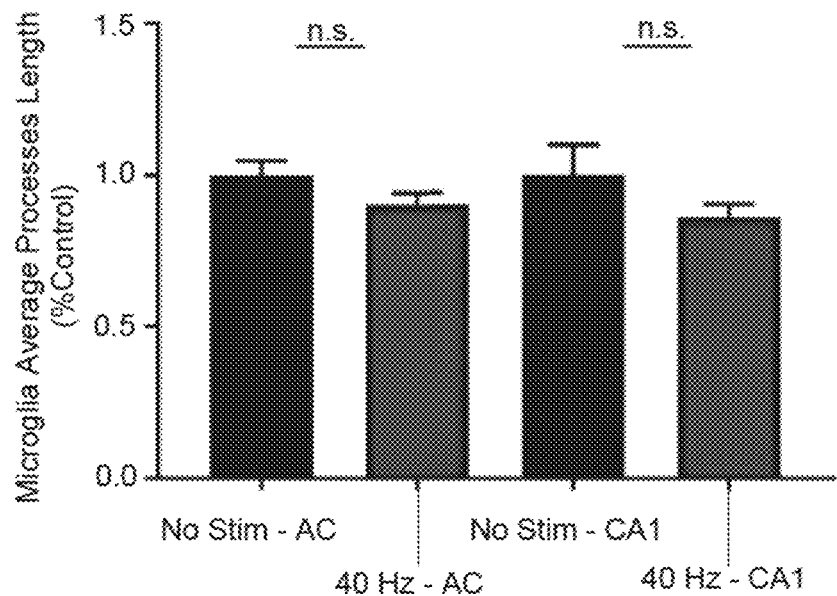

FIG. 11E shows average length of Iba1-positive microglia primary processes in AC and CA1 in 6-month old 5XFAD mice following 7 days no stimulation post auditory GENUS for 1 hour per day for 7 days, normalized to non-stimulation control (n=6 mice per group, mean s.e.m. in bar graphs, n.s.=not significant, unpaired Mann-Whitney test).

Figure 11F:
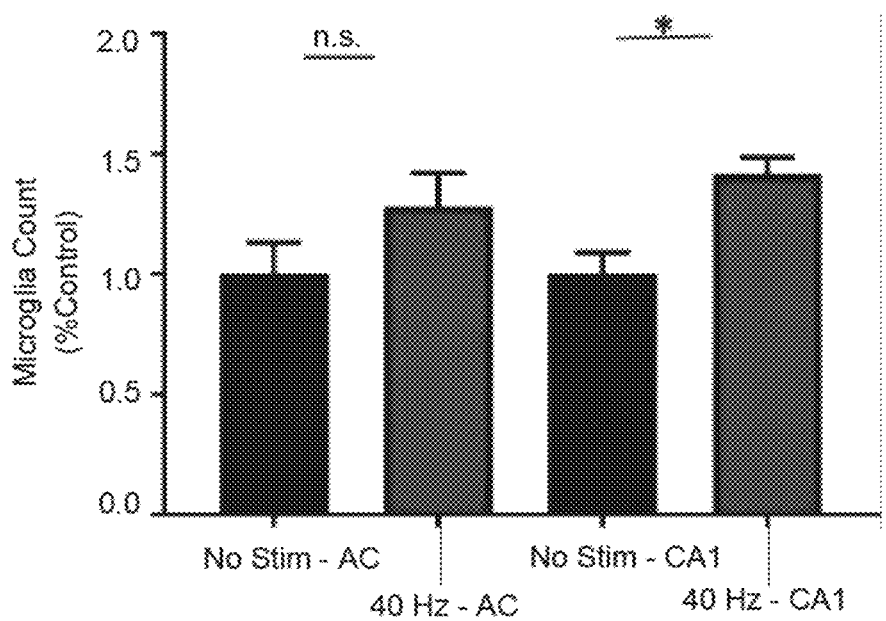

FIG. 11F shows number of Iba1-positive microglia in AC and CA1 in 6-month old 5XFAD mice following 7 days no stimulation post auditory GENUS for 1 hour per day for 7 days, normalized to non-stimulation control (n=6 mice per group, mean s.e.m. in bar graphs, *P<0.05, n.s.=not significant, unpaired Mann-Whitney test).

Figure 11G:
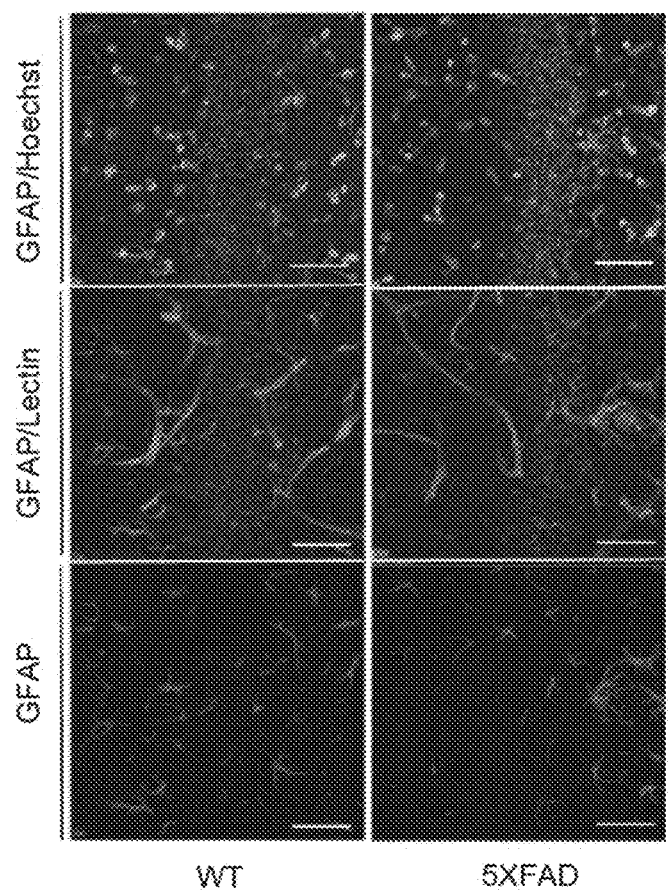

FIG. 11G shows immunohistochemistry of CLARITY treated brain sections with anti-GFAP (ab4674, red) and lectin stain (DL-1174, green) antibodies in CA1 of 6-month-old WT and 5XFAD mice (n=5 mice per group, scale bar, 50 μm).

Figure 11H:
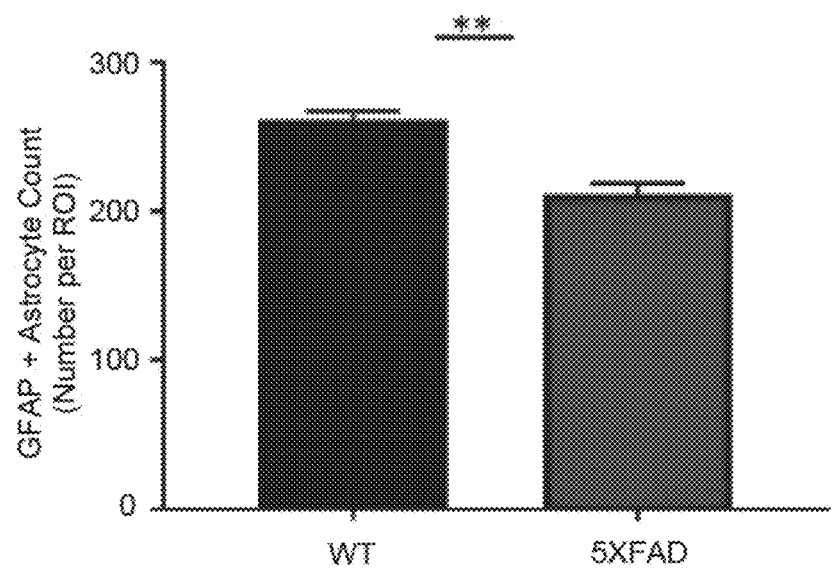

FIG. 11H shows number of GFAP positive cells (per image of interest, using IMAMS) in CA1 of 6-month-old WT and 5XFAD mice (n=5 mice per group, mean s.e.m. in bar graphs, **P<0.01, unpaired Mann-Whitney test).

Figure 12A:
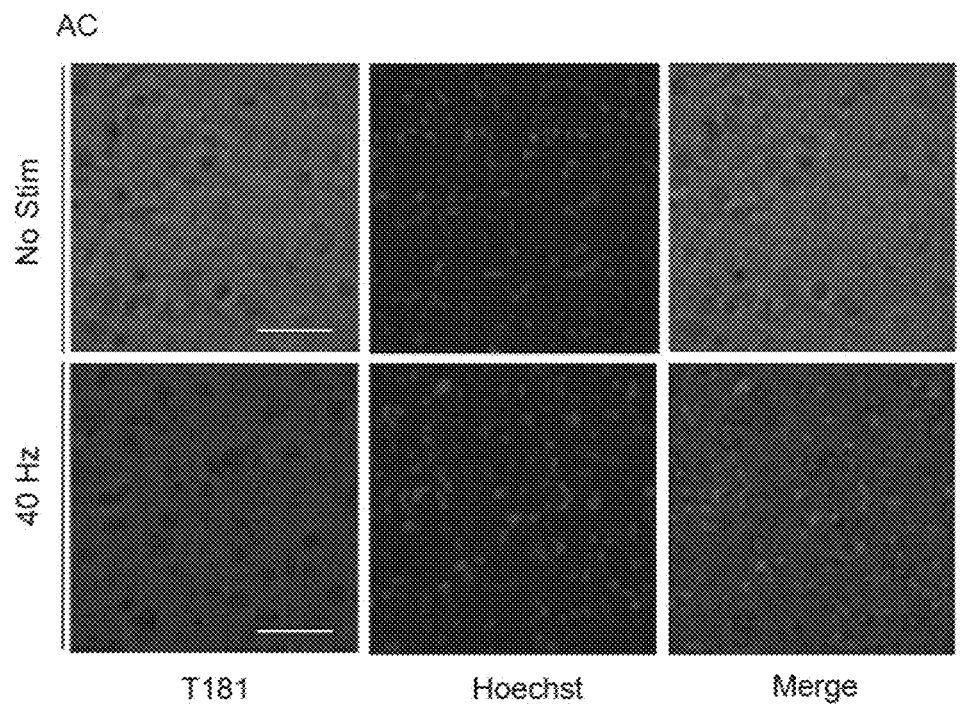
FIG. 12A-12L show auditory GENUS reduces phosphorylated tau in P301S mice.

FIG. 12A shows immunohistochemistry with anti-pTau (T181, red) antibodies in AC of 6-month-old P301S mice after 7 days of 1 hour per day no stimulation or auditory GENUS (image taken with 40× objective, scale bar, 50 μm).

Figure 12B:
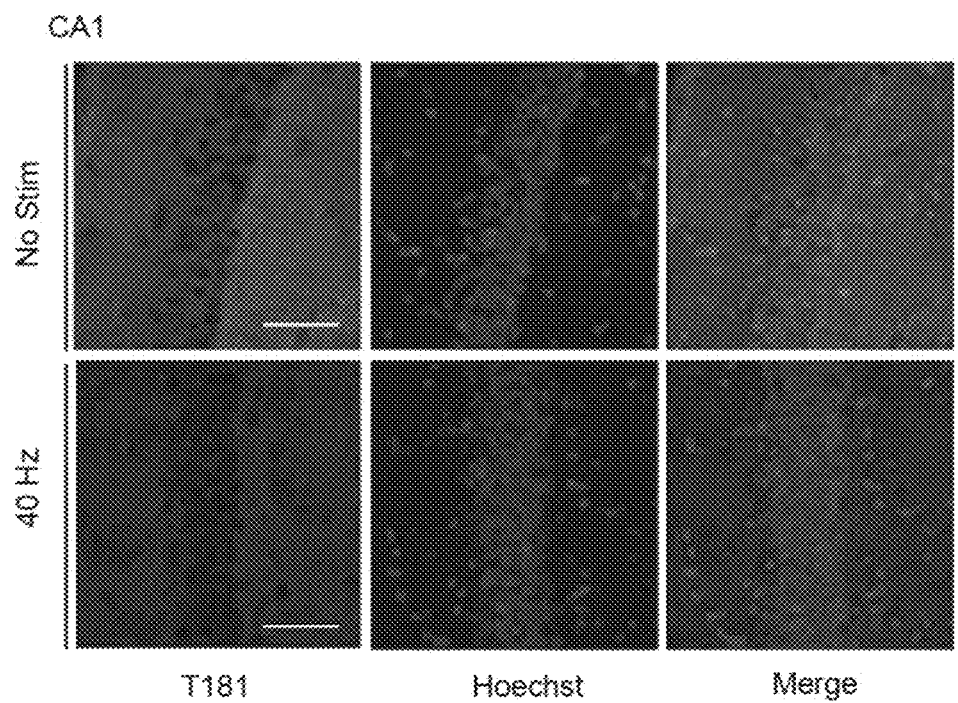

FIG. 12B shows as in FIG. 12A for CA1.

Figure 12C:
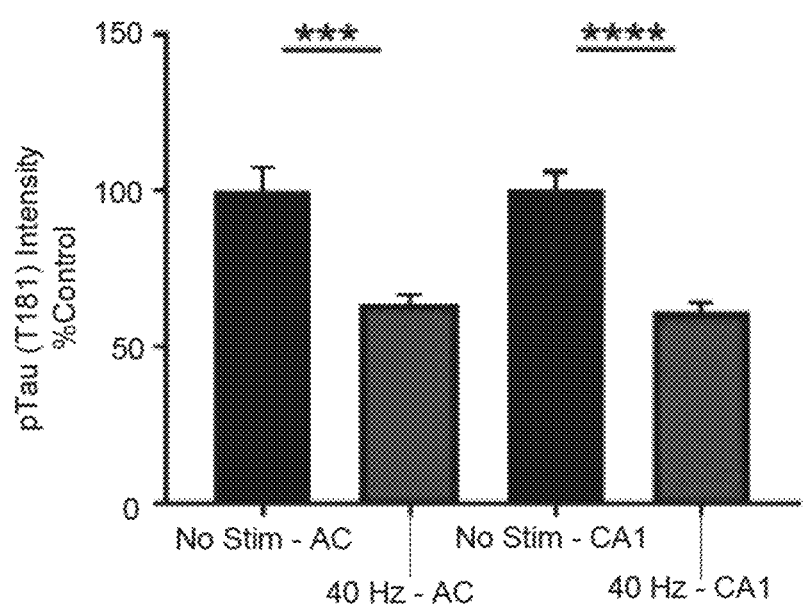

FIG. 12C shows relative pTau (T181) intensity levels in AC and CA1 of P301S mice after 7 days of 1 hour per day no stimulation or auditory GENUS normalized to non-stimulation control (n=10 mice per group, *P<0.001, **P<0.0001; unpaired Mann-Whitney test).

Figure 12D:
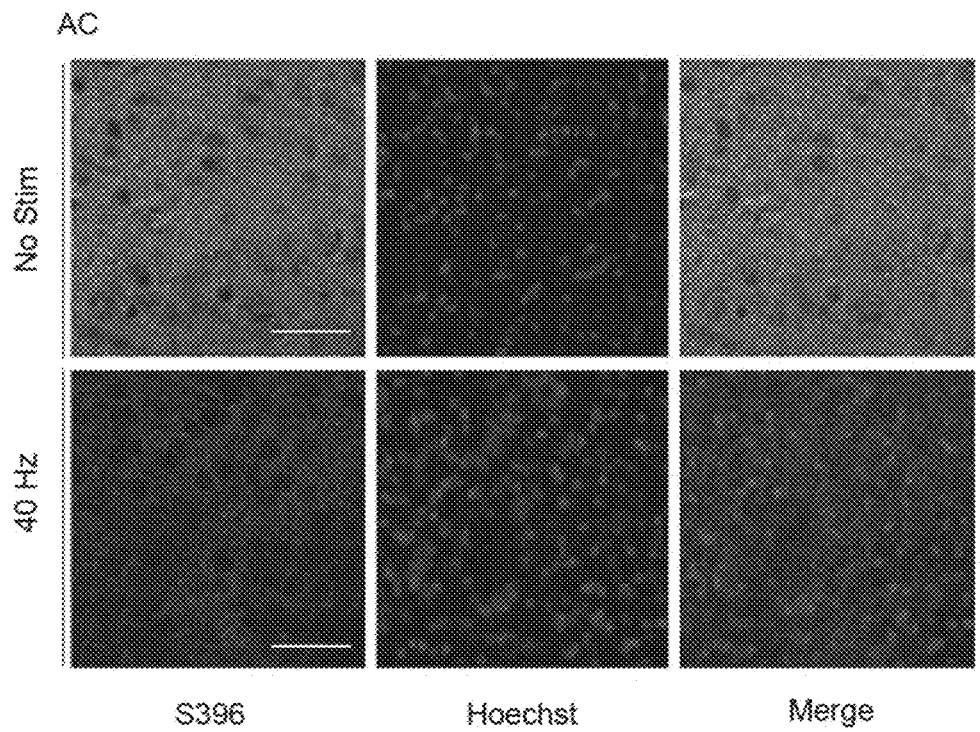

FIG. 12D shows immunohistochemistry with anti-pTau (S396, green) antibodies in AC of 6-month-old P301S mice after 7 days of 1 h per day no stimulation or auditory GENUS (scale bar, 50 μm).

Figure 12E:
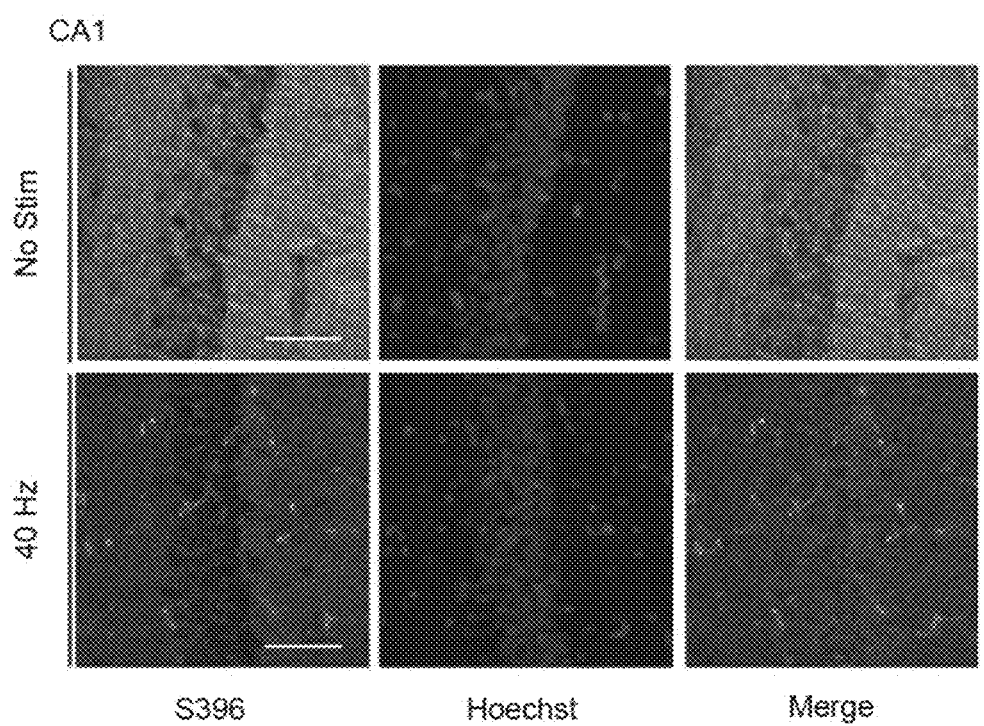

FIG. 12E shows as in FIG. 12D for CA1.

Figure 12F:
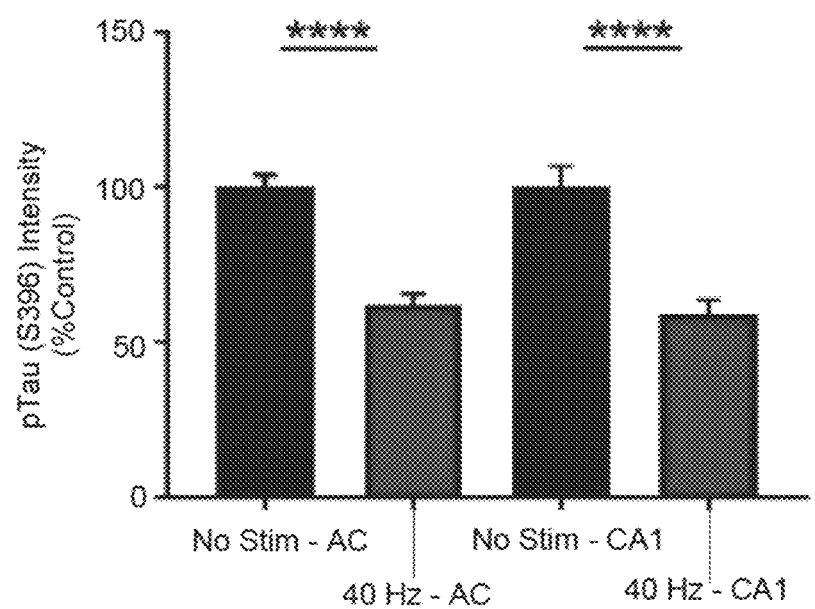

FIG. 12F shows relative pTau (S396) intensity levels in P301S mice in AC and CA1 after 7 days of 1 hour per day no stimulation or auditory GENUS normalized to non-stimulation control (n=10 mice per group, ****P<0.0001; unpaired Mann-Whitney test).

Figure 12G:
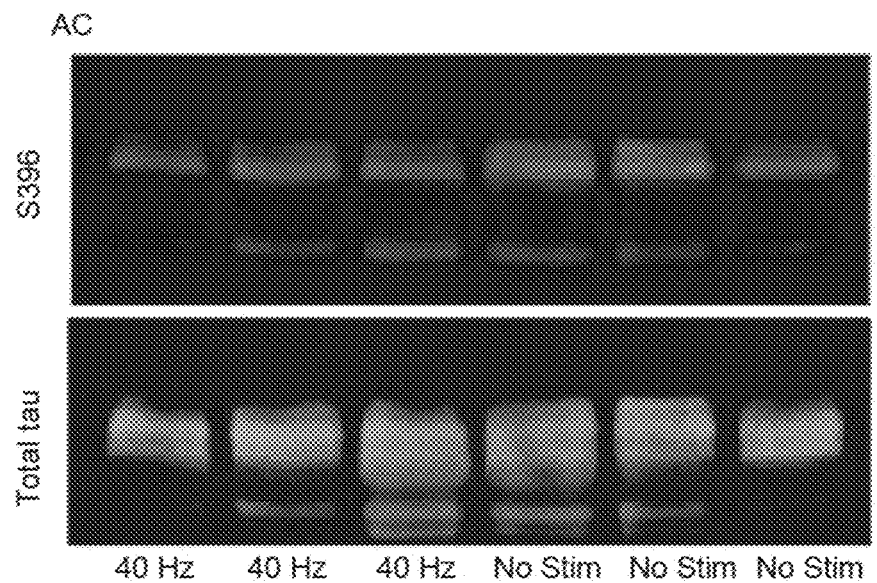

FIG. 12G shows representative western blot showing levels of pTau (S396) and total tau in AC of 6-month-old P301S mice after 7 days of 1 hour per day no stimulation or auditory GENUS.

Figure 12H:
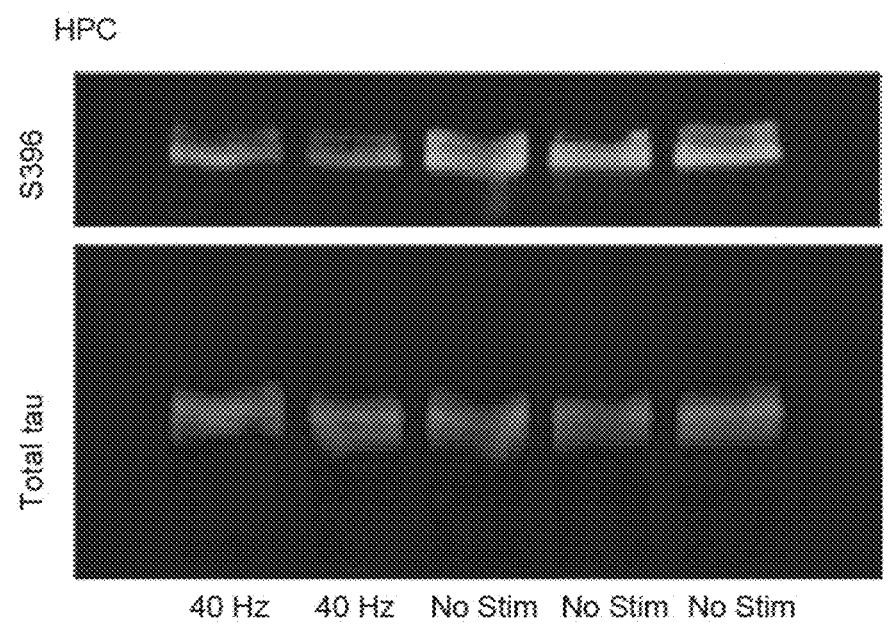

FIG. 12H shows as in FIG. 12G for hippocampus.

Figure 12I:
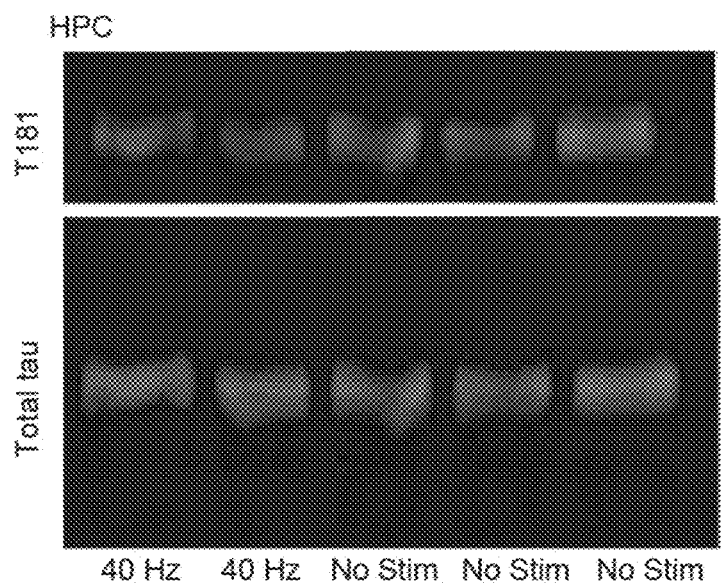

FIG. 12I shows representative western blot showing levels of pTau (T181) and total tau in hippocampus of 6-month-old P301S mice after 7 days of 1 hour per day no stimulation or auditory GENUS.

Figure 12J:
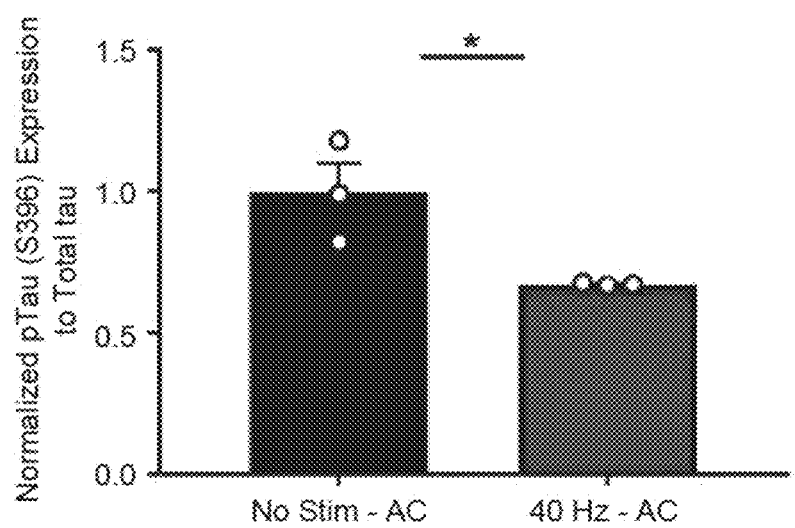

FIG. 12J shows relative immunoreactivity of pTau (S396) normalized to total tau in AC of P301S mice (from western blot in G) after 7 days of 1 hour per day no stimulation or auditory GENUS (n=3 mice per group, mean s.e.m. in bar graphs, *P<0.05; unpaired Mann-Whitney test).

Figure 12K:
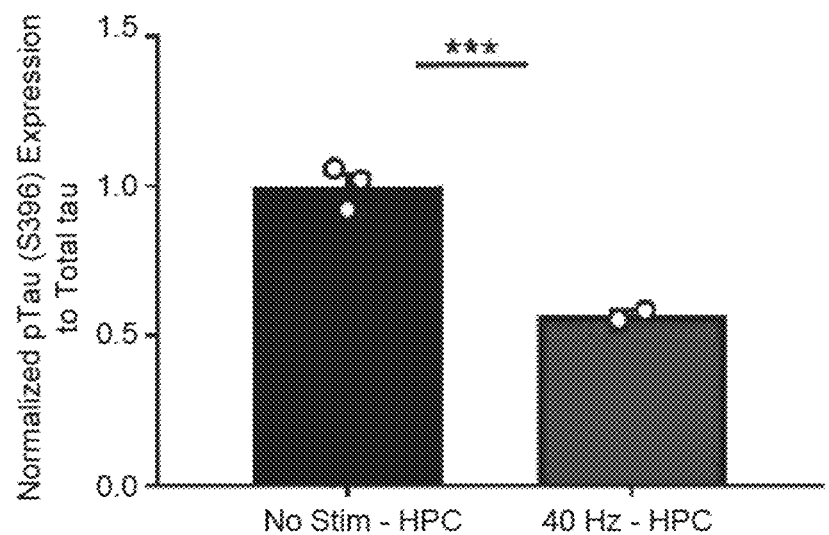

FIG. 12K shows relative immunoreactivity of pTau (S396) normalized to total tau in HPC of P301S mice (from western blot in H) after 7 days of 1 hour per day no stimulation or auditory GENUS (n=2 mice in 40 Hz group and n=3 in non-stimulation group, mean s.e.m. in bar graphs, ***P<0.001; unpaired Mann-Whitney test).

Figure 12L:
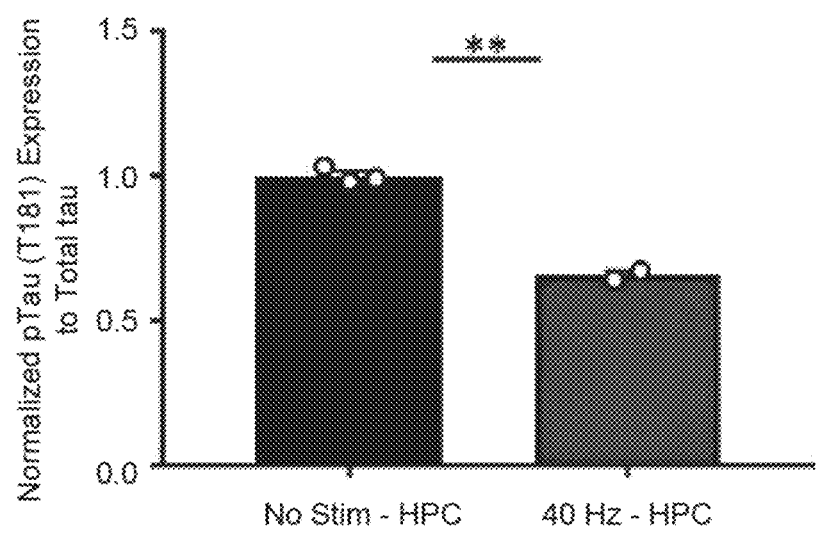

FIG. 12L shows relative immunoreactivity of pTau (T181) normalized to total tau in hippocampus of P301S mice (from western blot in I) after 7 days of 1 hour per day no stimulation or auditory GENUS (n=2 mice in 40 Hz group and n=3 in non-stimulation group, mean s.e.m. in bar graphs, **P<0.01; unpaired Mann-Whitney test).

Figure 13A:
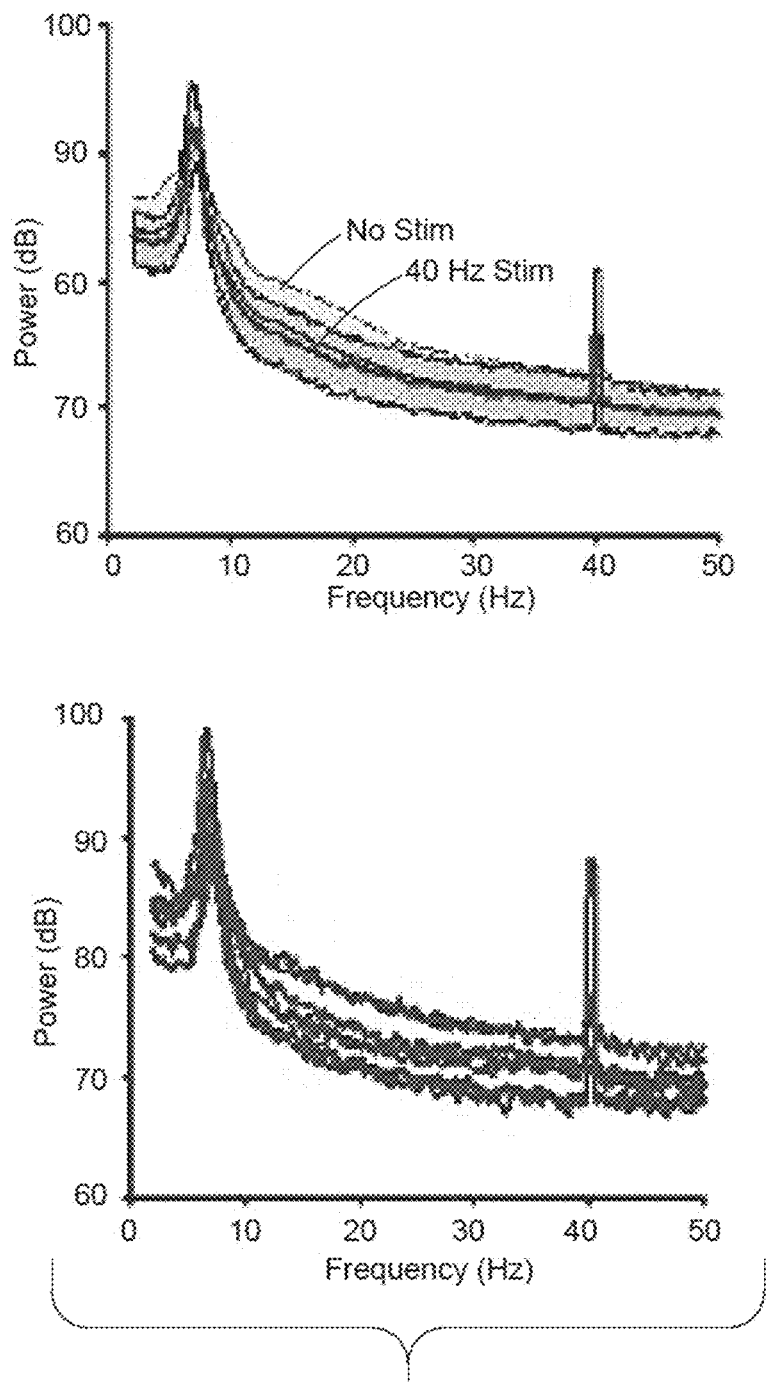
FIG. 13A-13U show 40 Hz combined auditory and visual stimulation modulates spiking activity in AC, CA1, and mPFC.

FIG. 13A shows power spectral density (PSD) response to 40 Hz audio-visual flicker stimuli and no stimulation periods, with mean and standard deviation across recording days (left), power spectrum LFP response to audio-visual flicker stimulation of all recording days in AC (recording site with largest 40 Hz peak during 40 Hz audio-visual flicker per recording depth is shown, see Methods) (right).

Figure 13B:
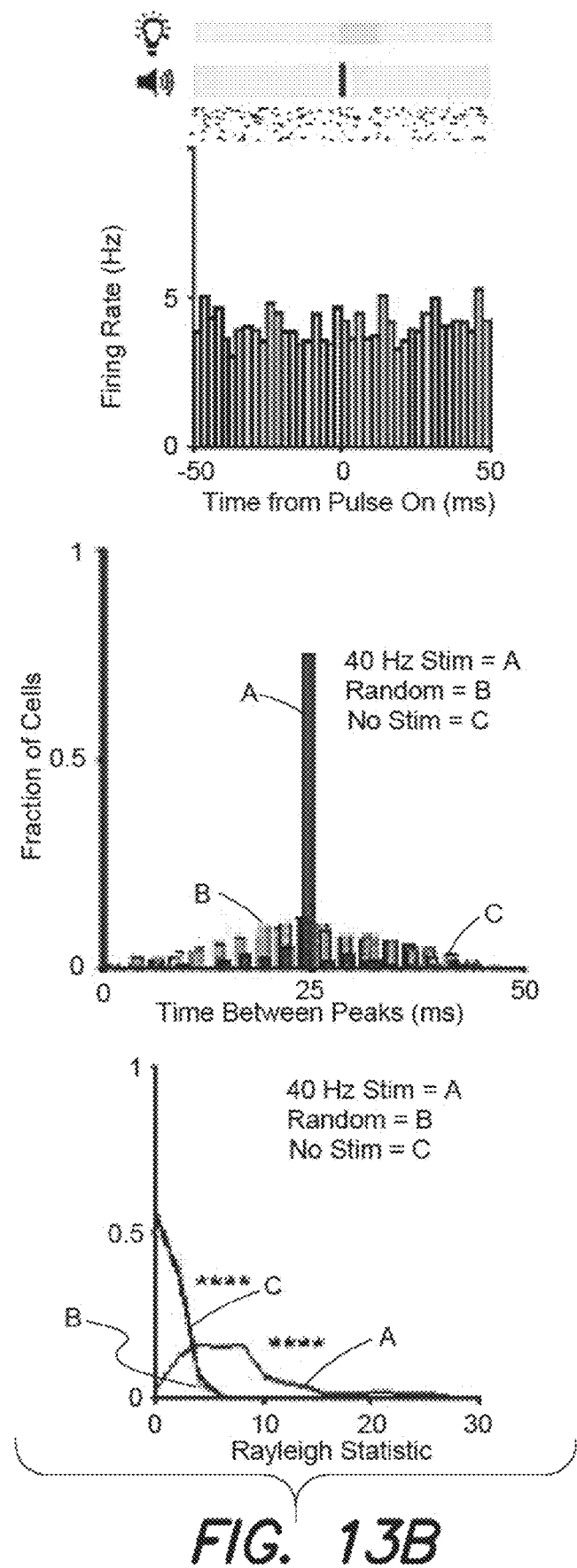

FIG. 13B shows firing rate modulation, below, of putative single unit shown in FIG. 13A to audio-visual random stimulation; raster plot, above, shows spiking of the single unit to 10 s of random stimulation (left). Distribution of intervals between peaks in firing rate response to audio-visual stimulation in AC (center, proportion of intervals around inter-stimulus interval: P=0 40 Hz vs. No stim, P=0 40 Hz vs. Random; z-Test for two proportions), Rayleigh statistic distribution of single unit response to 40 Hz audio-visual stimulation (right, ****P<0.0001, P=2×10$^{-79}$ 40 Hz vs. No Stim, P=1×10$^{-72}$40 Hz vs. Random; Kolmogorov-Smirnov test; 20 units had 40 Hz stim RS values greater than 30; 2 units had random stim RS values greater than 30).

Figure 13C:
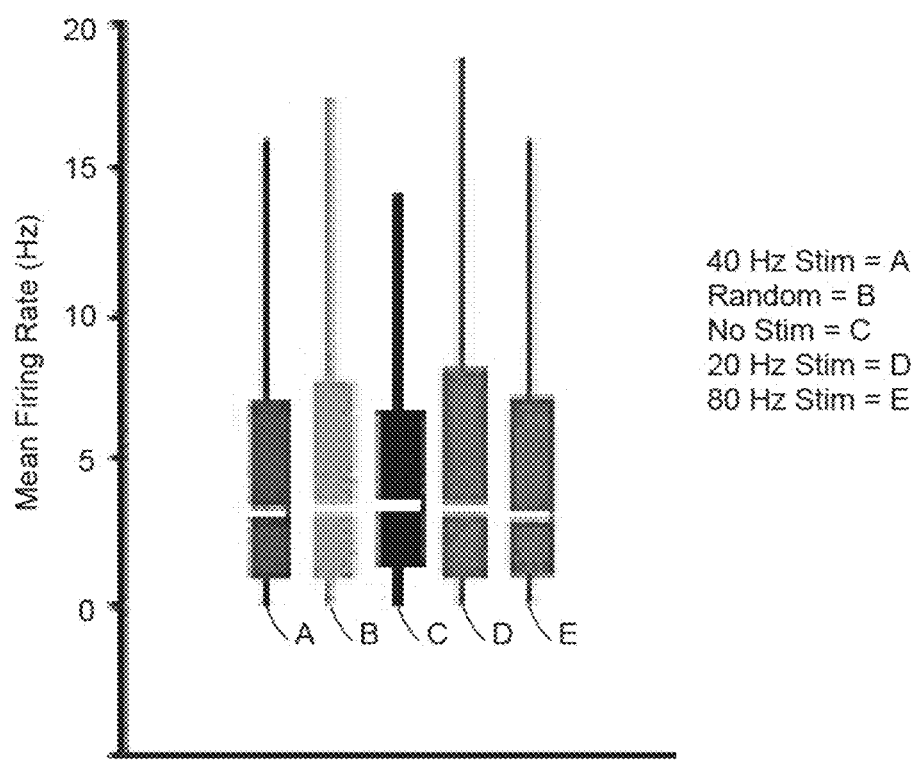

FIG. 13C shows single unit mean firing rate during all audio-visual stimulation conditions.

Figure 13D:
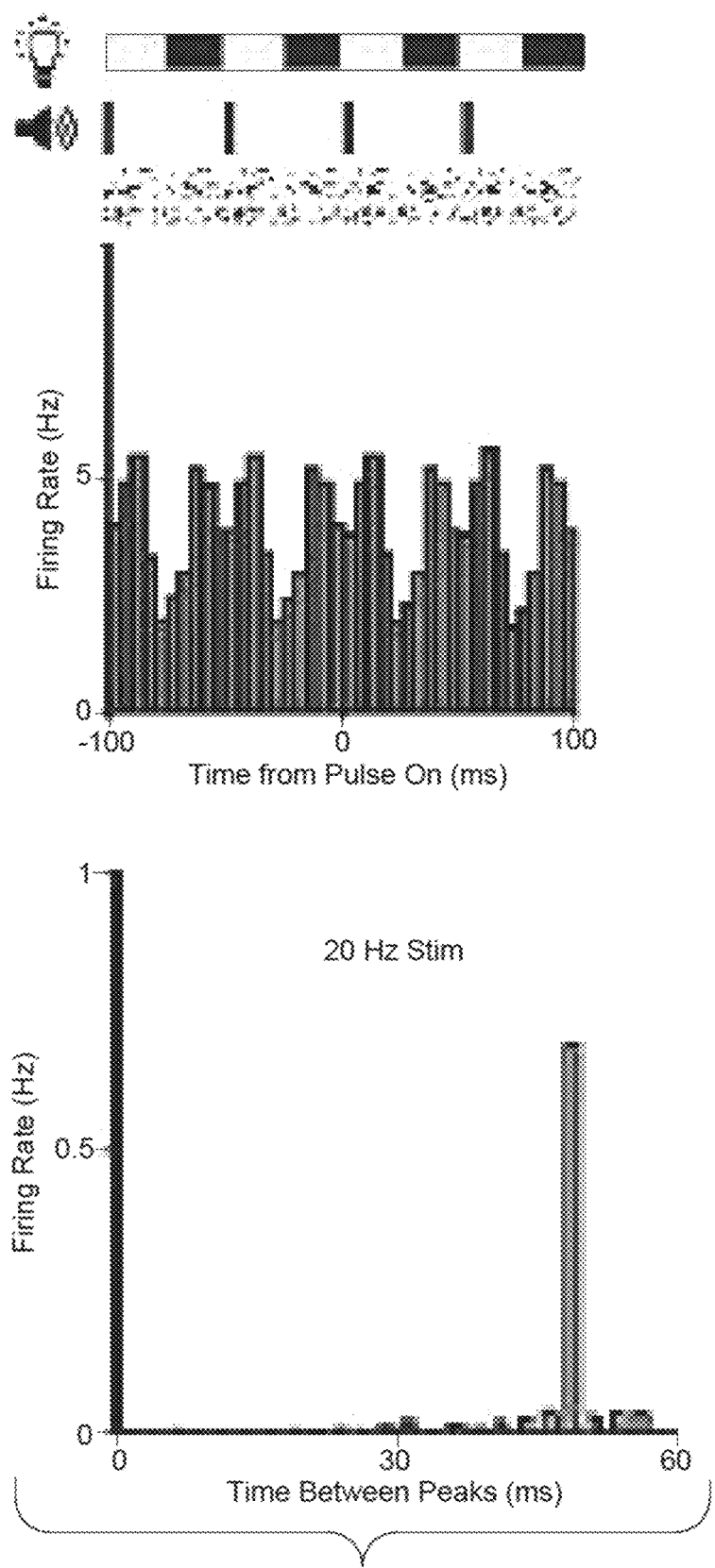

FIG. 13D shows firing rate modulation of a putative single unit in response to 20 Hz audio-visual flicker stimulation (left, below), raster plot shows spiking in response to 10 s of stimulation (left, above). Distribution of intervals between peaks in firing rate response to 20 Hz audio-visual stimulation (right, proportion of intervals around inter-stimulus interval: P=0 20 Hz vs. No stim; z-Test for two proportions).

FIG. 13E shows firing rate modulation of the same unit shown in D in response to 80 Hz audio-visual flicker stimulation (left, below), raster plot shows spiking in response to 10 s of stimulation (left, above). Distribution of intervals between peaks in firing rate response to 80 Hz audio-visual stimulation (right, proportion of intervals around inter-stimulus interval: P=0 80 Hz vs. No stim; z-Test for two proportions).

Figure 13F:
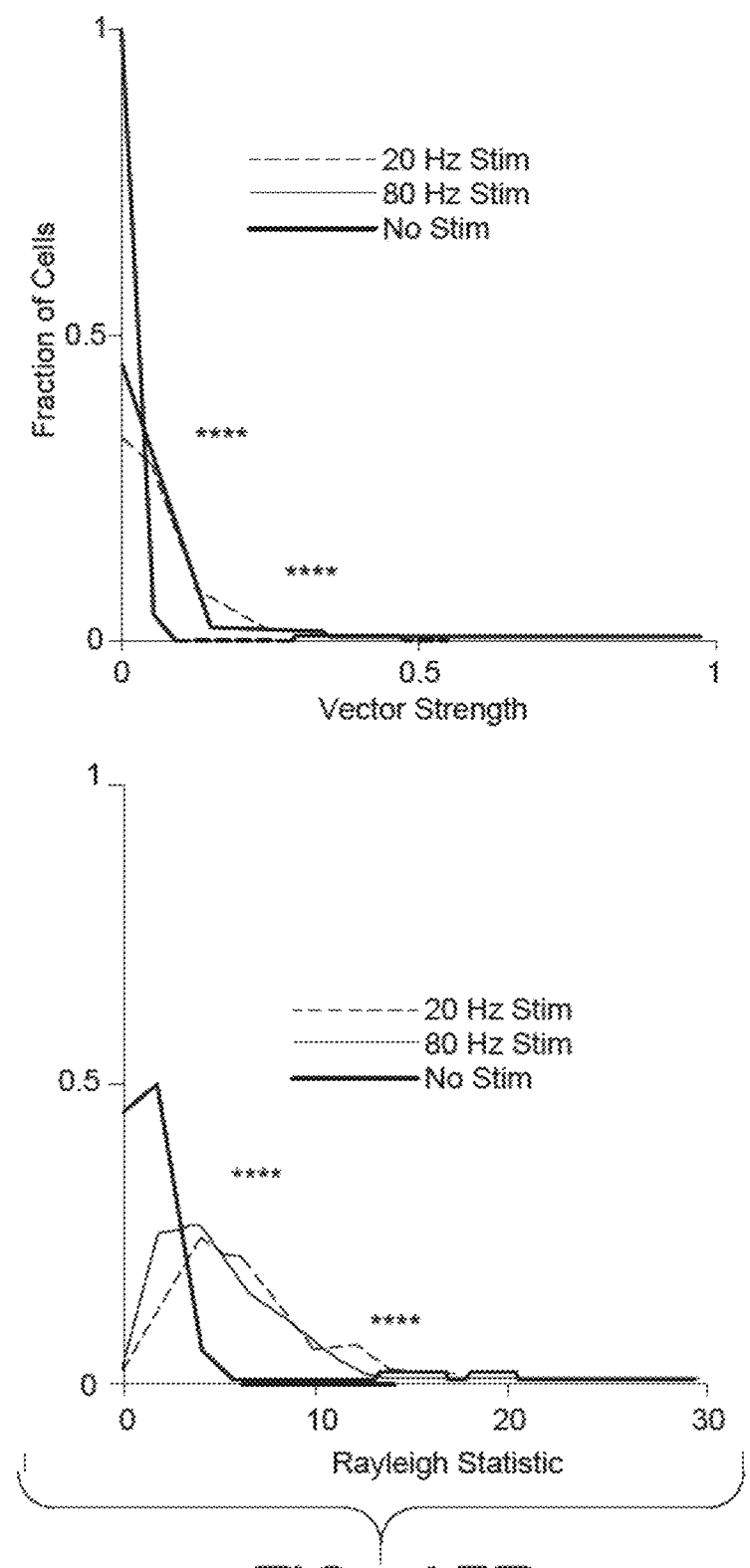

FIG. 13F shows vector strength distribution of 20 Hz and 80 Hz auditory stimulation is higher than no stimulation condition (left, **P<0.0001, P=2×10$^{-63}$20 Hz vs. No Stim, P=1×10$^{-56}$ 80 Hz vs. No Stim; Kolmogorov-Smirnov test), and Rayleigh statistic distribution of 20 Hz and 80 Hz auditory stimulation higher than no stimulation (right, **P<0.0001, P=1×10$^{-88}$ 20 Hz vs. No Stim, P=5×10$^{-72}$ 80 Hz vs. No Stim; Kolmogorov-Smirnov test; 50 units had 20 Hz stim RS values greater than 30; 19 units had 80 Hz stim RS values greater than 30).

Figure 13G:
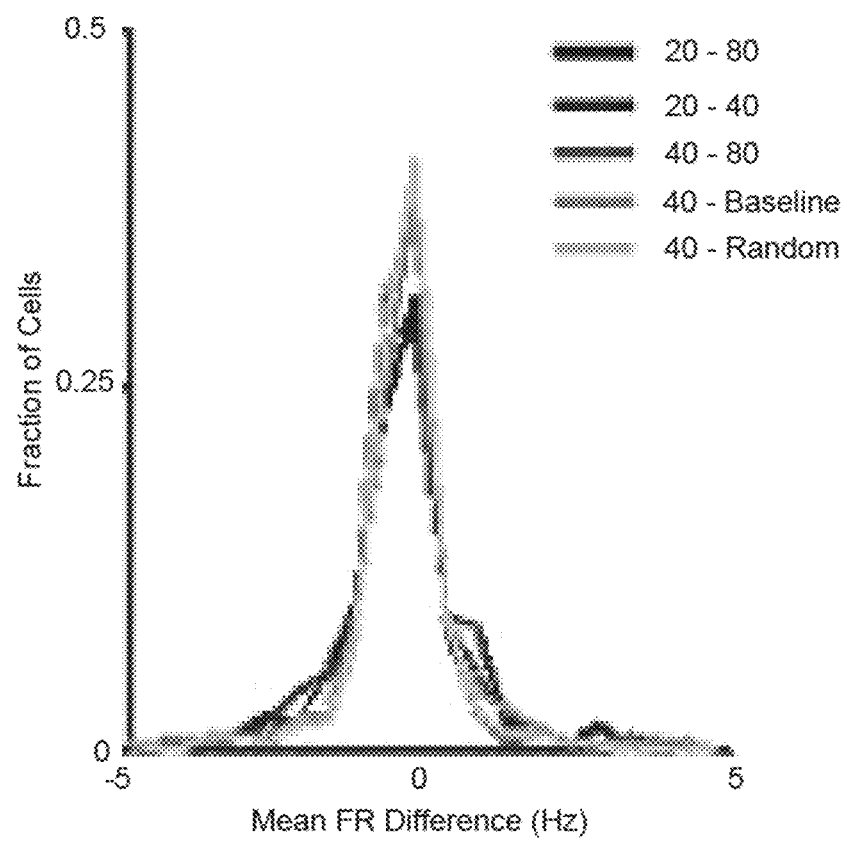

FIG. 13G shows mean firing rate difference of single units between multiple stimulation conditions in AC centers around 0 Hz (*P<0.05 20 Hz-80 Hz, *P<0.05 20 Hz-40 Hz, all others n.s.; Wilcoxon signed rank test for zero median).

Figure 13H:
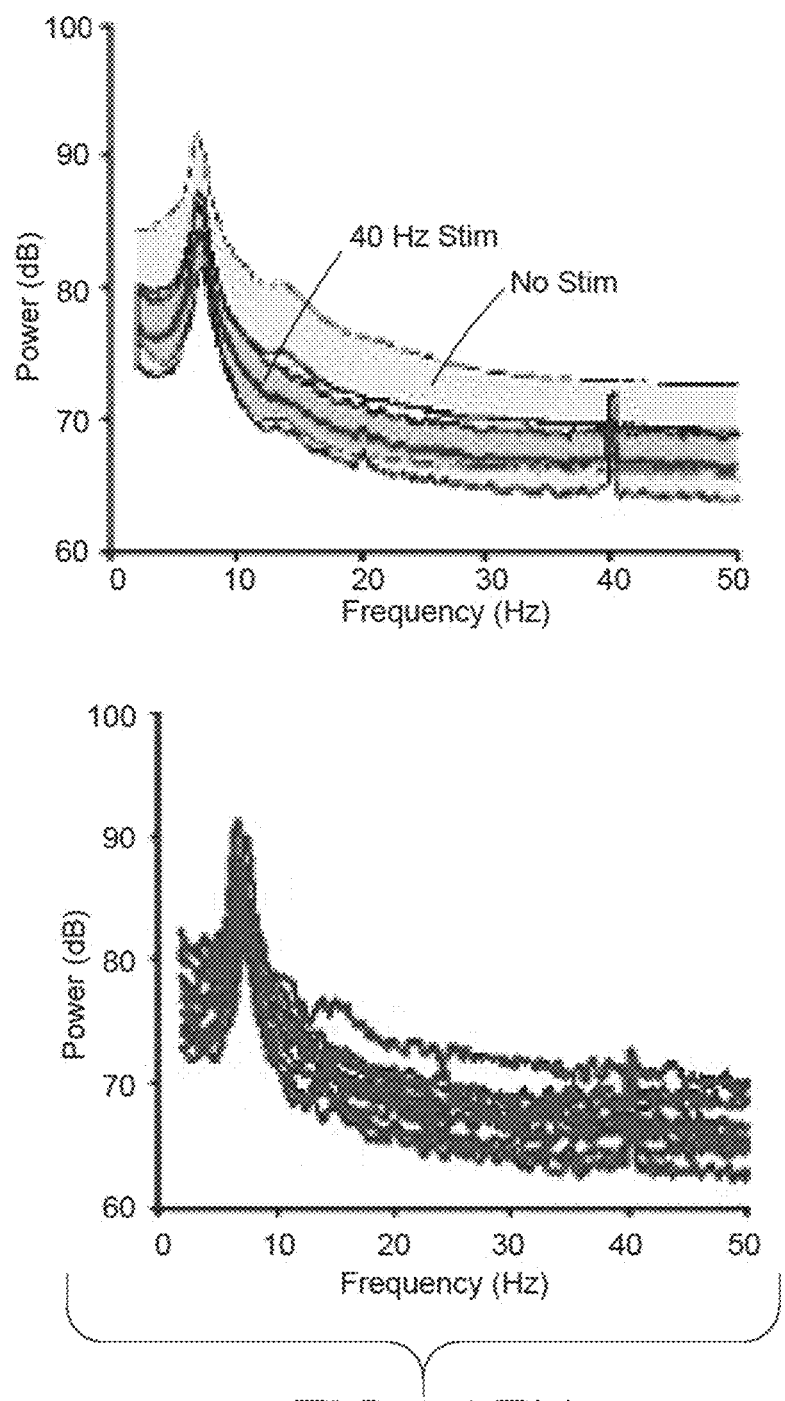

FIG. 13H shows same as A for CA1.

Figure 13I:
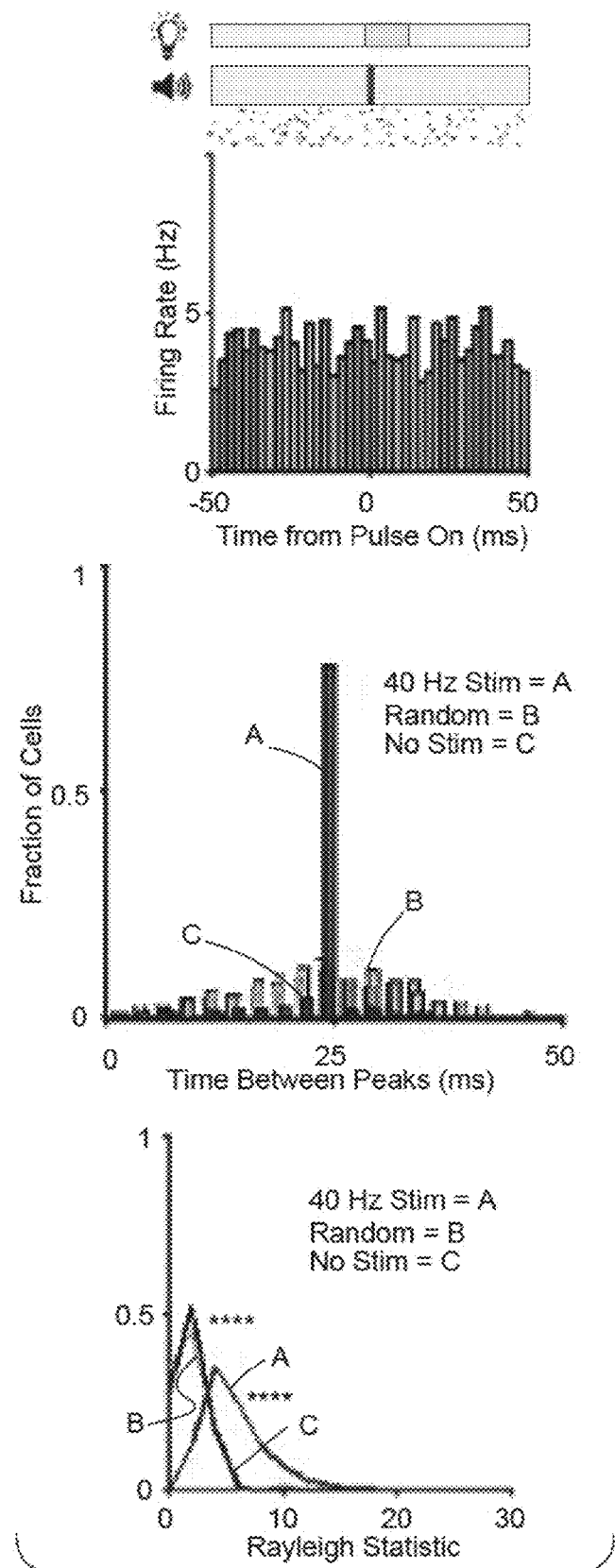

FIG. 13I shows same as B for CA1 (right, ****P<0.0001, P=1×10$^{-71}$ 40 Hz vs. No Stim, P=1×10$^{-71}$ 40 Hz vs. Random; Kolmogorov-Smirnov test. Center, proportion of intervals around inter-stimulus interval: P=0 40 Hz vs. No stim, P=0 40 Hz vs. Random; z-Test for two proportions).

Figure 13J:
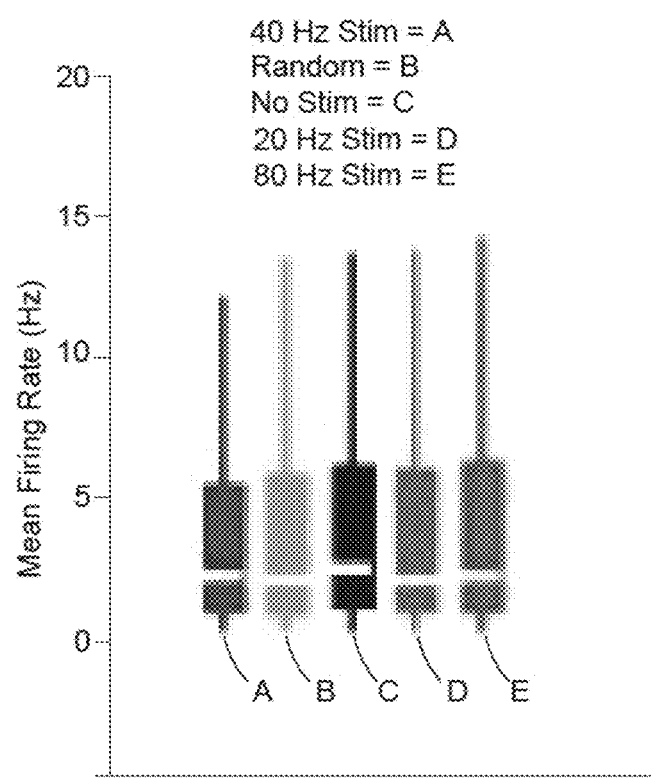

FIG. 13J shows same as C for CA1.

FIG. 13K shows same as D for CA1 (right, P=0 20 Hz vs. No stim; z-Test for two proportions).

FIG. 13L shows same as E for CA1 (right, P=0 80 Hz vs. No stim; z-Test for two proportions).

Figure 13M:
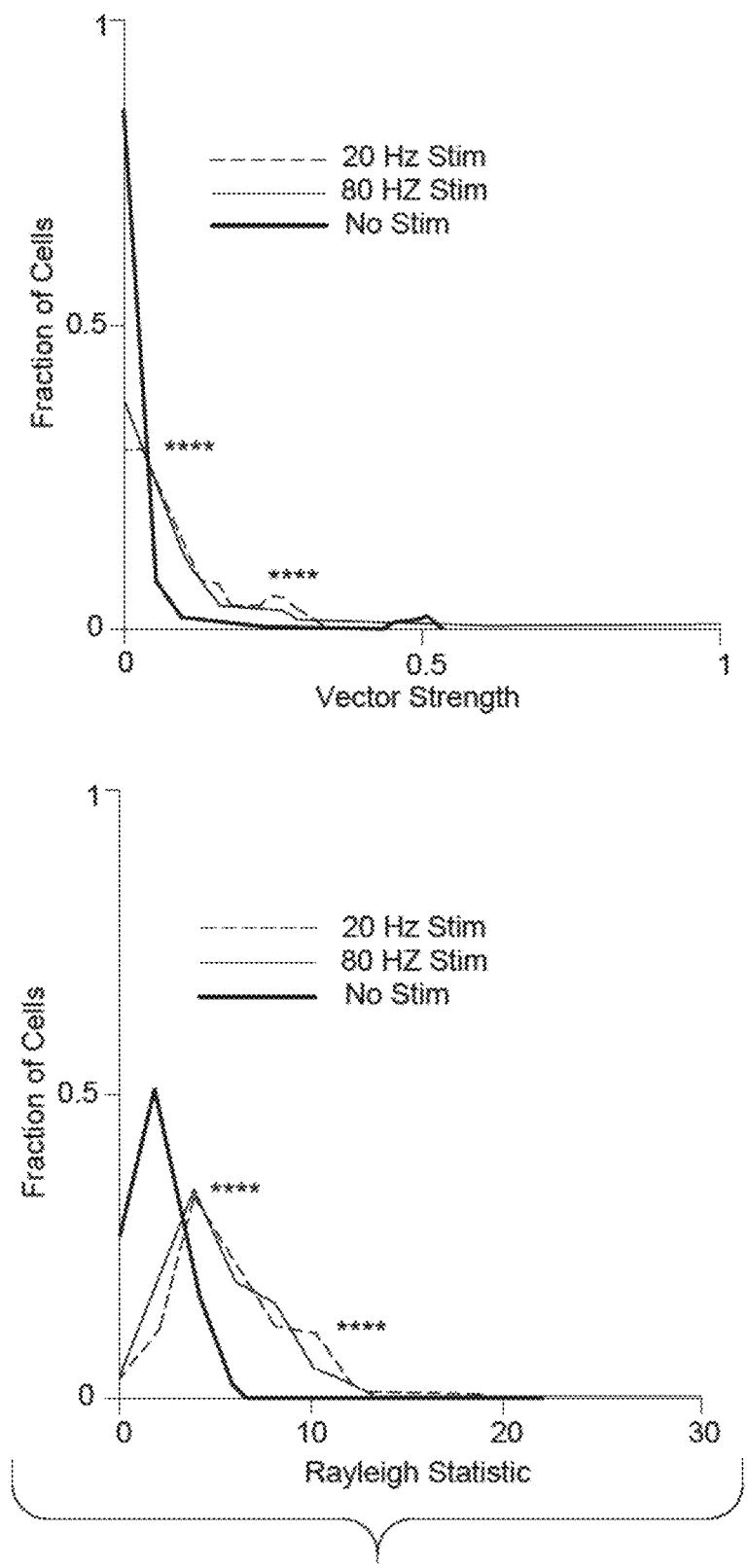

FIG. 13M shows same as F for CA1 (left, **P<0.0001, P=8×10$^{-43}$ 20 Hz vs. No Stim, P=8×10$^{-40}$ 80 Hz vs. No Stim; Kolmogorov-Smirnov test; right, **P<0.0001, P=2×10$^{-70}$ 20 Hz vs. No Stim, P=1×10$^{-57}$ 80 Hz vs. No Stim; Kolmogorov-Smirnov test).

Figure 13N:
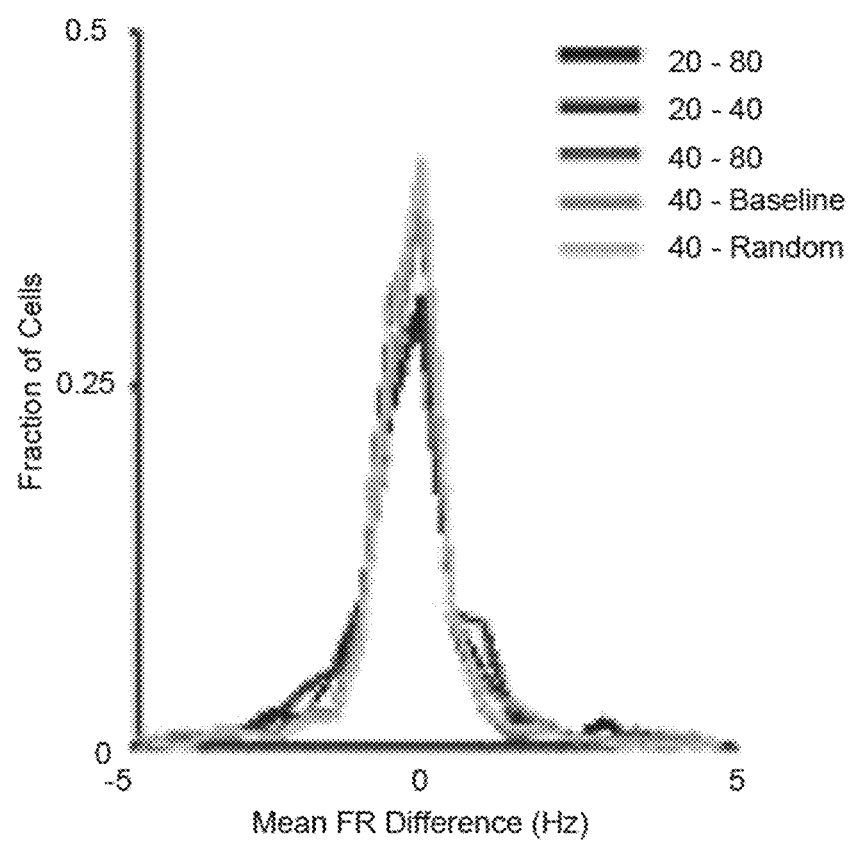
Figure 130:
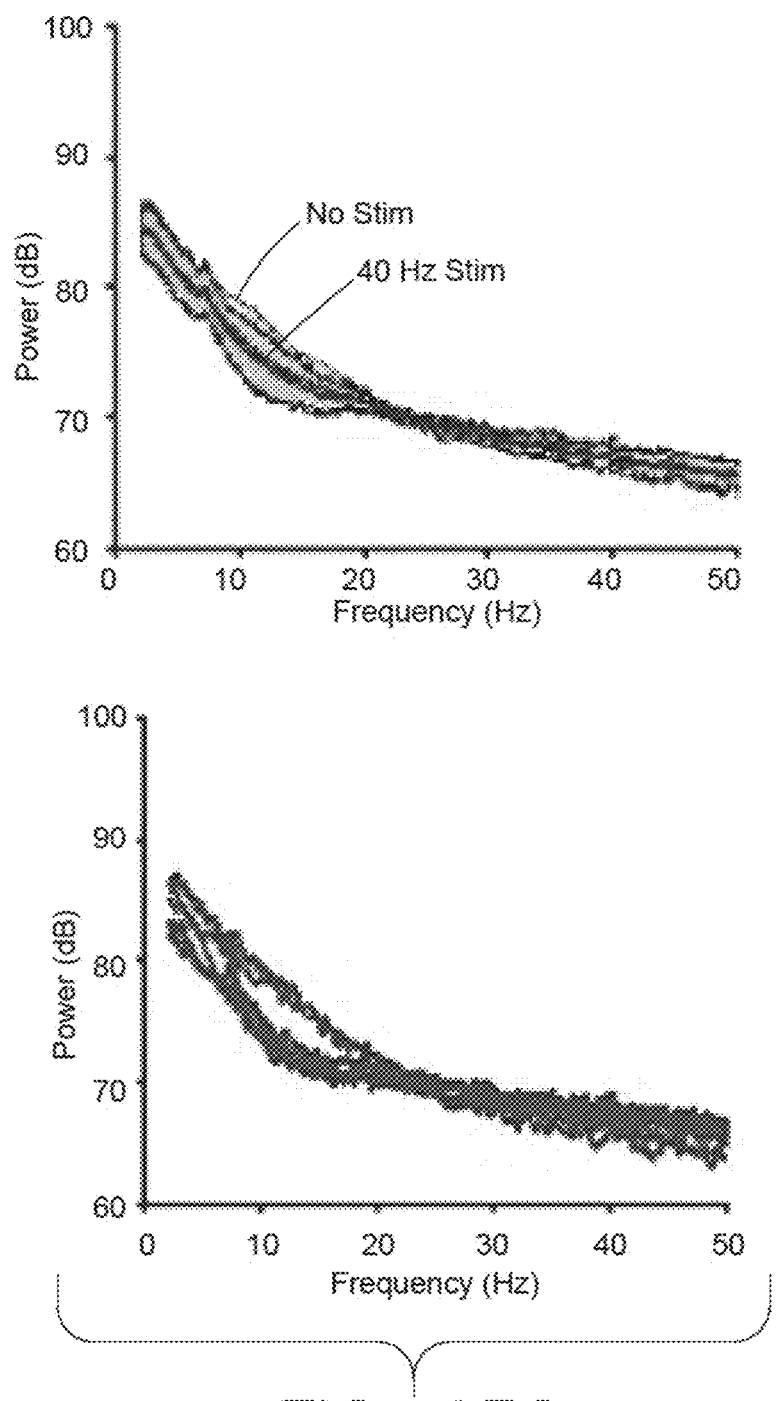

FIG. 13N shows same as G for CA1 (all n.s.; Wilcoxon signed rank test for zero median).

FIG. 13O shows same as A for mPFC.

Figure 13P:
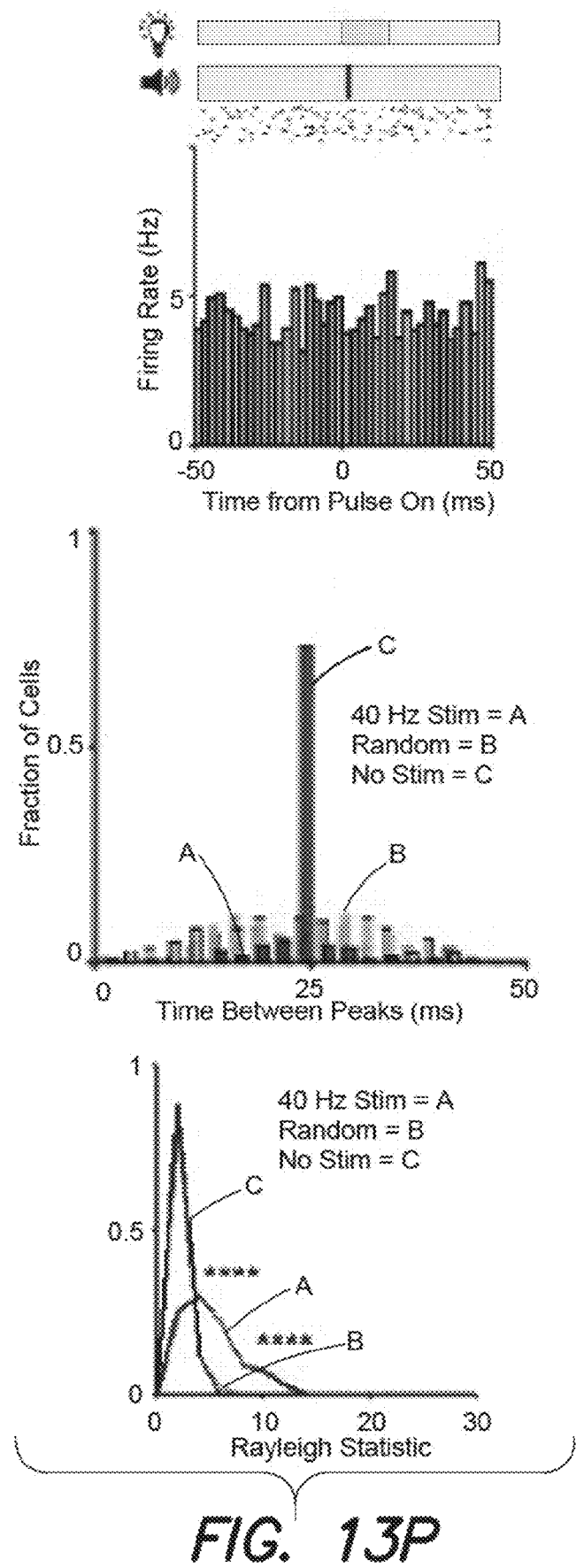

FIG. 13P shows same as B for mPFC (right, ****P<0.0001, P=5×10$^{-23}$ 40 Hz vs. No Stim, P=3×10$^{-21}$ 40 Hz vs. Random; Kolmogorov-Smirnov test. Center, proportion of intervals around inter-stimulus interval: P=0 40 Hz vs. No stim, P=0 40 Hz vs. Random; z-Test for two proportions).

Figure 13Q:
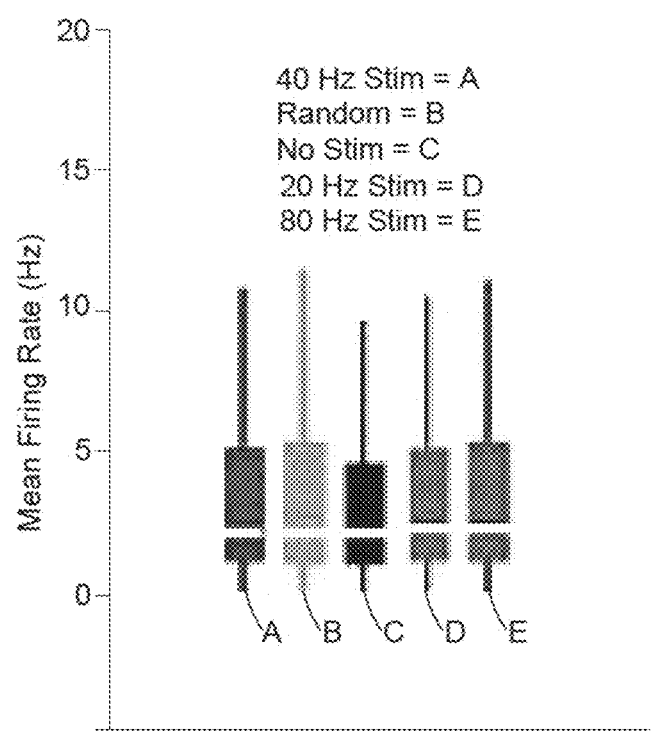

FIG. 13Q shows same as C for mPFC.

FIG. 13R shows same as D for mPFC (right, P=0 20 Hz vs. No stim; z-Test for two proportions).

Figure 13S:
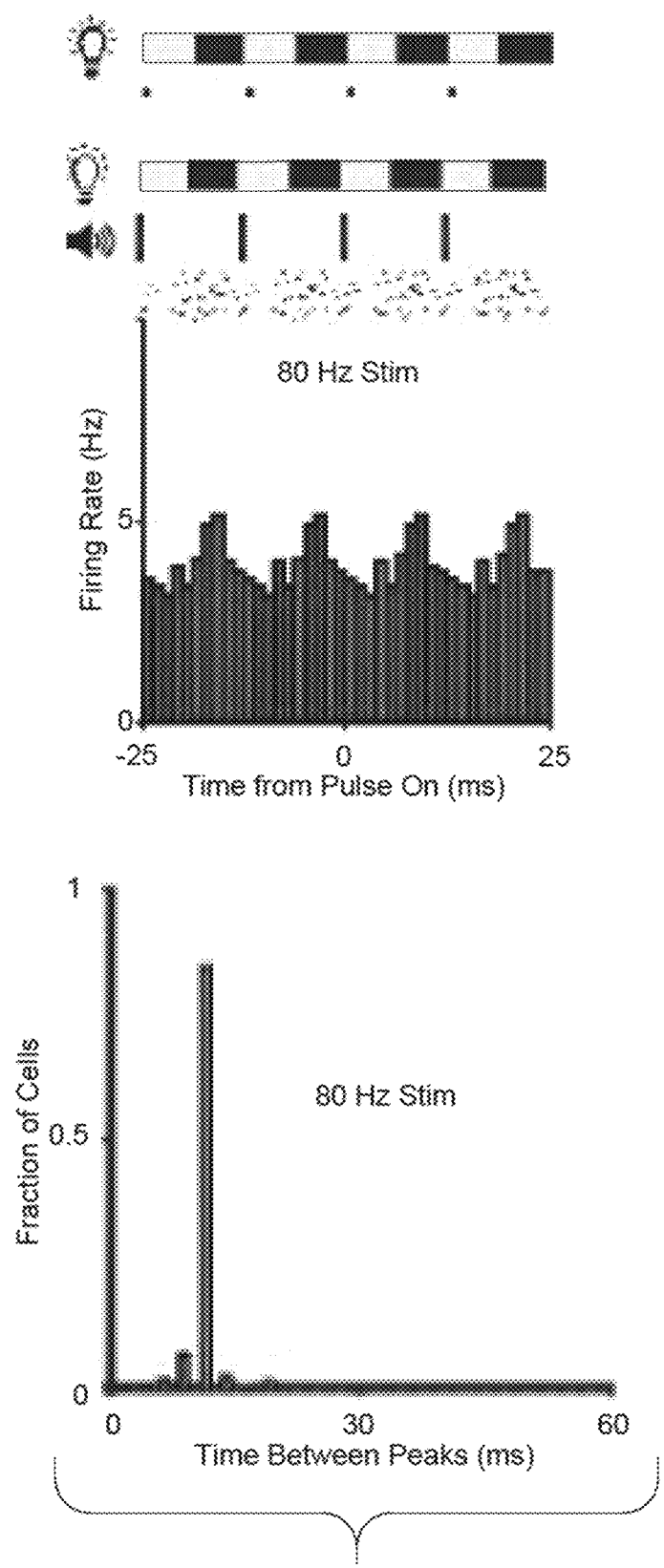

FIG. 13S shows same as E for mPFC (right, P=0 80 Hz vs. No stim; z-Test for two proportions).

Figure 13T:
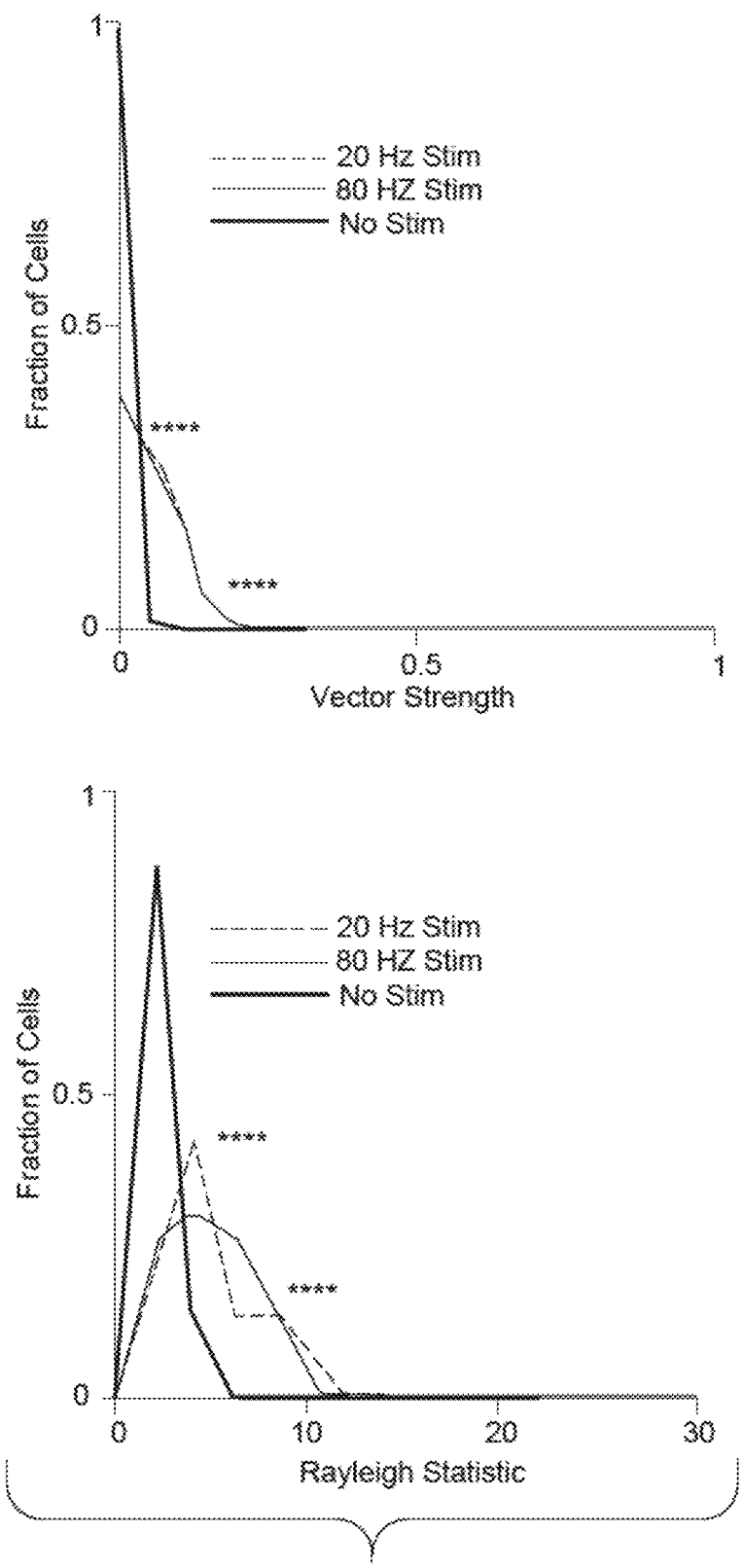

FIG. 13T shows same as F for mPFC (left, **P<0.0001, P=1×10$^{-23}$ 20 Hz vs. No Stim, P=2×10$^{-25}$ 80 Hz vs. No Stim; Kolmogorov-Smirnov test; right, **P<0.0001, P=1×10$^{-23}$ 20 Hz vs. No Stim, P=8×10$^{-25}$ 80 Hz vs. No Stim; Kolmogorov-Smirnov test).

Figure 13U:
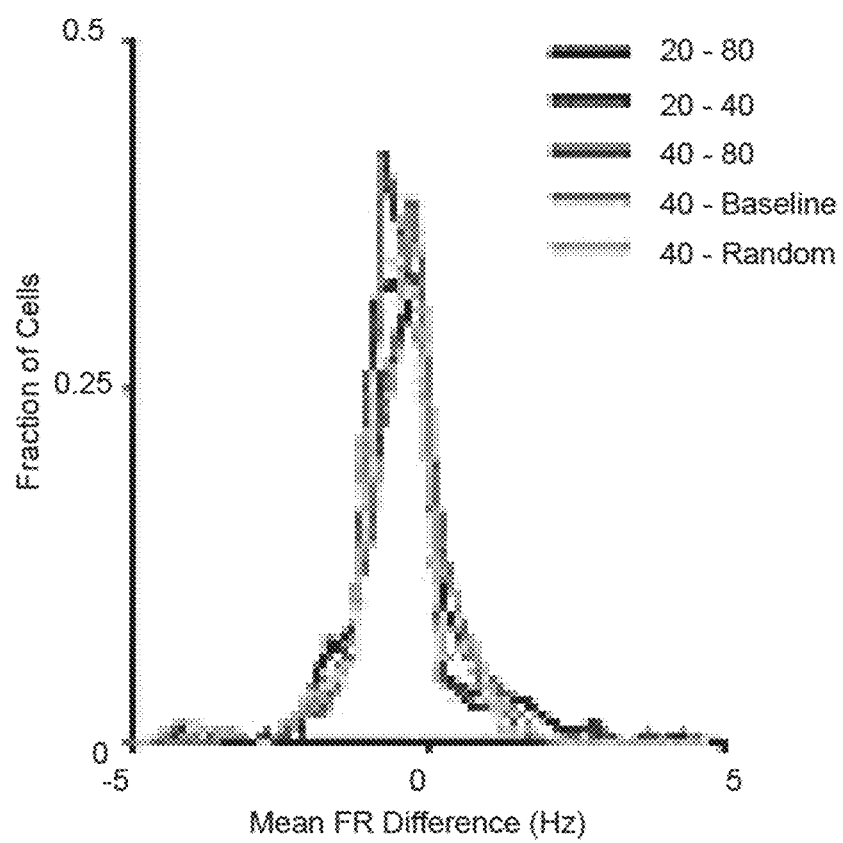

FIG. 13U shows same as G for mPFC (*P<0.05 40 Hz—No Stim, all others n.s.; Wilcoxon signed rank test for zero median).

Figure 14A:
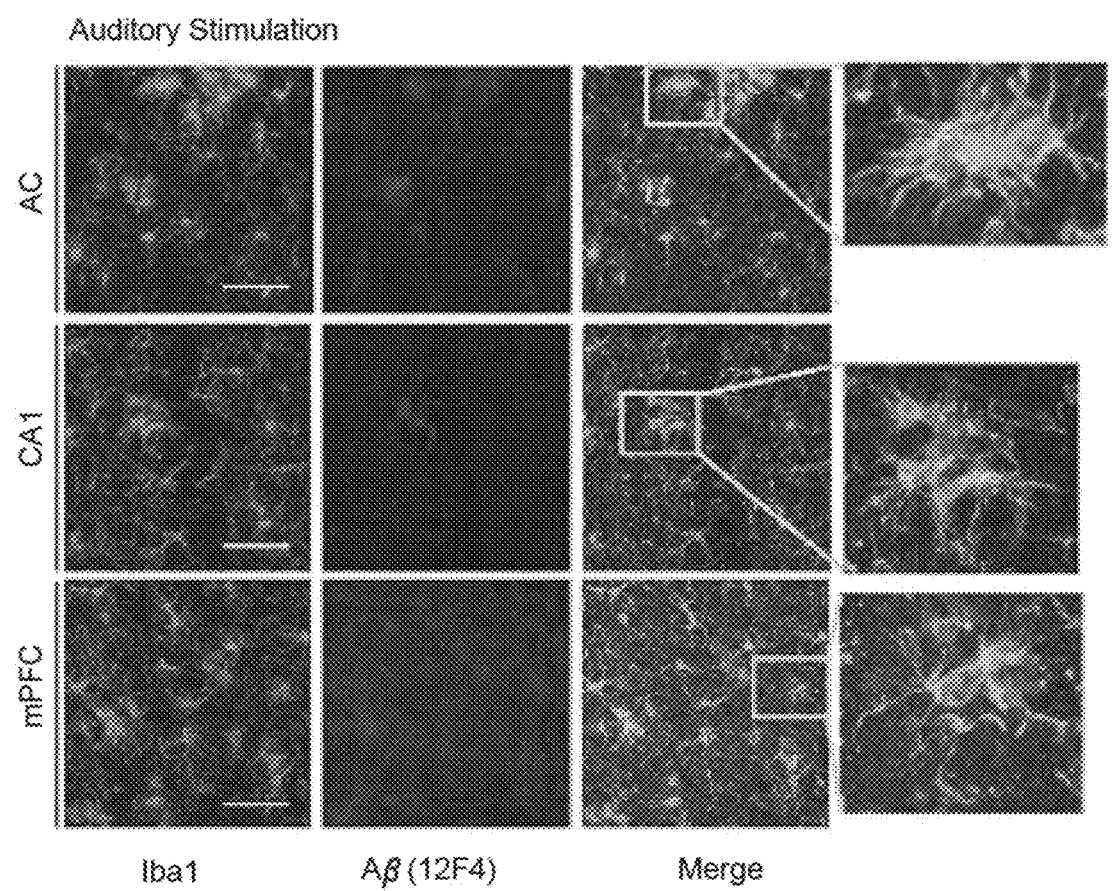
FIG. 14A-14V show 1-week of auditory or visual GENUS only do not affect mPFC pathology.

FIG. 14A shows immunohistochemistry of anti-Iba1 (019-19741, green) and anti-Aβ (12F4, red) antibodies in AC, CA1, and mPFC of 6-month-old 5XFAD mice after 7 days of 1 hour per day of auditory GENUS (inset magnification, 100×; scale bar, 50 μm).

Figure 14B:
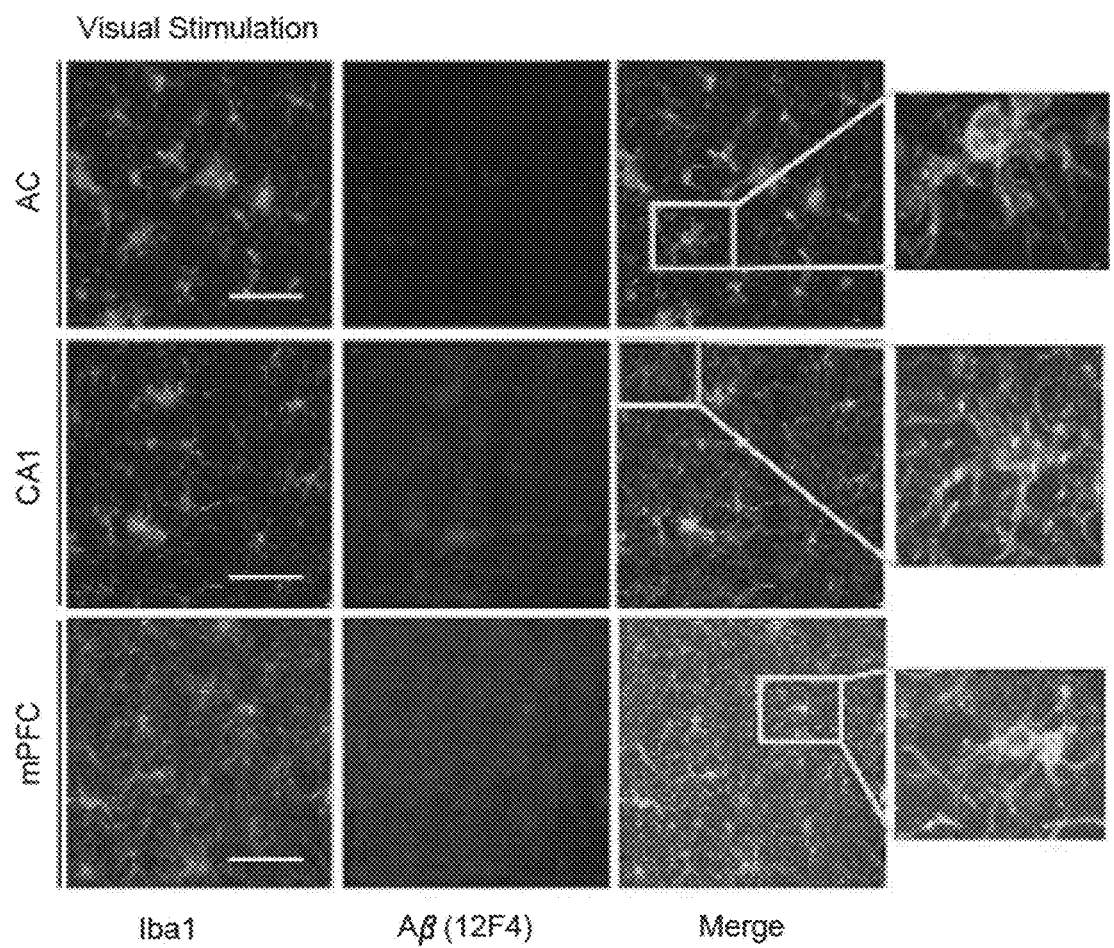

FIG. 14B shows immunohistochemistry of anti-Iba1 (019-19741, green) and anti-Aβ (12F4, red) antibodies in VC, CA1, and mPFC of 6-month-old 5XFAD mice after 7 days of 1 hour per day of visual GENUS (inset magnification, 100×; scale bar, 50 μm).

Figure 14C:
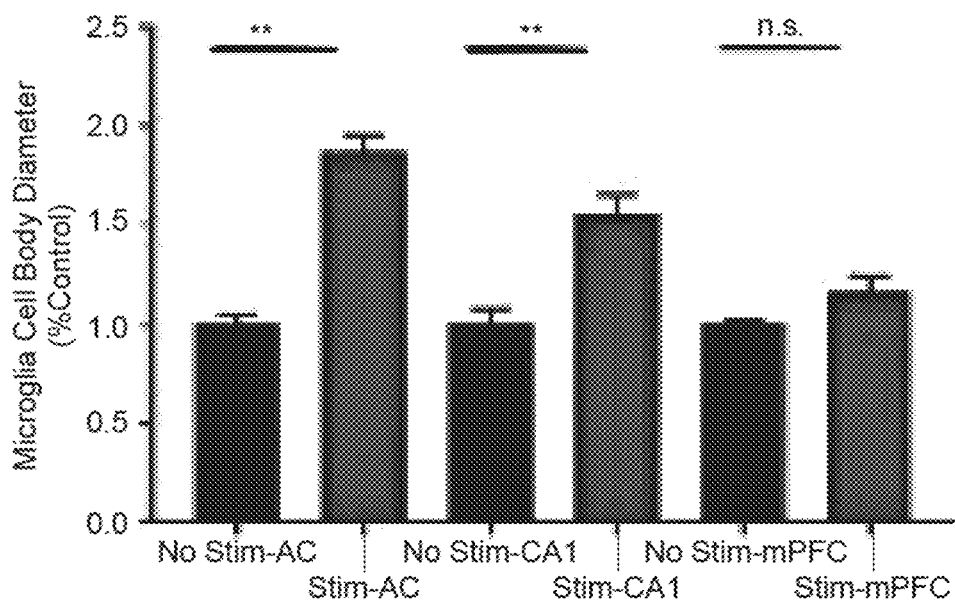

FIG. 14C shows average microglia cell body diameter in AC, CA1, and mPFC of 6-month-old 5XFAD mice after 7 days of 1 hour per day of auditory GENUS, normalized to no stimulation control (n=6 mice per group, mean s.e.m. in bar graphs, n.s.=not significant, **P<0.01, unpaired Mann-Whitney test).

Figure 14D:
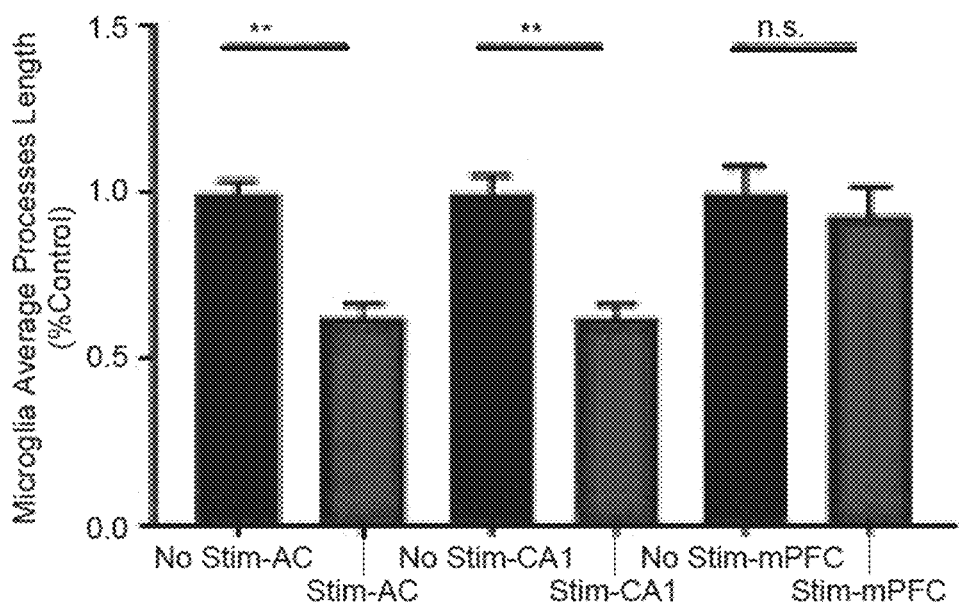

FIG. 14D shows average microglia process length in AC, CA1, and mPFC of 6-month-old 5XFAD mice after 7 days of 1 hour per day of auditory GENUS, normalized to no stimulation control (n=6 mice per group, mean s.e.m. in bar graphs, n.s.=not significant, **P<0.01, unpaired Mann-Whitney test).

Figure 14E:
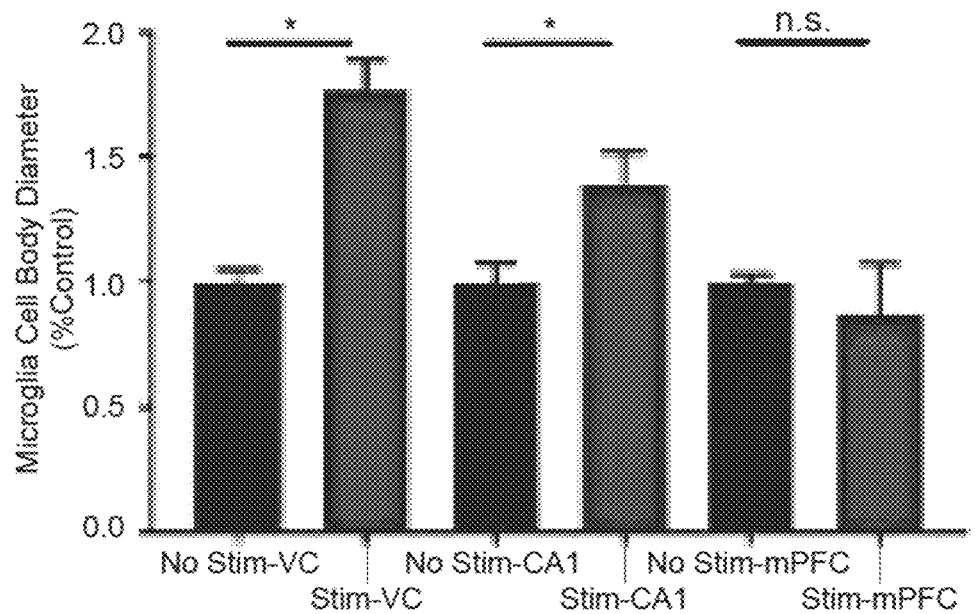

FIG. 14E shows microglia count per region of interest in AC, CA1, and mPFC of 6-month-old 5XFAD mice after 7 days of 1 hour per day of auditory GENUS (n=6 mice per group, mean s.e.m. in bar graphs, n.s.=not significant, **P<0.01, unpaired Mann-Whitney test).

Figure 14F:
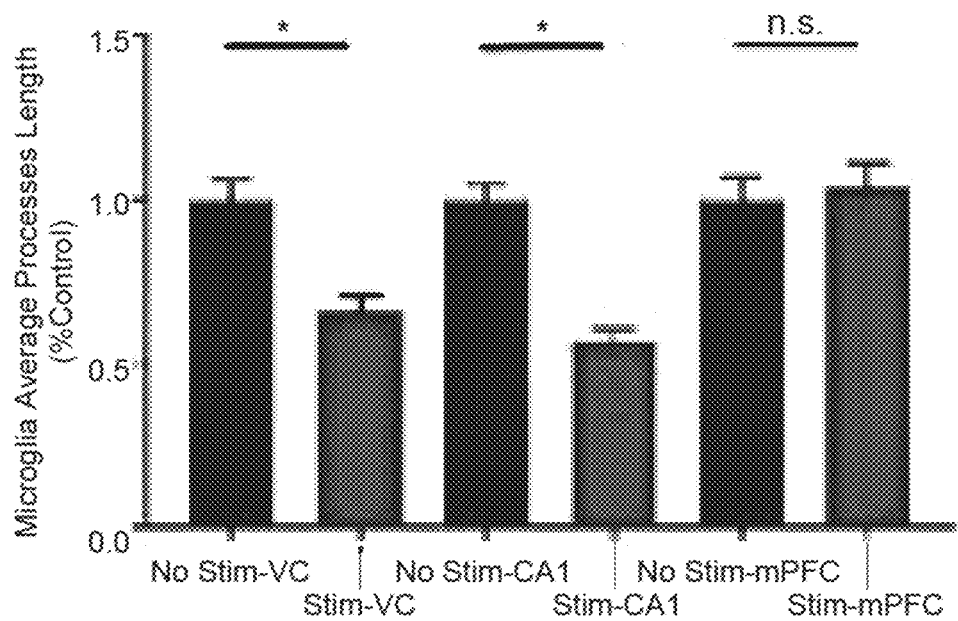

FIG. 14F shows average number of microglia surrounding 25 μm radium of a plaque in AC, CA1, and mPFC following no stimulation or auditory GENUS (n=6 mice per group, mean s.e.m. in bar graphs, n.s.=not significant, unpaired Mann-Whitney test).

Figure 14G:
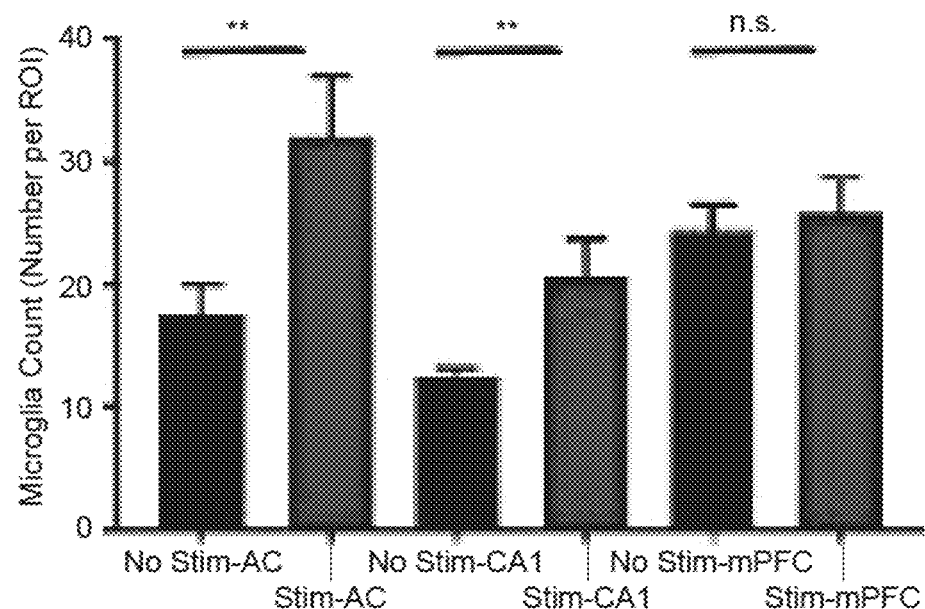

FIG. 14G shows average microglia cell body diameter in VC, CA1, and mPFC of 6-month-old 5XFAD mice after 7 days of 1 hour per day of visual GENUS, normalized to no stimulation control (n=6 mice per group, mean s.e.m. in bar graphs, n.s.=not significant, *P<0.05; unpaired Mann-Whitney test).

Figure 14H:
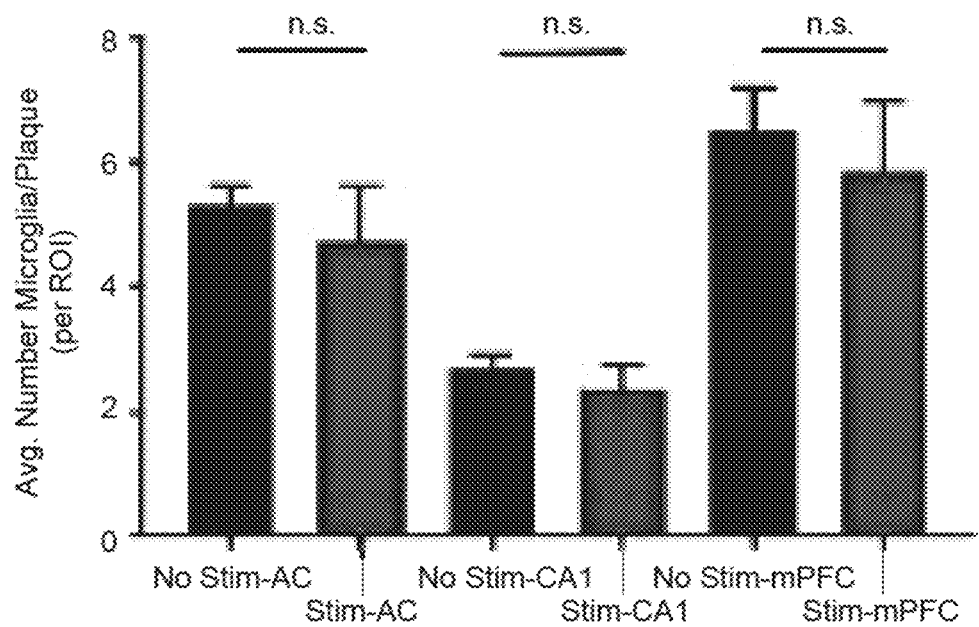

FIG. 14H shows average microglia process length in VC, CA1, and mPFC of 6-month-old 5XFAD mice after 7 days of 1 hour per day of visual GENUS, normalized to no stimulation control (n=6 mice per group, mean s.e.m. in bar graphs, n.s.=not significant, *P<0.05; unpaired Mann-Whitney test).

Figure 14I:
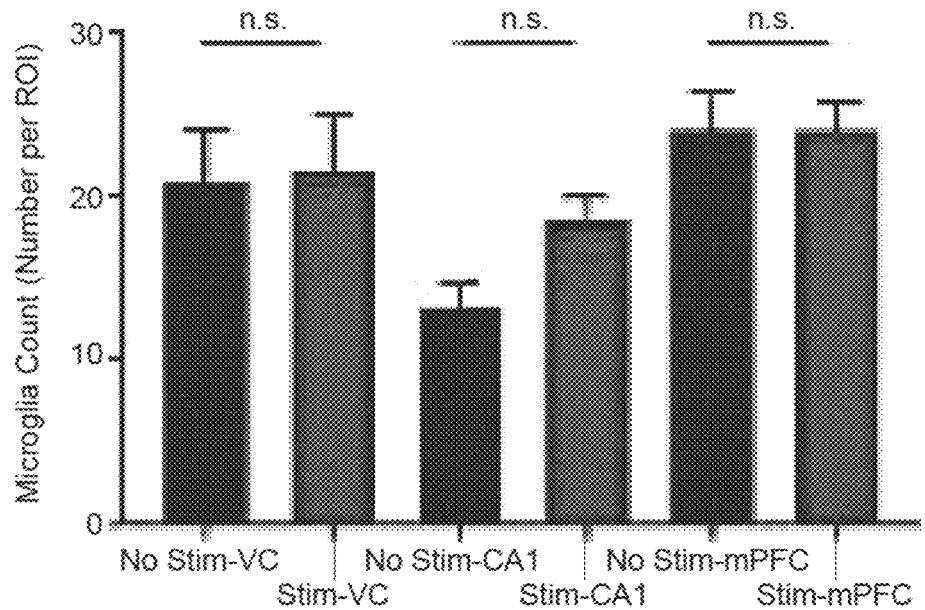

FIG. 14I shows microglia count per region of interest in VC, CA1, and mPFC of 6-month-old 5XFAD mice after 7 days of 1 hour per day of visual GENUS (n=6 mice per group, mean s.e.m. in bar graphs, n.s.=not significant, unpaired Mann-Whitney test).

Figure 14J:
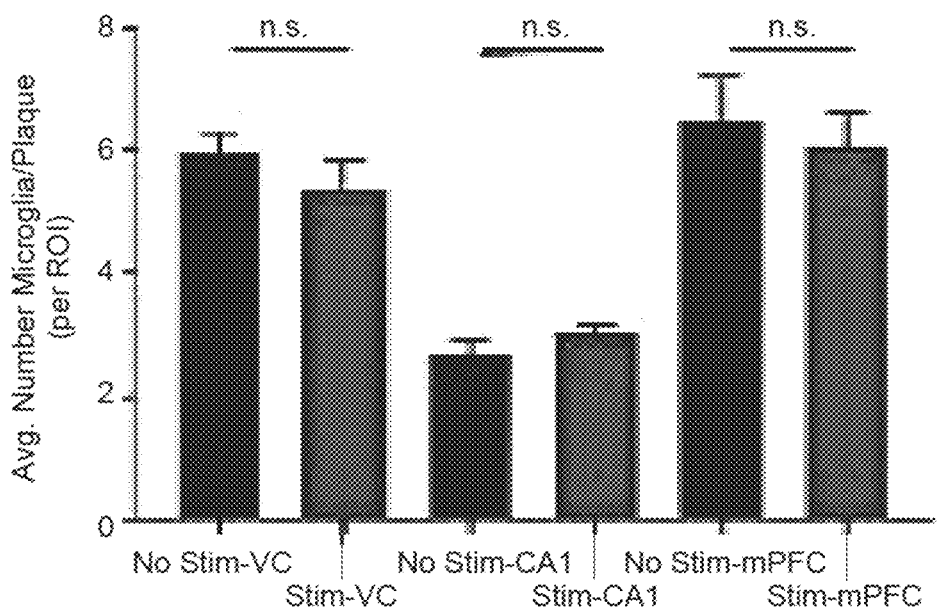

FIG. 14J shows average number of microglia surrounding 25 µm radium of a plaque in VC, CA1, and mPFC following no stimulation or visual GENUS (n=6 mice per group, mean s.e.m. in bar graphs, n.s.=not significant, unpaired Mann-Whitney test).

Figure 14K:
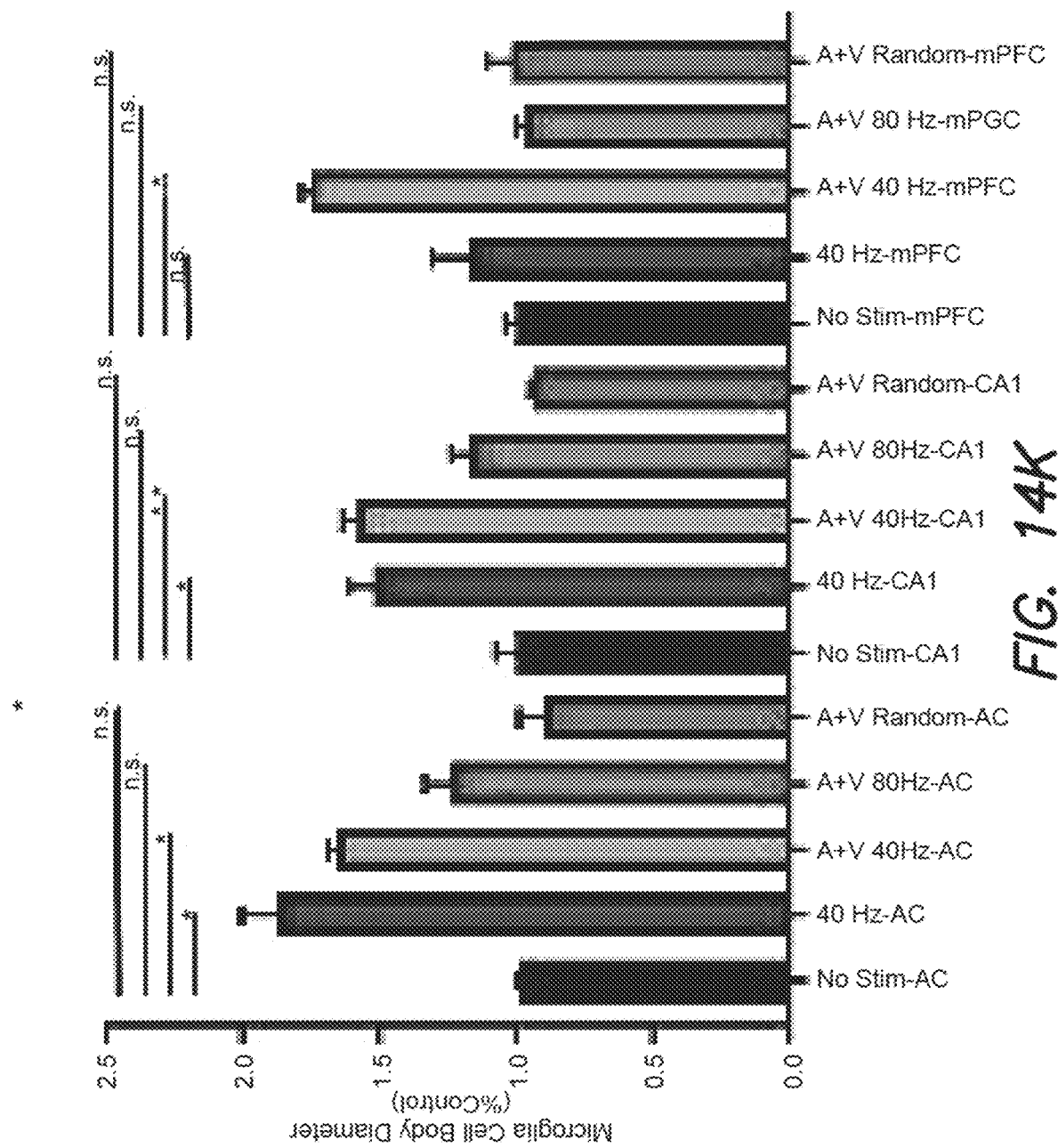

FIG. 14K shows average microglia cell body diameter in AC, CA1, and mPFC of 6-month-old 5XFAD mice following 7 days of 1 hour per day 40 Hz auditory stimulation, combined (A+V) GENUS, combined (A+V) 80 Hz, or combined (A+V) random frequency stimulation, normalized to non-stimulation control (n=6 mice per group, mean s.e.m. in bar graphs, n.s.=not significant, *P<0.05, **P<0.01; unpaired Mann-Whitney test).

Figure 14L:
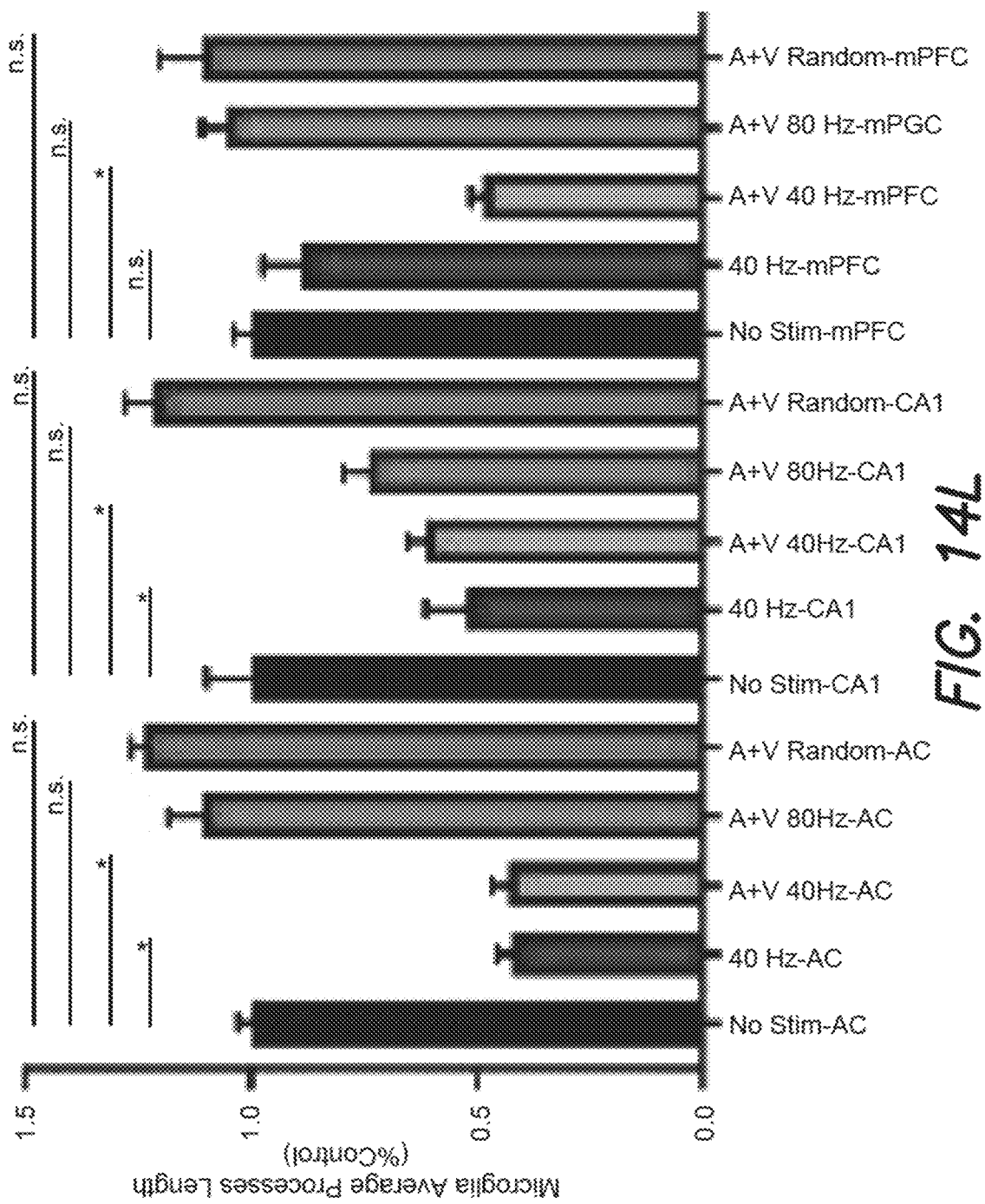

FIG. 14L shows average microglia process length in AC, CA1, and mPFC of 6-month-old 5XFAD mice following 7 days of 1 hour per day 40 Hz auditory stimulation, combined (A+V) GENUS, combined (A+V) 80 Hz, or combined (A+V) random frequency stimulation, normalized to non-stimulation control (n=6 mice per group, mean s.e.m. in bar graphs, n.s.=not significant, *P<0.05, unpaired Mann-Whitney test).

Figure 14M:
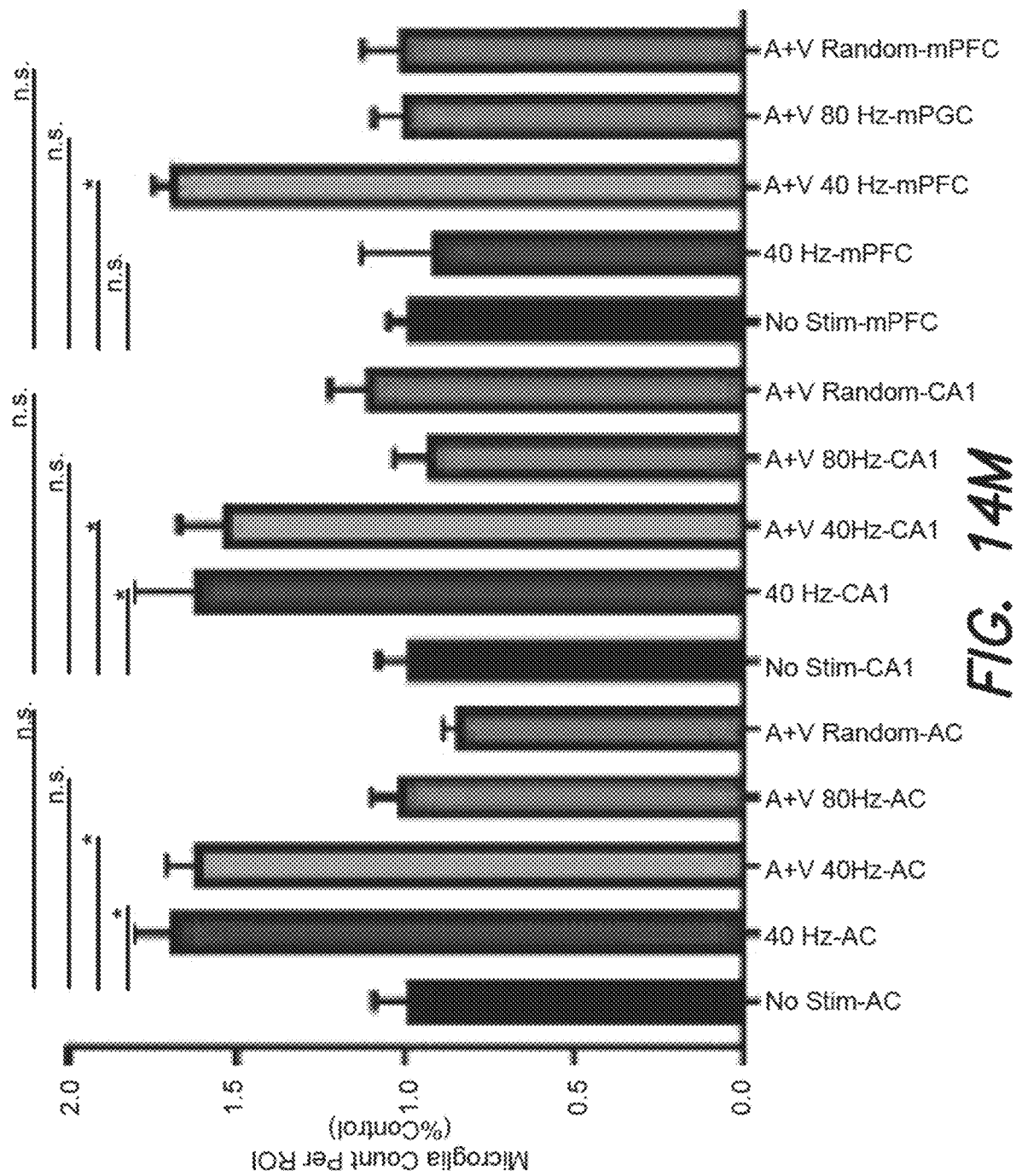

FIG. 14M shows microglia count per region of interest in AC, CA1, and mPFC of 6-month-old 5XFAD mice following 7 days of 1 hour per day 40 Hz auditory stimulation, combined (A+V) GENUS, combined (A+V) 80 Hz, or combined (A+V) random frequency stimulation, normalized to non-stimulation control (n=6 mice per group, mean s.e.m. in bar graphs, n.s.=not significant, *P<0.05, unpaired Mann-Whitney test).

Figure 14N:
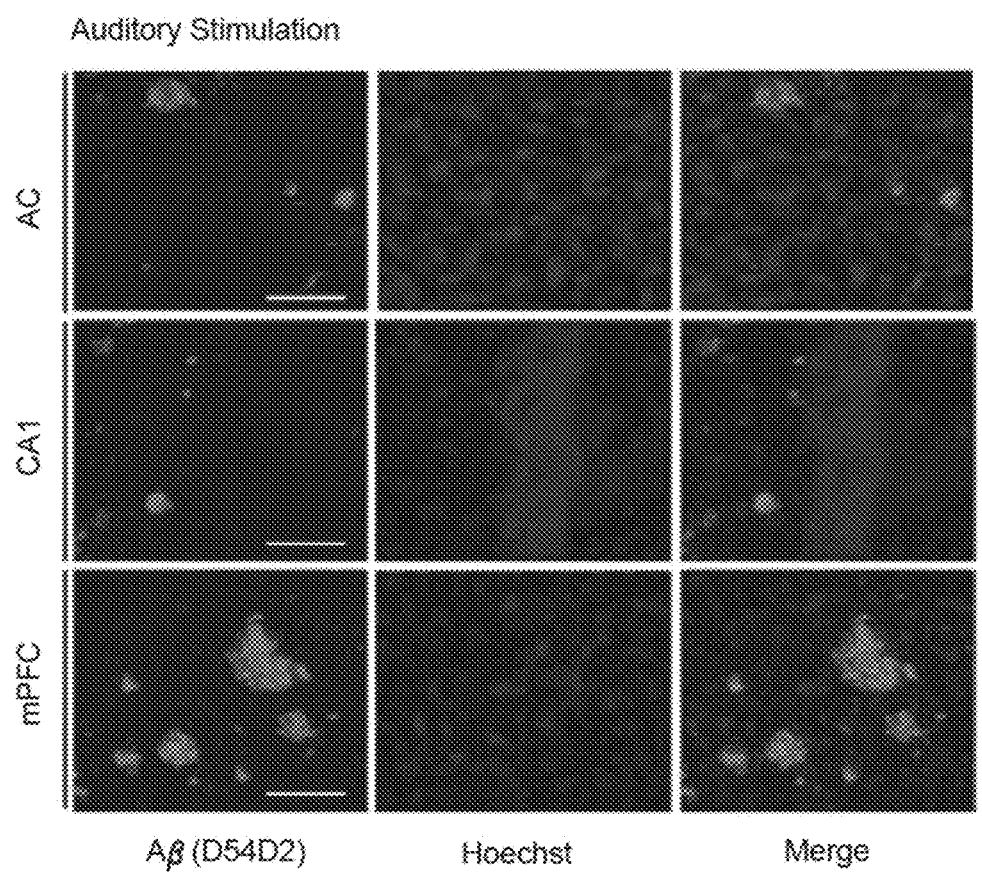
Figure 140:
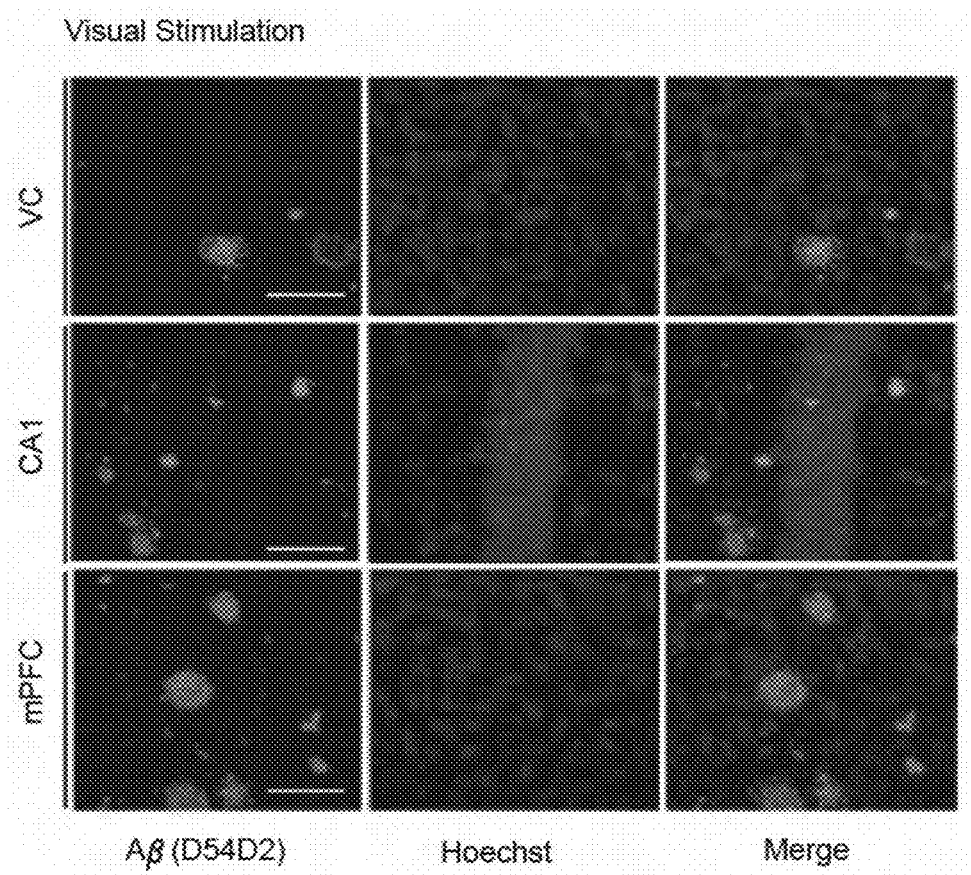

FIG. 14N shows immunohistochemistry of anti-Aβ plaques (D54D2, green) antibodies in AC, CA1, and mPFC of 6-month-old 5XFAD mice after 7 days of 1 hour per day of auditory GENUS (n=6 mice per group, scale bar, 50 µm).

FIG. 14O shows immunohistochemistry of anti-Aβ plaques (D54D2, green) antibodies in VC, CA1, and mPFC of 6-month-old 5XFAD mice after 7 days of 1 hour per day of visual GENUS (n=6 mice per group, scale bar, 50 µm).

Figure 14P:
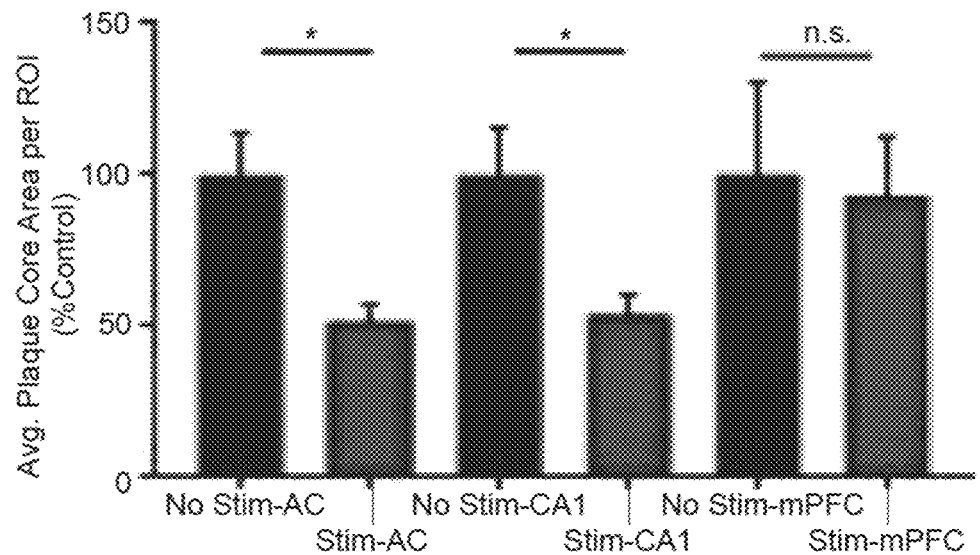

FIG. 14P shows average plaque core area per region of interest, normalized to no stimulation control (n=6 per group, mean s.e.m. in bar graphs, n.s.=not significant, *P<0.05, unpaired Mann-Whitney test).

Figure 14Q:
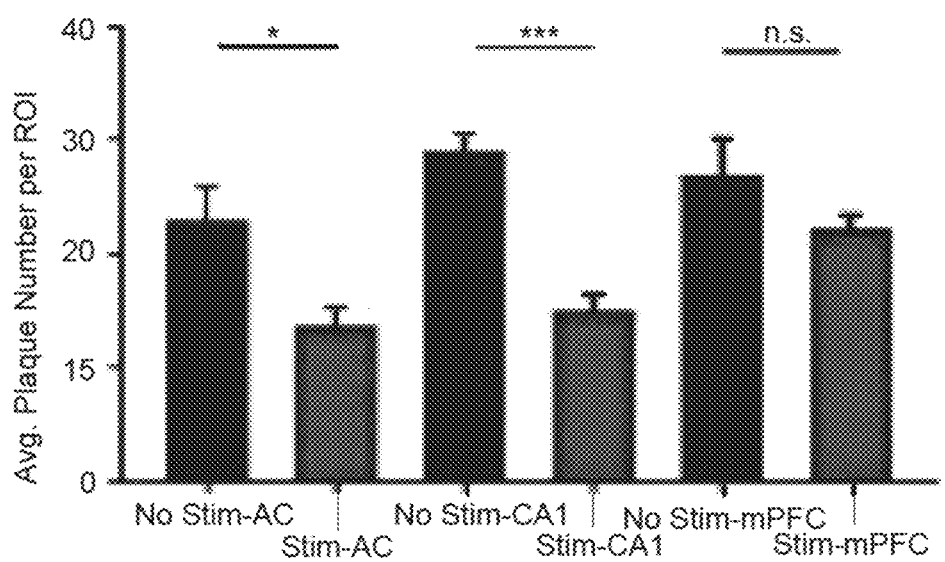

FIG. 14Q shows average number of plaques in AC, CA1, and mPFC following auditory GENUS normalized to no stimulation control (n=6 per group, mean s.e.m. in bar graphs, n.s.=not significant, *P<0.05, ***P<0.001, unpaired Mann-Whitney test).

Figure 14R:
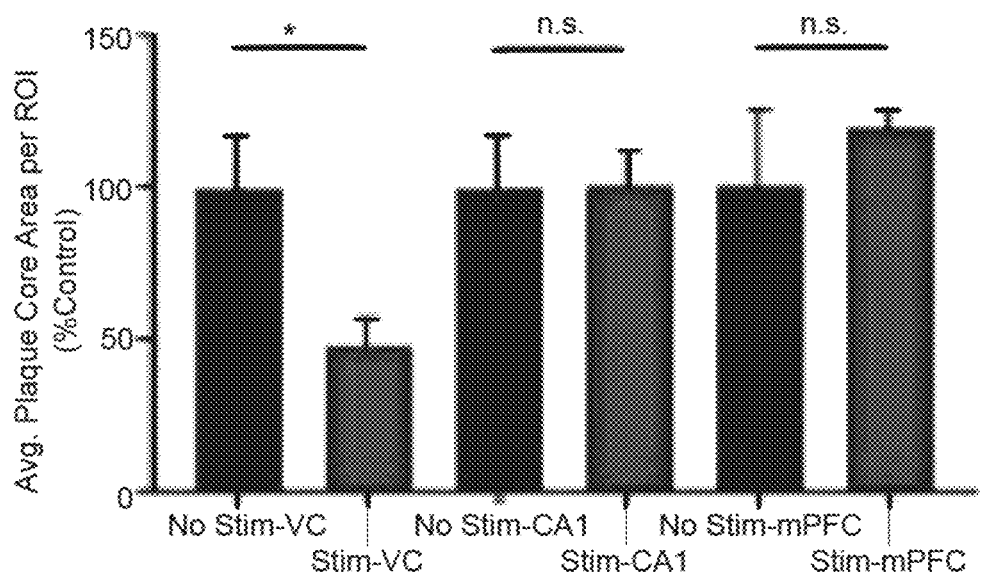

FIG. 14R shows average plaque core area per region of interest, normalized to no stimulation control (n=6 per group, mean s.e.m. in bar graphs, n.s.=not significant, *P<0.05, unpaired Mann-Whitney test).

Figure 14S:
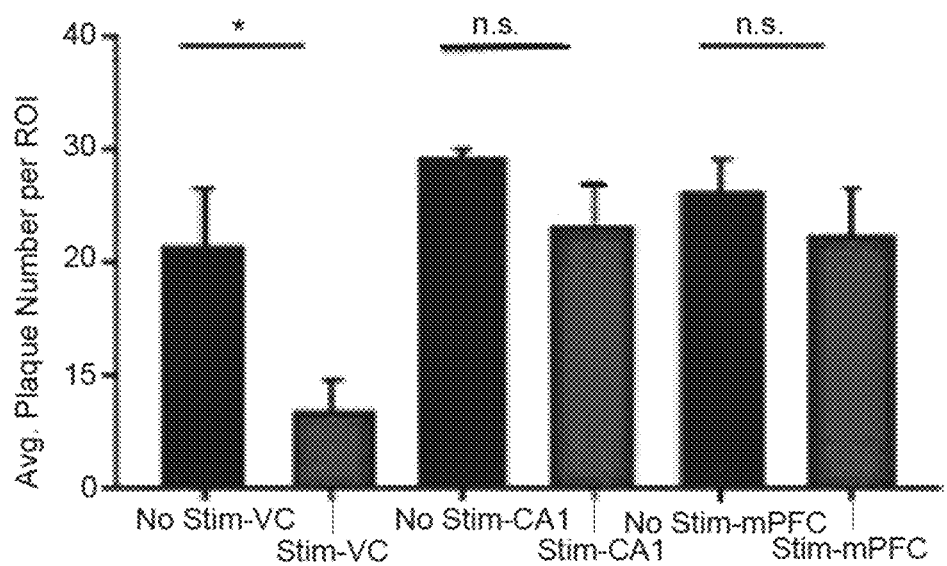

FIG. 14S shows average number of plaques in VC, CA1, and mPFC following visual GENUS normalized to no stimulation control (n=6 per group, mean s.e.m. in bar graphs, n.s.=not significant, *P<0.05, unpaired Mann-Whitney test).

Figure 14T:
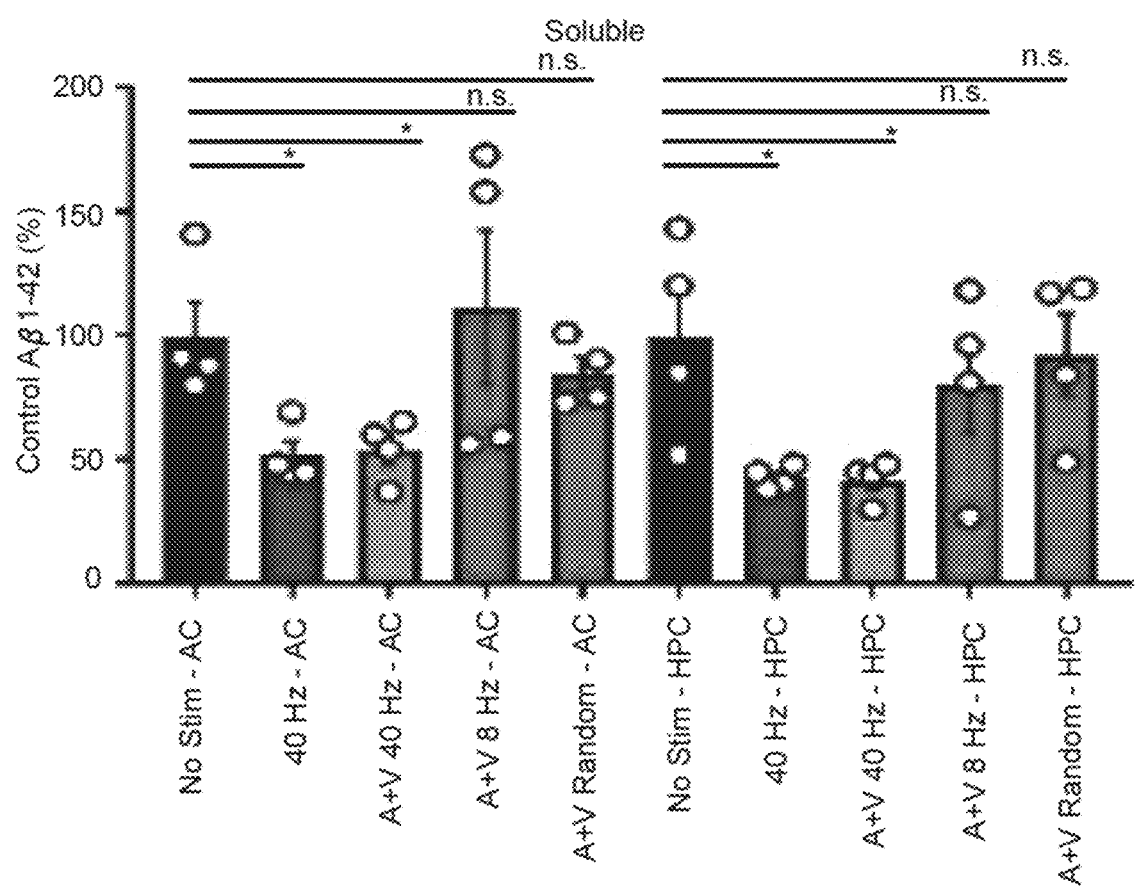

FIG. 14T shows relative soluble $A\beta_{1-42}$ levels in AC and HPC in 6-month-old 5XFAD mice after 7 days of 1 hour per day no stimulation, 40 Hz auditory stimulation, combined (A+V) GENUS, combined (A+V) 8 Hz, and combined (A+V) random frequency stimulation, normalized to no stimulation control (n=4-5 per group, mean s.e.m. in bar graphs, n.s.=not significant, *P<0.05, Kruskal-Wallis test with Dunn's multiple comparison test).

Figure 14U:
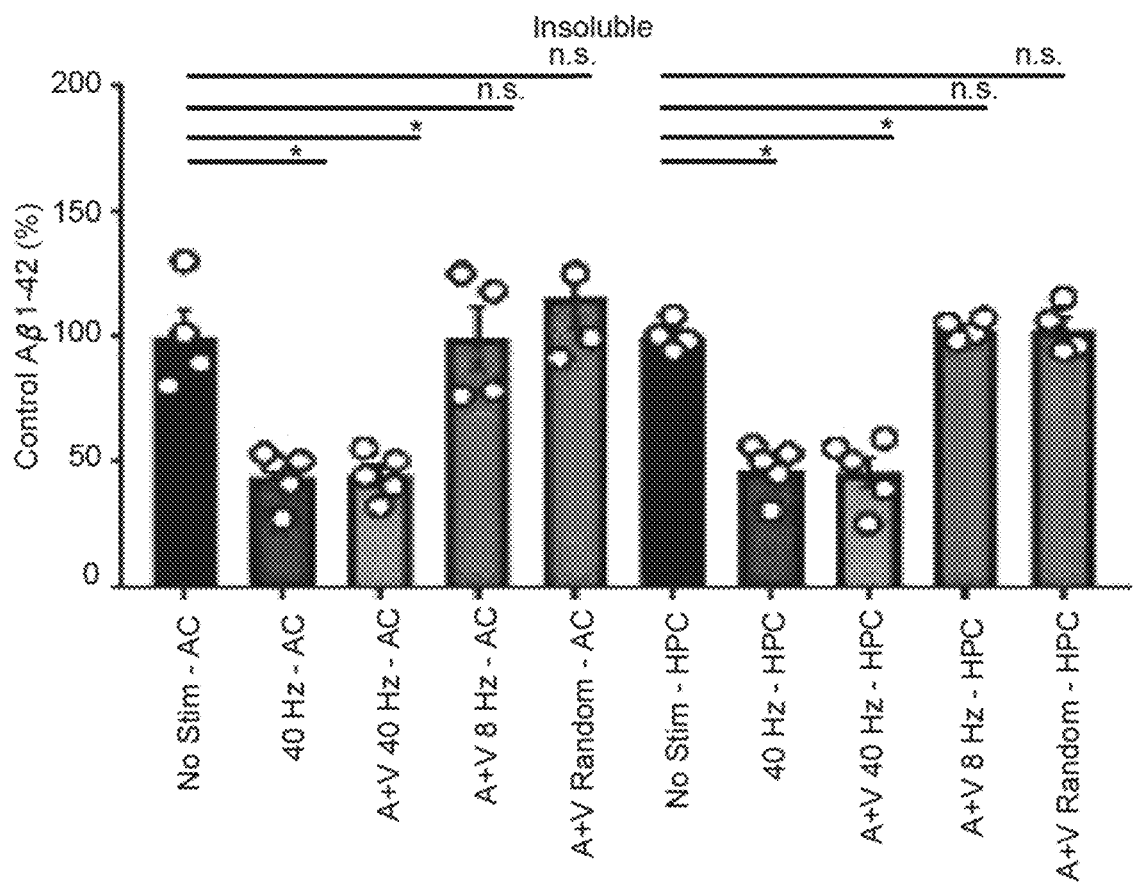

FIG. 14U shows relative insoluble $A\beta_{1-42}$ levels in AC and HPC in 6-month-old 5XFAD mice after 7 days of 1 hour per day no stimulation, 40 Hz auditory stimulation, combined (A+V) GENUS, combined (A+V) 8 Hz, and combined (A+V) random frequency stimulation, normalized to no stimulation control (n=4-5 per group, mean s.e.m. in bar graphs, n.s.=not significant, *P<0.05, Kruskal-Wallis test with Dunn's multiple comparison test).

Figure 14V:
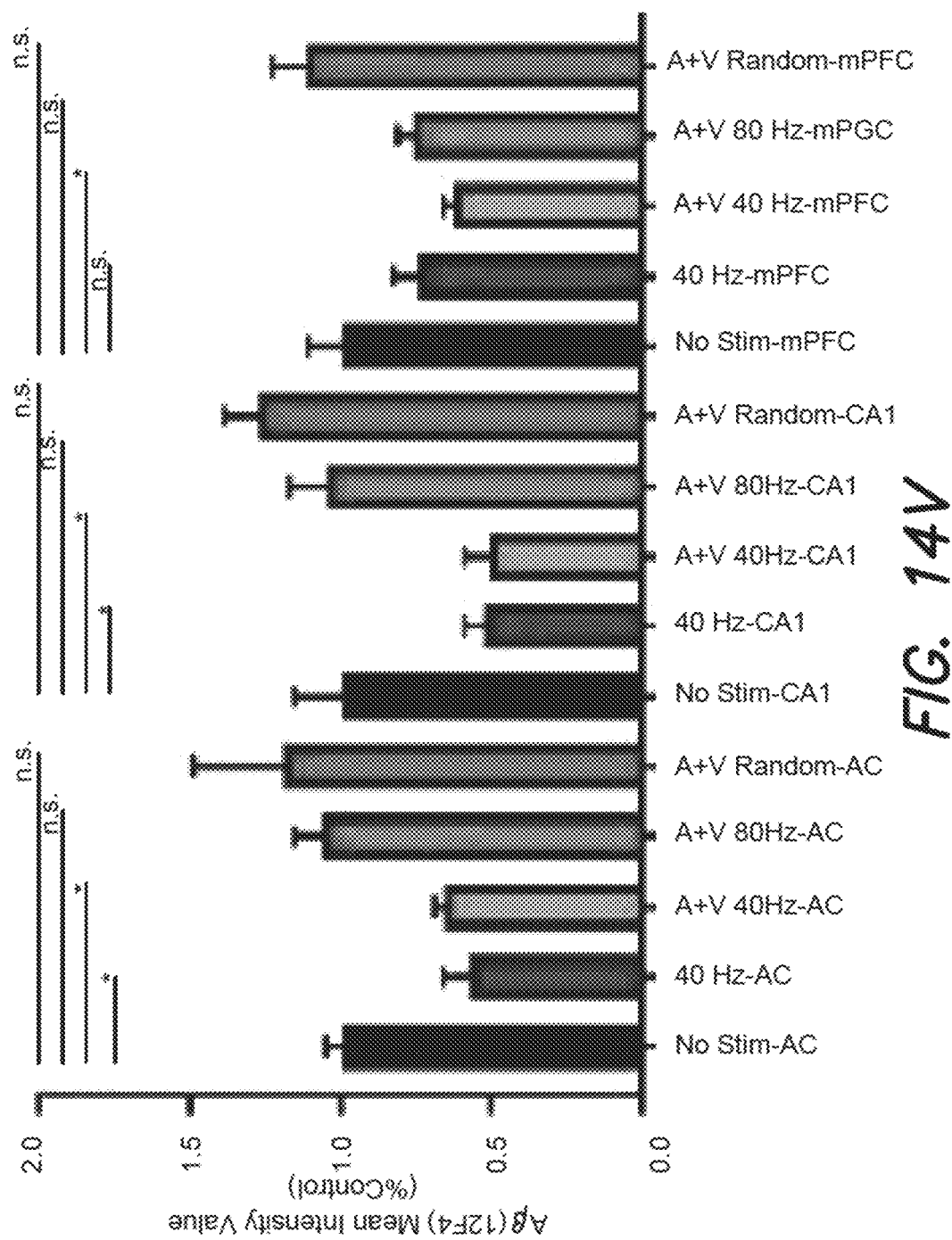

FIG. 14V shows Aβ (12F4) mean intensity value (12F4 antibody) in AC, CA1, and mPFC in 6-month old 5XFAD mice following 7 days of 1 hour per day no stimulation, 40 Hz auditory stimulation, combined (A+V) GENUS, combined (A+V) 80 Hz, and combined (A+V) random frequency stimulation, normalized to no stimulation control (n=4-5 mice per group, mean s.e.m. in bar graphs, n.s.=not significant, *P<0.05, Kruskal-Wallis test with Dunn's multiple comparison test).

Auditory Stimulation at 40 Hz Modulates Spiking Activity in AC, CA1, and mPFC

We first determined whether auditory tone stimulation could produce GENUS in auditory cortex (AC), hippocampal subregion CA1, and in medial prefrontal cortex (mPFC). We presented animals with trains of tones at 20 Hz, 40 Hz, 80 Hz, or with trains of randomly spaced tones (1 ms-long, 10 kHz tones played every 12.5 ms, 25 ms, 50 ms, or with randomized inter-tone intervals that averaged 25 ms, henceforward referred to as "auditory flicker stimulation"). During tone presentation we performed electrophysiological recordings using 32 channel silicon probes in AC, CA1, and mPFC of 3-8 month old male wild-type (C57BL6J) mice running or resting on a spherical treadmill. To locate AC a series of 50 ms auditory mapping tones, henceforward referred to as "mapping stimuli," were played at varying depths until a transient LFP response was detected around 20 ms after tone onset (FIG. 8A). CA1 was located based on electrophysiological hallmarks, and mPFC recording location was confirmed with histology after the final recording in each animal (FIGS. 8G and 8M).

After we reached the target region, animals were presented with interleaved periods of quiet and auditory flicker stimuli while neural activity was recorded. Stimulus blocks rotated between 20 Hz, 40 Hz, 80 Hz, and random auditory flicker stimuli. The firing rate of putative single units increased and decreased periodically with each tone thereby entraining to the 40 Hz auditory flicker stimulation (FIGS. 1A, 1E, and 1I, blue). Units were also modulated by random stimulation. When all random pulses were aligned, there was a change in firing rate modulation following the stimulus, indicating that single units responded to the random stimuli pulses. However, the random train of auditory tones did not induce periodic firing modulation (FIGS. 1A, 1E, and 1I, orange). Entrainment varied between single units, in both phase distribution and amplitude. During flicker stimulation, neurons fired as a function of the stimulus, but they did not fire on every cycle and often fired at a wide range of phases (FIGS. 1A, 1E, and 1I). The interval between peaks in firing rate during the auditory flicker stimulation was around 25 ms (equivalent to 40 Hz) in the majority of single units; 75% in AC, 79% in CA1, and 74% in mPFC. (FIGS. 1B, 1F, and 1J).

In contrast, during baseline periods with no tones and periods with random tones the interval between peaks had a broad distribution with less than 11% of cells in AC, 12% of cells in CA1, and 16% of cells in mPFC having peak intervals of around 25 ms (i.e. the firing rate was not modulated at 40 Hz; FIGS. 1B, 1F, and 1J). Modulation strength was quantified by considering single unit firing rate as a function of the stimulus phase and calculating its vector strength (VS) (FIGS. 1C, 1G, and 1K, left). Vector strength values range from 0 to 1, with 0 representing a uniform distribution of firing that is not modulated by the stimulus (VS=0) and 1 representing a distribution in which a neuron only fired to a specific stimulus phase (VS=1). The distribution of vector strengths of single-unit response to 40 Hz auditory stimulation ranged from 0.002 to 1 in AC, 0.0005 to 1 in HPC, and 0.1 to 0.6 in PFC, and was significantly higher than no stimulation, as well as than that of random stimulation (FIGS. 1C, 1G, and 1K, center). Random stimulation vector strengths were also significantly higher than the no stimulation condition, because vector strength measures modulation by a stimulus. However, vector strength does not quantify periodicity of modulation, and while random stimulation did elicit a single unit response, it did not induce periodic firing modulation.

Similarly, the distribution of Rayleigh statistics for single units during 40 Hz auditory stimulation was significantly higher than that of the no stimulation and random stimulation controls (FIGS. 1C, 1G and 1K, right). The mean firing rate of single neurons was similar between 40 Hz auditory flicker stimulation and controls of no stimulation, random stimulation, 20 Hz and 80 Hz auditory flicker stimulation (FIGS. 1D, 1H, and 1L; FIGS. 8C, 1I, and 1O, right). Local field potentials in AC displayed elevated power at 40 Hz during the auditory flicker stimulation, but the effects varied between recording locations, recording sessions, and response latency to mapping tones (FIGS. 8B, 1H, and 1N). These findings suggest that 40 Hz auditory flicker stimulation induces GENUS robustly in AC, CA1, and mPFC.

Auditory GENUS Improves Memory Performance in 5XFAD Mice

Given that auditory GENUS is able to influence hippocampal neural activity, we next assessed its effects on hippocampus-dependent learning and memory in 6-month-old 5XFAD mice (FIG. 2A). We used 6-month-old 5XFAD animals as that is when behavioral impairments first become evident. We performed 1-week of auditory GENUS for all subsequent experiments; specifically, mice were placed in a quiet chamber and exposed to a train of 1 ms-long 10 kHz auditory tones for 1 hr/day for 7 days at a frequency of 40 Hz (thus, 40 (10 kHz) tones/second). We began by habituating the mice to the behavior chamber 24 hours prior to testing novel object recognition (NOR) and novel object location (NOL) memory performance, which evaluate the ability to remember the identity or placement of an object in a specific context, a behavior known to be affected in human AD subjects. These tests measure behavior performance using a recognition index, which is the percent of time spent exploring the novel object or object in new location, respectively, over the entire duration of exploration.

During habituation, neither auditory GENUS, random frequency, nor non-stimulated groups showed significant changes in average velocity, total distance, time spent in the center, or time spent in the periphery, indicating the three groups did not show differences in general activity or anxiety-like behavior (FIG. 9E-9H). Following auditory GENUS, 5XFAD mice exhibited a significantly higher recognition index of 65.50±1.40% for object and 61.41±2.0% for location memory tasks, whereas the non-stimulated and random frequency control groups did not display a preference for the novel object nor the newly-displaced object in the two tests, respectively (FIGS. 2B and 2E). There was no significant difference in distance traveled or average velocity during the task periods between the three groups, indicating that these effects were not due to general differences in activity (FIGS. 2C, 2D, 2F, and 2G).

The amount of time spent exploring the novel and familiar objects during NOR was examined; we observed that mice following auditory GENUS spent a significantly higher amount of time with the novel object whereas the non-stimulated and random frequency control groups did not exhibit an exploration preference (FIG. 9A). Similarly, we observed that mice following auditory GENUS spent a significantly higher amount of time with an object in a novel location (NOL), whereas the non-stimulated and random frequency control groups did not exhibit an exploration preference (FIG. 9C). As an additional control measure to examine differences in exploration activity, we measured the amount of time (min) mice spent to reach the object exploration requirement of 20 s during the object tasks. We observed no significant difference in the time taken to reach the object exploration requirement between the three groups (FIGS. 9B and 9D).

To further characterize the effects of auditory GENUS on hippocampus-dependent behavior, we performed the Morris water maze test, which measures the ability to remember the location of a hidden platform with respect to surrounding context cues. Mice gradually learn the location of the hidden platform over successive trials, and their spatial memory of the platform location is measured by the escape latency, which is the amount of time it takes for the individual mouse to find the hidden platform. During the training phase, all three groups were able to successfully learn the location of the hidden platform, however the escape latency for the group receiving auditory GENUS was consistently and significantly shorter than both the non-stimulated and random frequency control groups (FIG. 2H). There was no significant difference in swim velocity between the three groups (FIG. 9I). During the probe trial, or when the hidden platform is removed from the tank, mice that received auditory GENUS spent a significantly longer period of time exploring the quadrant containing the missing platform, and displayed a higher number of crossings over the previous platform location, when compared to both the non-stimulated and random frequency control groups (FIGS. 2I and 2J).

As a final behavioral measure, we examined the activity of 5XFAD mice during 1-hr auditory GENUS, no stimulation, or random frequency stimulation and observed no significant differences in average velocity (cm/s) and distance traveled (cm) (FIGS. 9J and 9K). To explore whether there are differences in 'sleep' states, or periods of quiescence, we measured the amount of time mice spent under 2 cm/s during the 1-hr stimulation groups. We observed no significant difference between the three groups (FIG. 9L). Together, these results show that auditory GENUS can improve recognition and spatial memory in 6-month-old 5XFAD mice.

Auditory GENUS Reduces Amyloid Load in AC and Hippocampus in 5XFAD Mice

The beneficial effects of auditory GENUS on cognitive function led us to investigate whether underlying amyloid pathology could be modified in the 5XFAD mouse model. Previously, we showed the ameliorative effect of visual GENUS on amyloid load in younger 3-month-old mice. Here, our aim was to further study the effect of auditory GENUS on 6-month old mice, which are in a more progressive state of AD and exhibit higher amyloid plaque loads. Mice were placed in a quiet chamber and exposed to a series of different auditory tone-train frequencies, including 40 Hz, 8 Hz, 80 Hz, random frequency stimulation, or to no stimulation. 24 hrs after the completion of the 7-day stimulation, we analyzed amyloid load in AC and whole hippocampus (HPC) by Aβ enzyme-linked immunosorbent assay (ELISA). Following 40 Hz auditory stimulation, we observed that soluble $A\beta_{1-42}$ levels were reduced by 51.84±4.98% in AC and 46.89±3.89% in HPC, whereas soluble $A\beta_{1-40}$ levels in AC and HPC were reduced by 20.65±3.21% and 34.15±4.83%, respectively, when compared with no tone or additional frequency controls (FIG. 3A and FIG. 10A). Similarly, insoluble $A\beta_{1-42}$ levels were reduced by 36.68±3.21% in AC and 43.84±2.42% in HPC (FIG. 3B). Insoluble $A\beta_{1-40}$ was not detectable via ELISA in both auditory GENUS or no stimulation controls.

Our results indicate that the observed reduction in amyloid is specific to 40 Hz stimulation as neither 8 Hz, 80 Hz, nor random frequency stimulation significantly change Aβ levels when compared to non-stimulation control. To determine whether these effects apply to other AD-mouse models, and whether our results are specific to our 5XFAD model, we examined Aβ levels of 6-month-old APP/PS1 transgenic mice, a well-validated AD model, following 7 days of auditory GENUS. We found that soluble $A\beta_{1-42}$ was significantly reduced by 48.39±3.50% in AC and by 35.54±4.27% in HPC when compared to no stimulation control (FIG. 10B).

We next examined plaque load in the 5XFAD mouse model with immunohistochemical analysis using a β-amyloid specific antibody (Cell Signaling Technology; D54D2) (FIGS. 3C and 3D). Plaque number was significantly reduced following 7 days of auditory GENUS, by 45.73±2.818% and 59.30±2.083% in AC and CA1 respectively, compared to no stimulation controls (FIG. 3E). Plaque size was also significantly reduced, by 54.37±5.603% and 40.70±5.321% in AC and CA1, respectively (FIG. 3F). Analysis of $A\beta_{1-42}$ specific immunostaining indicated a substantial reduction in $A\beta_{1-42}$ deposits by 45.35±0.011% and 43.21±0.0285% in AC and CA1, respectively (FIG. 3G-3I). To examine the dynamics of plaque load after 40 Hz stimulation, we performed immunohistochemistry analysis using a β-amyloid specific antibody (Cell Signaling Technology; D54D2) in 5XFAD mice that were first subjected to a week of auditory GENUS and then left unstimulated for the next 7 days. We observed slight decreases in average plaque number, area, and amyloid intensity, however these differences were not significant (See FIG. 10F-10H). To examine plaque load following auditory GENUS in another AD model, we used 9-month-old APP/PS1 mice, as 6-month-old mice do not exhibit significant plaque development.

We observed plaque number was significantly reduced in AC by 52.65±7.53% and CA1 by 62.90±15.5%. Plaque size was significantly reduced in AC by 67.90±6.18% and CA1 by 64.06±15.2%. Analysis of $A\beta_{1-42}$ specific immunostaining using an $A\beta_{1-42}$ antibody (BioLegend; 12F4) indicated a substantial reduction in $A\beta_{1-42}$ deposits by 38.77±4.21% and 47.63±6.08% in AC and CA1, respectively, compared to no-stimulation control (FIG. 10C-10E). Collectively, these results demonstrate that auditory GENUS can entrain gamma activity in AC and CA1 and reduce amyloid load in AD mouse models.

Auditory GENUS Induces a Glia and Blood Vessel Response in 5XFAD Mice

Accumulating evidence suggests that microglia are responsive to changes in neuronal activity, and play a role in AD pathology (Allen and Barres, 2005, Mosher and Wyss-Coray, 2014, Walker and Lue, 2015). Our ability to reduce amyloid load in AC and HPC led us to examine whether auditory GENUS could stimulate a change in microglia response in 6-month-old 5XFAD mice. Microglia have been shown to change their cellular morphology during activation states involving engulfment (Davies et al., 2016) and indeed, our earlier study demonstrated that 1 hr of visual GENUS was sufficient to induce a morphological change in microglia consistent with activation and increased phagocytic activity in VC (Iaccarino et al., 2016). Using an antibody against the microglia marker Iba1 (FIGS. 4A and 4B), we observed approximately 60% more microglia in both AC and CA1 in the auditory GENUS group when compared with no stimulation controls (FIG. 4C). Microglia cell body area increased by 70.60±4.78% in AC and 117.17±10.4% in CA1, following auditory GENUS when compared with no stimulation controls (FIG. 4D). We further found a decrease in microglia process length by 46.44±3.2% (AC) and 50.875±4.8% (CA1) as well as a 36.00±9.5% (AC) and 143.813±29.9% (CA1) increase in process arborization, when compared with no stimulation controls (FIGS. 4E and 4F). To evaluate microglia uptake of Aβ, we measured the co-localization of Aβ within microglia by co-immunostaining tissue sections with Iba1 and an Aβ antibody specific for $A\beta_{1-42}$ (12F4, see Methods). We observed that the percentage of microglia whose cell bodies were co-localized with Aβ increased by 58.75±1.25% in AC and 61.33±3.71% in CA1 following auditory GENUS when compared with no stimulation controls (FIG. 4G).

To examine whether microglia response following auditory GENUS occurs in other AD mouse models, we measured microglia morphology from 9-month old APP/PS1 mice following 7 days of auditory GENUS. Similar to our results seen in 5XFAD microglia following 7 days of auditory GENUS (See FIG. 4A-4G), we observed a significant increase in microglia cell body diameter and count, as well as a significant decrease in average processes length in AC and CA1 when compared to no stimulation control (FIG. 11A-11C).

In order to understand the longitudinal effects of microglia response in 5XFAD mice following auditory GENUS, we examined microglia morphology following 7 days of no stimulation post a week of auditory GENUS. We observed a similar trend as from amyloid (FIG. 10F-10H), specifically a non-significant increase in microglia cell body diameter, decrease in average processes length, and increase in microglia count in the auditory cortex (See FIG. 11D-11F). We did however see a significant increase (by 41.70±6.75%) in microglia count in CA1 when compared to non-stimulation control.

Astrocytes are another primary glial cell in the central nervous system, and are critical for homeostatic maintenance, synaptic pruning, waste clearance, and other important biological processes such as regulating cerebral blood flow (Chung et al., 2015, Kisler et al., 2017). Reactive-like astrocytes express glial fibrillary acidic protein (GFAP) (Eng et al., 1971). To investigate whether there are any baseline changes in the number of reactive astrocytes between 6-month-old 5XFAD and WT littermate control mice, we performed CLARITY on 100 μm CA1 brain sections stained against GFAP antibodies (FIG. 11G). We observed that 5XFAD mice had a significantly lower number of GFAP-positive astrocytes when compared to WT controls (FIG. 11H). This observation is consistent with reports that show other AD transgenic mouse models with similar glia atrophy (Rodriguez et al., 2009). To determine whether auditory GENUS could affect the reactivity of astrocytes, we subjected 6-month-old 5XFAD mice to 7 days of either 1 hr/day auditory GENUS or no stimulation control, and then immunostained their brain sections using antibodies against GFAP and S100 calcium-binding protein B (S100B), another protein shown to be expressed in reactive-like astrocytes (FIGS. 4II and 4I). Astrocytes positive for GFAP increased by 27.66±0.954% and 18.14±0.799% in AC and CA1, respectively, and S100B-positive astrocytes increased by 21.83±1.07% in AC and 15.57±0.869% in CA1 (FIGS. 4J and 4K). This observed change in astrocyte number following auditory GENUS may be indicative of a potential increase in astrocyte survival.

Astrocytes are known to play an important role in regulating the brain's vascular network, and accumulating evidence suggests dysfunction of this network in AD may exacerbate pathology. Amyloid clearance from the brain is multifaceted and various processes via the vasculature have been proposed, such as through the glymphatic system and via transport by the endocytic receptor lipoprotein receptor-related protein 1 (LRP1).

To investigate potential changes in the vasculature, we first used tomato lectin (*Lycopersicon esculentum*), an effective marker of the blood vessel endothelium to stain 5XFAD brain slices following auditory GENUS (FIGS. 5A and 5B). Interestingly, we observed a 49.70±7.80% (AC) and 104.70±10.96% (CA1) increase in blood vessel diameter following auditory GENUS, when compared with no stimulation controls (FIG. 5C). We further explored whether amyloid-blood vessel interactions change following auditory GENUS. We examined whether auditory GENUS could affect Aβ co-localization with LRP1, which has been shown to play an important role in Aβ transport and systemic elimination through the vasculature (Storck et al., 2016), by staining for LRP1 and Aβ in brain slices from 5XFAD mice that were either exposed to the 1 hr/day auditory GENUS or no stimulation for 7 days (FIGS. 5D and 5E). In no stimulation controls, we observed a 8.17±2.70% (AC) and 6.97±1.73% (CA1) co-localization of Aβ with LRP1, whereas in the auditory GENUS group, co-localization of Aβ with LRP1 increased significantly to 17.71±2.78% and 16.50±3.90% in AC and CA1, respectively (FIG. 5F). Together, these results suggest that one explanation for reduced Aβ levels in AC and CA1 following auditory GENUS may be through increased clearance of Aβ through microglia and changes in the vasculature.

Auditory GENUS Reduces Tau Phosphorylation in AC and Hippocampus

Another classical pathological hallmark of AD is the accumulation of phosphorylated tau aggregates. Tau phosphorylation at specific amino acid residues associated with AD has been demonstrated to alter its cytoskeletal support functions and to reduce its solubility, and is thus suggested to be a major neuronal insult. To investigate whether auditory GENUS could impact pathology in another AD-associated mouse model, we used Tau P301S mice. Because tau P301S mice begin exhibiting spatial and contextual learning deficits at 6-months-old, we examined whether auditory GENUS could lead to a reduction in phosphorylated tau in AC and HPC in 6-month-old tau P301S mice. Immunohistochemical analysis of brain slices from these mice (FIGS. 12A, 12B, 12D, and 12E) indicated that auditory GENUS reduced tau phosphorylation at threonine-181 (T181) by 36.20±2.828% (AC) and 38.70±2.737% (CA1), and at serine-396 (S396) by 37.90±3.469% (AC) and 40.80±4.528% (CA1) (FIGS. 12C and 12F). Western blot (WB) experiments confirmed the immunohistochemistry results of tau phosphorylation at S396, showing a 33.83±0.20% and 43.20±1.50% reduction in phosphorylation in AC and whole hippocampus tissue, respectively, when compared with total tau (FIGS. 12G, 12H, 12J, and 12K). WB analysis indicated a reduction in phosphorylated T181 tau in hippocampus by 34.50±1.61%, although the difference was not significant in AC (FIGS. 12I and 12L). Altogether, our results show that auditory GENUS can reduce the levels of AD-related hyperphosphorylated tau epitopes, and that auditory GENUS can affect pathology in a tauopathy mouse model.

Combined Auditory and Visual GENUS Induces a Clustering Phenotype Response by Microglia Our findings thus far demonstrate that auditory GENUS can reduce amyloid levels and induce glial and vasculature changes in cortical sensory areas and in hippocampus. This prompted us to investigate whether combining auditory with visual GENUS could elicit more profound cellular effects. We first determined whether a combination of 40 Hz auditory tone stimulation with 40 Hz light flicker could entrain neural responses in AC, CA1, and mPFC. We presented 3-8 month old male wild-type (C57BL6J) mice with a combination of 1 ms-long auditory tones and 12.5 ms-long light pulses at a frequency of 40 Hz while recording neural activity in AC, CA1, and mPFC using 32-channel silicon probes as animals ran or rested on a spherical treadmill. Spiking increased and decreased periodically with each tone and light-on period, thus entraining to 40 Hz during combined auditory-visual stimulation (FIG. 6A-6C, left). Vector strength distributions were significantly higher during 40 Hz auditory-visual stimulation than in random stimulation or no stimulation conditions (FIG. 6A-6C, right). Therefore, the spiking of single neurons in AC, CA1, and mPFC was entrained to 40 Hz significantly more during auditory-visual stimulation periods than during baseline periods. Local field potentials in AC, HPC, and mPFC displayed elevated power at 40 Hz during audio-visual flicker stimulation, however the effect was very small in mPFC (FIGS. 13A, 13H, and 13O). Thus, 40 Hz tone plus light stimulation induced GENUS in AC, CA1, and mPFC.

While small, we observe differences between auditory and combined auditory-visual stimulation in mPFC in the local field potential (LFP) response and in single unit mean firing rates. There was a small increase in power in the LFP at 40 Hz during combined stimulation, but not during auditory only stimulation (FIG. 8N and FIG. 6O). Additionally, the distribution of mean firing rate differences between combined stimulation and baseline had a median that was significantly different from zero, while this did not differ significantly from zero with auditory only stimulation (FIG. 8O and FIG. 6U).

Following 1 hr/day for 7 days of combined GENUS, we examined the morphological features of microglia and their interactions with Aβ in AC, VC, and CA1 (FIGS. 6D and 6E). Because higher-order cognitive regions are known to process multi-modal sensory stimuli, we examined whether combined GENUS could elicit a microglia effect in the medial prefrontal cortex (mPFC) as well. We found that microglia exhibited a significant increase in soma area whereas projection length significantly decreased when compared with non-stimulated controls (FIGS. 6F and 6G). Microglia number also significantly increased following combined GENUS in AC, VC, CA1, and mPFC (FIG. 6H). Microglia in the auditory or visual stimulation groups alone (FIGS. 14A-14D, 14G, and 14H) displayed reduced projection length and enlarged soma area in AC, VC, and CA1, but not in mPFC.

In contrast to visual GENUS, auditory GENUS showed a significant increase in microglia count in CA1; but neither auditory nor visual GENUS alone elicited a significant change in microglia count in the mPFC (FIGS. 14E and 14I). These findings show that following 1-week of GENUS, only combined auditory and visual stimulation, and not auditory or visual stimulation alone, promoted a microglia response in mPFC.

Interestingly, microglia in the combined GENUS group appeared to show a change in activity by displaying an encapsulating effect surrounding amyloid deposits. To better resolve the clustering microglia-Aβ phenotype, we created three-dimensional (3D) renderings from AC, VC, CA1, and mPFC images, taken from 5XFAD brain slices following combined GENUS and no stimulation control (Shown in '3D reconstruction' column in FIGS. 6D and 6E). Using IMARIS imaging software (see Methods), we created 3D surfaces of amyloid deposits (red spots) and microglia cells (green spots), and quantified the proximity and number of microglia within a 25 μm radius of an amyloid deposit (far right inset, FIGS. 6D and 6E, example videos showing the clustering microglia-Aβ phenotype following combined GENUS and no stimulation control are provided in supplementary videos 1 and 2.) We observed a significant increase of 48.88±0.651% in AC, 31.56±1.11% in VC, and 38.64±0.959% in mPFC in the number of microglia surrounding a 25 μm radius around amyloid plaques following combined GENUS, when compared to no stimulation control (FIG. 6I). We also observed a non-significant increase in CA1 by 33.05±2.65%. To examine whether the clustering microglia-Aβ phenotype is a specific phenotype following combined-GENUS, we analyzed the number of microglia within a 25 μm radius of an amyloid deposit following auditory or visual GENUS alone. We observed no significant difference in the number of microglia per plaque between GENUS and non-stimulated mice (FIGS. 14F and 14J).

We next addressed the frequency specificity of microglia response in 6-month-old 5XFAD mice following 7-days of 40 Hz auditory GENUS, combined GENUS, 80 Hz, or random frequency stimulation in AC, CA1, and mPFC. We observed significant increases in microglia cell body diameter and count, as well as a significant decrease in average processes length in AC and CA1 following both 40 Hz auditory stimulation and combined GENUS when compared to additional frequency and non-stimulation controls.

Only combined GENUS resulted in a microglia response in the mPFC when compared to 40 Hz auditory stimulation, additional frequency and non-stimulation controls (FIG. 14K-14M). These results provide show that combined GENUS enhances microglia response through changes in neuronal activity. Therefore, we conclude combined GENUS induces an extended microglia clustering response in AC, VC and mPFC.

Concurrent Auditory and Visual GENUS, but not Auditory or Visual Alone, Reduces Amyloid Load in the mPFC Our observation of a microglia response in AC, VC, CA1, and mPFC prompted us to investigate whether combined GENUS could also change amyloid levels in those regions following 7 days of 1 hr stimulation. Immunohistochemical analysis using an anti-Aβ antibody (D54D2) demonstrated a reduction in plaque area (56.34±6.35% in AC, 71.50±6.51% in VC, and 69.73±6.48% in CA1) and number (50.02±3.74% in AC, 50.60±10.9% in VC, and 48.80±11.1% in CA1) following combined GENUS when compared to no stimulation control. Surprisingly, our results demonstrate a 59.64±8.71% reduction in plaque size and a 2-fold decrease in plaque number in the mPFC in the combined GENUS group, compared to the non-stimulated controls (FIG. 7A-7D). Neither auditory nor visual GENUS alone could elicit a reduction in amyloid plaque staining in the mPFC, suggesting a response specific to combined GENUS (FIG. 14N-14S). Visual GENUS also did not show changes in plaque size or number in CA1. Both auditory only and combined GENUS treatments showed reductions in soluble $A\beta_{1-42}$ and insoluble $A\beta_{1-42}$ levels as measured by Aβ-ELISA in AC and HPC, whereas combined random flicker, 8 Hz, or 80 Hz stimuli did not have a significant effect in amyloid levels in AC or HPC (FIGS. 14T and 14U).

We next treated 6-month-old 5XFAD mice with sensory stimulation at various frequencies in order to determine whether the reduction of Aβ in the mPFC was specific to the type (auditory only vs combined) or frequency of the stimulus. Using Aβ-ELISA to measure changes in amyloid levels in mPFC, we observed no significant differences in soluble or insoluble $A\beta_{1-42}$ among combined 8 Hz, 40 Hz auditory stimulation, combined random frequency stimulation, or no stimulation groups. In contrast, the combined GENUS group showed a 59.58±7.26% reduction in soluble $A\beta_{1-42}$, and a 34.17±8.20% reduction in insoluble $A\beta_{1-42}$ in the mPFC compared to the no stimulation group (FIGS. 7E and 7F).

Furthermore, we measured plaque load via immunohistochemical analysis using a β-amyloid specific antibody (Cell Signaling Technology; D54D2) in 6-month-old 5XFAD mice following 7-days of 40 Hz auditory GENUS, combined GENUS, 80 Hz, or random frequency stimulation. We observed a significant decrease in average plaque number in AC and CA1 following 40 Hz auditory stimulation and combined GENUS, however, only combined GENUS resulted in a significant reduction in plaque number in the mPFC when compared to additional frequency controls and non-stimulation control (FIGS. 7C and 7D). Analysis of $A\beta_{1-42}$ specific immunostaining using an $A\beta_{1-42}$ antibody indicated a substantial reduction in Aβ in AC and CA1 following 40 Hz auditory stimulation and combined GENUS, however, only combined GENUS resulted in a significant reduction in immunostaining intensity in the mPFC (FIG. 14V).

Reduced amyloid load in the mPFC suggests that combined GENUS affects broader cortical regions. To determine the overall effect of combined GENUS on amyloid plaque abundance in the whole cortex, we performed whole brain SHIELD processing (Methods) in 6-month-old 5XFAD mice following 1-week of combined GENUS and immunostained for amyloid plaques (using D54D2 antibody) (FIGS. 7G and 7H). Using light sheet microscopy to analyze plaques in 3D, we found a 37% and 34% reduction in total plaque volume and number, respectively, in the neocortex when compared to non-stimulation control (FIGS. 7I and 7J, example videos showing 3D whole brain SHIELD samples immunostained for plaques following combined GENUS and no stimulation control are provided in supplementary videos 3 and 4). Together, these results indicate that combined GENUS significantly reduces amyloid plaque load across the neocortex of the 5XFAD mouse model.

Methods

Animals

All animal work was approved by the Committee for Animal Care of the Division of Comparative Medicine at the Massachusetts Institute of Technology and by the Institutional Animal Care and Use Committee at Georgia Institute of Technology. Mice were housed in groups no larger than five on a standard 12-hour light/12-hour dark cycle; all experiments were performed during the light cycle. Electrophysiology experiments were performed at Georgia Institute of Technology, male (1-3 month old) WT mice (C57Bl/6) were obtained from the Jackson laboratory. Mice were housed on a reverse 12 h light/12 h dark cycle and all experiments were performed during the dark cycle. Food and water were provided without restriction.

Surgical Procedures

All surgeries were performed as described in Iaccarino and Singer et al., 2016. In brief, adult (2-3-month-old) mice were anesthetized with isoflurane before headplate placement surgery. A custom stainless steel headplate was fixed using dental cement (C&B Metabond, Parkell) and the target craniotomy site for LFP recordings was marked on the skull (in mm, from bregma: −2.0 anterior/posterior, +/−1.8 medial/lateral for targeting CA1, −2.0 to −3.0 anterior/posterior, +/−1.8 medial/lateral for targeting auditory cortex, and +1.3 to +1.4 anterior/posterior, +/−1.0 medial/lateral for targeting prefrontal cortex). A craniotomy was later performed in 3-8 month old mice. Before the first recording session, craniotomies (200-500 µm diameter) were made by thinning the skull with a dental drill and then making a hole with a 27-gauge needle. When not recording, the craniotomy was sealed with a sterile silicon elastomer (Kwik-Sil WPI).

Electrophysiology Recordings

During recordings, head-fixed animals ran on an air-floating 8-inch spherical treadmill. All animals had previously learned to maneuver on the treadmill until they were comfortable while occasionally receiving sweetened condensed milk (1:2 water dilution). Animals were on the ball for a maximum of 5 hours and had multiple periods of running and rest during this time. Single shank 32-channel probes (NeuroNexus) were advanced to the target location. Recording sites spanned 250 µm. For auditory cortex recordings, the probe was advanced at a 45° angle from vertical parallel to the coronal plane to a depth of 3-4.15 mm. A series of 50 ms tones of 5, 10, 15, and 20 kHz were presented to detect auditory response in the mean LFP. For CA1 recordings, the probe was advanced vertically through the craniotomy to a depth of 1.14-2.05 mm until hippocampal pyramidal layer electrophysiology characteristics were observed (large theta waves and sharp wave ripples, 150+µV spikes on multiple channels). For prefrontal cortex recordings, the probe was advanced at a 20° angle from vertical, at a 49° angle from the coronal plane to a depth of 1.48-2.15 mm. If data were collected at multiple depths during the same recording session; new depths were mapped in order to ensure the location of the recording sites remained in the target location (n=9 recording depths from 9 sessions in 5 mice for AC and 12 recording depths from 10 sessions in 5 mice for CA1, n=7 recording depths from 7 sessions in 4 mice for mPFC). Data were acquired with a sampling rate of 20 kHz using an Intan RHD2000 Evaluation System using a ground pellet as reference.

Auditory and Visual Stimuli for Electrophysiology Recordings

Animals were presented with 10 s stimulation blocks interleaved with 10 s baseline periods. Stimulation blocks rotated between auditory-only or auditory and visual stimulation at 20 Hz, 40 Hz, 80 Hz, or with random stimulation (pulses were delivered with randomized inter-pulse intervals determined from a uniform distribution with an average interval of 25 ms). Stimuli blocks were interleaved to ensure the results observed were not due to changes over time in the neuronal response. All auditory pulses were 1 ms-long 10 kHz tones. All visual pulses were 50% duty cycle of the stimulation frequency (25 ms, 12.5 ms, or 6.25 ms in length). For combined stimulation, auditory and visual pulses were aligned to the onset of each pulse.

Data Acquisition

Data were acquired with a sampling rate of 20 kHz using an Intan RHD2000 Evaluation System.

Spike Detection

Raw traces were bandpass filtered between 300-6,000 Hz. Spikes were then detected by a threshold of the median of the filtered signal plus five times the estimated standard deviation (median/0.675).

Spike Sorting and Single Unit Stability

Spike detection and sorting was carried out using MountainSort automated spike sorting followed by manual curation based on visual inspection of waveforms and cross-correlograms. Prior to manual curation, quality thresholds were applied to only include units with peak SNR greater than or equal to 1, less than 10% overlap with noise, and greater than 95% isolation against other units which resulted in well-isolated single units. To account for periods of instability in the recordings during which single units were lost, stability criteria were applied such that only stable periods (no sudden loss of a single unit's firing rate) would be considered in analysis. Firing rate (FR) for each unit was computed over the course of the recording session. Firing rate was clustered into two distributions, low FR and high FR, using k-means clustering. For units with FR that dropped below 10% of the high FR mean, further analyses identified a stable recording period defined as the longest length of time that the FR was 2 standard deviations above the low FR mean.

Local Field Potential

LFP was obtained by downsampling raw traces to 2 kHz and bandpass filtering between 1-300 Hz.

Recording Sites for Analysis

The data in AC and CA1 were analyzed on multiple channels. In AC, the lower 16 of 32 channels were utilized spanning 375 µm, as the lowest channel on the probe was used to determine the location of AC, and the highest 16 channels were determined to not be in the primary area of interest. For CA1, all functioning channels on the probe were analyzed (27/32 or 31/32) spanning 250 µm. The highest channel on the probe in both AC and CA1 was used as the probe reference for power spectral analysis. Similar results were obtained using the ground as reference.

Prefrontal Cortex Histology

During the final mPFC recording in each animal, the probe was coated with DiI and inserted to target depth. Mice were transcardially perfused with 4% paraformaldehyde in phosphate buffered saline (PBS) under anesthesia (isoflurane), and the brains were post-fixed overnight in 4% paraformaldehyde in 1×PBS. Brains were sectioned 100 µm thick with a Leica VT1000S vibratome (Leica). Sections were stained with 0.2% 1 mMol DAPI in 1×PBS and mounted onto microscopy slides with Vectashield mounting medium. Images were acquired on a Zeiss Axio Observer Z1 inverted epifluorescent microscope with the accompanying Zen Blue 2 software.

Power Spectrum

Power spectral density analysis was performed using multitaper methods from the Chronux toolbox (time-bandwidth product=3, number of tapers=5). LFP traces were divided into 10 s trials of each stimulation condition. The average power spectral density was computed for each animal (within the same recording day and recording depth) over these trials, referencing to a ground pellet in saline above the skull. Power spectral density analysis was initially computed for all recording sites in AC, CA1, and mPFC. From each recording depth, the traces with the largest 40 Hz peak in response to 40 Hz flicker stimuli were included in the analysis. The per-depth traces displayed in the presented data had the largest 40 Hz peak in response to auditory flicker stimuli.

Firing During Flicker Stimulation

The single unit peri-stimulus time histograms (PSTH) for each stimulus frequency encompassed four stimulus cycles $$\left(\text{where one cycle} = \frac{1}{\text{stimulus frequency}} \text{ sec}\right),$$

with 10 bins per cycle, to show spiking across trains of stimuli. PSTHs were computed for all single units by binning spikes for 2 stimulus cycles before and after the start of each light-on or audio-on pulse. No stimulation histograms were calculated using randomly distributed pulse times, as in the random stimulation condition. Firing rate was computed in each bin by dividing the number of spikes per bin by the total number of pulses and the bin size. To quantify firing rate periodicity in relation to the stimulus frequency, the time interval between firing rate peaks was calculated for all single unit histograms. The peaks of each PSTH was the maximum firing rate within one stimulus interval. To quantify firing rate modulation by the stimulus and compute circular statistics, peri-stimulus spike times were converted into radians: (peri-stimulus spike time)*$2\pi$*(stimulus frequency). Vector strength was computed using methods from the CircStat toolbox; the Rayleigh statistic was computed using the equation $RS=2nVS^2$, where n is total spike count, and VS is vector strength (Berens, 2009, Ma et al., 2013).

Mean Firing Rate

Mean firing rate was computed for each single unit for each stimulus condition. Only stable periods for each unit contributed to the mean FR calculation (see Spike sorting and single unit stability, above). Difference in mean firing rate between stimulus conditions was computed within each unit by taking the difference in mean FR in each condition for that unit.

40 Hz Visual Flicker Stimulation Protocol

For biochemical and Immunohistochemical analysis, 5XFAD mice were placed in a dark chamber illuminated by a light-emitting diode (LED) bulb and were exposed to one of four stimulation conditions: dark, 8 Hz, 40 Hz (12.5 ms light on, 12.5 ms light off, 60 W), or random (light pulses were delivered with a random interval determined by a uniform distribution with a mean of 25 ms) stimulation for 1-hour for seven days.

40 Hz Auditory Tone Train Stimulation Protocol

For biochemical, Immunohistochemical, or behavioral analysis, 5XFAD, APP/PS1, or P301S mice were placed in a dimly lit chamber in a quiet room insulated with soundproof foam (McMaster-Carr, 5692T49). Speakers (AYL, AC-48073) were placed out-of-reach from the mouse above the chambers. Mice were exposed to one of five stimulation conditions: no tones, tones at 8 Hz, tones at 40 Hz, tones at 80 Hz, or tone delivered at random (auditory tones were delivered with a random interval determined by a uniform distribution with a mean of 25 ms) stimulation. Tones for the stimulation conditions consisted of a 10 kHz tone that was 1 ms in duration and delivered at 60 dB. For electrophysiology recordings, after probe placement, the lights in the room were turned off and the animals were presented with alternating 10 s periods of audio-only and visual-audio stimulation interleaved with 10 s periods of no light or tones. For audio-only stimulation, a 10 kHz tone was played at 40 Hz with a 4% duty cycle. For visual-audio stimulation, the audio stimulation was accompanied with surrounding light flickered at 40 Hz for 10 s periods with a 50% duty cycle. Stimuli were presented in this manner for 20 min sessions, with 1-10 min pauses in between sessions to check on the animals' behavior.

Concurrent 40 Hz Auditory and Visual Stimulation Protocol

For biochemical, Immunohistochemical, or behavioral analysis, 5XFAD mice were placed in a dark chamber illuminated by an LED bulb and exposed to an auditory tone train, simultaneously. Mice were exposed to one of four stimulations: dark/quiet, 40 Hz light flicker, 40 Hz auditory tone train, concurrent 40 Hz light flicker and auditory tone, or random light flicker/tone stimulations.

Immunohistochemistry

Mice were transcardially perfused with 4% paraformaldehyde in phosphate buffered saline (PBS) under anesthesia (2:1 of ketamine/xylazine), and the brains were post-fixed overnight in 4% paraformaldehyde in PBS. Brains were sectioned 40 µm thick with a Leica VT1000S vibratome (Leica). Sections were permeabilized and blocked in PBS with 0.3% Triton X-100 and 10% donkey serum at room temperature for 2-hours. Sections were incubated overnight at 4° C. in primary antibody containing PBS with 0.3% Triton X-100 and 10% donkey serum. Primary antibodies were: anti-β-amyloid (Cell Signaling Technology; D54D2), anti-Iba1 (Wako Chemicals; 019-19741), anti-glial fibrillary acidic protein (GFAP)(Abcam; ab4674), anti-S100B (Abcam; ab868), anti-LRP1 (Abcam; 28320), DyLight 488 labeled *Lycopersicon esculentum* (tomato) lectin (Vector laboratories; DL-1174), anti-amyloid oligomer (Millipore Sigma; AB9234), anti-phospho-tau (Ser396) (Cell Signaling Technology; 9632), anti-phospho-tau (Thr181) (Cell Signaling Technology, 12885), Hoechst 33342 (Thermo Fisher Scientific; H3570). The anti-Aβ antibody 12F4 was used because it does not react with APP, allowing us to determine whether our labelling was specific to Aβ, as well as allowing for co-labelling with Iba1. Anti-amyloid oligomer antibody AB9234 was used for co-labelling with LRP1. The following day, brain sections were incubated with fluorescently conjugated secondary antibodies (Jackson ImmunoResearch) for 2 hours at room temperature, and nuclei were stained with Hoechst 33342 (Invitrogen). Images were acquired using a confocal microscope (LSM 710; Zeiss) with a 40× objective at identical settings for all conditions. Images were quantified using ImageJ 1.42q by an experimenter blind to treatment groups. For each experimental condition, two coronal sections from each animal were used for quantification. Scale bars are 50 µm unless otherwise noted in figure legends. ImageJ was used to measure the diameter of Iba1+ cell bodies and to trace the processes for length measurement. In addition, the Coloc2 plugin was used to measure co-localization of Iba1 and Aβ. Microglia processes arborization was quantified using Imarisx64 8.1.2 (Bitplane, Zurich, Switzerland). The 'analyze particles' function in ImageJ was used for counting plaque number and area, deposits of at least 10 µm were included and a set threshold was used for both control and experimental groups.

Vasculature-Aβ Colocalization Analysis

ImarisColoc module was used to quantify colocalization of signal between two separate source channels (i.e. Lectin and AB, Lectin and LRP1) in 3D. These source channels were thresholded to mask any intensity coming from noise or background signal. ImarisColoc then generates a new channel containing only voxels that colocalize within the thresholds set for the source channels, and presents the associated statistical analyses.

Microglia-Aβ Clustering Analysis

IMARIS was used to analyze the microglial clustering pattern around amyloid plaques in 40 uM slices. The surfaces module was utilized to detect and 3D render plaques (red) based on 12F4 signal. Iba1-positive microglia were then counted using the spots module, placing a sphere at the soma of each cell (green). Finally, the Spots Close To Surface XTension was run to find the subset of spots that are closer to the surface objects than the defined 25 uM threshold, and exclusion of spots that fall outside this range. The algorithm measures the distance from the center of the spot to the nearest point of the surface object in 3D space, allowing for the quantification of microglial aggregation near plaques.

CLARITY Immunostaining in Brain Slices

Mice were perfused with ice-cold PBS (1×) followed by ice-cold 4% PFA, 1% glutaraldehyde in 1×PBS. Brains were dissected out and post-fixed in 4% PFA/1% glutaraldehyde solution for 72 hours at 4° C. Fixation was terminated by incubating brains in inactivation solution (4% acrylamide, 1 M glycine, 0.1% triton-X100 in 1×PBS) for 48 hours at RT. After washing in 1×PBS, brains were sliced into 100 uM coronal sections on a vibratome (Leica VT100S) in 1×PBS. Sections containing regions of interest (i.e. auditory cortex and hippocampus) were selected, with reference to the Allen Mouse Brain Atlas, and incubated in clearing buffer (pH 8.5-9.0, 200 mM sodium dodecylsulfate, 20 mM lithium hydroxide monohydrate, 4 mM boric acid in ddH2O) for 2-4 hours, shaking at 55° C. Cleared sections were washed 3×15 mins in 1×PBST (0.1% Triton-X100/1×PBS) and put into blocking solution (2% bovine serum albumin/1×PBST) overnight at RT. Subsequently, three 1 hour washes in 1×PBST were performed, shaking at RT. Sections were incubated in weak binding buffer (pH 8.5-9.0, 37.75 mM Na2HPO4, 3.53 mM KH2PO4, 0.02% sodium azide in PBST) for 1 hour at RT, then transferred to primary antibody, diluted to 1:100 in 1× weak binding buffer for 12 hours at 37° C. Reversal buffer (pH 7.4, 37.75 mM Na2HPO4, 3.53 mM KH2PO4 in 0.02% sodium azide in PBST) is then added in even hourly aliquots over 6 hours, to equal the volume of primary antibody solution plus the volume of the tissue. Another set of 3×1 hour washes in 1×PBST was conducted before sections were incubated for 12 hours at RT, in a mixture of Hoechst 33258 (1:250) (Sigma-Aldrich, 94403) and secondary antibody (1:100) in 1×PBS. Sections were then washed overnight in 1×PBS and incubated in RIMS (Refractive Index Matching Solution: 75 g Histodenz, 20 mL 0.1M phosphate buffer, 60 mL ddH2O) for 1 hour at RT prior to mounting. Brain sections were mounted onto microscopy slides with coverslips (VWR VistaVision, VWR International, LLC, Radnor, PA) in RIMS.

Images were acquired on a Zeiss LSM 880 microscope with the accompanying Zen Black 2.1 software (Carl Zeiss Microscopy, Jena, Germany). Z-stack images were taken with a step size of 0.4-0.5 pixel dwell 4.1 ms, averaging of 2, resolution 1024×1024 suitable for 3D reconstruction. Imarisx64 8.3.1 (Bitplane, Zurich, Switzerland) was used for 3-D rendering and analysis.

Whole Mouse Brain Processing and Clearing

5XFAD mouse brains were processed according to the SHIELD protocol. Briefly, 5XFAD mice were transcardially perfused with ice-cold PBS followed by 20 mLs of SHIELD-OFF solution containing 4% PFA. Brains were dissected and post-fixed in the same solution for 24 hours at 4° C. Brains were then incubated overnight in SHIELD-OFF solution without PFA at 4° C. Brains were then incubated in the SHIELD-ON solution for 24 hours at 37° C. Following fixation, brains were incubated in an aqueous clearing solution containing 200 mM sodium dodecyl sulfate (SDS), 20 mM lithium hydroxide monohydrate, 40 mM boric acid, pH 8.5-9.0. Brains were then cleared using SmartClear Pro (LifeCanvas Technologies, Cambridge, MA) based on stochastic electrotransport (Kim et al., PNAS, 2015) for several days, until transparent.

Immunostaining of Cleared Whole Hemispheres

Cleared hemispheres were stained with 15 ul of beta-amyloid antibody conjugated with Alexa Fluor-488 (CST, #51374) over 2 days, using a eTANGO, a modified stochastic electrotransport method (Kim et al., PNAS, 2015).

Light-Sheet Microscopy

Immunostained samples were incubated with hProtos (3 g diatrizoic acid, 5 g N-methyl-d-glutamine, 125 g iohexol in 105 ml DI-water) for optical clearing and then mounted to acrylic holder using 2% low-temperature melting agarose in hProtos. Custom-made light-sheet microscope equipped with 10× CLARITY-optimized objective was used to image whole hemispheres using the 488 channel for beta-amyloid visualization and the 647 channel for autofluorescence.

Cleared Whole Brain Image Processing, Plaque Detection, and Atlas Alignment

Acquired image data were illumination corrected using CIDRE, an open-source software package implemented in Matlab, and the resulting processed images were stitched together using Terastitcher in Imaris™ (Bitplane®) was used for 3D visualizations, and ImageJ (National Institutes of Health) was used to create representative slice-by-slice 2D visualizations. Automated plaque detection was performed using a combination of the open-source ClearMap software, a custom cell classification neural network model, and Elastix. Candidate plaques were located as "spots" with ClearMap's spot detection module. First, background subtraction was done slice-by-slice by using a grey-scale morphological top-hat transformation with a disk structure element with major and minor diameter pixel sizes of (21,21). Next, local maxima of the data are detected by applying a 3D maxima filter with disk structure element of size (7,7,4), and these local maxima are filtered with an intensity threshold of 100. The pixel volumes corresponding to each spot center location are also computed using a 3D watershed transform with spot centers as seed points. All candidate plaques with volume less than a sphere with 10-micron diameter were then filtered out. True plaques were identified from the candidate plaques using a convolutional neural network (CNN) model as a categorical plaque/non-plaque classifier implemented in Keras™ with a Theano™ backend. The CNN input is a 32-by-32 pixel bounding box centered at a candidate plaque center, and the output is a two element one-hot vector representing the plaque and non-plaque categories. The architecture consists of 12 total convolutional layers, each with a rectified linear unit (ReLU) activation and followed by batch normalization: 3 with 64 2×2 kernels, 3 with 128 2×2 kernels, followed by 3 with 192 2×2 kernels, 1 with 256 2×2 kernels, 1 with 256 1×1 kernels, and 1 with 2 1×1 kernels. 2×2 subsampling is done after the third, sixth, and ninth convolutional layer, and Dropout with a rate of 0.5 is applied after the last nine convolutional/batch normalization layers for regularization. After the final convolutional layer, global average pooling followed by softmax activation is applied to generate the final categorical vector. During training, a categorical cross entropy loss was used with the Adam optimizer with default parameters. The CNN was trained for 400 epochs with batch size of 64 on ~10,000 manual plaque annotations augmented with random rotations, shears, and reflections using the Keras™ Image Data Generator. The resulting model was then used to classify plaques from detected spots for all samples. To perform atlas alignment, autofluorescence channel images were first downsampled to the atlas resolution, and then Elastix was used to calculate affine and B-spline transformation parameters to do 3D image registration, with the resampled autofluorescence image as the fixed image and the atlas as moving image. The resulting alignment parameters were applied on the plaque locations (output from the CNN model) to transform the plaques into the atlas space, after which a CSV file with plaque count and volume information for each brain region (segmentation according to the Allen Brain Atlas) is generated.

Western Blot

Hippocampus and auditory cortex were dissected and lysates were prepared from 6-month-old male 5XFAD. Tissue was homogenized in 1 ml RIPA (50 mM Tris HCl pH 8.0, 150 mM NaCl, 1% NP-40, 0.5% sodium deoxycholate, 0.1% SDS) buffer with a hand homogenizer (Sigma), incubated on ice for 15 min, and rotated at 4° C. for 30 min. Cell debris was isolated and discarded by centrifugation at 14,000 r.p.m. for 10 min. Lysates were quantitated using a nanodrop, and 25 μg protein was loaded on a 10% acrylamide gels. Protein was transferred from acrylamide gels to PVDF membranes (Invitrogen) at 100 V for 120 min. Membranes were blocked using bovine serum albumin (5% w/v) diluted in TBS:Tween. Membranes were incubated in primary antibodies overnight at 4° C. and secondary antibodies at room temperature for 90 min. Primary antibodies were anti-phospho-tau (Ser396) and anti-phospho-tau (Thr181). Secondary antibodies were LI-COR IRDye secondary antibodies. Signal intensities were quantified using ImageJ 1.46a and normalized to values of total tau Tau5 (Thermo Fisher Scientific; AHB0042).

ELISA

Primary auditory cortices, medial prefrontal cortices, and hippocampi were isolated from 6-month-old 5XFAD males and subjected to Aβ measurement using $A\beta_{42}$ or $A\beta_{40}$ ELISA kits (Invitrogen) according to the manufacturer's instructions. Insoluble Aβ was treated with 5M guanidine/50 mM Tris HCL (pH 8.0) buffer before ELISA measurement.

Behavioral Experiments

Novel Object Recognition

The novel object recognition (NOR) task consisted of a habituation phase followed by training and testing performed the following day, as previously described (Leger et al., 2013). 24 hours before training, mice were habituated to an open testing arena (40 cm L×40 cm W×35 cm H) for 5 min, during which total distance (cm), time in the center (s), and velocity (cm/s) were calculated (TSE Systems). During training, mice were placed into the same box with two identical objects placed in opposite corners. Mice were allowed a total of 20 seconds of object interaction time (within a maximum time frame of 10 minutes), and then immediately removed from the arena. Object memory was tested 1 hr later using the same procedure during training, except one object was replaced with a novel one in its place. Object exploration was recorded when the snout contacted either object and was calculated by a recognition index, $RI=T_{novel}/(T_{novel}+T_{familiar})$, where $T_{novel}$ and $T_{familiar}$ indicate the time spent with the novel and familiar object, respectively.

Novel Object Location

The novel location recognition (NOL) task was performed using the same procedure as the object recognition task, except two identical objects were used for both training and testing, and one object was displaced to a novel location during testing.

Morris Water Maze Test

Spatial reference memory testing was performed in a circular tank (diameter, 1.2 m) filled with white opaque water at approximately 22° C. Reference cues consisting of different colors and shapes were placed along the walls surrounding the tank. Within the tank was a fixed platform (diameter, 10 cm) located in a target quadrant. During testing, the platform was submerged and the mice were placed into the tank at one of seven points randomly facing the wall of the tank. Mice were provided 60 s to search for the platform, which if not found, were gently guided to it. Animals were kept on the platform for 15 s. Two trials a day were conducted with a 1 hour interatrial interval. Between the trails, mice were gently padded dry and warmed on a heating pad. Mouse behavior was video-recorded using TSE Systems. The escape latency, or the time it took for the mouse to reach the platform, was scored for each trial and averaged per testing day. On day 6, the platform was removed and a memory test (probe test) was performed. The time spent in each of the 4 quadrants and the number of crossing of the area where the platform used to be was recorded. Swimming velocity was recorded automatically.

CONCLUSION

Inventive aspects of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will see, e.g., the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for treating dementia or Alzheimer's disease in a subject in need thereof, the method comprising:
    (a) delivering a combined auditory stimulus and visual stimulus having a frequency of about 20 Hz to about 60 Hz to the subject, wherein the visual stimulus and the auditory stimulus are synchronized and have a phase relationship of from −180 to 0 degrees or from 0 to 180 degrees;
    (b) increasing, in response to (a), blood vessel diameter in the auditory cortex and/or the hippocampus of the subject; and
    (c) increasing, in response to (a), clearance of amyloid-beta (Aβ) plaque in the auditory cortex and/or the hippocampus of the subject via vasculature relative to absence of the auditory and visual stimuli.

2. The method of claim 1, the method further comprising:
    (d) reducing, in response to (a), tau phosphorylation in the auditory cortex and/or the hippocampus of the subject.

3. The method of claim 1, the method further comprising:
    (d) increasing, in response to (a), co-localization of Aβ with lipoprotein receptor-related protein 1 (LRP1) in the auditory cortex and/or the hippocampus of the subject.

4. The method of claim 1, the method further comprising:
    (d) increasing, in response to (a), a number of microglia in the auditory cortex and/or the hippocampus of the subject.

5. The method of claim 1, the method further comprising:
    (d) increasing, in response to (a), cell body area of microglia in the auditory cortex and/or the hippocampus of the subject.

6. The method of claim 1, the method further comprising:
    (d) decreasing, in response to (a), process length of microglia in the auditory cortex and/or the hippocampus of the subject.

7. The method of claim 1, the method further comprising:
    (d) increasing, in response to (a), process arborization of microglia in the auditory cortex and/or the hippocampus of the subject.

8. The method of claim 1, the method further comprising:
    (d) increasing, in response to (a), uptake of Aβ plaque by microglia in the auditory cortex and/or the hippocampus of the subject.

9. The method of claim 1, wherein the frequency is in a range from about 35 Hz to about 45 Hz.

10. The method of claim 9, wherein the frequency is about 40 Hz.

11. The method of claim 1, wherein the auditory stimulus includes a 10 kHz tone played at 40 Hz with a duty cycle of about 4% to about 80%.

12. The method of claim 1, wherein (a) comprises delivering the combined auditory stimulus and visual stimulus non-invasively.

13. The method of claim 1, further comprising delivering the combined auditory stimulus and visual stimulus for no more than about 6 hours each day for at least seven days.

14. A system comprising:
    a signal generator to generate a signal having a frequency of approximately 20 Hz to approximately 60 Hz;
    an auditory emitter, coupled to the signal generator, to administer an auditory stimulus to a subject, based on the signal generated by the signal generator; and
    a visual stimulator, coupled to the signal generator, to administer a visual stimulus to the subject, based on the signal generated by the signal generator, wherein the visual stimulus is synchronized to the auditory stimulus and has a phase relationship to the auditory stimulus of from −180 to 0 degrees or from 0 to 180 degrees, the visual stimulus adapted in combination with the auditory stimulus to induce increases in blood vessel diameter in the auditory cortex and/or the hippocampus of the subject, such that clearance of amyloid-beta (Aβ) plaque in the auditory cortex and/or the hippocampus of the subject via vasculature is increased relative to absence of the auditory and visual stimuli.

15. The method of claim 1, wherein (c) comprises reducing, in response to (a), an area and/or an amount of Aβ plaque in the auditory cortex and/or the hippocampus of the subject.

16. The method of claim 1, wherein the Aβ plaque comprises at least one of isoform $A\beta_{1-40}$ and isoform $A\beta_{1-42}$.

17. The method of claim 1, wherein (b) comprises about a 50% increase in blood vessel diameter in the auditory cortex.

18. The method of claim 1, wherein (b) comprises about a 105% increase in blood vessel diameter in the hippocampus.

19. The method of claim 1, further comprising:
(d) inducing, in response to (a), periodic spiking response in 5% or more of recording sites in the auditory cortex and/or the hippocampus of the subject.

20. The method of claim 1, further comprising:
(d) inducing, in response to (a), local field potential (LFP) at 40 Hz in the auditory cortex and/or the hippocampus of the subject.

21. The method of claim 1, further comprising:
(d) increasing clearance of Aβ plaque in at least one brain region of the subject via the glymphatic system.

22. The method of claim 1, further comprising:
(d) inducing, in response to (a), local field potential (LFP) at 40 Hz in the medial prefrontal cortex (mPFC) of the subject.

23. The method of claim 1, further comprising:
(d) delivering the combined auditory stimulus and visual stimulus for no more than about 6 hours each day for at least seven days; and
(e) increasing, in response to (a) and (d), clearance of Aβ plaque in the mPFC of the subject relative to absence of the visual and auditory stimuli.

24. The method of claim 23, wherein (e) comprises reducing, in response to (a) and (d), an area and/or an amount of Aβ plaque in the mPFC.

25. The method of claim 23, further comprising:
(f) increasing, in response to (a) and (d), a number of microglia in the mPFC of the subject.

26. The method of claim 23, further comprising:
(f) increasing, in response to (a) and (d), cell body diameter of microglia in the mPFC of the subject.

27. The method of claim 23, further comprising:
(f) decreasing, in response to (a) and (d), process length of microglia in the mPFC of the subject.

28. The method of claim 1, wherein the visual stimulus and the auditory stimulus are out of phase.

29. The method of claim 28, wherein the phase relationship is less than about 0 degrees.

30. The method of claim 28, wherein the phase relationship is greater than about 0 degrees.

31. The method of claim 1, wherein the phase relationship is 0 degrees.

32. The method of claim 31, further comprising:
(d) reducing, in response to (a), tau phosphorylation in the auditory cortex and/or the hippocampus of the subject.

33. The method of claim 31, further comprising:
(d) increasing, in response to (a), co-localization of Aβ with lipoprotein receptor-related protein 1 (LRP1) in the auditory cortex and/or the hippocampus of the subject.

34. The method of claim 31, further comprising:
(d) increasing, in response to (a), a number of microglia in the auditory cortex and/or the hippocampus of the subject.

35. The method of claim 31, further comprising:
(d) increasing, in response to (a), cell body area of microglia in the auditory cortex and/or the hippocampus of the subject.

36. The method of claim 31, further comprising:
(d) decreasing, in response to (a), process length of microglia in the auditory cortex and/or the hippocampus of the subject.

37. The method of claim 31, further comprising:
(d) increasing, in response to (a), process arborization of microglia in the auditory cortex and/or the hippocampus of the subject.

38. The method of claim 31, further comprising:
(d) increasing, in response to (a), uptake of Aβ plaque by microglia in the auditory cortex and/or the hippocampus of the subject.

39. The method of claim 31, wherein (c) comprises reducing, in response to (a), an area and/or an amount of Aβ plaque in the auditory cortex and/or the hippocampus of the subject.

40. The method of claim 31, wherein the Aβ plaque comprises at least one of isoform $A\beta_{1-40}$ and isoform $A\beta_{1-42}$.

41. The method of claim 31, wherein (b) comprises about a 50% increase in blood vessel diameter in the auditory cortex.

42. The method of claim 31, wherein (b) comprises about a 105% increase in blood vessel diameter in the hippocampus.

43. The method of claim 31, further comprising:
(d) inducing, in response to (a), periodic spiking response in 5% or more of recording sites in the auditory cortex and/or the hippocampus of the subject.

44. The method of claim 31, further comprising:
(d) inducing, in response to (a), local field potential (LFP) at 40 Hz in the auditory cortex and/or the hippocampus of the subject.

45. The method of claim 31, further comprising:
(d) inducing, in response to (a), local field potential (LFP) at 40 Hz in the medial prefrontal cortex (mPFC) of the subject.

46. The method of claim 31, further comprising:
(d) delivering the combined auditory stimulus and visual stimulus no more than about 6 hours each day for at least seven days; and
(e) increasing, in response to (a), clearance of Aβ plaque in the medial prefrontal cortex (mPFC) of the subject relative to absence of the visual and auditory stimuli.

47. The method of claim 46, wherein (e) comprises reducing, in response to (a) and (d), an area and/or an amount of Aβ plaque in the mPFC.

48. The method of claim 46, further comprising:
(f) increasing, in response to (a) and (d), a number of microglia in the mPFC of the subject.

49. The method of claim 46, further comprising:
(f) increasing, in response to (a) and (d), cell body diameter of microglia in the mPFC of the subject.

50. The method of claim 46, further comprising:
(f) decreasing, in response to (a) and (d), process length of microglia in the mPFC of the subject.

51. The method of claim 31, further comprising:
(d) increasing clearance of Aβ plaque in at least one brain region of the subject via the glymphatic system.

52. The system of claim 14, wherein the auditory stimulus is a click train.

53. The system of claim 14, wherein the frequency is in a range from about 35 Hz to about 45 Hz.

54. The system of claim 53, wherein the frequency is about 40 Hz.

55. The system of claim 14, wherein the auditory emitter is configured to administer the auditory stimulus non-invasively and the visual stimulator is configured to administer the visual stimulus non-invasively.

56. The system of claim 55, further comprising a noise canceling device to reduce ambient sound at least one ear of the subject.

57. The system of claim 14, further comprising a light blocking device to reduce ambient light to an eye of the subject.

58. The system of claim 14, wherein the visual stimulator comprises at least one light-emitting diode to emit the visual stimulus.

* * * * *